(12) United States Patent
Canne Bannen et al.

(10) Patent No.: US 8,367,667 B2
(45) Date of Patent: Feb. 5, 2013

(54) PYRROLE DERIVATIVES AS PHARMACEUTICAL AGENTS

(75) Inventors: Lynne Canne Bannen, Pacifica, CA (US); Jeff Chen, San Francisco, CA (US); Lisa Esther Dalrymple, San Francisco, CA (US); Brenton T Flatt, Poway, CA (US); Timothy Patrick Forsyth, Hayward, CA (US); Xiao-Hui Gu, San Diego, CA (US); Morrison B Mac, San Francisco, CA (US); Larry W Mann, Richland, MI (US); Grace Mann, Brisbane, CA (US); Richard Martin, San Diego, CA (US); Raju Mohan, Encinitas, CA (US); Brett Murphy, Lake Elsinore, CA (US); Michael Charles Nyman, San Diego, CA (US); William C Stevens, Escondido, CA (US); Tie-Lin Wang, San Diego, CA (US); Yong Wang, Foster City, CA (US); Jason H Wu, San Diego, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 13/214,665

(22) Filed: Aug. 22, 2011

(65) Prior Publication Data
US 2011/0301128 A1 Dec. 8, 2011

Related U.S. Application Data

(62) Division of application No. 11/572,962, filed as application No. PCT/US2005/026916 on Jul. 30, 2005, now Pat. No. 8,026,237.

(60) Provisional application No. 60/592,469, filed on Jul. 30, 2004, provisional application No. 60/592,439, filed on Jul. 30, 2004.

(51) Int. Cl.
*A61K 31/40* (2006.01)
*A61K 31/4439* (2006.01)
*A61K 31/454* (2006.01)
*A61K 31/5377* (2006.01)
*A61K 31/506* (2006.01)

(52) U.S. Cl. .............. 514/235.5; 514/256; 514/326; 514/343; 514/423

(58) Field of Classification Search .............. 514/427, 514/235.5, 256, 423, 326, 343
See application file for complete search history.

(56) References Cited

U.S. PATENT DOCUMENTS

| 6,479,531 | B1 | 11/2002 | Kalindjian et al. |
| 6,747,047 | B2 | 6/2004 | Lahm et al. |
| 2003/0236254 | A1 | 12/2003 | Lohray et al. |
| 2004/0102511 | A1 | 5/2004 | Sattigeri et al. |
| 2004/0267028 | A1 | 12/2004 | Smith et al. |

FOREIGN PATENT DOCUMENTS

| EP | 1298029 | 3/2004 |
| JP | 62-289557 A | 5/1987 |
| JP | 4-145078 A | 5/1992 |
| JP | 4-520351 A | 7/2004 |
| WO | 03/007993 A1 | 1/2003 |
| WO | 03/015777 | 2/2003 |
| WO | 03/016280 A1 | 2/2003 |
| WO | 03/016288 | 2/2003 |
| WO | 03/027069 A1 | 4/2003 |
| WO | 2004/005250 A1 | 1/2004 |
| WO | 2004/058249 A1 | 7/2004 |
| WO | 2004/060870 A1 | 7/2004 |

OTHER PUBLICATIONS

Vippagunta, et al., Advanced Drug Delivery Reviews, p. 1, (2001).
Wu, et al, Toxicology, 236:1-6, 2007.
Kato, et al, Heterocycles, 1978, vol. 10, p. 261-4.
STN preliminary search report, U.S. Appl. No. 11/572,962.
Supplementary Partial European Search Report for EP 05 80 3281, (2008).

*Primary Examiner* — Yong Chu
(74) *Attorney, Agent, or Firm* — McDonnell Boehnen Hulbert & Berghoff LLP

(57) ABSTRACT

Compounds, compositions and methods for modulating the activity of receptors are provided. In particular compounds and compositions are provided for modulating the activity of receptors and for the treatment, prevention, or amelioration of one or more symptoms of disease or disorder directly or indirectly related to the activity of the receptors.

33 Claims, No Drawings

# PYRROLE DERIVATIVES AS PHARMACEUTICAL AGENTS

CROSS REFERENCE TO RELATED APPLICATIONS

This application is a divisional application of U.S. Ser. No. 11/572,962, filed on Dec. 3, 2007, now U.S. Pat. No. 8,026,237 which is a US national phase of international application PCT/US2005/026916 filed on Jul. 30, 2005, which claims priority to U.S. Provisional Patent Application Ser. No. 60/592,469 filed on Jul. 30, 2004 and U.S. Provisional Patent Application Ser. No. 60/592,439 filed on Jul. 30, 2004, the disclosures of which are incorporated herein by reference.

FIELD OF THE INVENTION

Compounds, compositions and methods are provided for modulating the activity of receptors and for the treatment, prevention, or amelioration of one or more symptoms of disease or disorder related to the activity of the receptors.

BACKGROUND OF THE INVENTION

The nuclear receptor (NR) superfamily comprises more than 150 different proteins, most of which are believed to function as ligand activated transcription factors, exerting widely different biological responses by regulating gene expression (for review, see Di Croce et al, EMBO J1 8:6201-6210 (1999); Mangelsdorf, et al Cell 83:825-839 (1995); Perlmann, et al, Cell 90:391-397 (1997)). Members of this family include receptors for endogenous small, lipophilic molecules, such as steroid hormones, retinoids, vitamin D and thyroid hormone.

The classical steroid receptors include the mineralocorticoid receptor (MR) (or aldosterone receptor), the estrogen receptors, ER alpha and ER beta, the androgen receptor (AR), the progesterone receptor (PR) and the glucocorticoid receptor (GR). Also closely related in structure are the estrogen related receptors (ERRs) ERR1, ERR2 and ERR3. The steroid receptors perform important functions in the body related to the transcriptional homeostasis of electrolyte and water balance, growth, development and wound healing, fertility, stress responses, immunological function, and cognitive functioning (see, Assay Drug Dev. Technol., 1 (6): 843-52 (2003)). Accordingly, compounds that modulate (i.e. antagonize, agonize, partially antagonize, partially agonize) the activity of steroid nuclear receptors are important pharmaceutical agents that have specific utility in a number of methods, as well as for the treatment and prevention of a wide range of diseases and disorders modulated by the activity of steroid nuclear receptors.

Members of the steroid nuclear receptor sub-family exhibit significant homology to each other and possess closely related DNA and ligand binding domains. Given the close similarity in ligand binding domains of the steroid nuclear receptors, it is not surprising that many naturally occurring and synthetic molecules possess the ability to modulate the activity of more than one steroid nuclear receptor. For example the naturally occurring glucocorticoids cortisol and corticosterone are able to modulate both the glucocorticoid receptor and the mineralocorticoid receptor under physiological conditions.

Accordingly, one approach to developing compounds that are steroid nuclear receptor modulators is to identify a core chemical scaffold that exhibits a common structural motif that provides for the ability to bind to a steroid nuclear receptor, and which in certain embodiments possesses the ability to selectively modulate one or more of the other steroid nuclear receptors. Such compounds are useful for the local or systemic treatment or prophylaxis of human and veterinary diseases, disorders and conditions that are modulated, or otherwise affected by one or more steroid nuclear receptors, or in which steroid nuclear receptor activity, is implicated.

A well-characterized example of the classical steroid receptor sub-family that is amenable to this approach is the mineralocorticoid receptor (aldosterone receptor). The mineralocorticoid receptor plays an important role in regulating electrolyte balance and blood pressure in the body (Adv. Physiol. Educ., 26(1): 8-20 (2002), and its activity is modulated in vivo through the secretion of aldosterone.

Traditionally, it was thought that aldosterone was secreted by the zona glomerulosa of the adrenal gland in response to angiotensin II, potassium and adrenocorticotropic hormone (ACTH), and acted primarily on the epithelial cells of the kidney and colon to regulate sodium and potassium transport. More recently, it has been appreciated that aldosterone is also synthesized by endothelial cells and in vascular smooth muscle cells (VSMCs), the brain, blood vessels and myocardium where it may play a paracrine or autocrine role (Ann. N.Y. Acad. Sci. 970 89-100 (2002)).

Tissue specificity for aldosterone is conferred by the local expression of the mineralocorticoid receptor and by the activity of 11-beta hydroxysteroid dehydrogenase type 2 (11 β-HSD2), which acts to convert the cross-reactive glucocorticoids cortisol and corticosterone into cortisone and 11-dehydrocorticosterone which have significantly reduced affinity for the MR (Science, 242: 583-585 (1988)).

In humans, elevated plasma aldosterone concentrations are usually associated with hypertension, typically mediated through the effect of the hormone on sodium retention and blood volume. Hypertension affects about 5 million Americans, approximately a third of which are unaware of their condition and are not receiving treatment. Hypertension is associated with the development of cardiovascular, cardiac and renal diseases, including chronic and congestive heart failure (J. Postgrad. Med. J., 79:634-642 (2003)), progressive renal failure (J. Am. Soc. Nephrol., 14:2395-2401 (2003)) and chronic and end stage renal failure (Am. J. Kid. Dis., 37 (4): 677-688 (2001)). In these conditions, elevated blood pressure appears to enhance and amplify the progressive decline in organ function in these diseases.

Aldosterone also has direct effects on brain, heart, vascular and renal tissues. In the heart, vascular and renal tissues, aldosterone action can also play a significant role in the development and progression of inflammation, scarring and fibrosis (the generation of fibrotic tissue) independently of the effects on blood pressure (Clin. Cardiol., 23:724-730 (2000); Adv. Physiol. Educ., 26(1): 8-20 (2002); Hypertension, 26:101-111 (1995)).

In the brain, aldosterone has been linked to various cognitive dysfunctions, and aldosterone antagonists have been shown to be useful for improving cognitive function (US Application UA2002/0111337), and treating cognitive & mood dysfunctions.

In chronic heart failure (CHF), impaired cardiac function triggers a train of compensatory mechanisms, including aldosterone secretion, that ultimately leads to a worsening of symptoms and reduced survival (J. Clin. Endo & Meta, 88: (6) 2376-2383 (2003)). These changes are primarily mediated by the renin-angiotensin-aldosterone system (RAAS) and sympathetic nervous system. Activation of the RAAS leads to increases in renin, angiotensin II and aldosterone. Angiotensin II acts as a vasoconstrictor, promotes aldosterone production, and stimulates norepinephrine release from sympathetic nerve terminals to increase the heart rate. Aldosterone acts to increase blood volume, and hence blood pressure, through its action in the kidney to retain sodium.

While the net effect of these factors is to restore blood pressure, the increased peripheral vascular resistance also increases the load against which the heart works. Ultimately the increased cardiac pressure results in cardiac re-modeling, leading to lung stiffness, pulmonary edema, and breathlessness. Additionally peripheral vasoconstriction results in reduced blood flow to the skeletal muscles contributing to fatigue during exercise.

Current drug treatments for CHF are focused on relieving the symptoms of the disease, improving the quality of life, slowing disease progression, preventing hospital admission, prolonging active life, and reducing mortality. Such therapeutic approaches include the use of diuretics, angiotensin converting enzyme inhibitors (ACE inhibitors), beta adrenergic receptor blockers (beta blockers), AT antagonists and calcium channel blockers to suppress the harmful effects of the neuroendocrine compensatory mechanisms such as the RAAS and beta adrenergic (symphathetic) nervous system. (Postgrad. Med. J. 79 634-642 (2003)).

Diuretics act to reduce water retention, reduce blood pressure and can act as vasodilators to reduce circulatory resistance. ACE inhibitors and beta blockers have been shown to reduce mortality and improve symptom status in CHF in part by reducing angiotensin II and aldosterone levels. However angiotensin II and aldosterone typically return to normal levels with chronic therapy. Accordingly, angiotensin II receptor antagonists, which selectively block the AT1 angiotensin receptor, and aldosterone antagonists, which selectively block the mineralocorticoid receptor, provide significant therapeutic benefit for the treatment of CHF (Circulation, 100:1056-1064 (1999); N. Eng. J. Med., 341 (10):709-718 (1999)).

In addition to aldosterone and angiotensin II, calcium channels play an important role in heart failure. In both vascular and cardiac tissue, muscle cell contraction occurs when cells are depolarized from the influx of calcium through calcium channels in the cell. Calcium channel blockers inhibit muscle contraction and promote relaxation. In vascular smooth muscle this results in vessel dilation, reduced blood pressure (anti-hypertensive effect) and a reduction in the force required to pump blood by the heart. Calcium channel blockers also act on the heart to improve filling by promoting relaxation of cardiac muscle in diastole. However, calcium channel blockers also reduce the force of contraction during systole (negative inotropy) and therefore are often not the drug of choice for treating heart failure.

Hypertension is not only a primary cause of the development of cardiovascular, cardiac and renal diseases, but a risk factor for the progression of these diseases initiated by other mechanisms such as atherosclerosis, cardiovascular disease, ischemic heart disease, diabetes, diabetic nephropathy, chronic glomerulonephritis and polycystic kidney disease (J. Am. Soc. Nephrol., 14:2395-2401 (2003)).

In renal failure, as with the case of chronic heart failure, a number of clinical trials have established that interruption of the RAAS cascade with ACE inhibitors is beneficial in limiting renal disease (Am. J. Kid. Dis., 37 (4): 677-688 (2001). Additional studies have also established that aldosterone antagonists can attenuate proteinuria and renal damage typically observed in progressive renal disease and offer further therapeutic benefit compared to ACE inhibitors alone (Hypertension., 31:451-458 (1998)).

Many aldosterone antagonists are known. For example spironolactone, the first approved aldosterone antagonist, has been used for blocking aldosterone-dependent sodium transport in the distal tubule of the kidney in order to reduce edema and to treat essential hypertension and primary hyperaldosteronism (F. Mantero et al, Clin. Sci. Mol. Med., 45 (Suppl 1), 219s-224s (1973)). Spironolactone is also used commonly in the treatment of other hyperaldosterone-related diseases such as liver cirrhosis, renal failure and congestive heart failure (F. J. Saunders et al, Aldactone; Spironolactone: A Comprehensive Review, Searle, N.Y. (1978)).

However, spironolactone is not very selective for the MR over other steroid receptors, including the androgen and progesterone receptors. This cross reactivity leads to undesired side effects such as menstrual irregularity in women, and gynecomastia in men (Circulation, 107:2512-2518 (2003)). Eplerenone is a derivative of spironolactone that is more selective for the MR than spironolactone (Nature Reviews, 2: 177-178 (2003)). However, eplerenone has relatively low potency for the MR, induces hyperkalemia, and is primarily eliminated via the kidney, making it unsuitable for patients with progressive renal failure.

Accordingly, there is a need for new modulators that are useful in the prevention, treatment, or amelioration of one or more of the symptoms of diseases or disorders associated with mineralocorticoid receptor activity. Such diseases or disorders include, but are not limited to fluid retention, edema, primary hyperaldosteronism, Conn's syndrome, hypertension, high blood pressure, liver cirrhosis, cardiovascular disease, heart failure, chronic heart failure, cardiac disease, renal disease, chronic kidney disease, fibrosis, and cognitive dysfunctions.

SUMMARY OF THE INVENTION

Compounds for use in pharmaceutical compositions and methods for modulating the activity of one or more steroid nuclear receptors are provided. In one embodiment, the compounds for use in the compositions and methods provided herein have formula (I):

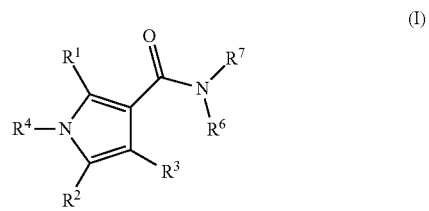

wherein:
$R^1$ and $R^2$ are each independently hydrogen, halo, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroaralkyl, optionally substituted heterocyclyl, optionally substituted heterocyclylalkyl, —OR$^9$, —SR$^9$, —N(R$^9$)$_2$, —C(O)OR$^9$ or —C(O)N(R$^9$)$_2$;
$R^3$ is independently hydrogen, halo, cyano, optionally substituted alkyl, optionally substituted alkenyl or optionally substituted alkynyl;
$R^4$ is hydrogen, —C(O)R$^9$ or —S(O)$_2$R$^9$; or $R^4$ is alkyl, alkenyl or alkynyl, where each is optionally substituted by one or more substituents selected from the group consisting of halo, haloalkyl, nitro, —OR$^9$, —SR$^9$, —S(O)$_t$R$^{10}$ (where t is 1 or 2), —N(R$^9$)$_2$, —CN, —C(O)R$^9$, —C(S)R$^9$, —C(NR$^9$)R$^9$, —C(O)OR$^9$, —C(S)OR$^9$, —C(NR$^9$)OR$^9$, —C(O)N(R$^9$)$_2$, —C(S)N(R$^9$)$_2$, —C(NR$^9$)N(R$^9$)$_2$, —C(O)SR$^9$, —C(S)SR$^9$, —C(NR$^9$)SR$^9$, —S(O)$_t$OR$^9$ (where t is 1 or 2), —S(O)$_t$N(R$^9$)$_2$ (where t is 1 or 2), —S(O)$_t$N(R$^9$)N(R$^9$)$_2$ (where t is 1 or 2), —S(O)$_t$N(R$^9$)N=C(R$^9$)$_2$, —S(O)$_t$N(R$^9$)C(O)R$^{10}$ (where t is 1 or 2), —S(O)$_t$N(R$^9$)C(O)N(R$^9$)$_2$ (where t is 1 or 2), —R$^8$—S(O)$_t$N(R$^9$)C(NR$^9$)N(R$^9$)$_2$ (where t is 1 or 2), —N(R$^9$)C(O)R$^{10}$, —N(R$^9$)C(O)OR$^{10}$, —N(R$^9$)C(O)SR$^{10}$, —N(R$^9$)C(NR$^9$)SR$^{10}$, —N(R$^9$)C(S)SR$^{10}$, —N(R$^9$)C(O)N(R$^9$)$_2$, —N(R$^9$)C(NR$^9$)N(R$^9$)$_2$, —N(R$^9$)C(S)N(R$^9$)$_2$, —N(R$^9$)S(O)$_t$R$^{10}$ (where t is 1 or 2), —OC(O)R$^{10}$, —OC(NR$^9$)R$^{10}$, —OC(S)R$^{10}$, —OC(O)OR$^{10}$, —OC(NR$^9$)OR$^{10}$, —OC(S)OR$^{10}$, —OC(O)SR$^9$, —OC(O)N(R$^9$)$_2$, —OC(NR$^9$)N(R$^9$)$_2$, —OC(S)N(R$^9$)$_2$, —C(O)—R$^{11}$—C(O)R$^9$, —C(O)—R$^{11}$—C(S)R$^9$, —C(O)—R$^{11}$—C(NR$^9$)R$^9$, —C(O)—R$^{11}$—C(O)OR$^9$, —C(O)—R$^{11}$—C(S)OR$^9$, —C(O)—R$^{11}$—C(NR$^9$)OR$^9$, —C(O)—R$^{11}$—C(O)N(R$^9$)$_2$, —C(O)—R$^{11}$—C(S)N(R$^9$)$_2$, —C(O)—R$^{11}$—C(NR$^9$)N(R$^9$)$_2$, —C(O)—R$^{11}$—C(O)SR$^9$, —C(O)—R$^{11}$—C(S)SR$^9$ and —C(O)—R$^{11}$—C(NR$^9$)SR$^9$;

or R$^4$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^8$—SR$^9$, —R$^8$—S(O)$_t$R$^{10}$ (where t is 1 or 2), —R$^8$—N(R$^9$)$_2$, —R$^8$—CN, —R$^8$—C(O)R$^9$, —R$^8$—C(S)R$^9$, —R$^8$—C(NR$^9$)R$^9$, —R$^8$—C(O)OR$^9$, —R$^8$—C(S)OR$^9$, —R$^8$—C(NR$^9$)OR$^9$, —R$^8$—C(O)N(R$^9$)$_2$, —R$^8$—C(S)N(R$^9$)$_2$, —R$^8$—C(NR$^9$)N(R$^9$)$_2$, —R$^8$—C(O)SR$^9$, —R$^8$—C(S)SR$^9$, —R$^8$—C(NR$^9$)SR$^9$, —R$^8$—S(O)$_t$OR$^9$ (where t is 1 or 2), —R$^8$—S(O)$_t$N(R$^9$)$_2$ (where t is 1 or 2), —R$^8$—S(O)$_t$N(R$^9$)N(R$^9$)$_2$ (where t is 1 or 2), —R$^8$—S(O)$_t$N(R$^9$)N=C(R$^9$)$_2$, —R$^8$—S(O)$_t$N(R$^9$)C(O)R$^{10}$ (where t is 1 or 2), —R$^8$—S(O)$_t$N(R$^6$)C(O)N(R$^9$)$_2$ (where t is 1 or 2), —R$^8$—S(O)$_t$N(R$^9$)C(NR$^9$)N(R$^9$)$_2$ (where t is 1 or 2), —R$^8$—N(R$^9$)C(O)R$^{10}$, —R$^8$—N(R$^9$)C(O)OR$^{10}$, —R$^8$—N(R$^9$)C(O)SR$^{10}$, —R$^8$—N(R$^9$)C(NR$^9$)SR$^{10}$, —R$^8$—N(R$^9$)C(S)SR$^{10}$, —R$^8$—N(R$^9$)C(O)N(R$^9$)$_2$, —R$^8$—N(R$^9$)C(NR$^9$)N(R$^9$)$_2$, —R$^8$—N(R$^9$)C(S)N(R$^9$)$_2$, —R$^8$—N(R$^9$)S(O)$_t$R$^{10}$ (where t is 1 or 2), —R$^8$—OC(O)R$^{10}$, —R$^8$—OC(NR$^9$)R$^{10}$, —R$^8$—OC(S)R$^{10}$, —R$^8$—OC(O)OR$^{10}$, —R$^6$—OC(NR$^9$)OR$^{10}$, —R$^6$—OC(S)OR$^{10}$, —R$^6$—OC(C)SR$^9$, —R$^8$—OC(O)N(R$^9$)$_2$, —R$^8$—OC(NR$^9$)N(R$^9$)$_2$, —R$^8$—OC(S)N(R$^9$)$_2$, —R$^8$—C(O)—R$^{11}$—C(O)R$^9$, —R$^8$—C(O)—R$^{11}$—C(S)R$^9$, —R$^8$—C(O)—R$^{11}$—C(NR$^9$)R$^9$, —R$^8$—C(O)—R$^{11}$—C(O)OR$^9$, —R$^6$—C(O)—R$^{11}$—C(S)OR$^9$, —R$^8$—C(O)—R$^{11}$—C(NR$^9$)OR$^9$, —R$^8$—C(O)—R$^{11}$—C(O)N(R$^9$)$_2$, —R$^8$—C(O)—R$^{11}$—C(S)N(R$^9$)$_2$, —R$^8$—C(O)—R$^{11}$—C(NR$^9$)N(R$^9$)$_2$, —R$^8$—C(O)—R$^{11}$—C(O)SR$^9$, —R$^8$—C(O)—R$^{11}$—C(S)SR$^9$ and —R$^8$—C(O)—R$^{11}$—C(NR$^9$)SR$^9$;

R$^6$ is hydrogen or optionally substituted alkyl;

R$^7$ is alkyl, alkenyl or alkynyl, where each is optionally substituted by one or more substituents selected from the group consisting of nitro, halo, —OR$^{14}$, —SR$^{14}$, —S(O)$_t$R$^{15}$ (where t is 1 or 2), —N(R$^{14}$)$_2$, —CN, —C(O)R$^{14}$, —C(S)R$^{14}$, —C(NR$^{14}$)R$^{14}$, —C(O)OR$^{14}$, —C(S)OR$^{14}$, —C(NR$^{14}$)OR$^{14}$, —C(O)N(R$^{14}$)$_2$, —C(S)N(R$^{14}$)$_2$, —C(NR$^{14}$)N(R$^{14}$)$_2$, —C(O)SR$^{14}$, —C(S)SR$^{14}$, —C(NR$^{14}$)SR$^{14}$, —S(O)$_t$OR$^{14}$ (where t is 1 or 2), —S(O)$_t$N(R$^{14}$)$_2$ (where t is 1 or 2), —S(O)$_t$N(R$^{14}$)N(R$^{14}$)$_2$ (where t is 1 or 2), —S(O)$_t$N(R$^{14}$)N=C(R$^{14}$)$_2$, —S(O)$_t$N(R$^{14}$)C(O)R$^{15}$ (where t is 1 or 2), —R$^8$—S(O)$_t$N(R$^{14}$)C(O)N(R$^{14}$)$_2$ (where t is 1 or 2), —R$^8$—S(O)$_t$N(R$^{14}$)C(NR$^{14}$)N(R$^{14}$)$_2$ (where t is 1 or 2), —N(R$^{14}$)C(O)R$^{15}$, —N(R$^{14}$)C(O)OR$^{15}$, —N(R$^{14}$)C(O)SR$^{15}$, —N(R$^{14}$)C(NR$^{14}$)SR$^{15}$, —N(R$^{14}$)C(S)SR$^{15}$, —N(R$^{14}$)C(O)N(R$^{14}$)$_2$, —N(R$^{14}$)C(NR$^{14}$)N(R$^{14}$)$_2$, —N(R$^{14}$)C(S)N(R$^{14}$)$_2$, —N(R$^{14}$)S(O)$_t$R$^{15}$ (where t is 1 or 2), —OC(O)R$^{15}$, —OC(NR$^{14}$)R$^{15}$, —OC(S)R$^{15}$, —OC(O)OR$^{15}$, —OC(NR$^{14}$)OR$^{15}$, —OC(S)OR$^{15}$, —OC(O)SR$^{14}$, —OC(O)N(R$^{14}$)$_2$, —OC(NR$^{14}$)N(R$^{14}$)$_2$, —OC(S)N(R$^{14}$)$_2$, —C(O)—R$^{16}$—C(O)R$^{14}$, —C(O)—R$^{16}$—C(S)R$^{14}$, —C(O)—R$^{16}$—C(NR$^{14}$)R$^{14}$, —C(O)—R$^{16}$—C(O)OR$^{14}$, —C(O)—R$^{16}$—C(S)OR$^{14}$, —C(O)—R$^{16}$—C(NR$^{14}$)OR$^{14}$, —C(O)—R$^{16}$—C(O)N(R$^{14}$)$_2$, —C(O)—R$^{16}$—C(S)N(R$^{14}$)$_2$, —C(O)—R$^{16}$—C(NR$^{14}$)N(R$^{14}$)$_2$, —C(O)—R$^{16}$—C(O)SR$^{14}$, —C(O)—R$^{16}$—C(S)SR$^{14}$ and —C(O)—R$^{16}$—C(NR$^{14}$)SR$^{14}$;

or R$^7$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of halo, nitro, dioxo, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^{13}$—OR$^{14}$, —R$^{13}$—SR$^{14}$, —R$^{13}$—S(O)$_t$R$^{15}$ (where t is 1 or 2), —R$^{13}$—N(R$^{14}$)$_2$, —R$^{13}$—CN, —R$^{13}$—C(O)R$^{14}$, —R$^{13}$—C(S)R$^{14}$, —R$^{13}$—C(NR$^{14}$)R$^{14}$, —R$^{13}$—C(O)OR$^{14}$, —R$^{13}$—C(S)OR$^{14}$, —R$^{13}$—C(NR$^{14}$)OR$^{14}$, —R$^{13}$—C(O)N(R$^{14}$)$_2$, —R$^{13}$—C(S)N(R$^{14}$)$_2$, —R$^{13}$—C(NR$^{14}$)N(R$^{14}$)$_2$, —R$^{13}$—C(O)SR$^{14}$, —R$^{13}$—C(S)SR$^{14}$, —R$^{13}$—C(NR$^{14}$)SR$^{14}$, —R$^{13}$—S(O)$_t$OR$^{14}$ (where t is 1 or 2), —R$^{13}$—S(O)$_t$N(R$^{14}$)$_2$ (where t is 1 or 2), —R$^{13}$—S(O)$_t$N(R$^{14}$)N(R$^{14}$)$_2$ (where t is 1 or 2), —R$^{13}$—S(O)$_t$N(R$^{14}$)N=C(R$^{14}$)$_2$, —R$^{13}$—S(O)$_t$N(R$^{14}$)C(O)R$^{15}$ (where t is 1 or 2), —R$^{13}$—S(O)$_t$N(R$^{14}$)C(NR$^{14}$)N(R$^{14}$)$_2$ (where t is 1 or 2), —R$^{13}$—N(R$^{14}$)C(O)R$^{18}$, —R$^{13}$—N(R$^{14}$)C(O)OR$^{15}$, —R$^{13}$—N(R$^{14}$)C(O)SR$^{15}$, —R$^{13}$—N(R$^{14}$)C(NR$^{14}$)SR$^{15}$, —R$^{13}$—N(R$^{14}$)C(S)SR$^{15}$, —R$^{13}$—N(R$^{14}$)C(O)N(R$^{14}$)$_2$, —R$^{13}$—N(R$^{14}$)C(NR$^{14}$)N(R$^{14}$)$_2$, —R$^{13}$—N(R$^{14}$)C(S)N(R$^{14}$)$_2$, —R$^{13}$—N(R$^{14}$)S(O)$_t$R$^{15}$ (where t is 1 or 2), —R$^{13}$—OC(O)R$^{15}$, —R$^{13}$—OC(NR$^{14}$)R$^{15}$, —R$^{13}$—OC(S)R$^{15}$, —R$^{13}$—OC(O)OR$^{15}$, —R$^{13}$—OC(NR$^{14}$)OR$^{15}$, —R$^{13}$—OC(S)OR$^{15}$, —R$^{13}$—OC(O)SR$^{14}$, —R$^{13}$—OC(O)N(R$^{14}$)$_2$, —R$^{13}$—OC(NR$^{14}$)N(R$^{14}$)$_2$, —R$^{13}$—OC(S)N(R$^{14}$)$_2$, —R$^{13}$—C(O)—R$^{16}$—C(O)R$^{14}$, —R$^{13}$—C(O)—R$^{16}$—C(S)R$^{14}$, —R$^{13}$—C(O)—R$^{16}$—C(NR$^{14}$)R$^{14}$, —R$^{13}$—C(O)—R$^{16}$—C(O)OR$^{14}$, —R$^{13}$—C(O)—R$^{16}$—C(S)OR$^{14}$, —R$^{13}$—C(O)—R$^{16}$—C(NR$^{14}$)OR$^{14}$, —R$^{13}$—C(O)—R$^{16}$—C(O)N(R$^{14}$)$_2$, —R$^{13}$—C(O)—R$^{16}$—C(S)N(R$^{14}$)$_2$, —R$^{13}$—C(O)—R$^{16}$—C(NR$^{14}$)N(R$^{14}$)$_2$, —R$^{13}$—C(O)—R$^{16}$—C(O)SR$^{14}$, —R$^{13}$—C(O)—R$^{16}$—C(S)SR$^{14}$ and —R$^{13}$—C(O)—R$^{16}$—C(NR$^{14}$)SR$^{14}$;

where each R$^8$ and R$^{13}$ are independently a direct bond, an optionally substituted straight or branched alkylene chain, or an optionally substituted straight or branched alkenylene chain;

where each $R^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two $R^9$s, together with the nitrogen to which they are attached, form an optionally substituted heterocyclyl;

where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two $R^{14}$s, together with the nitrogen to which they are attached, form an optionally substituted heterocyclyl;

where each $R^{10}$ and $R^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl;

where each $R^{11}$ and $R^{16}$ are independently an optionally substituted straight or branched alkylene chain or an optionally substituted straight or branched alkenylene chain; and as a single isomer, a mixture of isomers, or as a racemic mixture of isomers; or as a solvate or polymorph; or as a prodrug; or as a pharmaceutically acceptable salt thereof.

In another aspect, the invention includes compounds of formula (II);

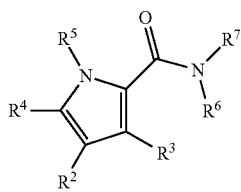

(II)

wherein:
$R^2$ is independently hydrogen, halo, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroaralkyl, optionally substituted heterocyclyl, optionally substituted heterocyclylalkyl, —$OR^9$, —$SR^9$, —$N(R^9)_2$, —$C(O)OR^9$ or —$C(O)N(R^9)_2$;

$R^3$ is independently hydrogen, halo, cyano, optionally substituted alkyl, optionally substituted alkenyl, or optionally substituted alkynyl;

$R^4$ is hydrogen; —$C(O)R^9$ or —$S(O)_2R^9$; or $R^4$ is alkyl, alkenyl or alkynyl, where each is optionally substituted by one or more substituents selected from the group consisting of halo, haloalkyl, nitro, —$OR^9$, —$SR^9$, —$S(O)_tR^{10}$ (where t is 1 or 2), —$N(R^9)_2$, —CN, —$C(O)R^9$, —$C(S)R^9$, —$C(NR^9)R^9$, —$C(O)OR^9$, —$C(S)OR^9$, —$C(NR^9)OR^9$, —$C(O)N(R^9)_2$, —$C(S)N(R^9)_2$, —$C(NR^9)N(R^9)_2$, —$C(O)SR^9$, —$C(S)SR^9$, —$C(NR^9)SR^9$, —$S(O)_tOR^9$ (where t is 1 or 2), —$S(O)_tN(R^9)_2$ (where t is 1 or 2), —$S(O)_tN(R^9)N(R^9)_2$ (where t is 1 or 2), —$S(O)_tN(R^9)N=C(R^9)_2$, —$S(O)_tN(R^9)C(O)R^{10}$ (where t is 1 or 2), —$R^8$—$S(O)_tN(R^9)C(O)N(R^9)_2$ (where t is 1 or 2), —$R^8$—$S(O)_tN(R^9)C(NR^9)N(R^9)_2$ (where t is 1 or 2), —$N(R^9)C(O)R^{10}$, —$N(R^9)C(O)OR^{10}$, —$N(R^9)C(O)SR^{10}$, —$N(R^9)C(NR^9)SR^{10}$, —$N(R^9)C(S)SR^{10}$, —$N(R^9)C(O)N(R^9)_2$, —$N(R^9)C(NR^9)N(R^9)_2$, —$N(R^9)C(S)N(R^9)_2$, —$N(R^9)S(O)_tR^{10}$ (where t is 1 or 2), —$OC(O)R^{10}$, —$OC(NR^9)R^{10}$, —$OC(S)R^{10}$, —$OC(O)OR^{10}$, —$OC(NR^9)OR^{10}$, —$OC(S)OR^{10}$, —$OC(O)SR^9$, —$OC(O)N(R^9)_2$, —$OC(NR^9)N(R^9)_2$, —$OC(S)N(R^9)_2$, —$C(O)$—$R^{11}$—$C(O)R^9$, —$C(O)$—$R^{11}$—$C(S)R^9$, —$C(O)$—$R^{11}$—$C(NR^9)R^9$, —$C(O)$—$R^{11}$—$C(O)OR^9$, —$C(O)$—$R^{11}$—$C(S)OR^9$, —$C(O)$—$R^{11}$—$C(NR^9)OR^9$, —$C(O)$—$R^{11}$—$C(O)N(R^9)_2$, —$C(O)$—$R^{11}$—$C(S)N(R^9)_2$, —$C(O)$—$R^{11}$—$C(NR^9)N(R^9)_2$, —$C(O)$—$R^{11}$—$C(O)SR^9$, —$C(O)$—$R^{11}$—$C(S)SR^9$ and —$C(O)$—$R^{11}$—$C(NR^9)SR^9$;

or $R^4$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^9)_2$, —$R^8$—CN, —$R^8$—$C(O)R^9$, —$R^8$—$C(S)R^9$, —$R^8$—$C(NR^9)R^9$, —$R^8$—$C(O)OR^9$, —$R^8$—$C(S)OR^9$, —$R^8$—$C(NR^9)OR^9$, —$R^8$—$C(O)N(R^9)_2$, —$R^8$—$C(S)N(R^9)_2$, —$R^8$—$C(NR^9)N(R^9)_2$, —$R^8$—$C(O)SR^9$, —$R^8$—$C(S)SR^9$, —$R^8$—$C(NR^9)SR^9$, —$R^8$—$S(O)_tOR^9$ (where t is 1 or 2), —$R^8$—$S(O)_tN(R^9)_2$ (where t is 1 or 2), —$R^8$—$S(O)_tN(R^9)N(R^9)_2$ (where t is 1 or 2), —$R^8$—$S(O)_tN(R^9)N=C(R^9)_2$, —$R^8$—$S(O)_tN(R^9)C(O)R^{10}$ (where t is 1 or 2), —$R^8$—$S(O)_tN(R^9)C(O)N(R^9)_2$ (where t is 1 or 2), —$R^8$—$N(R^9)C(O)R^{10}$, —$R^8$—$N(R^9)C(O)OR^{10}$, —$R^8$—$N(R^9)C(O)SR^{10}$, —$R^8$—$N(R^9)C(NR^9)SR^{10}$, —$R^8$—$N(R^9)C(S)SR^{10}$, —$R^8$—$N(R^9)C(O)N(R^9)_2$, —$R^8$—$N(R^9)C(NR^9)N(R^9)_2$, —$R^8$—$N(R^9)C(S)N(R^9)_2$, —$R^8$—$N(R^9)S(O)_tR^{10}$ (where t is 1 or 2), —$R^8$—$OC(O)R^{10}$, —$R^8$—$OC(NR^9)R^{10}$, —$R^8$—$OC(S)R^{10}$, —$R^8$—$OC(O)OR^{10}$, —$R^8$—$OC(NR^9)OR^{10}$, —$R^8$—$OC(S)OR^{10}$, —$R^8$—$OC(O)SR^9$, —$R^8$—$OC(O)N(R^9)_2$, —$R^8$—$OC(NR^9)N(R^9)_2$, —$R^8$—$OC(S)N(R^9)_2$, —$R^8$—$C(O)$—$R^{11}$—$C(O)R^9$, —$R^8$—$C(O)$—$R^{11}$—$C(S)R^9$, —$R^8$—$C(O)$—$R^{11}$—$C(NR^9)R^9$, —$R^8$—$C(O)$—$R^{11}$—$C(O)OR^9$, —$R^8$—$C(O)$—$R^{11}$—$C(S)OR^9$, —$R^8$—$C(O)$—$R^{11}$—$C(NR^9)OR^9$, —$R^8$—$C(O)$—$R^{11}$—$C(O)N(R^9)_2$, —$R^8$—$C(O)$—$R^{11}$—$C(S)N(R^9)_2$, —$R^8$—$C(O)$—$R^{11}$—$C(NR^9)N(R^3)_2$, —$R^8$—$C(O)$—$R^{11}$—$C(O)SR^9$, —$R^8$—$C(O)$—$R^{11}$—$C(S)SR^9$ and —$R^8$—$C(O)$—$R^{11}$—$C(NR^9)SR^9$;

$R^5$ is hydrogen, optionally substituted alkyl, optionally substituted cycloalkyl, optionally substituted cycloalkylalkyl, optionally substituted aryl, optionally substituted aralkyl, optionally substituted heteroaryl, optionally substituted heteroaralkyl, —$C(O)R^9$ or —$S(O)_2R^9$;

$R^6$ is hydrogen or optionally substituted alkyl;

$R^7$ is alkyl, alkenyl or alkynyl, where each is optionally substituted by one or more substituents selected from the group consisting of nitro, halo, optionally substituted cycloalkyl, optionally substituted heterocyclyl, optionally substituted aryl, optionally substituted heteroaryl, —OR$^{14}$, —SR$^{14}$, —S(O)$_t$R$^{15}$ (where t is 1 or 2), —N(R$^{14}$)$_2$, —CN, —C(O)R$^{14}$, —C(S)R$^{14}$, —C(NR$^{14}$)R$^{14}$, —C(O)OR$^{14}$, —C(S)OR$^{14}$, —C(NR$^{14}$)OR$^{14}$, —C(O)N(R$^{14}$)$_2$, —C(S)N(R$^{14}$)$_2$, —C(NR$^{14}$)N(R$^{14}$)$_2$, —C(O)SR$^{14}$, —C(S)SR$^{14}$, —C(NR$^{14}$)SR$^{14}$, —S(O)$_t$OR$^{14}$ (where t is 1 or 2), —S(O)$_t$N(R$^{14}$)$_2$ (where t is 1 or 2), —S(O)$_t$N(R$^{14}$)N(R$^{14}$)$_2$ (where t is 1 or 2), —S(O)$_t$N(R$^{14}$)N=C(R$^{14}$)$_2$, —S(O)$_t$N(R$^{14}$)C(O)R$^{15}$ (where t is 1 or 2), —R$^8$—S(O)$_t$N(R$^{14}$)C(O)N(R$^{14}$)$_2$ (where t is 1 or 2), —N(R$^{14}$)C(O)R$^{15}$, —N(R$^{14}$)C(O)OR$^{15}$, —N(R$^{14}$)C(O)SR$^{15}$, —N(R$^{14}$)C(NR$^{14}$)SR$^{15}$, —N(R$^{14}$)C(S)SR$^{15}$, —N(R$^{14}$)C(O)N(R$^{14}$)$_2$, —N(R$^{14}$)C(NR$^{14}$)N(R$^{14}$)$_2$, —N(R$^{14}$)C(S)N(R$^{14}$)$_2$, —N(R$^{14}$)S(O)$_t$R$^{15}$ (where t is 1 or 2), —OC(O)R$^{15}$, —OC(NR$^{14}$)R$^{15}$, —OC(S)R$^{15}$, —OC(O)OR$^{15}$, —OC(NR$^{14}$)OR$^{15}$, —OC(S)OR$^{15}$, —OC(O)SR$^{14}$, —OC(O)N(R$^{14}$)$_2$, —OC(NR$^{14}$)N(R$^{14}$)$_2$, —OC(S)N(R$^{14}$)$_2$, —R$^{13}$—C(O)—R$^{16}$—C(O)R$^{14}$, —R$^{13}$—C(O)—R$^{16}$—C(S)R$^{14}$, —R$^{13}$—C(O)—R$^{16}$—C(NR$^{14}$)R$^{14}$, —R$^{13}$—C(O)—R$^{16}$—C(O)OR$^{14}$, —R$^{13}$—C(O)—R$^{16}$—C(S)OR$^{14}$, —R$^{13}$—C(O)—R$^{16}$—C(NR$^{14}$)OR$^{14}$, —R$^{13}$—C(O)—R$^{16}$—C(O)N(R$^{14}$)$_2$, —R$^{13}$—C(O)—R$^{16}$—C(S)N(R$^{14}$)$_2$, —R$^{13}$—C(O)—R$^{16}$—C(NR$^{14}$)N(R$^{14}$)$_2$, —R$^{13}$—C(O)—R$^{16}$—C(O)SR$^{14}$, —R$^{13}$—C(O)—R$^{16}$—C(S)SR$^{14}$ and —R$^{13}$—C(O)—R$^{16}$—C(NR$^{14}$)SR$^{14}$;

or R$^7$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of halo, nitro, dioxo, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^{13}$—OR$^{14}$, —R$^{13}$—SR$^{14}$, —R$^{13}$—S(O)$_t$R$^{15}$ (where t is 1 or 2), —R$^{13}$—N(R$^{14}$)$_2$, —R$^{13}$—CN, —R$^{13}$—C(O)R$^{14}$, —R$^{13}$—C(S)R$^{14}$, —R$^{13}$—C(NR$^{14}$)R$^{14}$, —R$^{13}$—C(O)OR$^{14}$, —R$^{13}$—C(S)OR$^{14}$, —R$^{13}$—C(NR$^{14}$)OR$^{14}$, —R$^{13}$—C(O)N(R$^{14}$)$_2$, —R$^{13}$—C(S)N(R$^{14}$)$_2$, —R$^{13}$—C(NR$^{14}$)N(R$^{14}$)$_2$, —R$^{13}$—C(O)SR$^{14}$, —R$^{13}$—C(S)SR$^{14}$, —R$^{13}$—C(NR$^{14}$)SR$^{14}$, —R$^{13}$—S(O)$_t$OR$^{14}$ (where t is 1 or 2), —R$^{13}$—S(O)$_t$N(R$^{14}$)$_2$ (where t is 1 or 2), —R$^{13}$—S(O)$_t$N(R$^{14}$)N(R$^{14}$)$_2$ (where t is 1 or 2), —R$^{13}$—S(O)$_t$N(R$^{14}$)N=C(R$^{14}$)$_2$, —R$^{13}$—S(O)$_t$N(R$^{14}$)C(O)R$^{15}$, —R$^{13}$—N(R$^{14}$)C(O)R$^{15}$, —R$^{13}$—N(R$^{14}$)C(O)OR$^{15}$, —R$^{13}$—N(R$^{14}$)C(O)SR$^{15}$, —R$^{13}$—N(R$^{14}$)C(NR$^{14}$)SR$^{15}$, —R$^{13}$—N(R$^{14}$)C(S)SR$^{15}$, —R$^{13}$—N(R$^{14}$)C(O)N(R$^{14}$)$_2$, —R$^{13}$—N(R$^{14}$)C(NR$^{14}$)N(R$^{14}$)$_2$, —R$^{13}$—N(R$^{14}$)C(S)N(R$^{14}$)$_2$, —R$^{13}$—N(R$^{14}$)S(O)$_t$R$^{15}$ (where t is 1 or 2), —R$^{13}$—OC(O)R$^{15}$, —R$^{13}$—OC(NR$^{14}$)R$^{15}$, —R$^{13}$—OC(S)R$^{15}$, —R$^{13}$—OC(O)OR$^{15}$, —R$^{13}$—OC(NR$^{14}$)OR$^{15}$, —R$^{13}$—OC(S)OR$^{15}$, —R$^{13}$—OC(O)SR$^{14}$, —R$^{13}$—OC(O)N(R$^{14}$)$_2$, —R$^{13}$—OC(NR$^{14}$)N(R$^{14}$)$_2$, —R$^{13}$—OC(S)N(R$^{14}$)$_2$, —R$^{13}$—C(O)—R$^{16}$—C(O)R$^{14}$, —R$^{13}$—C(O)—R$^{16}$—C(S)R$^{14}$, —R$^{13}$—C(O)—R$^{16}$—C(NR$^{14}$)R$^{14}$, —R$^{13}$—C(O)—R$^{16}$—C(O)OR$^{14}$, —R$^{13}$—C(O)—R$^{16}$—C(S)OR$^{14}$, —R$^{13}$—C(O)—R$^{16}$—C(NR$^{14}$)OR$^{14}$, —R$^{13}$—C(O)—R$^{16}$—C(O)N(R$^{14}$)$_2$, —R$^{13}$—C(O)—R$^{16}$—C(S)N(R$^{14}$)$_2$, —R$^{13}$—C(O)—R$^{16}$—C(NR$^{14}$)N(R$^{14}$)$_2$, —R$^{13}$—C(O)—R$^{16}$—C(O)SR$^{14}$, —R$^{13}$—C(O)—R$^{16}$—C(S)SR$^{14}$ and —R$^{13}$—C(O)—R$^{16}$—C(NR$^{14}$)SR$^{14}$;

where each R$^8$ and R$^{13}$ are independently a direct bond, an optionally substituted straight or branched alkylene chain, or an optionally substituted straight or branched alkenylene chain;

where each R$^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two R$^9$s, together with the nitrogen to which they are attached, form an optionally substituted heterocyclyl;

where each R$^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two R$^{14}$s, together with the nitrogen to which they are attached, form an optionally substituted heterocyclyl;

where each R$^{10}$ and R$^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; and where each R$^{11}$ and R$^{16}$ are independently an optionally substituted straight or branched alkylene chain or an optionally substituted straight or branched alkenylene chain;

as a single isomer, a mixture of isomers, or as a racemic mixture of isomers; or as a solvate or polymorph; or as a prodrug; or as a pharmaceutically acceptable salt thereof.

In another aspect, the invention includes compounds of formula (III);

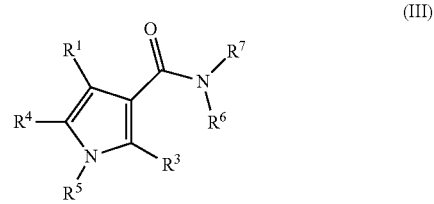

(III)

wherein:

R$^1$ is independently hydrogen, halo, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroaralkyl, optionally substituted heterocyclyl, optionally substituted heterocyclylalkyl, —OR$^9$, —SR$^9$, —N(R$^9$)$_2$, —C(O)OR$^9$ or —C(O)N(R$^9$)$_2$;

R$^3$ is independently hydrogen, halo, cyano, optionally substituted alkyl, optionally substituted alkenyl or optionally substituted alkynyl;

R$^4$ is hydrogen; —C(O)R$^9$ or —S(O)$_2$R$^9$; or R$^4$ is alkyl, alkenyl or alkynyl optionally substituted by one or more substituents selected from the group consisting of halo, haloalkyl, haloalkoxy, nitro, —OR$^9$, —SR$^9$, —S(O)$_t$R$^{10}$ (where t is 1 or 2), —N(R$^9$)$_2$, —CN, —C(O)R$^9$, —C(S)R$^9$, —C(NR$^9$)R$^9$, —C(O)OR$^9$, —C(S)OR$^9$, —C(NR$^9$)OR$^9$, —C(O)N(R$^9$)$_2$, —C(S)N(R$^9$)$_2$, —C(NR$^9$)N(R$^9$)$_2$, —C(O)SR$^9$, —C(S)SR$^9$, —C(NR$^9$)SR$^9$, —S(O)$_t$OR$^9$ (where t is 1 or 2), —S(O)$_t$N(R$^9$)$_2$ (where t is 1 or 2), —S(O)$_t$N(R$^9$)N(R$^9$)$_2$ (where t is 1 or 2), —S(O)$_t$N(R$^9$)N═C(R$^9$)$_2$, —S(O)$_t$N(R$^9$)C(O)R$^{10}$ (where t is 1 or 2), —R$^8$—S(O)$_t$N(R$^9$)C(O)N(R$^9$)$_2$ (where t is 1 or 2), —R$^8$—S(O)$_t$N(R$^9$)C(NR$^9$)N(R$^9$)$_2$ (where t is 1 or 2), —N(R$^9$)C(O)R$^{10}$, —N(R$^9$)C(O)OR$^{10}$, —N(R$^9$)C(O)SR$^{10}$, —N(R$^9$)C(NR$^9$)SR$^{10}$, —N(R$^g$)C(S)SR$^{10}$, —N(R$^9$)C(O)N(R$^9$)$_2$, —N(R$^9$)C(NR$^9$)N(R$^9$)$_2$, —N(R$^9$)C(S)N(R$^9$)$_2$, —N(R$^9$)S(O)$_t$R$^{10}$ (where t is 1 or 2), —OC(O)R$^{10}$, —OC(NR$^9$)R$^{10}$, —OC(S)R$^{10}$, —OC(O)OR$^{10}$, —OC(NR$^9$)OR$^{10}$, —OC(S)OR$^{10}$, —OC(O)SR$^9$, —OC(O)N(R$^9$)$_2$, —OC(NR$^9$)N(R$^9$)$_2$, —OC(S)N(R$^9$)$_2$, —C(O)—R$^{11}$—C(O)R$^9$, —C(O)—R$^{11}$—C(S)R$^9$, —C(O)—R$^{11}$—C(NR$^9$)R$^9$, —C(O)—R$^{11}$—C(O)OR$^9$, —C(O)—R$^{11}$—C(S)OR$^9$, —C(O)—R$^{11}$—C(NR$^9$)OR$^9$, —C(O)—R$^{11}$—C(O)N(R$^g$)$_2$, —C(O)—R$^{11}$—C(S)N(R$^9$)$_2$, —C(O)—R$^{11}$—C(NR$^9$)N(R$^9$)$_2$, —C(O)—R$^{11}$—C(O)SR$^9$, —C(O)—R$^{11}$—C(S)SR$^9$ and —C(O)—R$^{11}$—C(NR$^9$)SR$^9$;

or R$^4$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^8$—OR$^9$, —R$^8$—SR$^9$, —R$^8$—S(O)$_t$R$^{10}$ (where t is 1 or 2), —R$^8$—N(R$^9$)$_2$, —R$^8$—CN, —R$^8$—C(O)R$^9$, —R$^8$—C(S)R$^9$, —R$^8$—C(NR$^9$)R$^9$, —R$^8$—C(O)OR$^S$, —R$^8$—C(S)OR$^9$, —R$^8$—C(NR$^9$)OR$^9$, —R$^8$—C(O)N(R$^9$)$_2$, —R$^8$—C(S)N(R$^9$)$_2$, —R$^8$—C(NR$^9$)N(R$^9$)$_2$, —R$^8$—C(O)SR$^9$, —R$^8$—C(S)SR$^9$, —R$^8$—C(NR$^9$)SR$^9$, —R$^8$—S(O)$_t$OR$^9$ (where t is 1 or 2), —R$^8$—S(O)$_t$N(R$^9$)$_2$ (where t is 1 or 2), —R$^8$—S(O)$_t$N(R$^9$)N═C(R$^9$)$_2$, —R$^8$—S(O)$_t$N(R$^9$)C(O)R$^{10}$ (where t is 1 or 2), —R$^8$—S(O)$_t$N(R$^9$)C(O)N(R$^9$)$_2$ (where t is 1 or 2), —R$^8$—N(R$^9$)C(O)R$^{10}$, —R$^8$—N(R$^9$)C(O)OR$^{10}$, —R$^8$—N(R$^9$)C(O)SR$^{10}$, —R$^8$—N(R$^g$)C(NR$^9$)SR$^{10}$, —R$^8$—N(R$^9$)C(S)SR$^{10}$, —R$^8$—N(R$^9$)C(O)N(R$^9$)$_2$, —R$^8$—N(R$^9$)C(NR$^9$)N(R$^9$)$_2$, —R$^8$—N(R$^9$)C(S)N(R$^9$)$_2$, —R$^8$—N(R$^9$)S(O)$_t$R$^{10}$ (where t is 1 or 2), —R$^8$—OC(O)R$^{10}$, —R$^8$—OC(NR$^9$)R$^{10}$, —R$^8$—OC(S)R$^{10}$, —R$^8$—OC(O)OR$^{10}$, —R$^8$—OC(NR$^9$)OR$^{10}$, —R$^8$—OC(S)OR$^{10}$, —R$^8$—OC(O)SR$^9$, —R$^8$—OC(O)N(R$^9$)$_2$, —R$^8$—OC(NR$^9$)N(R$^9$)$_2$, —R$^8$—OC(S)N(R$^9$)$_2$, —R$^8$—C(O)—R$^{11}$—C(O)R$^9$, —R$^8$—C(O)—R$^{11}$—C(S)R$^9$, —R$^8$—C(O)—R$^{11}$—C(NR$^9$)R$^9$, —R$^8$—C(O)—R$^{11}$—C(O)OR$^9$, —R$^8$—C(O)—R$^{11}$—C(S)OR$^9$, —R$^8$—C(O)—R$^{11}$—C(NR$^9$)OR$^9$, —R$^6$—C(O)—R$^{11}$—C(O)N(R$^9$)$_2$, —R$^8$—C(O)—R$^{11}$—C(S)N(R$^9$)$_2$, —R$^8$—C(O)—R$^{11}$—C(NR$^9$)N(R$^9$)$_2$, —R$^8$—C(O)—R$^{11}$—C(O)SR$^9$, —R$^8$—C(O)—R$^{11}$—C(S)SR$^9$ and —R$^6$—C(O)—R$^{11}$—C(NR$^9$)SR$^9$;

R$^5$ is hydrogen, optionally substituted alkyl, optionally substituted cycloalkyl, optionally substituted cycloalkylalkyl, optionally substituted aryl, optionally substituted aralkyl, optionally substituted heteroaryl, optionally substituted heteroaralkyl, —C(O)R$^9$ or —S(O)$_2$R$^9$;

or R$^5$ is alkyl, alkenyl or alkynyl, where each is optionally substituted by one or more substituents selected from the group consisting of halo, haloalkyl, haloalkoxy, nitro, —OR$^9$, —SR$^9$, —S(O)$_t$R$^{10}$ (where t is 1 or 2), —N(R$^9$)$_2$, —CN, —C(O)R$^9$, —C(S)R$^9$, —C(NR$^9$)R$^9$, —C(O)OR$^9$, —C(S)OR$^9$, —C(NR$^9$)OR$^9$, —C(O)N(R$^9$)$_2$, —C(S)N(R$^9$)$_2$, —C(NR$^9$)N(R$^9$)$_2$, —C(O)SR$^9$, —C(S)SR$^9$, —C(NR$^9$)SR$^9$, —S(O)$_t$OR$^9$ (where t is 1 or 2), —S(O)$_t$N(R$^9$)$_2$ (where t is 1 or 2), —S(O)$_t$N(R$^9$)N(R$^9$)$_2$ (where t is 1 or 2), —S(O)$_t$N(R$^9$)N═C(R$^9$)$_2$, —S(O)$_t$N(R$^9$)C(O)R$^{10}$ (where t is 1 or 2), —S(O)$_t$N(R$^9$)C(O)N(R$^9$)$_2$ (where t is 1 or 2), —R$^8$—S(O)$_t$N(R$^9$)C(NR$^9$)N(R$^9$)$_2$ (where t is 1 or 2), —N(R$^9$)C(O)R$^{10}$, —N(R$^9$)C(O)OR$^{10}$, —N(R$^9$)C(O)SR$^{16}$, —N(R$^9$)C(NR$^9$)SR$^{10}$, —N(R$^9$)C(S)SR$^{10}$, —N(R$^9$)C(O)N(R$^9$)$_2$, —N(R$^9$)C(NR$^9$)N(R$^9$)$_2$, —N(R$^9$)C(S)N(R$^9$)$_2$, —N(R$^9$)S(O)$_t$R$^{10}$ (where t is 1 or 2), —OC(O)R$^{10}$, —OC(NR$^9$)R$^{10}$, —OC(S)R$^{10}$, —OC(O)OR$^{10}$, —OC(NR$^9$)OR$^{10}$, —OC(S)OR$^{10}$, —OC(O)SR$^9$, —OC(O)N(R$^9$)$_2$, —OC(NR$^9$)N(R$^9$)$_2$, —OC(S)N(R$^9$)$_2$, —C(O)—R$^{11}$—C(O)R$^9$, —C(O)—R$^{11}$—C(S)R$^9$, —C(O)—R$^{11}$—C(NR$^9$)R$^9$, —C(O)—R$^{11}$—C(O)OR$^9$, —C(O)—R$^{11}$—C(S)OR$^9$, —C(O)—R$^{11}$—C(NR$^9$)OR$^9$, —C(O)—R$^{11}$—C(O)N(R$^9$)$_2$, —C(O)—R$^{11}$—C(S)N(R$^9$)$_2$, —C(O)—R$^{11}$—C(NR$^9$)N(R$^9$)$_2$, —C(O)—R$^{11}$—C(O)SR$^9$, —C(O)—R$^{11}$—C(S)SR$^9$ and —C(O)—R$^{11}$—C(NR$^9$)SR$^9$;

R$^6$ is hydrogen, alkyl or optionally substituted alkyl;

R$^7$ is alkyl, alkenyl or alkynyl, where each is optionally substituted with one or more substituents selected from the group consisting of nitro, halo, optionally substituted cycloalkyl, optionally substituted heterocyclyl, optionally substituted aryl, optionally substituted heteroaryl, —OR$^{14}$, —SR$^{14}$, —S(O)$_t$R$^{15}$ (where t is 1 or 2), —N(R$^{14}$)$_2$, —CN, —C(O)R$^{14}$, —C(S)R$^{14}$, —C(NR$^{14}$)R$^{14}$, —C(O)OR$^{14}$, —C(S)OR$^{14}$, —C(NR$^{14}$)OR$^{14}$, —C(O)N(R$^{14}$)$_2$, —C(S)N(R$^{14}$)$_2$, —C(NR$^{14}$)N(R$^{14}$)$_2$, —C(O)SR$^{14}$, —C(S)SR$^{14}$, —C(NR$^{14}$)SR$^{14}$, —S(O)$_t$OR$^{14}$ (where t is 1 or 2), —S(O)$_t$N(R$^{14}$)$_2$ (where t is 1 or 2), —S(O)$_t$N(R$^{14}$)N(R$^{14}$)$_2$ (where t is 1 or 2), —S(O)$_t$N(R$^{14}$)N═C(R$^{14}$)$_2$, —S(O)$_t$N(R$^{14}$)C(O)R$^{15}$ (where t is 1 or 2), —S(O)$_t$N(R$^{14}$)C(O)N(R$^{14}$)$_2$ (where t is 1 or 2), —N(R$^{14}$)C(O)R$^{15}$, —N(R$^{14}$)C(O)OR$^{15}$, —N(R$^{14}$)C(O)SR$^{15}$, —N(R$^{14}$)C(NR$^{14}$)SR$^{15}$, —N(R$^{14}$)C(S)SR$^{15}$, —N(R$^{14}$)C(O)N(R$^{14}$)$_2$, —N(R$^{14}$)C(NR$^{14}$)N(R$^{14}$)$_2$, —N(R$^{14}$)C(S)N(R$^{14}$)$_2$, —N(R$^{14}$)S(O)$_t$R$^{15}$ (where t is 1 or 2), —OC(O)R$^{15}$, —OC(NR$^{14}$)R$^{15}$, —OC(S)R$^{15}$, —OC(O)OR$^{15}$, —OC(NR$^{14}$)OR$^{15}$, —OC(S)OR$^{15}$, —OC(O)SR$^{14}$, —OC(O)N(R$^{14}$)$_2$, —OC(NR$^{14}$)N(R$^{14}$)$_2$, —OC(S)N(R$^{14}$)$_2$, —C(O)—R$^{16}$—C(O)R$^{14}$, —C(O)—R$^{16}$—C(S)R$^{14}$, —C(O)—R$^{16}$—C(NR$^{14}$)R$^{14}$, —C(O)—R$^{16}$—C(O)OR$^{14}$, —C(O)—R$^{16}$—C(S)OR$^{14}$, —C(O)—R$^{16}$—C(NR$^{14}$)OR$^{14}$, —C(O)—R$^{16}$—C(O)N(R$^{14}$)$_2$, —C(O)—R$^{16}$—C(S)N(R$^{14}$)$_2$, —C(O)—R$^{16}$—C(NR$^{14}$)N(R$^{14}$)$_2$, —C(O)—R$^{16}$—C(O)SR$^{14}$, —C(O)—R$^{16}$—C(S)SR$^{14}$ and —C(O)—R$^{16}$—C(NR$^{14}$)SR$^{14}$;

or R$^7$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, dioxo, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^{13}$—OR$^{14}$, —R$^{13}$—SR$^{14}$, —R$^{13}$—S(O)$_t$R$^{15}$ (where t is 1 or 2), —R$^{13}$—N(R$^{14}$)$_2$, —R$^{13}$—CN, —R$^{13}$—C(O)R$^{14}$, —R$^{13}$—C(S)R$^{14}$, —R$^{13}$—C(NR$^{14}$)R$^{14}$, —R$^{13}$—C(O)OR$^{14}$, —R$^{13}$—C(S)OR$^{14}$, —R$^{13}$—C(NR$^{14}$)OR$^{14}$, —R$^{13}$—C(O)N(R$^{14}$)$_2$, —R$^{13}$—C(S)N(R$^{14}$)$_2$, —R$^{13}$—C(NR$^{14}$)N(R$^{14}$)$_2$, —R$^{13}$—C(O)SR$^{14}$, —R$^{13}$—C(S)SR$^{14}$, —R$^{13}$—C(NR$^{14}$)SR$^{14}$, —R$^{13}$—S(O)$_t$OR$^{14}$ (where t is 1 or 2), —R$^{13}$—S(O)$_t$N(R$^{14}$)$_2$ (where t is 1 or 2), —R$^{13}$—S(O)$_t$N(R$^{14}$)N(R$^{14}$)$_2$ (where t is 1 or 2), —R$^{13}$—S(O)$_t$N(R$^{14}$)N=C(R$^{14}$)$_2$, —R$^{13}$—S(O)$_t$N(R$^{14}$)C(O)R$^{15}$, —R$^{13}$—N(R$^{14}$)C(O)R$^{18}$, —R$^{13}$—N(R$^{14}$)C(O)OR$^{18}$, —R$^{13}$—N(R$^{14}$)C(O)SR$^{15}$, —R$^{13}$—N(R$^{14}$)C(NR$^{14}$)SR$^{15}$, —R$^{13}$—N(R$^{14}$)C(S)SR$^{15}$, —R$^{13}$—N(R$^{14}$)C(O)N(R$^{14}$)$_2$, —R$^{13}$—N(R$^{14}$)C(NR$^{14}$)N(R$^{14}$)$_2$, —R$^{13}$—N(R$^{14}$)C(S)N(R$^{14}$)$_2$, —R$^{13}$—N(R$^{14}$)S(O)$_t$R$^{15}$ (where t is 1 or 2), —R$^{13}$—OC(O)R$^{15}$, —R$^{13}$—OC(NR$^{14}$)R$^{15}$, —R$^{13}$—OC(S)R$^{15}$, —R$^{13}$—OC(O)OR$^{15}$, —R$^{13}$—OC(NR$^{14}$)OR$^{18}$, —R$^{13}$—OC(S)OR$^{15}$, —R$^{13}$—OC(O)SR$^{14}$, —R$^{13}$—OC(O)N(R$^{14}$)$_2$, —R$^{13}$—OC(NR$^{14}$)N(R$^{14}$)$_2$, —R$^{13}$—OC(S)N(R$^{14}$)$_2$—R$^{13}$—C(O)—R$^{16}$—C(O)R$^{14}$, —R$^{13}$—C(O)—R$^{16}$—C(S)R$^{14}$, —R$^{13}$—C(O)—R$^{16}$—C(NR$^{14}$)R$^{14}$, —R$^{13}$—C(O)—R$^{16}$—C(O)OR$^{14}$, —R$^{13}$—C(O)—R$^{16}$—C(S)OR$^{14}$, —R$^{13}$—C(O)—R$^{16}$—C(NR$^{14}$)OR$^{14}$, —R$^{13}$—C(O)—R$^{16}$—C(O)N(R$^{14}$)$_2$, —R$^{13}$—C(O)—R$^{16}$—C(S)N(R$^{14}$)$_2$, —R$^{13}$—C(O)—R$^{16}$—C(NR$^{14}$)N(R$^{14}$)$_2$, —R$^{13}$—C(O)—R$^{16}$—C(O)SR$^{14}$, —R$^{13}$—C(O)—R$^{16}$—C(S)SR$^{14}$ and —R$^{13}$—C(O)—R$^{16}$—C(NR$^{14}$)SR$^{14}$;

where each R$^8$ and R$^{13}$ are independently a direct bond, an optionally substituted straight or branched alkylene chain, or an optionally substituted straight or branched alkenylene chain;

where each R$^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two R$^9$s, together with the nitrogen to which they are attached, form an optionally substituted heterocyclyl;

where each R$^{14}$ is independently selected from the group consisting of hydrogen, optionally substituted alkyl, optionally substituted alkenyl, optionally substituted alkynyl, optionally substituted cycloalkyl, cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two R$^{14}$s, together with the nitrogen to which they are attached, form an optionally substituted heterocyclyl;

where each R$^{10}$ and R$^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each R$^{11}$ and R$^{16}$ are independently an optionally substituted straight or branched alkylene chain or an optionally substituted straight or branched alkenylene chain;

as a single isomer, a mixture of isomers, or as a racemic mixture of isomers; or as a solvate or polymorph; or as a prodrug; or as a pharmaceutically acceptable salt thereof.

In another aspect, the invention includes compounds of formula (IV):

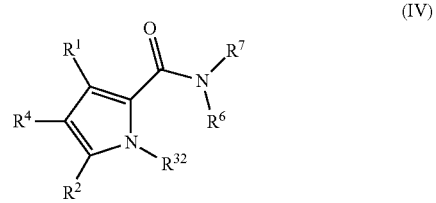

wherein:

R$^1$ and R$^2$ are each independently hydrogen, halo, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroaralkyl, optionally substituted heterocyclyl, optionally substituted heterocyclylalkyl, —OR$^9$, —SR$^9$, —N(R$^9$)$_2$, —C(O)OR$^9$ or —C(O)N(R$^9$)$_2$;

R$^4$ is hydrogen;

or R$^4$ is alkyl, alkenyl or alkynyl, where each is optionally substituted by one or more substituents selected from the group consisting of halo, haloalkyl, haloalkoxy, nitro, —OR$^9$, —SR$^9$, —S(O)$_t$R$^{10}$ (where t is 1 or 2), —N(R$^9$)$_2$, —CN, —C(O)R$^9$, —C(S)R$^9$, —C(NR$^9$)R$^9$, —C(O)OR$^9$, —C(S)OR$^9$, —C(NR$^9$)OR$^9$, —C(O)N(R$^9$)$_2$, —C(S)N(R$^9$)$_2$, —C(NR$^9$)N(R$^9$)$_2$, —C(O)SR$^9$, —C(S)SR$^9$, —C(NR$^9$)SR$^9$, —S(O)$_t$OR$^9$ (where t is 1 or 2), —S(O)$_t$N(R$^9$)$_2$ (where t is 1 or 2), —S(O)$_t$N(R$^9$)N(R$^9$)$_2$ (where t is 1 or 2), —S(O)$_t$N(R$^9$)N=C(R$^9$)$_2$, —S(O)$_t$N(R$^9$)C(O)R$^{10}$ (where t is 1 or 2), —R$^8$—S(O)$_t$N(R$^9$)C(O)N(R$^9$)$_2$ (where t is 1 or 2), —R$^8$—S(O)$_t$N(R$^9$)C(NR$^9$)N(R$^9$)$_2$ (where t is 1 or 2), —N(R$^9$)C(O)R$^{10}$, —N(R$^9$)C(O)OR$^{10}$, —N(R$^9$)C(O)SR$^{10}$, —N(R$^9$)C(NR$^9$)SR$^{10}$, —N(R$^9$)C(S)SR$^{10}$, —N(R$^9$)C(O)N(R$^9$)$_2$, —N(R$^9$)C(NR$^9$)N(R$^9$)$_2$, —N(R$^9$)C(S)N(R$^9$)$_2$, —N(R$^9$)S(O)$_t$R$^{10}$ (where t is 1 or 2), —OC(O)R$^{10}$, —OC(NR$^9$)R$^{10}$, —OC(S)R$^{10}$, —OC(O)OR$^{10}$, —OC(NR$^9$)OR$^{10}$, —OC(S)OR$^{10}$, —OC(O)SR$^9$, —OC(O)N(R$^9$)$_2$, —OC(NR$^9$)N(R$^9$)$_2$, —OC(S)N(R$^9$)$_2$, —C(O)—R$^{11}$—C(O)R$^9$, —C(O)—R$^{11}$—C(S)R$^9$, —C(O)—R$^{11}$—C(NR$^9$)R$^9$, —C(O)—R$^{11}$—C(O)OR$^9$, —C(O)—R$^{11}$—C(S)OR$^9$, —C(O)—R$^{11}$—C(NR$^9$)OR$^9$, —C(O)—R$^{11}$—C(O)N(R$^9$)$_2$, —C(O)—R$^{11}$—C(S)N(R$^9$)$_2$, —C(O)—R$^{11}$—C(NR$^9$)N(R$^9$)$_2$, —C(O)—R$^{11}$—C(O)SR$^9$, —C(O)—R$^{11}$—C(S)SR$^9$ and —C(O)—R$^{11}$—C(NR$^9$)SR$^9$;

or R$^4$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^8$—OR$^9$, —R$^8$—SR$^9$, —R$^8$—S(O)$_t$R$^{10}$ (where t is 1 or 2), —R$^8$—N(R$^9$)$_2$, —R$^8$—CN, —R$^8$—C(O)R$^9$, —R$^8$—C(S)R$^9$, —R$^8$—C(NR$^9$)R$^9$, —R$^8$—C(O)OR$^9$, —R$^8$—C(S)OR$^9$, —R$^8$—C(NR$^9$)OR$^9$, —R$^2$—C(O)N(R$^9$)$_2$, —R$^8$—C(S)N(R$^9$)$_2$, —R$^8$—C(NR$^9$)N(R$^9$)$_2$, —R$^8$—C(O)SR$^9$, —R$^8$—C(S)

$SR^9$, $-R^8-C(NR^9)SR^9$, $-R^8-S(O)_tOR^9$ (where t is 1 or 2), $-R^8-S(O)_tN(R^9)_2$ (where t is 1 or 2), $-R^8-S(O)_tN(R^9)N(R^9)_2$ (where t is 1 or 2), $-R^8-S(O)_tN(R^9)N=C(R^9)_2$, $-R^8-S(O)_tN(R^9)C(O)R^{10}$ (where t is 1 or 2), $-R^8-S(O)_tN(R^9)C(O)N(R^9)_2$ (where t is 1 or 2), $-R^8-N(R^9)C(O)R^{10}$, $-R^8-N(R^9)C(O)OR^{10}$, $-R^8-N(R^9)C(O)SR^{10}$, $-R^8-N(R^9)C(NR^9)SR^{10}$, $-R^8-N(R^9)C(S)SR^{10}$, $-R^8-N(R^9)C(O)N(R^9)_2$, $-R^8-N(R^9)C(NR^9)N(R^9)_2$, $-R^8-N(R^9)C(S)N(R^9)_2$, $-R^6-N(R^9)S(O)_tR^{10}$ (where t is 1 or 2), $-R^8-OC(O)R^{10}$, $-R^8-OC(NR^9)R^{10}$, $-R^8-OC(S)R^{10}$, $-R^8-OC(O)OR^{10}$, $-R^8-OC(NR^9)OR^{10}$, $-R^8-OC(S)OR^{10}$, $-R^8-OC(O)SR^9$, $-R^8-OC(O)N(R^9)_2$, $-R^8-OC(NR^9)N(R^9)_2$, $-R^8-OC(S)N(R^9)_2$, $-R^6-C(O)-R^{11}-C(O)R^9$, $-R^8-C(O)-R^{11}-C(S)R^9$, $-R^8-C(O)-R^{11}-C(NR^9)R^9$, $-R^8-C(O)-R^{11}-C(O)OR^9$, $-R^8-C(O)-R^{11}-C(S)OR^9$, $-R^8-C(O)-R^{11}-C(NR^9)OR^9$, $-R^6-C(O)-R^{11}-C(O)N(R^9)_2$, $-R^8-C(O)-R^{11}-C(S)N(R^9)_2$, $-R^6-C(O)-R^{11}-C(NR^9)N(R^9)_2$, $-R^8-C(O)-R^{11}-C(O)SR^9$, $-R^6-C(O)-R^{11}-C(S)SR^9$ and $-R^8-C(O)-R^{11}-C(NR^9)SR^9$;

$R^6$ is hydrogen or optionally substituted alkyl;

each $R^7$ is alkyl, alkenyl or alkynyl, where each is optionally substituted with one or more substituents selected from the group consisting of nitro, halo, optionally substituted cycloalkyl, optionally substituted heterocyclyl, optionally substituted aryl, optionally substituted heteroaryl, $-OR^{14}$, $-SR^{14}$, $-S(O)_tR^{15}$ (where t is 1 or 2), $-N(R^{14})_2$, $-CN$, $-C(O)R^{14}$, $-C(S)R^{14}$, $-C(NR^{14})R^{14}$, $-C(O)OR^{14}$, $-C(S)OR^{14}$, $-C(NR^{14})OR^{14}$, $-C(O)N(R^{14})_2$, $-C(S)N(R^{14})_2$, $-C(NR^{14})N(R^{14})_2$, $-C(O)SR^{14}$, $-C(S)SR^{14}$, $-C(NR^{14})SR^{14}$, $-S(O)_tOR^{14}$ (where t is 1 or 2), $-S(O)_tN(R^{14})_2$ (where t is 1 or 2), $-S(O)_tN(R^{14})N(R^{14})_2$ (where t is 1 or 2), $-S(O)_tN(R^{14})N=C(R^{14})_2$, $-S(O)_tN(R^{14})C(O)R^{15}$, $-N(R^{14})C(O)R^{15}$, $-N(R^{14})C(O)OR^{15}$, $-N(R^{14})C(O)SR^{15}$, $-N(R^{14})C(NR^{14})SR^{15}$, $-N(R^{14})C(S)SR^{15}$, $-N(R^{14})C(O)N(R^{14})_2$, $-N(R^{14})C(NR^{14})N(R^{14})_2$, $-N(R^{14})C(S)N(R^{14})_2$, $-N(R^{14})S(O)_tR^{15}$ (where t is 1 or 2), $-OC(O)R^{15}$, $-OC(NR^{14})R^{15}$, $-OC(S)R^{15}$, $-OC(O)OR^{15}$, $-OC(NR^{14})OR^{15}$, $-OC(S)OR^{15}$, $-OC(O)SR^{14}$, $-OC(O)N(R^{14})_2$, $-OC(NR^{14})N(R^{14})_2$, $-OC(S)N(R^{14})_2$, $-C(O)-R^{15}-C(O)R^{14}$, $-C(O)-R^{15}-C(S)R^{14}$, $-C(O)-R^{15}-C(NR^{14})R^{14}$, $-C(O)-R^{16}-C(O)OR^{14}$, $-C(O)-R^{16}-C(S)OR^{14}$, $-C(O)-R^{16}-C(NR^{14})OR^{14}$, $-C(O)-R^{16}-C(O)N(R^{14})_2$, $-C(O)-R^{16}-C(S)N(R^{14})_2$, $-C(O)-R^{16}-C(NR^{14})N(R^{14})_2$, $-C(O)-R^{16}-C(O)SR^{14}$, $-C(O)-R^{16}-C(S)SR^{14}$ and $-C(O)-R^{16}-C(NR^{14})SR^{14}$;

or each $R^7$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, dioxo, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, $-R^{13}-OR^{14}$, $-R^{13}-SR^{14}$, $-R^{13}-S(O)_tR^{15}$ (where t is 1 or 2), $-R^{13}-N(R^{14})_2$, $-R^{13}-CN$, $-R^{13}-C(O)R^{14}$, $-R^{13}-C(S)R^{14}$, $-R^{13}-C(NR^{14})R^{14}$, $-R^{13}-C(O)OR^{14}$, $-R^{13}-C(S)OR^{14}$, $-R^{13}-C(NR^{14})OR^{14}$, $-R^{13}-C(O)N(R^{14})_2$, $-R^{13}-C(S)N(R^{14})_2$, $-R^{13}-C(NR^{14})N(R^{14})_2$, $-R^{13}-C(O)SR^{14}$, $-R^{13}-C(S)SR^{14}$, $-R^{13}-C(NR^{14})SR^{14}$, $-R^{13}-S(O)_tOR^{14}$ (where t is 1 or 2), $-R^{13}-S(O)N(R^{14})_2$ (where t is 1 or 2), $-R^{13}-S(O)_tN(R^{14})N(R^{14})_2$ (where t is 1 or 2), $-R^{13}-S(O)_tN(R^{14})N=C(R^{14})_2$, $-R^{13}-S(O)_tN(R^{14})C(O)R^{18}$, $-R^{13}-N(R^{14})C(O)R^{15}$, $-R^{13}-N(R^{14})C(O)OR^{15}$, $-R^{13}-N(R^{14})C(O)SR^{18}$, $-R^{13}-N(R^{14})C(NR^{14})SR^{15}$, $-R^{13}-N(R^{14})C(S)SR^{18}$, $-R^{13}-N(R^{14})C(O)N(R^{14})_2$, $-R^{13}-N(R^{14})C(NR^{14})N(R^{14})_2$, $-R^{13}-N(R^{14})C(S)N(R^{14})_2$, $-R^{13}-N(R^{14})S(O)_tR^{15}$ (where t is 1 or 2), $-R^{13}-OC(O)R^{15}$, $-R^{13}-OC(NR^{14})R^{15}$, $-R^{13}-OC(S)R^{15}$, $-R^{13}-OC(O)OR^{15}$, $-R^{13}-OC(NR^{14})OR^{18}$, $-R^{13}-OC(S)OR^{18}$, $-R^{13}-OC(O)SR^{14}$, $-R^{13}-OC(O)N(R^{14})_2$, $-R^{13}-OC(NR^{14})N(R^{14})_2$, $-R^{13}-OC(S)N(R^{14})_2$, $-R^{13}-C(O)-R^{16}-C(O)R^{14}$, $-R^{13}-C(O)-R^{16}-C(S)R^{14}$, $-R^{13}-C(O)-R^{16}-C(NR^{14})R^{14}$, $-R^{13}-C(O)-R^{16}-C(O)OR^{14}$, $-R^{13}-C(O)-R^{16}-C(S)OR^{14}$, $-R^{13}-C(O)-R^{16}-C(NR^{14})OR^{14}$, $-R^{13}-C(O)-R^{16}-C(O)N(R^{14})_2$, $-R^{13}-C(O)-R^{16}-C(S)N(R^{14})_2$, $-R^{13}-C(O)-R^{16}-C(NR^{14})N(R^{14})_2$, $-R^{13}-C(O)-R^{16}-C(O)SR^{14}$, $-R^{13}-C(O)-R^{16}-C(S)SR^{14}$ and $-R^{13}-C(O)-R^{16}-C(NR^{14})SR^{14}$;

where each $R^8$ and $R^{13}$ are independently a direct bond, an optionally substituted straight or branched alkylene chain, or an optionally substituted straight or branched alkenylene chain;

where each $R^9$ is independently selected from the group consisting of hydrogen, optionally substituted alkyl, optionally substituted alkenyl, optionally substituted alkynyl, optionally substituted cycloalkyl, cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two $R^9$s, together with the nitrogen to which they are attached, form an optionally substituted heterocyclyl;

where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two $R^{14}$s, together with the nitrogen to which they are attached, form an optionally substituted heterocyclyl;

where each $R^{10}$ and $R^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl;

where each $R^{11}$ and $R^{16}$ are independently an optionally substituted straight or branched alkylene chain or an optionally substituted straight or branched alkenylene chain; and $R^{32}$ is independently hydrogen, halo, optionally substituted alkyl, optionally substituted alkenyl or optionally substituted alkynyl; as a single isomer, a mixture of isomers, or as a racemic mixture of isomers; or as a solvate or polymorph; or as a prodrug; or as a pharmaceutically acceptable salt thereof.

Such compounds can bind to one or more steroid nuclear receptors with high affinity and modulate their activity. Typically such compounds exhibit an $EC_{50}$ or $IC_{50}$ of less than 10 μM, and in certain embodiments, less than about 1 μM, 0.5 μM, 250 nM, 100 nM or 50 nM. In one aspect, the compounds provided herein are selective for a specific nuclear receptor, i.e. are at least 10, or in another aspect, at least 100 times more potent, as measured by any of the in vitro assays described herein, in binding to the desired steroid nuclear receptor than any other steroid receptor.

Also of interest are any pharmaceutically acceptable derivatives of the compounds disclosed herein, including without limitation salts, esters, enol ethers, enol esters, solvates, hydrates, polymorphs and prodrugs of the compounds described. In another embodiment are methods of using the disclosed compounds and compositions, or pharmaceutically acceptable derivatives thereof, for the local or systemic treatment or prophylaxis of human and veterinary diseases, disorders and conditions modulated or otherwise affected by one or more steroid nuclear receptors, or in which steroid nuclear receptor activity, is implicated, as defined herein.

Also provided are pharmaceutical compositions formulated for administration by an appropriate route and means containing effective concentrations of one or more of the compounds provided herein, or pharmaceutically acceptable derivatives thereof, and comprising at least one pharmaceutical carrier, vehicle, binder, diluent, disintegrating agent, lubricant, glidant, sweetening agent or flavoring agent. Such pharmaceutical compositions deliver amounts effective for the treatment, prevention, or amelioration of one or more symptoms of diseases or disorders that are modulated or otherwise affected by one or more steroid nuclear receptors, or in which steroid nuclear receptor activity, is implicated. Such diseases or disorders include without limitation:

a) Diseases or disorders associated with an excess or a deficiency of steroid receptor ligands, or steroid receptor activity, including, for example, Addison's disease, Cushing's syndrome, Conn's syndrome, Turner's syndrome, hormone replacement therapies, menopause, hypogonadism, somatopause, andropause, and viropause;

b) Diseases or disorders relating to cancer, including hormone dependent cancers such as breast cancer (U.S. Pat. No. 6,306,832), prostrate cancer (U.S. Pat. No. 5,656,651), benign prostatic hyperplasia (U.S. Pat. No. 5,656,651) ovarian cancer, endometrial cancer (U.S. Pat. No. 6,593,322), leukemia (U.S. Pat. No. 6,696,459) and lymphoma (U.S. Pat. No. 6,667,299);

c) Diseases or disorders related to infertility including endometriosis, the control of menstruation, dysfunctional uterine bleeding, dysmnenorrhea, endometriosis, meningiomas, leionyomas (uterine fibroids), the induction of labor (U.S. Pat. No. 6,358,947; U.S. Pat. No. 5,843,933) and as modulators of male and female fertility (e.g., as contraceptives or contragestational agents);

e) Diseases or disorders relating to metabolic syndromes including Syndrome X, hyperglycemia, insulin insensitivity, diabetes, obesity, fat storage or distribution, hyperlipidemia, hypercholesterolemia, hyperlipoproteinemia, hypertriglyceridemia, dyslipidemia, hyperinsulinemia, atherosclerosis and hyperuricemia (U.S. Pat. No. 6,699,893, U.S. Pat. No. 6,680,310; U.S. Pat. No. 6,593,480; US Patent Application No. 2003/0028910);

f) Diseases or disorders relating to bone or cartilage dysfunction, including osteoporosis, frailty, decreased bone density and hypercalcemia (U.S. Pat. No. 6,686,351; U.S. Pat. No. 6,660,468; US Application No. 2002/0187953);

g) Inflammatory diseases or disorders related to immune dysfunction, including, immunodeficiency, immunomodulation, autoimmune diseases, tissue rejection, wound healing, allergies, inflammatory bowel disease, Lupus Erythematosis, arthritis, osteoarthritis, rheumatoid arthritis, asthma and rhinitis (U.S. Pat. No. 6,699,893; U.S. Pat. No. 6,380,223; U.S. Pat. No. 6,716,829);

h) Diseases or disorders related to cognitive dysfunction, including psychosis, cognitive disorder, mood disorder, anxiety disorder, personality disorder and Parkinson's disease and Alzheimer's disease (U.S. Pat. No. 6,620,802; U.S. Pat. No. 6,734,211);

i) Disease or disorders related to high blood pressure, including fluid retention, edema, cardiovascular disease and hypertension (U.S. Pat. No. 6,608,047);

j) Disease or disorders related to heart disease, including ischemic heart disease, heart failure, systolic impairment, diastolic impairment, myocardial necrosis, pulmonary venous congestion, atrial fibrillation, myocardial infarction, myocardial fibrosis and chronic heart failure (U.S. Pat. No. 6,716,829; U.S. Pat. No. 6,391,867);

k) Diseases or disorders related to renal disease, including diabetic nephropathy, chronic glomerulonephritis, polycystic kidney disease, non-diabetic nephropathy and chronic kidney disease; (U.S. Pat. No. 6,716,829; U.S. Pat. No. 6,391,867);

l) Diseases or disorders related to fibrosis (U.S. Pat. No. 6,716,829; U.S. Pat. No. 6,391,867);

m) Diseases or disorders related to epidermal dysfunction including acne, hirsutism, alopecia and skin atrophy;

n) Diseases or disorders related to muscle wasting, low muscle mass, metabolic rate, and poor muscle mass to fat ratio.

Also provided are methods of modulating the activity of one or more steroid nuclear receptors in a cell, tissue or whole organism, using the compounds and compositions provided herein, or pharmaceutically acceptable derivatives thereof. Such methods also include methods of contraception, methods of regulating hair growth, methods of regulating muscle mass, methods of inducing weight loss, methods of regulating fat deposition or distribution, methods of stimulation of the metabolic rate, methods of altering the muscle mass to fat ratio, methods of regulating the development and growth of epidermal tissue, methods of regulating cognitive function, methods of regulating electrolyte balance, methods of regulating blood pressure and methods of regulating immunological function.

Also contemplated herein are combination therapies using one or more compounds or compositions provided herein, or pharmaceutically acceptable derivatives thereof, in combination with a wide variety of combination therapies to treat the diseases and disorders described above. Thus, the compounds and their pharmaceutically acceptable derivatives can be used in conjunction with other pharmaceutically active agents for the treatment of the diseases and disorders described herein.

In one embodiment, such additional pharmaceutical agents include one or more of the following: ACE inhibitors, Angiotensin II blockers, anti-cancer agents, anti-coagulants, anti-arrhythmics, anti-inflammatory agents, beta blockers, calcium channel antagonists, lipid-modulating agents, cytokine antagonists, digitalis medicines, diuretics, endothelin blockers, erythropoietin, vasodilators, and glucose lowering agents.

The compound or composition provided herein, or pharmaceutically acceptable derivative thereof, may be administered simultaneously with, prior to, or after administration of one or more of the above agents. Pharmaceutical compositions containing a compound provided herein and one or more of the above agents are also provided.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the diseases or disorders.

Also provided are articles of manufacture comprising a compound or composition, provided herein, or pharmaceutically acceptable derivative thereof; packaging material; and a label that indicates that the compound or composition, or pharmaceutically acceptable derivative thereof, is used for modulating the activity of a steroid nuclear receptor, or for treatment, prevention or amelioration of one or more symptoms of steroid nuclear receptor mediated diseases or disorders, or diseases or disorders in which steroid nuclear receptor activity is implicated.

DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain radical consisting solely of carbon and hydrogen atoms, containing no unsaturation, having from one to ten carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain radical consisting solely of carbon and hydrogen atoms, containing at least one double bond, having from two to ten carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain radical consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from one to eight carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

"Alkoxy" refers to the radical having the formula —OR wherein R is alkyl or haloalkyl. An "optionally substituted alkoxy" refers to the radical having the formula —OR wherein R is an optionally substituted alkyl as defined herein.

"Alkynylene" or "alkynylene chain" refers to a straight or branched chain unsaturated divalent radical consisting solely of carbon and hydrogen atoms, having from one to eight carbon atoms, wherein the unsaturation is present only as triple bonds and wherein the triple bond can exist between any two carbon atoms in the chain, e.g., ethynylene, prop-1-ynylene, but-2-ynylene, pent-1-ynylene, pent-3-ynylene and the like. The alkynylene chain may be attached to the rest of the molecule through any two carbons within the chain.

As used herein, "amidino" refers to a radical having the formula —C(=NR)N(R')R" where R, R' and R" are each independently hydrogen or alkyl "Amino" refers to a radical having the formula —NR'R" wherein R' and R" are each independently hydrogen, alkyl or haloalkyl. An "optionally substituted amino" refers to a radical having the formula —NR'R" wherein one or both of R' and R" are optionally substituted alkyl as defined herein.

"Androgen receptor" or "AR" refers to all mammalian isoforms, splice variants and polymorphisms of the nuclear receptor. Representative forms include, human, (Gene Bank Accession Number, P10275, rat, (Gene Bank Accession Number P15207), mouse (Gene Bank Accession Number P19091), and rabbit (Gene Bank Accession Number P49699).

"Angiotensin converting enzyme inhibitors" or "ACE inhibitors" refers to factors that act to decrease the conversion of angiotensin I to angiotensin II. A representative group of ACE inhibitors includes the following compounds: AB-103, ancovenin, benazeprilat, BRL-36378, BW-A575C, CGS-13928C, CL-242817, CV-5975, Equaten, EU-4865, EU-4867, EU-5476, foroxymithine, FPL 66564, FR-900456, Hoe-065, I5B2, indolapril, ketomethylureas, KRI-1177, KRI-1230, L-681176, libenzapril, MCD, MDL-27088, MDL-27467A, moveltipril, MS-41, nicotianamine, pentopril, phenacein, pivopril, rentiapril, RG-5975, RG-6134, RG-6207, RGH-0399, ROO-911, RS-10085-197, RS-2039, RS 5139, RS 86127, RU-44403, S-8308, SA-291, spiraprilat, SQ-26900, SQ-28084, SQ-28370, SQ-28940, SQ-31440, Synecor, utibapril, WF-10129, Wy-44221, Wy-44655, Y-23785, Yissum P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, 1-(-(1-carboxy-6-(4-piperidinyl)hexyl)amino)-1-oxopropyl octahydro-1H-indole-2-carboxylic acid, Bioproject BP1.137, Chiesi CHF 1514, Fisons FPL-66564, idrapril, Marion Merrell Dow MDL-100240, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat and spirapril. A group of ACE inhibitors of high interest includes the following compounds: alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat and spirapril.

"Angiotensin II blockers" or "AT1 antagonists" refers to factors that act to reduce the binding of angiotensin II to the Angiotensin II receptor. A group of AT1 antagonists of high interest includes the following compounds: Atacand (candesartan cilexetil), Avapro (irbesartan), Cozaar (losartan), Diovan (valsartan), Micardis (telmisartan), and Teveten (eprosartan mesylate).

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216, CI-973), anthracyclines (e.g., doxrubicin, daunorubicin), antitumor antibiotics (e.g., mitomycin, idarubicin, adriamycin, daunomycin), topoisomerase inhibitiors (e.g., etoposide, camptothecins) or any other cytotoxic agents, (estramustine phosphate, prednimustine), hormones or hormone agonists, antagonists, partial agonists or partial antagonists, and radiation treatment.

"Anticoagulants" refers to factors that act to reduce the clotting ability of blood. Examples available in the US include without limitation the brand names: Coumadin (warfarin), and Miradon (anisinidione).

"Antiarrhythmics" refer to factors that act to reduce abnormal heart rhythms. Examples available in the US include without limitation the brand names: Betapace (sotalol), Cardizem (diltiazem), Cordarone (amiodarone), Covera (verapamil), Inderal (propranolol), Isoptin (verapamil), Pacerone (amiodarone), Ethmozine (moricizine), Lopressor (metoprolol), Mexitil (mexiletine), Norpace (disopyramide), Procanbid (procainamide), Pronestyl (procainamide), Quinaglute Duratabs (quinidine gluconate), Quinidex Extentabs (quinidine sulfate), Rythmol (propafenone), Tambocor (flecamide), Tenormin (atenolol), Tiazac (diltiazem), Tikosyn (dofetilide), Tonocard (tocamide), and Toprol XL (metoprolol).

"Anti-inflammatory agents" refers to matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicyclic acid), COX-1 or COX-2 inhibitors), or glucocorticoid receptor agonists such as corticosteroids, methylprednisone, prednisone, or cortisone.

"Aryl" refers to a radical of carbocylic ring system wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Aralkyl" refers to a radical of the formula —$R_aR_b$ where $R_a$ is an alkyl radical as defined above, substituted by $R_b$, an aryl radical, as defined above, e.g., benzyl. Both the alkyl and aryl radicals may be optionally substituted as defined herein. "Aralkoxy" refers to a radical of the formula —$OR_aR_b$ where —$R_aR_b$ is an aralkyl radical as defined above. Both the alkyl and aryl radicals may be optionally substituted as defined herein.

"Atherosclerosis" refers to process whereby atherosclerotic plaques form within the inner lining of the artery wall leading to atherosclerotic cardiovascular diseases.

Atherosclerotic cardiovascular diseases can be recognized and understood by physicians practicing in the relevant fields of medicine, and include without limitation, restenosis, coronary heart disease (also known as coronary artery heart disease or ischemic heart disease), cerebrovascular disease including ischemic stroke, multi-infarct dementia, and peripheral vessel disease, including intermittent claudication, and erectile dysfunction.

"Beta blockers" refers to factors that act to reduce the activity of the sympathetic nervous system. Beta blockers typically act to selectively block the β-adrenergic receptor, but in some cases also block α 1 adrenoreceptor activity. Representative Beta blockers include the following Acc 9369, AMO-140, acebutolol, alprenolol, amosulalol, arotinolol, atenolol, befunolol, bevantolol, bisoprolol, bopindolol, bucumolol, bucindolol, bunitrolol, butofilolol, betaxolol, capsinolol, carazolol, CP-331684, carteolol, carvedilol, celiprolol, cloranolol, diprafenone, ersentilide, esmolol, esprolol, Fr-172516, indenolol, ISV-208, L-653328, labetalol, laniolol, levobunolol, LM-2616, levoprolol, mepindolol, metipranolol, metoprolol, nadolol, nebivolol, nifenalol, oxprenolol, penbutolol, pindolol, propranolol, sotalol, S-atenolol, SB-226552, SR-58894A, SR-59230A, talinolol, tertatolol, tilisolol, timolol, Toprol, TZC-5665, UK-1745, xamoterol, and, viskenit and YM-430. A group of Beta blockers of high interest includes the following compounds Betapace (sotalol), Blocadren (timolol), Brevibloc (esmolol), Cartrol (carteolol), Coreg (carvedilol), Corgard (nadolol), Inderal (propranolol), Inderal-LA (propranolol), Kerlone (betaxolol), Levatol (penbutolol), Lopressor (metoprolol), Normodyne (labetalol), Sectral (acebutolol), Tenormin (atenolol), Toprol-XL (metoprolol), Trandate (labetalol), Visken (pindolol), and Zebeta (bisoprolol). "Calcium channel antagonists" or "calcium channel blockers" refers to factors that act to reduce calcium channel activity. Examples include without limitation: Adalat (nifedipine), Calan (verapamil), Cardene (nicardipine), Cardizem (diltiazem), Cardizem CD (diltiazem), Cardizem SR (diltiazem), Cartia (diltiazem), Covera-HS (verapamil), Dilacor XR (diltiazem), Diltia XT (diltiazem), DynaCirc (isradipine), Isoptin (verapamil), Lotrel (amlodipine), Nimotop (nimodipine), Norvasc (amlodipine), Plendil (felodipine), Procardia (nifedipine), Procardia XL (nifedipine), Sular (nisoldipine), Teczem, Tiamate (diltiazem), Tiazac (diltiazem), Vascor (bepridil) Verelan (verapamil), aranidipine, atosiban, barnidipine, buflomedil, cilnidipine, docosahexaenoic acid, efonidipine HCL, fasudil, isradipine, lacidipine, lercanidipine, lomerizine, manidipine, nifelan, nilvadipine, nimodipine, nisoldipine, bepridil HCl. NS-7, NW-1015, SB-237376, SL-34.0829-08, terodiline, R-verapamil, bisaramil, CAI, ipenoxazone, JTV-519, S-312d, SD-3212, tamolarizine, TA-993, vintoperol, YM-430, CHF-1521, elgodipine, nitrendipine, furnidipine, L-651582, oxodipine, ranolazine, AE-0047, azelnidipine, dotarizine, lemildipine, pranidipine, semotiadil, temiverine HCl, tenosal, vatanidipine HCl, and ziconotide. A group of Calcium channel antagonists of high interest includes the following compounds: Adalat (nifedipine), Calan (verapamil), Cardene (nicardipine), Cardizem (diltiazem), Cardizem CD (diltiazem), Cardizem SR (diltiazem), Cartia (diltiazem), Covera-HS (verapamil), Dilacor XR (diltiazem), Diltia XT (diltiazem), DynaCirc (isradipine), Isoptin (verapamil), Lotrel (amlodipine), Nimotop (nimodipine), Norvasc (amlodipine), Plendil (felodipine), Procardia (nifedipine), Procardia XL (nifedipine), Sular (nisoldipine), Teczem, Tiamate (diltiazem), Tiazac (diltiazem), Vascor (bepridil) Verelan (verapamil).

"Chronic heart failure", or "CHF", or alternatively "congestive heart failure", refers to a disorder in which the heart exhibits a left ventricular ejection fraction of 40% or lower, as determined on echocardiography, or radionucleotide angiography. "Heart failure" refers to a disorder in which the heart exhibits a left ventricular ejection fraction of greater than 40%, but less than 90%, as determined on echocardiography, or radionucleotide angiography.

"Cognitive dysfunction" refers to psychosis, cognitive disorder, mood disorder, anxiety disorder and personality disorder. Psychosis includes symptoms characterized by one or more of the following: impairment of behavior, inability to think coherently, inability to comprehend reality, false belief, and abnormal sensations. Cognitive disorder includes symptoms characterized by one or more of the following: confusion, disorientation, memory disturbance, and behavioral disorganization. Mood disorder includes symptoms characterized by one or more of the following: depression, bipolar disorder, persistent abnormality of mood, altered activity rhythm, altered sleep, and altered appetite. Anxiety disorder includes symptoms characterized by one or more of the following: anxiety, panic, dysphoria, obsession, irrational fear, ritualistic behavior, compulsion, and pattern behavior.

"Cytokine Antagonists" refers to factors that act to block the activity of cytokines such as tumor necrosis factor. Examples include without limitation Pentoxifylline and Etanercept.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, norbornane, norbornene, adamantyl, bicyclo[2.2.2]octane and the like.

"Cycloalkylalkyl" refers to a radical of the formula —$R_aR_d$ where $R_a$ is an alkyl radical as defined above and $R_d$ is a cycloalkyl radical as defined above. The alkyl radical and the cylcoalkyl radical may be optionally substituted as defined herein.

"Diuretics" refers to factors that act to reduce blood pressure by reducing the amount of sodium and water in the body. Diuretics include, thiazide diuretics, potassium-sparing diuretics and loop-acting diuretics. Examples of thiazide diuretics of high interest include the following compounds: Aquatensen (methyclothiazide), Diucardin (hydroflumethiazide), Diulo (metolazone), Diuril (chlorothiazide), Enduron (methyclothiazide), Esidrix (hydrochlorothiazide), Hydrochlor (hydrochlorothiazide), Hydro-D (hydrochlorothiazide), HydroDIURIL (hydrochlorothiazide), Hydromox (quinethazone), Hygroton (chlorthalidone), Metahydrin (trichlormethiazide), Microzide (hydrochlorothiazide), Mykrox (metolazone), Naqua (trichlormethiazide), Naturetin (bendroflumethiazide), Oretic (hydrochlorothiazide), Renese (polythiazide), Saluron (hydroflumethiazide), Thalitone (chlorthalidone), Trichlorex (trichlormethiazide), and Zaroxolyn (metolazone). Examples of potassium-sparing diuretics of high interest includes the following compounds: Aldactone (spironolactone), Eplerenone, Dyrenium (triamterene), and Midamor (amiloride). Examples of loop-acting diuretics of high interest includes the following compounds: Bumex (bumetanide), Demadex (torsemide), Edecrin (ethacrynic acid), Lasix (furosemide), and Myrosemide (furosemide).

"Digitalis Medicines" refers to digoxin and related compounds. Examples of high interest include: Lanoxicaps (digoxin), Lanoxin (digoxin), Lanoxin Elixir Pediatric (digoxin), Lanoxin Injection (digoxin), and Lanoxin Injection Pediatric (digoxin).

"Dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL).

"$EC_{50}$" refers to a dosage, concentration or amount of a particular test compound that elicits a dose-dependent response at 50% of maximal expression of a particular response that is induced, provoked or potentiated by the particular test compound.

"Endothelin blockers" refers to factors that act to reduce the action of endothelin at the endothelin $ET_A$ or $ET_B$ endothelin receptors. Examples include without limitation, Bosentan Acetelion (Roche), Ro-61-0612 (Roche), SB217242, SB247083, Enrasentan, (SmithKline Beecham Pharmaceuticals), TBC-11251 (Texas Biotechnology Corp., Houston, Tex.), BMS187308 (Bristol-Myers Squibb Company, Princeton, N.J.), PD-145065 (Parke-Davis & Co.), TAK-044 (Takeda), Tarasentan (Abbott), ZD-1611 (Zeneca Group plc) and J-104132 (Banyu Pharmaceutical Co. Ltd).

"ER" or "ER family" refers to all species of ER alpha and ER beta. Representative ERα species include, without limitation the rat (Genbank Accession P06211), pig (Genbank Accession Q29040), and human (GenBank Accession P03372) forms of the receptor. Representative ER β species include, without limitation the rat (GenBank Accession Q62986), mouse (Genbank Accession O08537), and human (GenBank Accession Q92731) forms of the receptor.

"ERR" "ERRs" or "ERR subfamily" refers to all species of ERRα, ERRβ and ERRγ. Representative ERRα species include, without limitation the rat (Genbank Accession XM_215174), mouse (Genbank Accession NM_007953), and human (GenBank Accession NM_004451, XM_048286) forms of the receptor. Representative ERR β species include, without limitation the rat (GenBank Accession NM_011934), mouse (Genbank Accession NM_011934), and human (GenBank Accession NM_00452) forms of the receptor. Representative ERR γ species include, without limitation the rat (GenBank Accession XM_341170), mouse (Genbank Accession NM_011935), and human (GenBank Accession NM_001438) forms of the receptor. As used herein, "guanidino" refers to a radical having the formula —N(R)C(=NR') NR"R''' wherein R, R', R" and R''' are each independently hydrogen or alkyl.

"Fibrosis" refers to the formation fibrotic tissue associated with tissue damage and scarring. Examples include without limitation, cardiac fibrosis, vascular fibrosis, renal fibrosis and liver fibrosis.

"Glucose lowering agents" refers to factors that act to reduce, or help control plasma glucose levels in, for example, diabetes, insulin insensitivity or hyperglycemia. Examples include, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); dehydroepiandrosterone (also referred to as DHEA or its conjugated sulphate ester, DHEA-$SO_4$); antiglucocorticoids; TNFα-inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide) and insulin.

"Glucocorticoid receptor" or "GR" refers to all mammalian isoforms, splice variants and polymorphisms of the nuclear receptor. Representative forms include, human, (Gene Bank Accession Number, P04150), rat, (Gene Bank Accession Number P06536), and mouse (Gene Bank Accession Number P06537).

"Halo", "halogen" or "halide" refers to F, Cl, Br or I.

"Haloalkyl" refers to an alkyl group in which one or more of the hydrogen atoms are replaced by halogen. Such groups include, but are not limited to, chloromethyl, trifluoromethyl and 1-chloro-2-fluoroethyl.

"Haloalkenyl" refers to an alkenyl group in which one or more of the hydrogen atoms are replaced by halogen. Such groups include, but are not limited to, 1-chloro-2-fluoroethenyl.

"Heart disease" or "cardiac disease" refers to all forms of ischaemic heart disease, heart failure, systolic impairment, diastolic impairment, myocardial necrosis, pulmonary venous congestion, atrial fibrillation, myocardial infarction, myocardial fibrosis and chronic heart failure.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated or aromatic. The heterocyclic ring system may be attached to the main structure at any heteroatom or carbon atom which results in the creation of a stable compound. Examples of such heterocyclic radicals include, but are not limited to: acridinyl, azepinyl, benzimidazolyl, benzindolyl, benzisoxazinyl, benzo[4,6]imidazo[1,2-a]pyridinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazotyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thiophenyl, triazinyl, triazolyl and 1,3,5-trithianyl.

"Heteroaralkyl" refers to a radical of the formula —$R_aR_f$ where $R_a$ is an alkyl radical as defined above and $R_f$ is a heteroaryl radical as defined herein. The alkyl radical and the heteroaryl radical may be optionally substituted as defined herein.

"Heteroaralkoxy" refers to a radical of the formula —$OR_aR_f$ where —$R_aR_f$ is a heteroaralkyl radical as defined above. The alkyl radical and the heteroaryl radical may be optionally substituted as defined herein.

"Heteroaryl" refers to a heterocyclyl radical as defined above which is aromatic. The heteroaryl radical may be attached to the main structure at any heteroatom or carbon atom which results in the creation of a stable compound. Examples of such heteroaryl radicals include, but are not limited to: acridinyl, benzimidazolyl, benzindolyl, benzisoxazinyl, benzo[4,6]imidazo[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuranyl, furanyl, imidazolyl, imidazopyridinyl, imidazothiazolyl, indazolyl, indolinyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thiophenyl, triazinyl and triazolyl.

"Heterocyclylalkyl" refers to a radical of the formula —$R_aR_e$ wherein $R_a$ is an alkyl radical as defined above and $R_e$ is a heterocyclyl radical as defined herein. The alkyl radical and the heterocyclyl radical may be optionally substituted as defined herein.

"Heterocyclylalkoxy" refers to a radical of the formula —$OR_aR_e$ wherein —$R_aR_e$ is a heterocyclylalkyl radical as defined above. The alkyl radical and the heterocyclyl radical may be optionally substituted as defined herein.

"Hyperlipidemia" refers to the presence of an abnormally elevated level of lipids in the blood. Hyperlipidemia can appear in at least three forms: (1) hypercholesterolemia, i.e., an elevated LDL cholesterol level above normal (2) hypertriglyceridemia, i.e., an elevated triglyceride level above normal and (3) combined hyperlipidemia, i.e., a combination of hypercholesterolemia and hypertriglyceridemia.

"Hypertension" refers to a seated diastolic blood pressure of 90 mm Hg or greater, and/or, a systolic blood pressure of 140 mm Hg or greater.

"$IC_{50}$" refers to an amount, concentration or dosage of a particular test compound that achieves a 50% inhibition of a maximal response, such as modulation of MR transcriptional activity measured via any of the in-vivo or in vitro assays described herein.

"Imine" or "imino" refers to =NR, wherein R is hydrogen or alkyl.

"Lipid-modulating agents" refer to factors that act to reduce cholesterol (LDL cholesterol, total cholesterol, or HDL cholesterol) and/or trigylceride levels in the plasma. Examples include without limitation: HMG-CoA reductase inhibitors (including statins such as lovastatin, simvastatin, pravastatin, fluvastatin, atorvastatin and rivastatin), bile acid sequestrants (resins), nicotinic acid (niacin) and fibric acid derivatives (fibrates).

"Meta" as used in the claims refers to the position on the benzene ring that is meta with respect to the attachment point of the benzene moiety to the rest of the molecule.

"Mineralocorticoid receptor" or "aldosterone receptor" or "MR" refers to all mammalian isoforms, splice variants and polymorphisms of the nuclear receptor, (including the non-nuclear rapid response receptor). Representative forms include, human, (Gene Bank Accession Number, AAA59571, isoforms NP_000892 and P08235), rat, (Gene Bank Accession Number P22199), mouse (Gene Bank Accession Number CAC86375), chicken (Gene Bank Accession Number Q8QH12) and sheep (Gene Bank Accession Number 99BDJ7).

"Natriuretic peptides" refers to naturally occurring forms or analogs of natriuretic peptides that are activated in CHF as a result of ventricular and atrial wall stretch.

"Optionally substituted alkyl", "optionally substituted alkenyl" and "optionally substituted alkynyl" refer to alkyl radicals, alkenyl radicals and alkynyl radicals, respectively, that may be optionally substituted by one or more substituents independently selected from the group consisting of nitro, halo, azido, cyano, cycloalkyl, heteroaryl, heterocyclyl, —$OR^x$, —$N(R^y)(R^z)$, —$SR^x$, —$C(J)R^x$, —$C(J)OR^x$, —$C(J)N(R^y)(R^z)$, —$C(J)SR^x$, —$S(O)_tR^w$ (where t is 1 or 2), —$OC(J)R^x$, —$OC(J)OR^x$, —$OC(J)N(R^y)(R^z)$, —$OC(J)SR^x$, —$N(R^x)C(J)R^x$, —$N(R^x)C(J)OR^x$, —$N(R^x)C(J)N(R^y)(R^z)$, —$N(R^x)C(J)SR^x$, —$Si(R^w)_3$, —$N(R^x)S(O)_2R^w$, —$N(R^x)S(O)_2N(R^y)(R^z)$, —$S(O)_2N(R^y)(R^z)$, —$P(O)(R^w)_2$, —$OP(O)$ $(R^v)_2$, —C(J)N(R$^x$)S(O)$_2$R$^w$, —C(J)N(R$^x$)N(R$^x$)S(O)$_2$R$^w$, —C(R$^x$)=N(OR$^x$), and —C(R$^x$)=NN(R$^y$)(R$^z$), wherein:

R$^x$ is hydrogen, alkyl, alkenyl, alkynyl, cycloalkyl, cycloalkylalkyl, heterocyclyl, heterocyclylalkyl, aryl, aralkyl, heteroaryl, or heteroaralkyl;

R$^y$ and R$^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl; or R$^y$ and R$^z$, together with the nitrogen atom to which they are attached, form a heterocyclyl or heteroaryl;

R$^w$ is alkyl, alkenyl, alkynyl, cycloalkyl, cycloalkylalkyl, heterocyclyl, heterocyclylalkyl, aryl, aralkyl, heteroaryl, or heteroaralkyl;

R$^v$ is alkyl, alkenyl, alkynyl, cycloalkyl, cycloalkylalkyl, heterocyclyl, heterocyclylalkyl, aryl, aralkyl, heteroaryl, heteroaralkyl, hydroxy, —OR$^x$ or —N(R$^y$)(R$^z$); and J is O, NR$^x$ or S. Unless stated otherwise specifically in the specification, it is understood that the substitution can occur on any carbon of the alkyl, alkenyl or alkynyl group.

"Optionally substituted aryl", "optionally substituted cycloalkyl", "optionally substituted heteroaryl" and "optionally substituted heterocyclyl" refers to aryl, cycloalkyl, heterocyclyl and heteroaryl radicals, respectively, that are optionally substituted by one or more substituents selected from the group consisting of nitro, halo, haloalkyl, haloalkenyl, azido, cyano, oxo, thioxo, imino, alkyl, alkenyl, alkynyl, cycloalkyl, cycloalkylalkyl, heterocyclyl, heterocyclylalkyl, heteroaryl, heteroaralkyl, —R$^u$—OR$^x$, —R$^u$—N(R$^y$)(R$^z$), —R$^u$—SR$^x$, —R$^u$—C(J)R$^x$, —R$^u$—C(J)OR$^x$, —R$^u$—C(J)N(R$^y$)(R$^z$), —R$^u$—C(J)SR$^x$, —R$^u$—S(O)$_t$R$^w$ (where t is 1 or 2), —R$^u$—OC(J)R$^x$, —R$^u$—OC(J)OR$^x$, —R$^u$—OC(J)N(R$^y$)(R$^z$), —R$^u$—OC(J)SR$^x$, —R$^u$—N(R$^x$)C(J)R$^x$, —R$^u$—N(R$^x$)C(J)OR$^x$, —R$^u$—N(R$^x$)C(J)N(R$^y$)(R$^z$), —R$^u$—N(R$^x$)C(J)SR$^x$, —R$^u$—Si(R$^w$)$_3$, —R$^u$—N(R$^x$)S(O)$_2$R$^w$, —R$^u$—N(R$^x$)S(O)$_2$N(R$^y$)(R$^z$), —R$^u$—S(O)$_2$N(R$^y$)(R$^z$), —R$^u$—P(O)(R$^v$)$_2$, —R$^u$—OP(O)(R$^v$)$_2$, —R$^u$—C(J)N(R$^x$)S(O)$_2$R$^w$, —R$^u$—C(J)N(R$^x$)N(R$^x$)S(O)$_2$R$^w$, —R$^u$—C(R$^x$)=N(OR$^x$) and —R$^u$—C(R$^x$)=NN(R$^y$)(R$^z$), wherein:

each R$^u$ is independently alkylene or a direct bond;

each R$^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, —OR$^x$ or —N(R$^y$)(R$^z$);

R$^w$ is alkyl, alkenyl, alkynyl, cycloalkyl, cycloalkylalkyl, heterocyclyl, heterocyclylalkyl, aryl, aralkyl, heteroaryl, or heteroaralkyl;

each R$^x$ is independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

R$^y$ and R$^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

R$^y$ and R$^z$, together with the nitrogen atom to which they are attached, form a heterocycle or heteroaryl; and J is O, NR$^x$ or S.

Unless stated otherwise specifically in the specification, it is understood that the substitution can occur on any atom of the cycloalkyl, heterocyclyl, aryl or heteroaryl group.

"Oxo" refers to =O.

"Ortho" as used in the claims refers to the position on the benzene ring that is ortho to the attachment point of the benzene moiety to the rest of the molecule.

"Para" as used in the claims refers to the position on the benzene ring that is para with respect to the attachment point of the benzene moiety to the rest of the molecule.

"Pharmaceutically acceptable derivatives" of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

Pharmaceutically acceptable solvates and hydrates are complexes of a compound with one or more solvent or water molecules, or 1 to about 100, or 1 to about 10, or one to about 2, 3 or 4, solvent or water molecules.

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability.

"Prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

"Progesterone receptor" or "PR" refers to all mammalian isoforms, splice variants and polymorphisms of the nuclear receptor. Representative forms include, human, (Gene Bank Accession Number, P06401), and mouse (Gene Bank Accession Number Q63449).

"Renal disease" or "Kidney disease", or refers to diabetic nephropathy, chronic glomerulonephritis, polycystic kidney disease, non diabetic nephropathy and all forms of chronic kidney disease. "Chronic Kidney Disease" or "CKD" or "renal failure" or "kidney failure" is typically characterized based on glomerular filtration rate or GFR: Typically Chronic Kidney Disease is suggested when the GFR is 90 or less.

"Steroid receptors" or "steroid nuclear receptors" refers to all mammalian splice variants and isoforms of the steroid nuclear receptors AR(NR3C4), PR(NR3C3), ERα (NR3A1), ERβ (NR3A2), GR(NR3C1), and MR(NR3C2), as well as, the orphan nuclear receptors ERR1 (NR3B1), ERR2 (NR3B2), and ERR3 (NR3B3).

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

"Sulfide" refers to the radical having the formula —SR wherein R is an alkyl or haloalkyl group. An "optionally substituted sulfide" refers to the radical having the formula —SR wherein R is an optionally substituted alkyl as defined herein.

"Thioxo" refers to =S.

"Vasodilators" refers to compounds that act to cause vasodilation of blood vessels thereby increasing blood flow. Vasodilators of high interest includes the following compounds: IMDUR (isosorbide mononitrate), ISMO (isosorbide mononitrate), Isordil (isosorbide dinitrate), Monoket (isosorbide mononitrate), Nitro-Dur (nitroglycerin), Nitrolingual (nitroglycerin), Nitrostat (nitroglycerin), and Sorbitrate (isosorbide dinitrate). Unless specifically stated otherwise, where a compound may assume alternative tautomeric, regioisomeric and/or stereoisomeric forms, all alternative isomers are intended to be encompassed within the scope of the present invention. For example, where a compound is described as having one of two tautomeric forms, it is intended that the both tautomers be encompassed within the scope of the present invention. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

It is to be understood that the compounds provided herein may contain chiral centers. Such chiral centers may be of either the (R) or (S) configuration, or may be a mixture thereof.

Optically active (+) and (−), (R)- and (S)-, or (D)- and (L)-isomers may be prepared using chiral synthons or chiral reagents, or resolved using conventional techniques, such as reverse phase HPLC.

Where the number of any given substituent is not specified (e.g., haloalkyl), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem., 1972, 11:942-944).

| | |
|---|---|
| AcOH | acetic acid |
| anhyd | Anhydrous |
| aq | aqueous |
| CDCl$_3$ | Deuterochloroform |
| conc | Concentrated |
| DCM | Dichloromethane |
| DMF | N,N-dimethylformamide |
| DMSO | dimethyl sulfoxide |
| Et$_2$O | diethyl ether |
| EtOAc | ethyl acetate |
| EtOH | ethanol (100%) |
| Hex | Hexanes |
| MeOH | Methanol |
| Pd/C | palladium on activated carbon |
| satd | Saturated |
| THF | Tetrahydrofuran |

B. Formulation of Pharmaceutical Compositions

The pharmaceutical compositions provided herein contain therapeutically effective amounts of one or more of the compounds or compositions, or pharmaceutically acceptable derivatives thereof, provided herein that are useful in the prevention, treatment, or amelioration of human and veterinary diseases, disorders and conditions mediated by, or otherwise affected by one or more steroid nuclear receptors, or in which steroid nuclear receptor activity, is implicated, as defined herein. The compounds, compositions, or pharmaceutically acceptable derivatives thereof are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126; Remington's Pharmaceutical Sciences, Mack Publishing Company, Easton, Pa., 15th Edition, 1975).

In the pharmaceutical compositions, effective concentrations of one or more compounds or pharmaceutically acceptable derivatives thereof is (are) mixed with at least one suitable pharmaceutical carrier, vehicle, diluent, or solvent.

Dosage forms or compositions containing active ingredient in the range of 0.005% to 100% with the balance made up from non-toxic carrier may be prepared. The contemplated compositions may contain 0.001%-100% active ingredient, preferably 0.1-85%, typically 75-95%. In addition, the compounds may be formulated as the sole pharmaceutically active ingredient in the composition or may be combined with other active ingredients.

The active compound is included in the pharmaceutically acceptable carrier in an amount sufficient to exert a therapeutically useful effect in the absence of undesirable side effects on the patient treated. The therapeutically effective concentration may be determined empirically by testing the compounds using in vitro and in vivo systems described herein and in International Patent Application Publication Nos. 99/27365 and 00/25134 and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with nuclear receptor activity or in which nuclear receptor activity is implicated, as described herein.

Typically, a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time by a suitable route, including orally, parenterally, rectally, topically and locally. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using co-solvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses that are not segregated in packaging.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, celluloses, polyvinyl pyrrolidone, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol, carboxymethylcellulose and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether.

In all embodiments, tablets and capsules formulations may be coated as known by those of skill in the art in order to modify or sustain dissolution of the active ingredient. If oral administration is desired, the compound could be provided in a composition that protects it from the acidic environment of the stomach. Thus, for example, they may be coated with a conventional enterically digestible coating, such as phenylsalicylate, waxes and cellulose acetate phthalate. Emetic-coatings also include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active ingredient can also be mixed with other materials which do not impair the desired action, or with materials that supplement the desired action, such as antacids, H2 blockers, and diuretics. The active ingredient is a compound or pharmaceutically acceptable derivative thereof as described herein.

Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. No. Re 28,819 and U.S. Pat. No. 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

Injectables, Solutions and Emulsions

Parenteral administration, generally characterized by injection, either subcutaneously, intramuscularly or intravenously is also contemplated herein. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Sustained Release Formulations

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Compositions for Other Routes of Administration

Other routes of administration, such as transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Articles of Manufacture

The compounds or pharmaceutically acceptable derivatives may be packaged as articles of manufacture comprising packaging material, a compound or composition, or pharmaceutically acceptable derivative thereof provided herein, and a label that indicates that the compound or composition, or pharmaceutically acceptable derivative thereof, is used for modulating the activity of a steroid nuclear receptor, or for treatment, prevention or amelioration of one or more symptoms of a steroid nuclear receptor mediated diseases or disorder, or diseases or disorders in which steroid nuclear activity is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

EMBODIMENTS OF THE INVENTION

Of the various aspects of the invention set forth above in the Summary of the Invention, certain embodiments are described herein. One embodiment are compounds of formula (I):

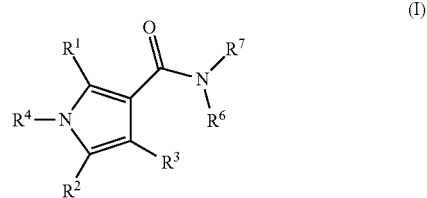

wherein:

$R^1$ and $R^2$ are each independently hydrogen, halo, cyano, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl, optionally substituted heteroaralkyl, optionally substituted heterocyclyl, optionally substituted heterocyclylalkyl, —$OR^9$, —$SR^9$, —$N(R^9)_2$, —$C(O)OR^9$ or —$C(O)N(R^9)_2$;

$R^3$ is independently hydrogen or halo;

$R^4$ is aryl or heteroaryl, where each is optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^9)_2$, —$R^8$—CN, —$R^8$—$C(O)R^9$, —$R^8$—$C(S)R^9$, —$R^8$—$C(NR^9)R^9$, —R⁸—C(O)OR⁹, —R⁸—C(S)OR⁹, —R⁸—C(NR⁹)OR⁹, —R⁸—C(O)N(R⁹)₂, —R⁸—C(S)N(R⁹)₂, —R⁸—C(NR⁹)N(R⁹)₂, —R⁸—C(O)SR⁹, —R⁸—C(S)SR⁹, —R⁸—C(NR⁹)SR⁹, —R⁸—S(O)ₜOR⁹ (where t is 1 or 2), —R⁸—S(O)ₜN(R⁹)₂ (where t is 1 or 2), —R⁸—S(O)ₜN(R⁹)N(R⁹)₂ (where t is 1 or 2), —R⁸—S(O)ₜN(R⁹)N═C(R⁹)₂, —R⁸—S(O)ₜN(R⁹)C(O)R¹⁰ (where t is 1 or 2), —R⁸—S(O)ₜN(R⁹)C(O)N(R⁹)₂ (where t is 1 or 2), —R⁸—S(O)ₜN(R⁹)C(NR⁹)N(R⁹)₂ (where t is 1 or 2), —R⁸—N(R⁹)C(O)R¹⁰, —R⁸—N(R⁹)C(O)OR¹⁰, —R⁸—N(R⁹)C(O)SR¹⁰, —R⁸—N(R⁹)C(NR⁹)SR¹⁰, —R⁸—N(R⁹)C(S)SR¹⁰, —R⁸—N(R⁹)C(O)N(R⁹)₂, —R⁸—N(R⁹)C(NR⁹)N(R⁹)₂, —R⁸—N(R⁹)C(S)N(R⁹)₂, —R⁸—N(R⁹)S(O)ₜR¹⁰ (where t is 1 or 2), —R⁸—OC(O)R¹⁰, —R⁸—OC(NR⁹)R¹⁰, —R⁸—OC(S)R¹⁰, —R⁸—OC(O)OR¹⁰, —R⁸—OC(NR⁹)OR¹⁰, —R⁸—OC(S)OR¹⁰, —R⁸—OC(O)SR⁹, —R⁸—OC(O)N(R⁹)₂, —R⁸—OC(NR⁹)N(R⁹)₂, —R⁸—OC(S)N(R⁹)₂, —R⁸—C(O)—R¹¹—C(O)R⁹, —R⁸—C(O)—R¹¹—C(S)R⁹, —R⁸—C(O)—R¹¹—C(NR⁹)R⁹, —R⁸—C(O)—R¹¹—C(O)OR⁹, —R⁸—C(O)—R¹¹—C(S)OR⁹, —R⁸—C(O)—R¹¹—C(NR⁹)OR⁹, —R⁸—C(O)—R¹¹—C(O)N(R⁹)₂, —R⁸—C(O)—R¹¹—C(S)N(R⁹)₂, —R⁸—C(O)—R¹¹—C(NR⁹)N(R⁹)₂, —R⁸—C(O)—R¹¹—C(O)SR⁹, —R⁸—C(O)—R¹¹—C(S)SR⁹ and —R⁸—C(O)—R¹¹—C(NR⁹)SR⁹;

R⁶ is hydrogen or optionally substituted alkyl;

R⁷ is aryl or heteroaryl, where each is optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R¹³—OR¹⁴, —R¹³—SR¹⁴, —R¹³—S(O)ₜR¹⁵ (where t is 1 or 2), —R¹³—N(R¹⁴)₂, —R¹³—CN, —R¹³—C(O)R¹⁴, —R¹³—C(S)R¹⁴, —R¹³—C(NR¹⁴)R¹⁴, R¹³—C(O)OR¹⁴, —R¹³—C(S)OR¹⁴, —R¹³—C(NR¹⁴)OR¹⁴, —R¹³—C(O)N(R¹⁴)₂, —R¹³—C(S)N(R¹⁴)₂, —R¹³—C(NR¹⁴)N(R¹⁴)₂, —R¹³—C(O)SR¹⁴, —R¹³—C(S)SR¹⁴, —R¹³—C(NR¹⁴)SR¹⁴, —R¹³—S(O)ₜOR¹⁴ (where t is 1 or 2), —R¹³—S(O)ₜN(R¹⁴)₂ (where t is 1 or 2), —R¹³—S(O)ₜN(R¹⁴)N(R¹⁴)₂ (where t is 1 or 2), —R¹³—S(O)ₜN(R¹⁴)N═C(R¹⁴)₂, —R¹³—S(O)ₜN(R¹⁴)C(O)R¹⁵ (where t is 1 or 2), —R¹³—S(O)ₜN(R¹⁴)C(NR¹⁴)N(R¹⁴)₂ (where t is 1 or 2), —R¹³—N(R¹⁴)C(O)R¹⁵, —R¹³—N(R¹⁴)C(O)OR¹⁵, —R¹³—N(R¹⁴)C(O)SR¹⁵, —R¹³—N(R¹⁴)C(NR¹⁴)SR¹⁵, —R¹³—N(R¹⁴)C(S)SR¹⁵, —R¹³—N(R¹⁴)C(O)N(R¹⁴)₂, —R¹³—N(R¹⁴)C(NR¹⁴)N(R¹⁴)₂, —R¹³—N(R¹⁴)C(S)N(R¹⁴)₂, —R¹³—N(R¹⁴)S(O)ₜR¹⁵ (where t is 1 or 2), —R¹³—OC(O)R¹⁵, —R¹³—OC(NR¹⁴)R¹⁵, —R¹³—OC(S)R¹⁵, —R¹³—OC(O)OR¹⁵, —R¹³—OC(NR¹⁴)OR¹⁵, —R¹³—OC(S)OR¹⁵, —R¹³—OC(O)SR¹⁴, —R¹³—OC(O)N(R¹⁴)₂, —R¹³—OC(NR¹⁴)N(R¹⁴)₂, —R¹³—OC(S)N(R¹⁴)₂, —R¹³—C(O)—R¹⁵—C(O)R¹⁴, —R¹³—C(O)—R¹⁵—C(S)R¹⁴, —R¹³—C(O)—R¹⁶—C(NR¹⁴)R¹⁴, —R¹³—C(O)—R¹⁶—C(O)OR¹⁴, —R¹³—C(O)—R¹⁶—C(S)OR¹⁴, —R¹³—C(O)—R¹⁶—C(NR¹⁴)OR¹⁴, —R¹³—C(O)—R¹⁶—C(O)N(R¹⁴)₂, —R¹³—C(O)—R¹⁶—C(S)N(R¹⁴)₂, —R¹³—C(O)—R¹⁶—C(NR¹⁴)N(R¹⁴)₂, —R¹³—C(O)—R¹⁶—C(O)SR¹⁴, —R¹³—C(O)—R¹⁶—C(S)SR¹⁴ and —R¹³—C(O)—R¹⁶—C(NR¹⁴)SR¹⁴;

where each R⁸ and R¹³ are independently a direct bond, an optionally substituted straight or branched alkylene chain, or an optionally substituted straight or branched alkenylene chain;

where each R⁹ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two R⁹s, together with the nitrogen to which they are attached, form an optionally substituted heterocyclyl;

where each R¹⁴ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or two R¹⁴s, together with the nitrogen to which they are attached, form an optionally substituted heterocyclyl;

where each R¹⁰ and R¹⁵ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl;

where each R¹¹ is independently an optionally substituted straight or branched alkylene chain or an optionally substituted straight or branched alkenylene chain; and as a single isomer, a mixture of isomers, or as a racemic mixture of isomers; or as a solvate or polymorph; or as a prodrug; or as a pharmaceutically acceptable salt thereof.

Another embodiment are compounds of formula (II):

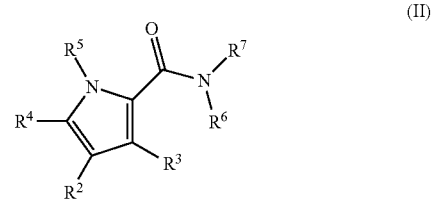

wherein:
R² is cyano, halo, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl or optionally substituted heteroaralkyl;

R³ is hydrogen or halo;

R⁴ is aryl or heteroaryl, where each is optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^3)_2$, —$R^8$—$CN$, —$R^8$—$C(O)R^3$, —$R^8$—$C(S)R^9$, —$R^8$—$C(NR^9)R^9$, —$R^8$—$C(O)OR^3$, —$R^8$—$C(S)OR^9$, —$R^8$—$C(NR^9)OR^9$, —$R^8$—$C(O)N(R^9)_2$, —$R^8$—$C(S)N(R^9)_2$, —$R^8$—$C(NR^9)N(R^9)_2$, —$R^8$—$C(O)SR^9$, —$R^8$—$C(S)SR^9$, —$R^8$—$C(NR^9)SR^9$, —$R^8$—$S(O)_tOR^3$ (where t is 1 or 2), —$R^8$—$S(O)_tN(R^9)_2$ (where t is 1 or 2), —$R^8$—$S(O)_tN(R^9)N(R^9)_2$ (where t is 1 or 2), —$R^8$—$S(O)_tN(R^9)N=C(R^9)_2$, —$R^8$—$S(O)_tN(R^3)C(O)R^{10}$ (where t is 1 or 2), —$R^8$—$S(O)_tN(R^9)C(O)N(R^3)_2$ (where t is 1 or 2), —$R^8$—$S(O)_tN(R^3)C(NR^3)N(R^3)_2$ (where t is 1 or 2), —$R^8$—$N(R^9)C(O)R^{10}$, —$R^8$—$N(R^9)C(O)OR^{10}$, —$R^8$—$N(R^9)C(O)SR^{10}$, —$R^8$—$N(R^3)C(NR^3)SR^{10}$, —$R^8$—$N(R^3)C(S)SR^{10}$, —$R^8$—$N(R^9)C(O)N(R^9)_2$, —$R^8$—$N(R^9)C(NR^9)N(R^9)_2$, —$R^8$—$N(R^9)C(S)N(R^9)_2$, —$R^8$—$N(R^9)S(O)_tR^{10}$ (where t is 1 or 2), —$R^8$—$OC(O)R^{10}$, —$R^8$—$OC(NR^9)R^{10}$, —$R^8$—$OC(S)R^{10}$, —$R^8$—$OC(O)OR^{10}$, —$R^8$—$OC(NR^3)OR^{10}$, —$R^8$—$OC(S)OR^{10}$, —$R^8$—$OC(O)SR^9$, —$R^8$—$OC(O)N(R^9)_2$, —$R^8$—$OC(NR^9)N(R^9)_2$, —$R^8$—$OC(S)N(R^9)_2$, —$R^8$—$C(O)$—$R^{11}$—$C(O)R^9$, —$R^8$—$C(O)$—$R^{11}$—$C(S)R^9$, —$R^3$—$C(O)$—$R^{11}$—$C(NR^9)R^9$, —$R^8$—$C(O)$—$R^{11}$—$C(O)OR^9$, —$R^8$—$C(O)$—$R^{11}$—$C(S)OR^3$, —$R^8$—$C(O)$—$R^{11}$—$C(NR^9)OR^3$, —$R^8$—$C(O)$—$R^{11}$—$C(O)N(R^9)_2$, —$R^8$—$C(O)$—$R^{11}$—$C(S)N(R^9)_2$, —$R^8$—$C(O)$—$R^{11}$—$C(NR^9)N(R^9)_2$, —$R^8$—$C(O)$—$R^{11}$—$C(O)SR^9$, —$R^8$—$C(O)$—$R^{11}$—$C(S)SR^3$ or —$R^8$—$C(O)$—$R^{11}$—$C(NR^9)SR^3$;

$R^5$ is optionally substituted alkyl, optionally substituted cycloalkyl, optionally substituted cycloalkylalkyl, optionally substituted aryl, optionally substituted aralkyl, optionally substituted heteroaryl or optionally substituted heteroaralkyl;

$R^6$ is hydrogen;

$R^7$ is aryl or heteroaryl, where each is optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^{13}$—$OR^{14}$, —$R^{13}$—$SR^{14}$, —$R^{13}$—$S(O)_tR^{15}$ (where t is 1 or 2), —$R^{13}$—$N(R^{14})_2$, —$R^{13}$—$CN$, —$R^{13}$—$C(O)R^{14}$, —$R^{13}$—$C(S)R^{14}$, —$R^{13}$—$C(NR^{14})R^{14}$, $C(O)OR^{14}$, —$R^{13}$—$C(S)OR^{14}$, —$R^{13}$—$C(NR^{14})OR^{14}$, —$R^{13}$—$C(O)N(R^{14})_2$, —$R^{13}$—$C(S)N(R^{14})_2$, —$R^{13}$—$C(NR^{14})N(R^{14})_2$, —$R^{13}$—$C(O)SR^{14}$, —$R^{13}$—$C(S)SR^{14}$, —$R^{13}$—$C(NR^{14})SR^{14}$, —$R^{13}$—$S(O)_tOR^{14}$ (where t is 1 or 2), —$R^{13}$—$S(O)_tN(R^{14})_2$ (where t is 1 or 2), —$R^{13}$—$S(O)_tN(R^{14})N(R^{14})_2$ (where t is 1 or 2), —$R^{13}$—$S(O)N(R^{14})N=C(R^{14})_2$, —$R^{13}$—$S(O)_tN(R^{14})C(O)R^{18}$ (where t is 1 or 2), —$R^{13}$—$S(O)_tN(R^{14})C(O)N(R^{14})_2$ (where t is 1 or 2), —$R^{13}$—$S(O)_tN(R^{14})C(NR^{14})N(R^{14})_2$ (where t is 1 or 2) and —$R^{13}$—$N(R^{14})S(O)_tR^{18}$ (where t is 1 or 2);

where each $R^8$ and $R^{13}$ are independently a direct bond, an optionally substituted straight or branched alkylene chain, or an optionally substituted straight or branched alkenylene chain;

where each $R^9$ is independently selected from the group consisting of hydrogen, optionally substituted alkyl, optionally substituted alkenyl, optionally substituted alkynyl, optionally substituted cycloalkyl, cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^9$s, together with the nitrogen atom to which they are attached, form an optionally substituted heterocyclyl;

where each $R^{14}$ is independently selected from the group consisting of hydrogen, optionally substituted alkyl, optionally substituted alkenyl, optionally substituted alkynyl, optionally substituted cycloalkyl, cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^{14}$s, together with the nitrogen atom to which they are attached, form an optionally substituted heterocyclyl;

where each $R^{10}$ and $R^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each $R^{11}$ is independently an optionally substituted straight or branched alkylene chain or an optionally substituted straight or branched alkenylene chain;

as a single isomer, a mixture of isomers, or a racemic mixture of isomers; or as a solvate or polymorph; or as a prodrug; or as a pharmaceutically acceptable salt thereof.

Another embodiment of the invention are compounds of formula (III):

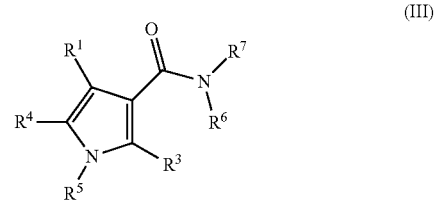

(III)

wherein:

$R^1$ is independently hydrogen, halo, cyano, optionally substituted alkyl, optionally substituted alkenyl or optionally substituted alkynyl, optionally substituted cycloalkyl, optionally substituted cycloalkylalkyl, optionally substituted aryl, optionally substituted aralkyl, optionally substituted heteroaryl, optionally substituted heteroaralkyl, optionally substituted heterocycyl, optionally substituted heterocyclyalkyl —$OR^9$, —$SR^9$, —$N(R^9)_2$, —$C(O)OR^9$ or —$C(O)N(R^9)_2$;

$R^3$ is independently hydrogen, halo, cyano, optionally substituted alkyl, optionally substituted alkenyl or optionally substituted alkynyl;

$R^4$ is hydrogen; —C(O)$R^9$ or —S(O)$_2R^9$;

or $R^4$ is alkyl, alkenyl or alkynyl optionally substituted by one or more substituents selected from the group consisting of halo, haloalkoxy, nitro, —O$R^9$, —S$R^9$, —S(O)$_tR^{10}$ (where t is 1 or 2), —N($R^9$)$_2$, —CN, —C(O)$R^9$, —C(S)$R^9$, —C(N$R^9$)$R^9$, —C(O)O$R^9$, —C(S)O$R^9$, —C(N$R^9$)O$R^9$, —C(O)N($R^9$)$_2$, —C(S)N($R^9$)$_2$, —C(N$R^9$)N($R^9$)$_2$, —C(O)S$R^9$, —C(S)S$R^9$, —C(N$R^9$)S$R^9$, —S(O)$_t$O$R^9$ (where t is 1 or 2), —S(O)$_t$N($R^9$)$_2$ (where t is 1 or 2), —S(O)$_t$N($R^9$)N($R^9$)$_2$ (where t is 1 or 2), —S(O)$_t$N($R^9$)N=C($R^9$)$_2$, —S(O)$_t$N($R^9$)C(O)$R^{10}$ (where t is 1 or 2), —$R^9$—S(O)$_t$N($R^9$)C(O)N($R^9$)$_2$ (where t is 1 or 2), —$R^8$—S(O)$_t$N($R^9$)C(N$R^9$)N($R^9$)$_2$ (where t is 1 or 2), —N($R^9$)C(O)$R^{10}$, —N($R^9$)C(O)O$R^{10}$, —N($R^9$)C(O)S$R^{10}$, —N($R^9$)C(N$R^9$)S$R^{10}$, —N($R^9$)C(S)S$R^{10}$, —N($R^9$)C(O)N($R^9$)$_2$, —N($R^9$)C(N$R^9$)N($R^9$)$_2$, —N($R^9$)C(S)N($R^9$)$_2$, —N($R^9$)S(O)$_tR^{10}$ (where t is 1 or 2), —OC(O)$R^{10}$, —OC(N$R^9$)$R^{10}$, —OC(S)$R^{10}$, —OC(O)O$R^{10}$, —OC(N$R^9$)O$R^{10}$, —OC(S)O$R^{10}$, —OC(O)S$R^9$, —OC(O)N($R^9$)$_2$, —OC(N$R^9$)N($R^9$)$_2$, —OC(S)N($R^9$)$_2$, —C(O)—$R^{11}$—C(O)$R^9$, —C(O)—$R^{11}$—C(S)$R^9$, —C(O)—$R^{11}$—C(N$R^9$)$R^9$, —C(O)—$R^{11}$—C(O)O$R^9$, —C(O)—$R^{11}$—C(S)O$R^9$, —C(O)—$R^{11}$—C(N$R^9$)O$R^9$, —C(O)—$R^{11}$—C(O)N($R^9$)$_2$, —C(O)—$R^{11}$—C(S)N($R^9$)$_2$, —C(O)—$R^{11}$—C(N$R^9$)N($R^9$)$_2$, —C(O)—$R^{11}$—C(O)S$R^9$, —C(O)—$R^{11}$—C(S)S$R^9$ and —C(O)—$R^{11}$—C(N$R^9$)S$R^9$;

or $R^4$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—O$R^9$, —$R^8$—S$R^9$, —$R^8$—S(O)$_tR^{10}$ (where t is 1 or 2), —$R^8$—N($R^9$)$_2$, —$R^8$—CN, —$R^8$—C(O)$R^9$, —$R^8$—C(S)$R^9$, —$R^8$—C(N$R^9$)$R^9$, —$R^8$—C(O)O$R^9$, —$R^8$—C(S)O$R^9$, —$R^8$—C(N$R^9$)O$R^9$, —$R^8$—C(O)N($R^9$)$_2$, —$R^8$—C(S)N($R^9$)$_2$, —$R^8$—C(N$R^9$)N($R^9$)$_2$, —$R^8$—C(O)S$R^9$, —$R^8$—C(S)S$R^9$, —$R^8$—C(N$R^9$)S$R^9$, —$R^8$—S(O)$_t$O$R^9$ (where t is 1 or 2), —$R^8$—S(O)$_t$N($R^9$)$_2$ (where t is 1 or 2), —$R^8$—S(O)$_t$N($R^9$)N($R^9$)$_2$ (where t is 1 or 2), —$R^8$—S(O)$_t$N($R^9$)N=C($R^9$)$_2$, —$R^8$—S(O)$_t$N($R^9$)C(O)$R^{10}$ (where t is 1 or 2), —$R^8$—S(O)$_t$N($R^9$)C(O)N($R^9$)$_2$ (where t is 1 or 2), —$R^8$—N($R^9$)C(O)$R^{10}$, —$R^8$—N($R^9$)C(O)O$R^{10}$, —$R^8$—N($R^9$)C(O)S$R^{10}$, —$R^8$—N($R^9$)C(N$R^9$)S$R^{10}$, —$R^8$—N($R^9$)C(S)S$R^{10}$, —$R^8$—N($R^9$)C(O)N($R^9$)$_2$, —$R^8$—N($R^9$)C(N$R^9$)N($R^9$)$_2$, —$R^8$—N($R^9$)C(S)N($R^9$)$_2$, —$R^8$—N($R^9$)S(O)$_tR^{10}$ (where t is 1 or 2), —$R^8$—OC(O)$R^{10}$, —$R^8$—OC(N$R^9$)$R^{10}$, —$R^8$—OC(S)$R^{10}$, —$R^8$—OC(O)O$R^{10}$, —$R^8$—OC(N$R^9$)O$R^{10}$, —$R^8$—OC(S)O$R^{10}$, —$R^8$—OC(O)S$R^9$, —$R^8$—OC(O)N($R^9$)$_2$, —$R^8$—OC(N$R^9$)N($R^9$)$_2$, —$R^8$—OC(S)N($R^9$)$_2$, —$R^8$—C(O)—$R^{11}$—C(O)$R^9$, —$R^8$—C(O)—$R^{11}$—C(S)$R^9$, —$R^8$—C(O)—$R^{11}$—C(N$R^9$)$R^9$, —$R^8$—C(O)—$R^{11}$—C(O)O$R^9$, —$R^8$—C(O)—$R^{11}$—C(S)O$R^9$, —$R^8$—C(O)—$R^{11}$—C(N$R^9$)O$R^9$, —$R^8$—C(O)—$R^{11}$—C(O)N($R^9$)$_2$, —$R^8$—C(O)—$R^{11}$—C(S)N($R^9$)$_2$, —$R^8$—C(O)—$R^{11}$—C(N$R^9$)N($R^9$)$_2$, —$R^8$—C(O)—$R^{11}$—C(O)S$R^9$, —$R^8$—C(O)—$R^{11}$—C(S)S$R^9$ and —$R^8$—C(O)—$R^{11}$—C(N$R^9$)S$R^9$;

$R^5$ is hydrogen, optionally substituted alkyl, optionally substituted cycloalkyl, optionally substituted cycloalkylalkyl, optionally substituted aryl, optionally substituted aralkyl, optionally substituted heteroaryl, optionally substituted heteroaralkyl, C(O)$R^9$ or —S(O)$_2R^9$;

$R^5$ is alkyl, alkenyl or alkynyl, where each is optionally substituted by one or more substituents selected from the group consisting of halo, haloalkyl, haloalkoxy, nitro, —O$R^9$, —S$R^9$, —S(O)$_tR^{10}$ (where t is 1 or 2), —N($R^9$)$_2$, —CN, —C(O)$R^9$, —C(S)$R^9$, —C(N$R^9$)$R^9$, —C(O)O$R^9$, —C(S)O$R^9$, —C(N$R^9$)O$R^9$, —C(O)N($R^9$)$_2$, —C(S)N($R^9$)$_2$, —C(N$R^9$)N($R^9$)$_2$, —C(O)S$R^9$, —C(S)S$R^9$, —C(N$R^9$)S$R^9$, —S(O)$_t$O$R^9$ (where t is 1 or 2), —S(O)$_t$N($R^9$)$_2$ (where t is 1 or 2), 7S(O)$_t$N($R^9$)N($R^9$)$_2$ (where t is 1 or 2), —S(O)$_t$N($R^9$)N=C($R^9$)$_2$, —S(O)$_t$N($R^9$)C(O)$R^{10}$ (where t is 1 or 2), —S(O)$_t$N($R^9$)C(O)N($R^9$)$_2$ (where t is 1 or 2), —$R^8$—S(O)$_t$N($R^9$)C(N$R^9$)N($R^9$)$_2$ (where t is 1 or 2), —N($R^9$)C(O)$R^{10}$, —N($R^9$)C(O)O$R^{10}$, —N($R^9$)C(O)S$R^{10}$, —N($R^9$)C(N$R^9$)S$R^{10}$, —N($R^9$)C(S)S$R^{10}$, —N($R^9$)C(O)N($R^9$)$_2$, —N($R^9$)C(N$R^9$)N($R^9$)$_2$, —N($R^9$)C(S)N($R^9$)$_2$, —N($R^9$)S(O)$_tR^{10}$ (where t is 1 or 2), —OC(O)$R^{10}$, —OC(N$R^9$)$R^{10}$, —OC(S)$R^{10}$, —OC(O)O$R^{10}$, —OC(N$R^9$)O$R^{10}$, —OC(S)O$R^{10}$, —OC(O)S$R^9$, —OC(O)N($R^9$)$_2$, —OC(N$R^9$)N($R^9$)$_2$, —OC(S)N($R^9$)$_2$, —C(O)—$R^{11}$—C(O)$R^9$, —C(O)—$R^{11}$—C(S)$R^9$, —C(O)—$R^{11}$—C(N$R^9$)$R^9$, —C(O)—$R^{11}$—C(O)O$R^9$, —C(O)—$R^{11}$—C(S)O$R^9$, —C(O)—$R^{11}$—C(N$R^9$)O$R^9$, —C(O)—$R^{11}$—C(O)N($R^9$)$_2$, —C(O)—$R^{11}$—C(S)N($R^9$)$_2$, —C(O)—$R^{11}$—C(N$R^9$)N($R^9$)$_2$, —C(O)—$R^{11}$—C(O)S$R^9$, —C(O)—$R^{11}$—C(S)S$R^9$ and —C(O)—$R^{11}$—C(N$R^9$)S$R^9$;

or $R^5$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, alkoxy, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—O$R^9$, —$R^8$—S$R^9$, —$R^8$—S(O)$_tR^{10}$ (where t is 1 or 2), —$R^8$—N($R^9$)$_2$, —$R^8$—CN, —$R^8$—C(O)$R^9$, —$R^8$—C(S)$R^9$, —$R^8$—C(N$R^9$)$R^9$, —$R^8$—C(O)O$R^9$, —$R^8$—C(S)O$R^9$, —$R^8$—C(N$R^9$)O$R^9$, —$R^8$—C(O)N($R^9$)$_2$, —$R^8$—C(S)N($R^9$)$_2$, —$R^8$—C(N$R^9$)N($R^9$)$_2$, —$R^8$—C(O)S$R^9$, —$R^8$—C(S)S$R^9$, —$R^8$—C(N$R^9$)S$R^9$, —$R^8$—S(O)$_t$O$R^9$ (where t is 1 or 2), —$R^8$—S(O)$_t$N($R^9$)$_2$ (where t is 1 or 2), —$R^8$—S(O)$_t$N($R^9$)N($R^9$)$_2$ (where t is 1 or 2), —$R^8$—S(O)$_t$N($R^9$)N=C($R^9$)$_2$, —$R^8$—S(O)$_t$N($R^9$)C(O)$R^{10}$ (where t is 1 or 2), —$R^8$—S(O)$_t$N($R^9$)C(O)N($R^9$)$_2$ (where t is 1 or 2), —$R^8$—S(O)$_t$N($R^9$)C(N$R^9$)N($R^9$)$_2$ (where t is 1 or 2), —$R^8$—N($R^9$)C(O)$R^{10}$, —$R^8$—N($R^9$)C(O)O$R^{10}$, —$R^8$—N($R^9$)C(O)S$R^{10}$, —$R^8$—N($R^9$)C(N$R^9$)S$R^{10}$, —$R^8$—N($R^9$)C(S)S$R^{10}$, —$R^8$—N($R^9$)C(O)N($R^9$)$_2$, —$R^8$—N($R^9$)C(N$R^9$)N($R^9$)$_2$, —$R^8$—N($R^9$)C(S)N($R^9$)$_2$, —$R^8$—N($R^9$)S(O)$_tR^{10}$ (where t is 1 or 2), —$R^8$—OC(O)$R^{10}$, —$R^8$—OC(N$R^9$)$R^{10}$, —$R^6$—OC(S)$R^{10}$, —$R^8$—OC(O)O$R^{10}$, —$R^8$—OC(N$R^9$)O$R^{10}$, —$R^8$—OC(S)O$R^{10}$, —$R^8$—OC(O)S$R^9$, —$R^8$—OC(O)N($R^9$)$_2$, —$R^8$—OC(N$R^9$)N($R^9$)$_2$, —$R^8$—OC(S)N($R^9$)$_2$, —$R^8$—C(O)—$R^{11}$—C(O)$R^9$, —$R^8$—C(O)—$R^{11}$—C(S)$R^9$, —$R^8$—C(O)—$R^{11}$—C (NR$^9$)R$^9$, —R$^8$—C(O)—R$^{11}$—C(O)OR$^9$, —R$^9$—C(O)—R$^{11}$—C(S)OR$^9$, —R$^8$—C(O)—R$^{11}$—C(NR$^9$)OR$^9$, —R$^8$—C(O)—R$^{11}$—C(O)N(R$^9$)$_2$, —R$^8$—C(O)—R$^{11}$—C(S)N(R$^9$)$_2$, —R$^8$—C(O)—R$^{11}$—C(NR$^9$)N(R$^9$)$_2$, —R$^8$—C(O)—R$^{11}$—C(O)SR$^9$, —R$^8$—C(O)—R$^{11}$—C(S)SR$^9$ and —R$^8$—C(O)—R$^{11}$—C(NR$^9$)SR$^9$;

R$^6$ is hydrogen, alkyl or optionally substituted alkyl;

R$^7$ is alkyl, alkenyl or alkynyl, where each is optionally substituted with one or more substituents selected from the group consisting of nitro, halo, optionally substituted cycloalkyl, optionally substituted heterocyclyl, optionally substituted aryl, optionally substituted heteroaryl, —OR$^{14}$, —SR$^{14}$, —S(O)$_t$R$^{15}$ (where t is 1 or 2), —N(R$^{14}$)$_2$, —CN, —C(O)R$^{14}$, C(NR$^{14}$)R$^{14}$, —C(O)OR$^{14}$, —C(S)OR$^{14}$, —C(NR$^{14}$)OR$^{14}$, —C(O)N(R$^{14}$)$_2$, —C(S)N(R$^{14}$)$_2$, —C(NR$^{14}$)N(R$^{14}$)$_2$, —C(O)SR$^{14}$, —C(S)SR$^{14}$, —C(NR$^{14}$)SR$^{14}$, —S(O)$_t$OR$^{14}$ (where t is 1 or 2), —S(O)$_t$N(R$^{14}$)$_2$ (where t is 1 or 2), —S(O)$_t$N(R$^{14}$)N(R$^{14}$)$_2$ (where t is 1 or 2), —S(O)$_t$N(R$^{14}$)N=C(R$^{14}$)$_2$, —S(O)$_t$N(R$^{14}$)C(O)R$^{15}$ (where t is 1 or 2), —S(O)$_t$N(R$^{14}$)C(O)N(R$^{14}$)$_2$ (where t is 1 or 2), —N(R$^{14}$)C(O)R$^{15}$, —N(R$^{14}$)C(O)OR$^{15}$, —N(R$^{14}$)C(O)SR$^{15}$, —N(R$^{14}$)C(NR$^{14}$)SR$^{15}$, —N(R$^{14}$)C(S)SR$^{15}$, —N(R$^{14}$)C(O)N(R$^{14}$)$_2$, —N(R$^{14}$)C(NR$^{14}$)N(R$^{14}$)$_2$, —N(R$^{14}$)C(S)N(R$^{14}$)$_2$, —N(R$^{14}$)S(O)$_t$R$^{15}$ (where t is 1 or 2), —OC(O)R$^{15}$, —OC(NR$^{14}$)R$^{15}$, —OC(S)R$^{15}$, —OC(O)OR$^{15}$, —OC(NR$^{14}$)OR$^{15}$, —OC(S)OR$^{15}$, —OC(O)SR$^{14}$, —OC(O)N(R$^{14}$)$_2$, —OC(NR$^{14}$)N(R$^{14}$)$_2$, —OC(S)N(R$^{14}$)$_2$, —C(O)—R$^{15}$—C(O)R$^{14}$, —C(O)—R$^{16}$—C(S)R$^{14}$, —C(O)—R$^{16}$—C(NR$^{14}$)R$^{14}$, C(O)—R$^{16}$—C(O)OR$^{14}$, —C(O)—R$^{16}$—C(S)OR$^{14}$, —C(O)—R$^{16}$—C(NR$^{14}$)OR$^{14}$, —C(O)—R$^{16}$—C(O)N(R$^{14}$)$_2$, —C(O)—R$^{16}$—C(S)N(R$^{14}$)$_2$, —C(O)—R$^{16}$—C(NR$^{14}$)N(R$^{14}$)$_2$, —C(O)—R$^{16}$—C(O)SR$^{14}$, —C(O)—R$^{16}$—C(S)SR$^{14}$ and —C(O)—R$^{16}$—C(NR$^{14}$)SR$^{14}$;

or R$^7$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, dioxo, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^{13}$—OR$^{14}$, —R$^{13}$—SR$^{14}$, —R$^{13}$—S(O)$_t$R$^{15}$ (where t is 1 or 2), —R$^{13}$—N(R$^{14}$)$_2$, —R$^{13}$—CN, —R$^{13}$—C(O)R$^{14}$, —R$^{13}$—C(S)R$^{14}$, —R$^{13}$—C(NR$^{14}$)R$^{14}$, —R$^{13}$—C(O)OR$^{14}$, —R$^{13}$—C(S)OR$^{14}$, —R$^{13}$—C(NR$^{14}$)OR$^{14}$, —R$^{13}$—C(O)N(R$^{14}$)$_2$, —R$^{13}$—C(S)N(R$^{14}$)$_2$, —R$^{13}$—C(NR$^{14}$)N(R$^{14}$)$_2$, —R$^{13}$—C(O)SR$^{14}$, —R$^{13}$—C(S)SR$^{14}$, —R$^{13}$—C(NR$^{14}$)SR$^{14}$, —R$^{13}$—S(O)$_t$OR$^{14}$ (where t is 1 or 2), —R$^{13}$—S(O)$_t$N(R$^{14}$)$_2$ (where t is 1 or 2), —R$^{13}$—S(O)$_t$N(R$^{14}$)N(R$^{14}$)$_2$ (where t is 1 or 2), —R$^{13}$—S(O)$_t$N(R$^{14}$)N=C(R$^{14}$)$_2$, —R$^{13}$—S(O)$_t$N(R$^{14}$)C(O)R$^{15}$, —R$^{13}$—N(R$^{14}$)C(O)R$^{15}$, —R$^{13}$—N(R$^{14}$)C(O)OR$^{15}$, —R$^{13}$—N(R$^{14}$)C(O)SR$^{15}$, —R$^{13}$—N(R$^{14}$)C(NR$^{14}$)SR$^{15}$, —R$^{13}$—N(R$^{14}$)C(S)SR$^{15}$, —R$^{13}$—N(R$^{14}$)C(O)N(R$^{14}$)$_2$, —R$^{13}$—N(R$^{14}$)C(NR$^{14}$)N(R$^{14}$)$_2$, —R$^{13}$—N(R$^{14}$)C(S)N(R$^{14}$)$_2$, —R$^{13}$—N(R$^{14}$)S(O)$_t$R$^{15}$ (where t is 1 or 2), —R$^{13}$—OC(O)R$^{15}$, —R$^{13}$—OC(NR$^{14}$)R$^{15}$, —R$^{13}$—OC(S)R$^{15}$, —R$^{13}$—OC(O)OR$^{15}$, —R$^{13}$—OC(NR$^{14}$)OR$^{15}$, —R$^{13}$—OC(S)OR$^{15}$, —R$^{13}$—OC(O)SR$^{14}$, —R$^{13}$—OC(O)N(R$^{14}$)$_2$, —R$^{13}$—OC(NR$^{14}$)N(R$^{14}$)$_2$, —R$^{13}$—OC(S)N(R$^{14}$)$_2$, —R$^{13}$—C(O)—R$^{16}$—C(O)R$^{14}$, —R$^{13}$—C(O)—R$^{16}$—C(S)R$^{14}$, —R$^{13}$—C(O)—R$^{16}$—C(NR$^{14}$)R$^{14}$, —R$^{13}$—C(O)R$^{16}$—C(O)OR$^{14}$, —R$^{13}$—C(O)—R$^{16}$—C(S)OR$^{14}$, —R$^{13}$—C(O)—R$^{16}$—C(NR$^{14}$)OR$^{14}$, —R$^{13}$—C(O)—R$^{16}$—C(O)N(R$^{14}$)$_2$, —R$^{13}$—C(O)—R$^{16}$—C(S)N(R$^{14}$)$_2$, —R$^{13}$—C(O)—R$^{16}$—C(NR$^{14}$)N(R$^{14}$)$_2$, —R$^{13}$—C(O)—R$^{16}$—C(O)SR$^{14}$, —R$^{13}$—C(O)—R$^{16}$—C(S)SR$^{14}$ and —R$^{13}$—C(O)—R$^{16}$—C(NR$^{14}$)SR$^{14}$;

where each R$^5$ and R$^{13}$ are independently a direct bond, an optionally substituted straight or branched alkylene chain, or an optionally substituted straight or branched alkenylene chain;

where each R$^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two R$^9$s, together with the nitrogen atom to which they are attached, form an optionally substituted heterocyclyl;

where each R$^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two R$^{14}$s, together with the nitrogen atom to which they are attached, form an optionally substituted heterocyclyl;

where each R$^{10}$ and R$^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each R$^{11}$ and R$^{16}$ are independently an optionally substituted straight or branched alkylene chain or an optionally substituted straight or branched alkenylene chain;

as a single isomer, a mixture of isomers, or as a racemic mixture of isomers; or as a solvate or polymorph; or as a prodrug; or as a pharmaceutically acceptable salt thereof.

Another embodiment of the invention are compounds of formula (III)

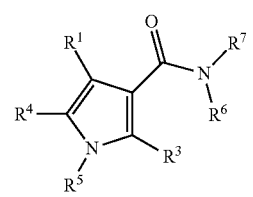

wherein:

$R^1$ is cyano, halo, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl or optionally substituted heteroaralkyl;

$R^3$ is hydrogen or halo;

$R^4$ is aryl or heteroaryl, where each is optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^9)_2$, —$R^8$—$C(O)R^9$, —$R^8$—$C(S)R^9$, —$R^8$—$C(NR^9)R^9$, —$R^8$—$C(O)OR^9$, —$R^8$—$C(S)OR^9$, —$R^8$—$C(NR^9)OR^9$, —$R^8$—$C(O)N(R^9)_2$, —$R^8$—$C(S)N(R^9)_2$, —$R^8$—$C(NR^9)N(R^9)_2$, —$R^8$—$C(O)SR^9$, —$R^8$—$C(S)SR^9$, —$R^8$—$C(NR^9)SR^9$, —$R^8$—$S(O)_tOR^9$ (where t is 1 or 2), —$R^8$—$S(O)_tN(R^9)_2$ (where t is 1 or 2), —$R^9$—$S(O)_tN(R^9)N(R^9)_2$ (where t is 1 or 2), —$R^8$—$S(O)_tN(R^9)N{=}C(R^9)_2$, —W—$S(O)_tN(R^9)C(O)R^{13}$ (where t is 1 or 2), —$R^8$—$S(O)_tN(R^9)C(O)N(R^9)_2$ (where t is 1 or 2), —W—$S(O)_tN(R^9)C(NR^9)N(R^9)_2$ (where t is 1 or 2), —$R^8$—$N(R^9)C(O)R^{13}$, —$R^8$—$N(R^9)C(O)OR^{10}$, —$R^8$—$N(R^9)C(O)SR^{10}$, —$R^8$—$N(R^9)C(NR^9)SR^{10}$, —$R^8$—$N(R^9)C(S)SR^{10}$, —$R^8$—$N(R^9)C(O)N(R^9)_2$, —$R^8$—$N(R^9)C(NR^9)N(R^9)_2$, —$R^9$—$N(R^9)C(S)N(R^9)_2$, —$R^8$—$N(R^9)S(O)_tR^{10}$ (where t is 1 or 2), —$R^8$—$OC(O)R^{10}$, —$R^8$—$OC(NR^9)R^{10}$, —$R^8$—$OC(S)R^{10}$, —$R^8$—$OC(O)OR^{10}$, —$R^8$—$OC(NR^9)OR^{10}$, —$R^8$—$OC(S)OR^{10}$, —$R^8$—$OC(O)SR^9$, —$R^8$—$OC(O)N(R^9)_2$, —$R^8$—$OC(NR^9)N(R^9)_2$, —$R^8$—$OC(S)N(R^9)_2$; —$R^8$—$C(O)$—$R^{11}$—$C(O)R^{14}$, —$R^8$—$C(O)$—$R^{11}$—$C(S)R^{14}$, —$R^8$—$C(O)$—$R^{11}$—$C(NR^{14})R^{14}$, —$R^8$—$C(O)$—$R^{11}$—$C(O)OR^{14}$, —$R^8$—$C(O)$—$R^{11}$—$C(S)OR^{14}$, —$R^8$—$C(O)$—$R^{11}$—$C(NR^{14})OR^{14}$, —$R^8$—$C(O)$—$R^{11}$—$C(O)N(R^{14})_2$, —$R^8$—$C(O)$—$R^{11}$—$C(S)N(R^{14})_2$, —$R^8$—$C(O)$—$R^{11}$—$C(NR^{14})N(R^{14})_2$, —$R^8$—$C(O)$—$R^{11}$—$C(O)SR^{14}$, —$R^8$—$C(O)$—$R^{11}$—$C(S)SR^{14}$ and —$R^8$—$C(O)$—$R^{11}$—$C(NR^{14})SR^{14}$;

$R^5$ is hydrogen, —$C(O)R^9$ or —$S(O)_2R^9$;

or $R^5$ is alkyl, alkenyl or alkynyl, where each is optionally substituted by one or more substituents selected from the group consisting of halo, nitro, —$OR^9$, —$SR^9$, —$S(O)_tR^{10}$ (where t is 1 or 2), —$N(R^9)_2$, —CN, —$C(O)R^9$, —$C(S)R^9$, —$C(NR^9)R^9$, —$C(O)OR^9$, —$C(S)OR^9$, —$C(NR^9)OR^9$, —$C(O)N(R^9)_2$, —$C(S)N(R^9)_2$, —$C(NR^9)N(R^9)_2$, —$C(O)SR^9$, —$C(S)SR^9$, —$C(NR^9)SR^9$, —$S(O)_tOR^9$ (where t is 1 or 2), —$S(O)_tN(R^9)_2$ (where t is 1 or 2), —$S(O)_tN(R^9)N(R^9)_2$ (where t is 1 or 2), —$S(O)_tN(R^9)N{=}C(R^9)_2$, —$S(O)_tN(R^9)C(O)R^{10}$ (where t is 1 or 2), —$S(O)_tN(R^9)C(O)N(R^9)_2$ (where t is 1 or 2), —$R^8$—$S(O)_tN(R^9)C(NR^9)N(R^9)_2$ (where t is 1 or 2), —$N(R^9)C(O)R^{10}$, —$N(R^9)C(O)OR^{10}$, —$N(R^9)$ $C(O)SR^{10}$, —$N(R^9)C(NR^9)SR^{10}$, —$N(R^9)C(S)SR^{10}$, —$N(R^9)C(O)N(R^9)_2$, —$N(R^9)C(NR^9)N(R^9)_2$, —$N(R^9)C(S)$ $N(R^9)_2$, —$N(R^9)S(O)_tR^{10}$ (where t is 1 or 2), —$OC(O)R^{10}$, —$OC(NR^9)R^{10}$, —$OC(S)R^{10}$, —$OC(O)OR^{10}$, —$OC(NR^9)$ $OR^{10}$, —$OC(S)OR^{10}$, —$OC(O)SR^9$, —$OC(O)N(R^9)_2$, —$OC(NR^9)N(R^9)_2$, —$OC(S)N(R^9)_2$, —$C(O)$—$R^{11}$—$C(O)R^9$, —$C(O)$—$R^{11}$—$C(S)R^9$, —$C(O)$—$R^{11}$—$C(NR^9)R^9$, —$C(O)$—$R^{11}$—$C(O)OR^9$, —$C(O)$—$R^{11}$—$C(S)OR^9$, —$C(O)$—$R^{11}$—$C(NR^9)OR^9$, —$C(O)$—$R^{11}$—$C(O)N(R^9)_2$, —$C(O)$—$R^{11}$—$C(S)N(R^9)_2$, —$C(O)$—$R^{11}$—$C(NR^9)N(R^9)_2$, —$C(O)$—$R^{11}$—$C(O)SR^9$, —$C(O)$—$R^{11}$—$C(S)SR^9$ and —$C(O)$—$R^{11}$—$C(NR^9)SR^9$;

or $R^5$ is cycloalkyl, cycloalkylalkyl, heterocyclyl, heterocyclylalkyl, aryl, aralkyl, heteroaryl or heteroaralkyl, where each is optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^9)_2$, —$R^8$—CN, —$R^8$—$C(O)R^9$, —$R^8$—$C(S)R^9$, —$R^8$—$C(NR^9)R^9$, —$R^8$—$C(O)OR^9$, —$R^8$—$C(S)OR^9$, —$R^8$—$C(NR^9)OR^9$, —$R^8$—$C(O)N(R^9)_2$, —$R^8$—$C(S)N(R^9)_2$, —$R^8$—$C(NR^9)N(R^9)_2$, —$R^8$—$C(O)SR^9$, —$R^8$—$C(S)SR^9$, —$R^8$—$C(NR^9)SR^9$, —$R^8$—$S(O)_tOR^9$ (where t is 1 or 2), —$R^8$—$S(O)_tN(R^9)_2$ (where t is 1 or 2), —$R^8$—$S(O)_tN(R^9)N(R^9)_2$ (where t is 1 or 2), —$R^8$—$S(O)_tN(R^9)N{=}C(R^9)_2$, —$R^8$—$S(O)_tN(R^9)C(O)R^{10}$ (where t is 1 or 2), —$R^8$—$S(O)_tN(R^9)C(O)N(R^9)_2$ (where t is 1 or 2), —$R^8$—$S(O)_tN(R^9)C(NR^9)N(R^9)_2$ (where t is 1 or 2), —$R^8$—$N(R^9)C(O)R^{10}$, —$R^8$—$N(R^9)C(O)OR^{10}$, —$R^8$—$N(R^9)C(O)SR^{10}$, —$R^8$—$N(R^9)C(NR^9)SR^{10}$, —$R^8$—$N(R^9)C(S)SR^{10}$, —$R^8$—$N(R^9)C(O)N(R^9)_2$, —$R^8$—$N(R^9)C(NR^9)N(R^9)_2$, —$R^8$—$N(R^9)C(S)N(R^9)_2$, —$R^8$—$N(R^9)S(O)_tR^{10}$ (where t is 1 or 2), —$R^8$—$OC(O)R^{10}$, —$R^8$—$OC(NR^9)R^{10}$, —$R^8$—$OC(S)R^{10}$, —$R^8$—$OC(O)OR^{10}$, —$R^8$—$OC(NR^9)OR^{10}$, —$R^8$—$OC(S)OR^{10}$, —$R^8$—$OC(O)SR^9$, —$R^8$—$OC(O)N(R^9)_2$, —$R^8$—$OC(NR^9)N(R^9)_2$, —$R^8$—$OC(S)N(R^9)_2$, —$R^8$—$C(O)$—$R^{11}$—$C(O)R^9$, —$R^8$—$C(O)$—$R^{11}$—$C(S)R^9$, —$R^8$—$C(O)$—$R^{11}$—$C(NR^9)R^9$, —$R^8$—$C(O)$—$R^{11}$—$C(O)OR^9$, —$R^8$—$C(O)$—$R^{11}$—$C(S)OR^9$, —$R^8$—$C(O)$—$R^{11}$—$C(NR^9)OR^9$, —$R^8$—$C(O)$—$R^{11}$—$C(O)N(R^9)_2$, —$R^8$—$C(O)$—$R^{11}$—$C(S)N(R^9)_2$, —$R^8$—$C(O)$—$R^{11}$—$C(NR^9)N(R^9)_2$, —$R^8$—$C(O)$—$R^{11}$—$C(O)SR^9$, —$R^8$—$C(O)$—$R^{11}$—$C(S)SR^9$ and —$R^8$—$C(O)$—$R^{11}$—$C(NR^9)SR^9$;

$R^6$ is hydrogen or optionally substituted alkyl;

$R^7$ is alkyl, alkenyl or alkynyl, where each is optionally substituted by one or more substituents selected from the group consisting of nitro, halo, —$OR^{14}$, —$SR^{14}$, —$S(O)_tR^{15}$ (where t is 1 or 2), —$N(R^{14})_2$, —CN, —$C(O)R^{14}$, —$C(S)R^{14}$, —$C(NR^{14})R^{14}$, —$C(O)OR^{14}$, —$C(S)OR^{14}$, —$C(NR^{14})OR^{14}$, —$C(O)N(R^{14})_2$, —$C(S)N(R^{14})_2$, —$C(NR^{14})N(R^{14})_2$, —$C(O)SR^{14}$, —$C(S)SR^{14}$, —$C(NR^{14})SR^{14}$, —$S(O)_tOR^{14}$ (where t is 1 or 2), —$S(O)_tN(R^{14})_2$ (where t is 1 or 2), —$S(O)_tN(R^{14})N(R^{14})_2$ (where t is 1 or 2), —$S(O)_tN(R^{14})N{=}C(R^{14})_2$, —$S(O)_tN(R^{14})C(O)R^{15}$ (where t is 1 or 2), —$R^8$—$S(O)_tN(R^{14})C(O)N(R^{14})_2$ (where t is 1 or 2), —$R^8$—$S(O)_tN(R^{14})C(NR^{14})N(R^{14})_2$ (where t is 1 or 2), —$N(R^{14})C(O)R^{15}$, —$N(R^{14})C(O)OR^{15}$, —$N(R^{14})C(O)SR^{15}$, —$N(R^{14})C(NR^{14})SR^{15}$, —$N(R^{14})C(S)SR^{15}$, —$N(R^{14})C(O)N(R^{14})_2$, —$N(R^{14})C(NR^{14})N(R^{14})_2$, —$N(R^{14})C(S)N(R^{14})_2$, —$N(R^{14})S(O)_tR^{15}$ (where t is 1 or 2), —$OC(O)R^{15}$, —$OC(NR^{14})R^{15}$, —$OC(S)R^{15}$, —$OC(O)OR^{15}$, —$OC(NR^{14})OR^{15}$, —$OC(S)OR^{15}$, —$OC(O)SR^{14}$, —$OC(O)N(R^{14})_2$, —$OC(NR^{14})N(R^{14})_2$, —$OC(S)N(R^{14})_2$, —$C(O)$—$R^{16}$—C $(O)R^{14}$, $-C(O)-R^{16}-C(S)R^{14}$, $-C(O)-R^{16}-C(NR^{14})$ $R^{14}$, $-C(O)-R^{16}-C(O)OR^{14}$, $-C(O)-R^{16}-C(S)OR^{14}$, $-C(O)-R^{16}-C(NR^{14})OR^{14}$, $-C(O)-R^{16}-C(O)$ $N(R^{14})_2$, $-C(O)-R^{16}-C(S)N(R^{14})_2$, $-C(O)-R^{16}-C(NR^{14})N(R^{14})_2$, $-C(O)-R^{16}-C(O)SR^{14}$, $-C(O)-R^{16}-C(S)SR^{14}$ and $-C(O)-R^{16}-C(NR^{14})SR^{14}$;

$R^6$ is hydrogen;

$R^7$ is aryl or heteroaryl, where each is optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, $-R^{13}-OR^{14}$, $-R^{13}-SR^{14}$, $-R^{13}-S(O)_tR^{15}$ (where t is 1 or 2), $-R^{13}-N(R^{14})_2$, $-R^{13}-CN$, $-R^{13}-C(O)R^{14}$, $-R^{13}-C(S)R^{14}$, $-R^{13}-C(NR^{14})-R^{13}-C(O)OR^{14}$, $-R^{13}-C(S)OR^{14}$, $-R^{13}-C(NR^{14})OR^{14}$, $-R^{13}-C(O)N(R^{14})_2$, $-R^{13}-C(S)N(R^{14})_2$, $-R^{13}-C(NR^{14})N(R^{14})_2$, $-R^{13}-C(O)SR^{14}$, $-R^{13}-C(S)SR^{14}$, $-R^{13}-C(NR^{14})SR^{14}$, $-R^{13}-S(O)_tOR^{14}$ (where t is 1 or 2), $-R^{13}-S(O)_tN(R^{14})_2$ (where t is 1 or 2), $-R^{13}-S(O)_tN(R^{14})N(R^{14})_2$ (where t is 1 or 2), $-R^{13}-S(O)_tN(R^{14})N=C(R^{14})_2$, $-R^{13}-S(O)_tN(R^{14})C(O)R^{18}$ (where t is 1 or 2), $-R^{13}-S(O)_tN(R^{14})C(O)N(R^{14})_2$ (where t is 1 or 2), $-R^{13}-S(O)_tN(R^{14})C(NR^{14})N(R^{14})_2$ (where t is 1 or 2) and $-R^{13}-N(R^{14})S(O)_tR^{18}$ (where t is 1 or 2);

where each $R^8$ and $R^{13}$ are independently a direct bond, an optionally substituted straight or branched alkylene chain, or an optionally substituted straight or branched alkenylene chain;

where each $R^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^9$s, together with the nitrogen atom to which they are attached, form an optionally substituted heterocyclyl; and where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^{14}$s, together with the nitrogen atom to which they are attached, form an optionally substituted heterocyclyl;

where each $R^{10}$ and $R^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each $R^{11}$ is independently an optionally substituted straight or branched alkylene chain or an optionally substituted straight or branched alkenylene chain; and as a single isomer, a mixture of isomers, or as a racemic mixture of isomers; or as a solvate or polymorph; or as a prodrug; or as a pharmaceutically acceptable salt thereof.

Another embodiment of the invention are compounds of formula (IV)

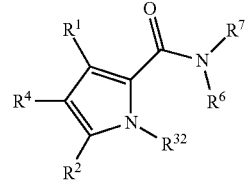

(IV)

wherein:

$R^1$ and $R^2$ are each independently cyano, halo, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heteroaryl or optionally substituted heteroaralkyl;

$R^{32}$ is hydrogen or halo;

$R^4$ is aryl or heteroaryl, where each is optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, $-R^8-OR^9$, $-R^8-SR^9$, $-R^8-S(O)_tR^{10}$ (where t is 1 or 2), $-R^8-N(R^9)_2$, $-R^8-CN$, $-R^8-C(O)R^9$, $-R^8-C(S)R^9$, $-R^8-C(NR^9)R^9$, $-R^8-C(O)OR^9$, $-R^8-C(S)OR^9$, $-R^8-C(NR^9)OR^9$, $-R^8-C(O)N(R^9)_2$, $-R^8-C(S)N(R^9)_2$, $-R^8-C(NR^9)N(R^9)_2$, $-R^8-C(O)SR^9$, $-R^8-C(S)SR^9$, $-R^8-C(NR^9)SR^9$, $-R^8-S(O)_tOR^9$ (where t is 1 or 2), $-R^8-S(O)_tN(R^9)_2$ (where t is 1 or 2), $-R^8-S(O)_tN(R^9)N(R^9)_2$ (where t is 1 or 2), $-R^8-S(O)_tN(R^9)N=C(R^9)_2$, $-R^8-S(O)_tN(R^9)C(O)R^{10}$ (where t is 1 or 2), $-R^8-S(O)_tN(R^9)C(O)N(R^9)_2$ (where t is 1 or 2), $-R^8-S(O)_tN(R^9)C(NR^9)N(R^9)_2$ (where t is 1 or 2), $-R^8-N(R^9)C(O)R^{10}$, $-R^8-N(R^9)C(O)OR^{10}$, $-R^8-N(R^9)C(O)SR^{10}$, $-R^8-N(R^9)C(NR^9)SR^{10}$, $-R^8-N(R^9)C(S)SR^{10}$, $-R^8-N(R^9)C(O)N(R^9)_2$, $-R^8-N(R^9)C(NR^9)N(R^9)_2$, $-R^8-N(R^9)C(S)N(R^9)_2$, $-R^8-N(R^9)S(O)_tR^{10}$ (where t is 1 or 2), $-R^8-OC(O)R^{10}$, $-R^8-OC(NR^9)R^{10}$, $-R^8-OC(S)R^{10}$, $-R^8-OC(O)OR^{10}$, $-R^8-OC(NR^9)OR^{10}$, $-R^9-OC(S)OR^{10}$, $-R^8-OC(O)SR^9$, $-R^8-OC(O)N(R^9)_2$, $-R^8-OC(NR^9)N(R^9)_2$, $-R^8-OC(S)N(R^9)_2$, $-R^8-C(O)-R^{11}-C$ (O)R⁹, —R⁸—C(O)—R¹¹—C(S)R⁹, —R⁸—C(O)—R¹¹—C(NR⁹)R⁹, —R⁸—C(O)—R¹¹—C(O)OR⁹, —R⁶—C(O)—R¹¹—C(S)OR⁹, —R⁸—C(O)—R¹¹—C(NR⁹)OR⁹, —R⁸—C(O)—R¹¹—C(O)N(R⁹)₂, —R⁸—C(O)—R¹¹—C(S)N(R⁹)₂, —R⁸—C(O)—R¹¹—C(NR⁹)N(R⁹)₂, —R⁸—C(O)—R¹¹—C(O)SR⁹, —R⁸—C(O)—R¹¹—C(S)SR⁹ and —R⁸—C(O)—R¹¹—C(NR⁹)SR⁹;

R⁶ is hydrogen;

R⁷ is aryl or heteroaryl, where each is optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R¹³—OR¹⁴, —R¹³—SR¹⁴, —R¹³—S(O)ₜR¹⁵ (where t is 1 or 2), —R¹³—N(R¹⁴)₂, —R¹³—CN, —R¹³—C(O)R¹⁴, —R¹³—C(S)R¹⁴, —R¹³—C(NR¹⁴)R¹⁴, C(O)OR¹⁴, —R¹³—C(S)OR¹⁴, —R¹³—C(NR¹⁴)OR¹⁴, —R¹³—C(O)N(R¹⁴)₂, —R¹³—C(S)N(R¹⁴)₂, —R¹³—C(NR¹⁴)N(R¹⁴)₂, —R¹³—C(O)SR¹⁴, —R¹³—C(S)SR¹⁴, —R¹³—C(NR¹⁴)SR¹⁴, —R¹³—S(O)ₜOR¹⁴ (where t is 1 or 2), —R¹³—S(O)ₜN(R¹⁴)₂ (where t is 1 or 2), —R¹³—S(O)ₜN(R¹⁴)N(R¹⁴)₂ (where t is 1 or 2), —R¹³—S(O)ₜN(R¹⁴)N=C(R¹⁴)₂, —R¹³—S(O)ₜN(R¹⁴)C(O)R¹⁵ (where t is 1 or 2), —R¹³—S(O)ₜN(R¹⁴)C(O)N(R¹⁴)₂ (where t is 1 or 2), —R¹³—S(O)ₜN(R¹⁴)C(NR¹⁴)N(R¹⁴)₂ (where t is 1 or 2) and —R¹³—N(R¹⁴)S(O)ₜR¹⁶ (where t is 1 or 2);

where each R⁸ and R¹³ are independently a direct bond, an optionally substituted straight or branched alkylene chain, or an optionally substituted straight or branched alkenylene chain;

where each R⁹ is independently selected from the group consisting of hydrogen, optionally substituted alkyl, optionally substituted alkenyl, optionally substituted alkynyl, optionally substituted cycloalkyl, cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; or where two R⁹s, together with the nitrogen atom to which they are attached, form an optionally substituted heterocyclyl;

R¹⁴ are independently selected from the group consisting of hydrogen, optionally substituted alkyl, optionally substituted alkenyl, optionally substituted alkynyl, optionally substituted cycloalkyl, cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; or where two R¹⁴s, together with the nitrogen atom to which they are attached, form an optionally substituted heterocyclyl;

where each R¹⁰ and R¹⁵ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; and where each R¹¹ is independently an optionally substituted straight or branched alkylene chain or an optionally substituted straight or branched alkenylene chain; and as a single isomer, a mixture of isomers, or as a racemic mixture of isomers; or as a solvate or polymorph; or as a prodrug; or as a pharmaceutically acceptable salt thereof.

Another embodiment are compounds of formulae (I)-(IV) wherein R⁴ is:

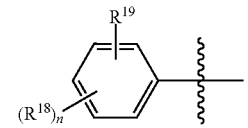

where:

n is 0 to 4;

each R¹⁸ is selected from the group consisting of halo, nitro, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R⁸—OR⁹, —R⁸—SR⁹, —R⁵—S(O)ₜR¹⁰ (where t is 1 or 2), —R⁸—N(R⁹)₂, —R⁸—CN, —R⁸—C(O)R⁹, —R⁸—C(S)R⁹, —R⁸—C(NR⁹)R⁹, —R⁸—C(O)OR⁹, —R⁸—C(S)OR⁹, —R⁸—C(NR⁹)OR⁹, —R⁸—C(O)N(R⁹)₂, —R⁸—C(S)N(R⁹)₂, —R⁸—C(NR⁹)N(R⁹)₂, —R⁸—C(O)SR⁹, —R⁸—C(S)SR⁹, —R⁸—C(NR⁹)SR⁹, —R⁸—S(O)ₜOR⁹ (where t is 1 or 2), —R⁸—S(O)ₜN(R⁹)₂ (where t is 1 or 2), —R⁸—S(O)ₜN(R⁹)N(R⁹)₂ (where t is 1 or 2), —R⁸—S(O)ₜN(R⁹)N=C(R⁹)₂, —R⁸—S(O)ₜN(R⁹)C(O)R¹⁰ (where t is 1 or 2), —R⁸—S(O)ₜN(R⁹)C(O)N(R⁹)₂ (where t is 1 or 2), —R⁸—N(R⁹)C(O)R¹⁰, —R⁸—N(R⁹)C(O)OR¹⁰, —R⁸—N(R⁹)C(O)SR¹⁰, —R⁸—N(R⁹)C(NR⁹)SR¹⁰, —R⁸—N(R⁹)C(S)SR¹⁰, —R⁸—N(R⁹)C(O)N(R⁹)₂, —R⁸—N(R⁹)C(NR⁹)N(R⁹)₂, —R⁸—N(R⁹)C(S)N(R⁹)₂, —R⁸—N(R⁹)S(O)ₜR¹⁰ (where t is 1 or 2), —R⁸—OC(O)R¹⁰, —R⁸—OC(NR⁹)R¹⁰, —R⁸—OC(S)R¹⁰, —R⁸—OC(O)OR¹⁰, —R⁸—OC(NR⁹)OR¹⁰, —R⁸—OC(S)OR¹⁰, —R⁸—OC(O)SR⁹, —R⁸—OC(O)N(R⁹)₂, —R⁸—OC(NR⁹)N(R⁹)₂, —R⁸—OC(S)N(R⁹)₂, —R⁸—C(O)—R¹¹—C(O)R⁹, —R⁸—C(O)—R¹¹—C(S)R⁹, —R⁸—C(O)—R¹¹—C(NR⁹)R⁹, —R⁸—C(O)—R¹¹—C(O)OR⁹, —R⁸—C(O)—R¹¹—C(S)OR⁹, —R⁸—C(O)—R¹¹—C(NR⁹)OR⁹, —R⁸—C(O)—R¹¹—C(O)N(R⁹)₂, —R⁸—C(O)—R¹¹—C(S)N(R⁹)₂, —R⁸—C(O)—R¹¹—C(NR⁹)N(R⁹)₂, —R⁸—C(O)—R¹¹—C(O)SR⁹, —R⁸—C(O)—R¹¹—C(S)SR⁹ and —R⁸—C(O)—R¹¹—C(NR⁹)SR⁹;

R¹⁹ is halo, optionally substituted alkyl, optionally substituted alkenyl, haloalkoxy, optionally substituted heterocyclyl, optionally substituted heterocyclylalkyl, optionally substituted aryl, optionally substituted aralkyl, optionally substituted aralkenyl, optionally substituted heteroaryl, optionally substituted heteroaralkyl, optionally substituted heteroaralkenyl, —R$^8$—C(O)R$^9$, —R$^8$—C(O)OR$^9$ or —R$^8$—C(O)N(R$^9$)$_2$;

where each R$^8$ is independently a direct bond, an optionally substituted straight or branched alkylene chain, or an optionally substituted straight or branched alkenylene chain;

where each R$^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two R$^9$s, together with the nitrogen atom to which they are attached, form an optionally substituted heterocyclyl;

where each R$^{10}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each R$^{11}$ is independently an optionally substituted straight or branched alkylene chain or an optionally substituted straight or branched alkenylene chain.

Another embodiment are compounds of formulae (I)-(IV) wherein R$^7$ is

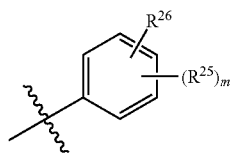

where m is 0 to 4; and

R$^{25}$ and R$^{26}$ are each independently selected from the group consisting of halo, nitro, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —R$^{13}$—OR$^{14}$, —R$^{13}$—SR$^{14}$, —R$^{13}$—S(O)$_t$R$^{15}$ (where t is 1 or 2), —R$^{13}$—N(R$^{14}$)$_2$, —R$^{13}$—CN, —R$^{13}$—C(O)R$^{14}$, —R$^{13}$—C(S)R$^{14}$, —R$^{13}$—C(NR$^{14}$)R$^{14}$, —R$^{13}$—C(O)OR$^{14}$, —R$^{13}$—C(S)OR$^{14}$, —R$^{13}$—C(NR$^{14}$)OR$^{14}$, —R$^{13}$—C(O)N(R$^{14}$)$_2$, —R$^{13}$—C(S)N(R$^{14}$)$_2$, —R$^{13}$—C(NR$^{14}$)N(R$^{14}$)$_2$, —R$^{13}$—C(O)SR$^{14}$, —R$^{13}$—C(S)SR$^{14}$, —R$^{13}$—C(NR$^{14}$)SR$^{14}$, —R$^{13}$—S(O)$_t$OR$^{14}$ (where t is 1 or 2), —R$^{13}$—S(O)$_t$N(R$^{14}$)$_2$ (where t is 1 or 2), —R$^{13}$—S(O)$_t$N(R$^{14}$)N(R$^{14}$)$_2$ (where t is 1 or 2), —R$^{13}$—S(O)$_t$N(R$^{14}$)N=C(R$^{14}$)$_2$, —R$^{13}$—S(O)$_t$N(R$^{14}$)C(O)R$^{15}$, (where t is 1 or 2), —R$^{13}$—S(O)$_t$N(R$^{14}$)C(O)N(R$^{14}$)$_2$ (where t is 1 or 2), —R$^{13}$—S(O)$_t$N(R$^{14}$)C(NR$^{14}$)N(R$^{14}$)$_2$ (where t is 1 or 2), —R$^{13}$—N(R$^{14}$)C(O)R$^{15}$, —R$^{13}$—N(R$^{14}$)C(O)OR$^{15}$, —R$^{13}$—N(R$^{14}$)C(O)SR$^{15}$, —R$^{13}$—N(R$^{14}$)C(NR$^{14}$)SR$^{15}$, —R$^{13}$—N(R$^{14}$)C(S)SR$^{15}$, —R$^{13}$—N(R$^{14}$)C(O)N(R$^{14}$)$_2$, —R$^{13}$—N(R$^{14}$)C(NR$^{14}$)N(R$^{14}$)$_2$, —R$^{13}$—N(R$^{14}$)C(S)N(R$^{14}$)$_2$, —R$^{13}$—N(R$^{14}$)S(O)$_t$R$^{15}$ (where t is 1 or 2), —R$^{13}$—OC(O)R$^{15}$, —R$^{13}$—OC(NR$^{14}$)R$^{15}$, —R$^{13}$—OC(S)R$^{15}$, —R$^{13}$—OC(O)OR$^{15}$, —R$^{13}$—OC(NR$^{14}$)OR$^{15}$, —R$^{13}$—OC(S)OR$^{15}$, —R$^{13}$—OC(O)SR$^{14}$, —R$^{13}$—OC(O)N(R$^{14}$)$_2$, —R$^{13}$—OC(NR$^{14}$)N(R$^{14}$)$_2$, —R$^{13}$—OC(S)N(R$^{14}$)$_2$, —R$^{13}$—C(O)—R$^{16}$—C(O)R$^{14}$, —R$^{13}$—C(O)—R$^{16}$—C(S)R$^{14}$, —R$^{13}$—C(O)—R$^{16}$—C(NR$^{14}$)R$^{14}$, —R$^{13}$—C(O)—R$^{16}$—C(O)OR$^{14}$, —R$^{13}$—C(O)—R$^{16}$—C(S)OR$^{14}$, —R$^{13}$—C(O)—R$^{16}$—C(NR$^{14}$)OR$^{14}$, —R$^{13}$—C(O)—R$^{16}$—C(O)N(R$^{14}$)$_2$, —R$^{13}$-C(O)—R$^{16}$-C(S)N(R$^{14}$)$_2$, —R$^{13}$—C(O)—R$^{16}$—C(NR$^{14}$)N(R$^{14}$)$_2$, —R$^{13}$—C(O)—R$^{16}$—C(O)SR$^{14}$, —R$^{13}$—C(O)—R$^{16}$—C(S)SR$^{14}$ and —R$^{13}$—C(O)—R$^{16}$—C(NR$^{14}$)SR$^{14}$;

where each R$^{13}$ is independently a direct bond, an optionally substituted straight or branched alkylene chain, or an optionally substituted straight or branched alkenylene chain;

where each R$^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two R$^{14}$s, together with the nitrogen atom to which they are attached, form an optionally substituted heterocyclyl;

where each R$^{15}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each R$^{16}$ is independently an optionally substituted straight or branched alkylene chain or an optionally substituted straight or branched alkenylene chain.

In another embodiment, the compounds for use in the compositions and methods provided are set forth in Table I.

C. Evaluation of the Activity of the Compounds

Standard physiological, pharmacological and biochemical procedures are available for testing the compounds to identify those that possess biological activities that selectively modulate the activity of steroid nuclear receptors. Such assays include, for example, biochemical assays such as binding assays, fluorescence polarization assays, fluorescence resonance energy transfer (FRET) based coactivator recruitment assays (see generally Glickman et al., *J. Biomolecular Screening*, 7 (1): 3-10 (2002)), as well as cell based assays including the co-transfection assay, the use of LBD-Gal 4 chimeras and protein-protein interaction assays (see, Lehmann. et al., *J. Biol. Chem.*, 272(6): 3137-3140 (1997).

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see for example, Owicki, J., Biomol Screen 2000 October; 5(5):297) scintillation proximity assays (SPA) (see for example, Carpenter et al., Methods Mol Biol 2002; 190:31-49) and FRET or time resolved FRET based coactivator recruitment assays (Mukherjee et al., J Steroid Biochem Mol Biol 2002 July; 81(3):217-25; (Zhou et al., Mol. Endocrinol. 1998 October; 12(10):1594-604). Generally such assays can be performed using either the full length receptor, or fragment including the isolated LBD. In the case of the mineralocorticoid receptor, a useful fragment comprises amino acids 671-984 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader. The ability of a compound to effect a ligand dependent interaction of a co-activator peptide with a nuclear receptor can also be assessed by fluorescence resonance energy transfer (FRET), or time resolved FRET, in order to characterize the agonist or antagonist activity of the compounds disclosed herein. Both approaches rely upon the fact that energy transfer from a donor molecule to an acceptor molecule only occurs when donor and acceptor are in close proximity. Typically the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically, GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor.

In addition a variety of cell based assay methodologies may be successfully used in screening assays to identify and profile the specificity of compounds of the present invention. These approaches include transfection assays, translocation assays, complementation assays and the use of gene activation technologies to over express endogenous nuclear receptors.

The basic co-transfection assay is based on the co-transfection into the cell of an expression plasmid to produce the nuclear receptor of interest in the cell with a reporter plasmid comprising a reporter gene whose expression is under the control of a hormone response element that is capable of interacting with that nuclear receptor. (See for example U.S. Pat. Nos. 5,071,773; 5,298,429, 6,416,957, WO 00/76523). Treatment of the transfected cells with an agonist for the nuclear receptor increases the transcriptional activity of that receptor which is reflected by an increase in expression of the reporter gene, which may be measured by a variety of standard procedures.

In one embodiment of this method, the host cell endogenously expresses the nuclear receptor and appropriate cofactors or heterodimeric partners. Typically, such a situation may occur with a primary cell or cell lines derived directly from a primary cell type, is used to characterize compounds of the present invention. Accordingly creation of the assay system requires only the transfection into the cell of a suitable reporter gene(s) as are described herein.

A cell line that endogenously expresses the MR includes, for example, the mouse collecting duct cell line described in Am. J. Physiol. Endocrinol Metab. 279 E336-E394 (2000). Alternatively the expression of endogenous genes (detected via RT-PCR) can be used to monitor MR transcriptional activity in response to the addition of a test compound.

In another aspect, the host cell may lack sufficient endogenous expression of a suitable nuclear receptor, in which case one may be introduced by transfection of the cell line with an expression plasmid, as described below. Typically, the expression plasmid comprises: (1) a promoter, such as an SV40 early region promoter, HSV tk promoter or phosphoglycerate kinase (pgk) promoter, CMV promoter, Srα promoter or other suitable control elements known in the art, (2) a cloned polynucleotide sequence, such as a cDNA encoding a receptor, co-factor, or a fragment thereof, ligated to the promoter in sense orientation so that transcription from the promoter will produce a RNA that encodes a functional protein, and (3) a polyadenylation sequence. As an example not to be construed as a limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. Genes & Development (1995) 9:1033-1045) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example see U.S. Pat. Nos. 6,534,261 and 6,503,7171) or a strong promoter or enhancer sequence together with a targeting sequence to enable homologous or non-homologous recombination of the activating sequence upstream of the gene of interest.

In one aspect of these methods, chimeras are used in place of the full-length nuclear receptor. Such chimeras typically comprise the ligand binding domain and hinge region of the nuclear receptor coupled to a heterologous DNA binding domain (DBD).

Typically for such chimeric constructs, heterologous DNA binding domains from distinct, well-defined nuclear receptors are used, or alternatively the DNA binding domains from yeast or bacterially derived transcriptional regulators such as members of the GAL 4 and Lex A (GenBank accession number ILEC)/Umud super families may be used.

GAL4 (GenBank Accession Number P04386) is a positive regulator for the expression of the galactose-induced genes. (see for example, Keegan et al., Science 231: 699-704 (1986)). Preferably the first 96 amino acids of the Gag protein are used, most preferably the first 147 amino acid residues of yeast Gal4 protein are used. For those receptors that can function as heterodimers with RXR, the method typically includes the use of expression plasmids for both the nuclear receptor of interest and RXR. Such sequences include, but are not limited to the following members of the RXR gene family, including RXRα, (GenBank Accession No. NM_002957), RXRβ. (GenBank Accession No. XM_042579) and RXRγ (GenBank Accession No. XM_053680).

To identify compounds that act to modulate co-factor, or nuclear receptor heterodimerization, a mammalian two-hybrid assay can be used (see, for example, U.S. Pat. Nos. 5,667,973, 5,283,173 and 5,468,614). This approach identifies protein-protein interactions in vivo through reconstitution of a strong transcriptional activator upon the interaction of two proteins, a "bait" and "prey" (Fields S and Song 0 (1989) Nature 340: 245; Willey et al., (1995) Gene & Development 9 1033-1045). This system relies on functional dimeric interactions between two fusion proteins, one carrying the GAL4 DNA-binding domain fusion with the ability to bind to a $GAL4_{UAS}$-containing reporter gene. The other carries the VP16 transactivation domain fusion. When expressed together, DNA binding and transcriptional activation is reconstituted in a single complex. Functional interaction, for example between a GAL-SRC-1 fusion protein and VP16-VDR fusion protein should lead to constitutive activation of a suitable reporter plasmid, such as luciferase reporter construct comprising GAL4 upstream Activating Sequences (UAS).

Such reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., (1987) Mol. Cell. Biol. 7 725-735) down stream from the herpes virus thymidine kinase promoter (located at nucleotides residues-105 to +51 of the thymidine kinase nucleotide sequence, pBLCAT2 (Luckow & Schutz (1987) Nucl. Acid. Res. 15 5490-5494)) which is linked in turn to the appropriate response elements.

Transactivation domains are well known in the art and can be readily identified by the artisan. Examples include the GAL4 activation domain, TAT, VP16, and analogs thereof.

Response elements (RE) are well known and have been thoroughly described in the art. Such response elements can include direct repeat structures or inverted repeat structures based on well defined hexad half sites, as described in greater detail below. Exemplary hormone response elements are composed of at least one direct repeat of two or more half sites, separated by a spacer having in the range of 0 up to 6 nucleotides. The spacer nucleotides can be randomly selected from any one of A, C, G or T. Each half site of response elements contemplated for use in the practice of the invention comprises the sequence: —RGBNNM-, wherein R is selected from A or G; B is selected from G, C, or T; each N is independently selected from A, T, C, or G; and M is selected from A or C; is with the proviso that at least 4 nucleotides of said —RGBNNM- sequence are identical with the nucleotides at corresponding positions of the sequence -AGGTCA-. Response elements employed to profile the compounds of the present invention can optionally be preceded by N, wherein x falls in the range of 0 up to 5. Preferred response elements useful in the methods of the present invention include hormone response elements such as the Glucocorticoid response element (GRE), for example as found in the MMTV LTR.

The choice of hormone response element is dependent upon the type of assay to be used. In the case of the use of a cell line endogenously expressing a steroid receptor, a known steroid RE would typically be used. In the case of a MR-LBD-Gal4 fusion, a GAL4 UAS would be used. Typically the GAL4 UAS would comprise the sequence 5'CGGRNNR-CYNYNCNCCG-3', where Y=C or T, R=A or G, and N=A, C, T or G, and would be present as a tandem repeat of 4 copies. Numerous reporter gene systems are known in the art and include, for example, alkaline phosphatase (see, Berger, J., et al., Gene (1988), Vol. 66, pp. 1-10; and Kain, S. R., Methods. Mol. Biol. (1997), Vol. 63, pp. 49-60), β-galactosidase (See, U.S. Pat. No. 5,070,012, issued Dec. 3, 1991 to Nolan et al., and Bronstein, I., et al., J. Chemilum. Biolum. (1989), Vol. 4, pp. 99-111), chloramphenicol acetyltransferase (See, Gorman et al., Mol. Cell. Biol. (1982), Vol. 2, pp. 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., Annu. Rev. Biochem. (1998), Vol. 67, pp. 509-44).

Numerous methods of co-transfecting the expression and reporter plasmids are known to those of skill in the art and may be used for the co-transfection assay to introduce the plasmids into a suitable cell type.

Any compound which is a candidate for the modulation of a steroid nuclear receptor activity may be tested by these methods. Generally, compounds are tested at several different concentrations to optimize the chances that modulation of receptor activity will be detected and recognized if present. Typically assays are performed in triplicate or quadruplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally, the compounds and compositions can be evaluated for their ability to increase or decrease the expression of genes known to be modulated by a steroid nuclear receptor and other nuclear receptors in vivo, using Northern-blot, RT PCR or oligonucleotide microarray analysis to analyze RNA levels. Western-blot analysis can be used to measure expression of proteins encoded by mineralocorticoid receptor target genes. Genes that are known or suspected to be regulated by the mineralocorticoid receptor, for example, include; sgk (serum and glucocorticoid regulated kinase (NM_005627)), Na/K ATPase, $\alpha 1,\beta 1$ subunits, ENaCalpha (epithelial Na channel (NM_001038)), GILZ (glucocorticoid induced leucine zipper (BC 061979)), and NDRG2, (N-myc downstream regulated gene 2 (NM_016250)).

Established animal models exist and these can be used to further profile and characterize the claimed compounds. These model systems for MR include the Kagawa bioassay of urinary electrolytes (Bhargava et al., Endocrinology 142(4): 1587-94, (2001)), the Goldblatt model (Nicoletti et al., Hypertension 26(1): 101-11, (1995)), the Cardiac fibrosis model described in Ramires et al., (J. Mol. Cell. Cardiol. March; 30 (3):475-83, (1998)), the Renal vascular injury in SHRSP saline-drinking stroke-prone spontaneously hypertensive rats described in Rocha et al., (Hypertension 33 (1 Pt 2): 232-7, (1999)), and Rodent model of myocardial necrosis and renal arteriopathy described in Rocha et al., (Endocrinology October; 141(10):3871-8 (2000)).

D. Methods of Use of the Compounds and Compositions

Also provided herein are methods of using the disclosed compounds and compositions for the local or systemic treatment or prophylaxis of human and veterinary diseases, disorders and conditions mediated by, or otherwise affected by one or more steroid nuclear receptors, or in which steroid nuclear receptor activity, is implicated, including without limitation:

(a) Diseases or disorders associated with an excess or a deficiency steroid receptor ligands or steroid receptor activity, including, for example, Addison's disease, Cushing's syndrome, Conn's syndrome, Turner's syndrome, hormone replacement therapies, menopause, hypogonadism, somatopause, andropause, and viropause;

(b) Diseases or disorders relating to cancer, including, for example, hormone dependent cancers such as breast cancer (U.S. Pat. No. 6,306,832), prostrate cancer (U.S. Pat. No. 5,656,651), benign prostatic hyperplasia (U.S. Pat. No. 5,656,651) ovarian cancer, endometrial cancer (U.S. Pat. No. 6,593,322), leukemia (U.S. Pat. No. 6,696,459) and lymphoma (U.S. Pat. No. 6,667,299);

(c) Diseases or disorders related to infertility including, for example, endometriosis, the control of menstruation, dysfunctional uterine bleeding, dysmnenorrhea, endometriosis, meningiomas, leionyomas (uterine fibroids), the induction of labor (U.S. Pat. No. 6,358, 947; U.S. Pat. No. 5,843,933) and as modulators of male and female fertility (e.g., as contraceptives or contragestational agents);

(d) Diseases or disorders relating to metabolic syndromes including, for example, Syndrome X, hyperglycemia, insulin insensitivity, diabetes, obesity, fat storage or distribution, hyperlipidemia, hypercholesterolemia, hyperlipoproteinemia, hypertriglyceridemia, dyslipidemia, hyperinsulinemia, atherosclerosis and hyperuricemia (U.S. Pat. No. 6,699,893, U.S. Pat. No. 6,680,310; U.S. Pat. No. 6,593,480; US Patent Application No. 2003/0028910);

(e) Diseases or disorders relating to bone or cartilage dysfunction, including, for example, osteoporosis, frailty, decreased bone density and hypercalcemia (U.S. Pat. No. 6,686,351; U.S. Pat. No. 6,660,468; US Application No. 2002/0187953);

(f) Inflammatory diseases or disorders related to immune dysfunction, including, for example, immunodeficiency, immunomodulation, autoimmune diseases, tissue rejection, wound healing, allergies, inflammatory bowel disease, Lupus Erythematosis, arthritis, osteoarthritis, rheumatoid arthritis, asthma and rhinitis (U.S. Pat. No. 6,699,893; U.S. Pat. No. 6,380,223; U.S. Pat. No. 6,716, 829);

(g) Diseases or disorders related to cognitive dysfunction, including for example, psychosis, cognitive disorder, mood disorder, anxiety disorder, personality disorder and Parkinson's disease and Alzheimer's disease (U.S. Pat. No. 6,620,802; U.S. Pat. No. 6,734,211);

(h) Disease or disorders related to high blood pressure, including, for example, fluid retention, edema, cardiovascular disease and hypertension (U.S. Pat. No. 6,608, 047);

(i) Disease or disorders related to heart disease, including, for example, ischemic heart disease, heart failure, systolic impairment, diastolic impairment, myocardial necrosis, pulmonary venous congestion, atrial fibrillation, myocardial infarction, myocardial fibrosis and chronic heart failure (U.S. Pat. No. 6,716,829; U.S. Pat. No. 6,391,867);

(j) Diseases or disorders related to renal disease, including, for example, diabetic nephropathy, chronic glomerulonephritis, polycystic kidney disease, non-diabetic nephropathy and chronic kidney disease; (U.S. Pat. No. 6,716,829; U.S. Pat. No. 6,391,867);

(k) Diseases or disorders related to fibrosis (U.S. Pat. No. 6,716,829; U.S. Pat. No. 6,391,867);

(l) Diseases or disorders related to epidermal dysfunction including, for example, acne, hirsutism, alopecia and skin atrophy;

(m) Diseases or disorders related to muscle wasting, including, for example, low muscle mass, muscle weakness, poor muscle mass to fat ratio.

Also provided are methods of using the disclosed compounds and compositions for of contraception, methods of regulating hair growth, methods of regulating muscle mass, methods of inducing weight loss, methods of regulating fat deposition or distribution, methods of stimulation of the metabolic rate, methods of altering the muscle mass to fat ratio, methods of regulating the development and growth of epidermal tissue, methods of regulating cognitive function, methods of regulating electrolyte balance, methods of regulating blood pressure and methods of regulating immunological function.

In one embodiment, such compounds or compositions exhibit selective agonist activity for at least one steroid nuclear receptor, in one of the in vitro assays described herein. In one embodiment the steroid nuclear receptor is MR. In another embodiment the steroid nuclear receptor is AR. In another embodiment the steroid nuclear receptor is PR. In another embodiment the steroid nuclear receptor is GR. In another embodiment the steroid nuclear receptor is ER. In another embodiment the steroid nuclear receptor is an ERR.

In another embodiment, such compounds or compositions exhibit selective partial agonist activity for at least one steroid nuclear receptor, in one of the in vitro assays described herein. In one embodiment the steroid nuclear receptor is MR. In another embodiment the steroid nuclear receptor is AR. In another embodiment the steroid nuclear receptor is PR. In another embodiment the steroid nuclear receptor is GR. In another embodiment the steroid nuclear receptor is PR. In another embodiment the steroid nuclear receptor is GR. In another embodiment the steroid nuclear receptor is ER. In another embodiment the steroid nuclear receptor is an ERR.

In another embodiment, such compounds or compositions exhibit selective partial antagonist activity for at least one steroid nuclear receptor, in one of the in vitro assays described herein. In one embodiment the steroid nuclear receptor is MR. In another embodiment the steroid nuclear receptor is AR. In another embodiment the steroid nuclear receptor is PR. In another embodiment the steroid nuclear receptor is GR. In another embodiment the steroid nuclear receptor is ER. In another embodiment the steroid nuclear receptor is an ERR.

In another embodiment, such compounds or compositions exhibit selective antagonist activity for at least one steroid nuclear receptor, in one of the in vitro assays described herein. In one embodiment the steroid nuclear receptor is MR. In another embodiment the steroid nuclear receptor is AR. In another embodiment the steroid nuclear receptor is GR. In another embodiment the steroid nuclear receptor is PR. In another embodiment the steroid nuclear receptor is ER. In another embodiment the steroid nuclear receptor is an ERR.

It will be understood by those skilled in the art that while the compounds, isomers, prodrugs and pharmaceutically acceptable derivatives thereof of the present invention will typically be employed as selective agonists, partial agonists, partial antagonists or antagonists, there may be instances where a compound with a mixed steroid nuclear receptor profile is preferred. In another embodiment, such compounds or compositions modulate at least two steroid nuclear receptors, in one of the in vitro assays described herein.

In one aspect, the two steroid receptors are MR and at least one other nuclear receptor selected from the group consisting of AR, PR, GR, ER and ERR. In another aspect such compounds or compositions modulate any combination of two nuclear receptors selected from AR, PR, GR, ER and ERR.

Also provided herein are methods of using the disclosed compounds and compositions, or pharmaceutically acceptable derivatives thereof, for the local or systemic treatment or prophylaxis of human and veterinary diseases, disorders and conditions modulated or otherwise affected by the MR, or in which MR activity, is implicated. In one embodiment such disorders and conditions include, for example, diseases associated with an excess, or a deficiency, of MR activity or mineralocorticoids in the body, heart disease, fibrosis, metabolic syndromes, cognitive dysfunction, renal disease, and high blood pressure.

Also provided herein are methods of using the disclosed compounds and compositions for the local or systemic treatment or prophylaxis of human and veterinary diseases, disorders and conditions modulated or otherwise affected by the PR, or in which PR activity, is implicated. In one embodiment such disorders and conditions include, for example, diseases associated with an excess, or a deficiency, of PR activity or progestins in the body, infertility, cognitive dysfunction, and cancers.

Also provided herein are methods of using the disclosed compounds and compositions for the local or systemic treatment or prophylaxis of human and veterinary diseases, disorders and conditions modulated or otherwise affected by the AR, or in which AR activity, is implicated. In one embodiment such disorders and conditions include, for example, diseases associated with an excess, or a deficiency, of AR activity or androgens in the body, heart disease, cognitive dysfunction, renal disease, cancers, infertility, anemia, epidermal dysfunction, constipation, dry eyes, periodontal disease, immune dysfunction, bone or cartilage dysfunction, low muscle mass and metabolic syndromes.

Also provided herein are methods of using the disclosed compounds and compositions for the local or systemic treatment or prophylaxis of human and veterinary diseases, disorders and conditions modulated or otherwise affected by the ER, or in which ER activity, is implicated. In one embodiment such disorders and conditions include, for example, diseases associated with an excess, or a deficiency, of ER activity or estrogens in the body, bone or cartilage dysfunction, infertility, epidermal dysfunction, metabolic syndromes, cancers, heart disease, and cognitive dysfunction.

Also provided herein are methods of using the disclosed compounds and compositions for the local or systemic treatment or prophylaxis of human and veterinary diseases, disorders and conditions modulated or otherwise affected by the GR, or in which GR activity, is implicated. In one embodiment such disorders and conditions include, for example, diseases associated with an excess, or a deficiency, of GR activity or glucocorticoids in the body, metabolic syndromes, hypertension, cognitive dysfunction, glaucoma, human immunodeficiency virus (HIV) or acquired immunodeficiency syndrome (AIDS), bone or cartilage dysfunction, immune dysfunction, post-surgical bone fracture, low muscle mass and prevention of muscle frailty.

Also provided herein are methods of using the disclosed compounds and compositions for the local or systemic treatment or prophylaxis of human and veterinary diseases, disorders and conditions modulated or otherwise affected by an ERR, or in which ERR activity, is implicated. In one embodiment such disorders and conditions include, for example, diseases associated with an excess, or a deficiency, of ERR activity in the body bone and cartilage dysfunction, metabolic syndromes, cancers, infertility, cognitive dysfunction, and epidermal dysfunction.

E. Combination Therapy

Furthermore, it will be understood by those skilled in the art that the compounds, isomers, prodrugs and pharmaceutically acceptable derivatives thereof of the present invention, including pharmaceutical compositions and formulations containing these compounds, can be used in a wide variety of combination therapies to treat the conditions and diseases described above. Thus, also contemplated herein is the use of compounds, isomers, prodrugs and pharmaceutically acceptable derivatives of the present invention in combination with other active pharmaceutical agents for the treatment of the disease/conditions described herein.

Also contemplated herein are combination therapies using one or more compounds or compositions provided herein, or pharmaceutically acceptable derivatives thereof, in combination with one or more of the following; ACE inhibitors, Angiotensin II blockers, anti-coagulants, anti-cancer agents, anti-arrhythmics, anti-inflammatory agents, beta blockers, calcium channel antagOnists, lipid-modulating agents, cytokine antagonists, digitalis medicines, diuretics, endothelin blockers, vasodilators, immune-suppressants, and glucose lowering agents.

The compound or composition provided herein, or pharmaceutically acceptable derivative thereof, may be administered simultaneously with, prior to, or after administration of one or more of the above agents.

Pharmaceutical compositions containing a compound provided herein or pharmaceutically acceptable derivative thereof, and one or more of the above agents are also provided.

Also provided is a combination therapy that treats the undesirable side effects of steroid treatment. These side effects include, but are not limited to, metabolic effects, weight gain, muscle wasting, decalcification of the skeleton, osteoporosis, thinning of the skin and thinning of the skeleton. However, according to the present invention, the compounds or compositions disclosed herein, or pharmaceutically acceptable derivatives thereof may be used in combination with steroid receptor agonists to block some of these side effects, without inhibiting the efficacy of the treatment.

Also provided is a combination therapy that treats or prevents the onset of the symptoms, or associated complications of cancer and related diseases and disorders comprising the administration to a subject in need thereof, of one of the compounds or compositions disclosed herein, or pharmaceutically acceptable derivatives thereof, with one or more anti-cancer agents.

Also provided is a combination therapy that treats or prevents the onset of the symptoms, or associated complications of infertility and related diseases and disorders, comprising the administration to a subject in need thereof, of one of the compounds or compositions disclosed herein, or pharmaceutically acceptable derivatives thereof, with one or more of the following active agents, estrogen agonists, and progesterone agonists.

Also provided is a combination therapy that treats or prevents the onset of the symptoms, or associated complications of metabolic syndromes and related diseases and disorders, comprising the administration to a subject in need thereof, of one of the compounds or compositions disclosed herein, or pharmaceutically acceptable derivatives thereof, with one or more of the following active agents, selected from the group consisting of phenylpropanolamine, phentermine, diethylpropion, mazindol; fenfluramine, dexfenfluramine, phentiramine, $\beta_3$ adrenoceptor agonist agents; sibutramine, gastrointestinal lipase inhibitors (such as orlistat), leptin, a glucose lower agent and lipid-modulating agent.

Also provided is a combination therapy that treats or prevents the onset of the symptoms, or associated complications of bone or cartilage dysfunction, and related diseases and disorders, comprising the administration to a subject in need thereof, of one of the compounds or compositions disclosed herein, or pharmaceutically acceptable derivatives thereof, with one or more of the following active agents, selected from the group consisting of immune-suppressants and anti-inflammatory agents.

Also provided is a combination therapy that treats or prevents the onset of the symptoms, or associated complications of immune dysfunction and related diseases and disorders, comprising the administration to a subject in need thereof, of one of the compounds or compositions disclosed herein, or pharmaceutically acceptable derivatives thereof, with one or more of the following active agents, selected from the group consisting of anti-inflammatory agents, immune-suppressants and cytokine antagonists.

Also provided is a combination therapy that treats or prevents the onset of the symptoms, or associated complications of cognitive dysfunction and related diseases and disorders, comprising the administration to a subject in need thereof, of one of the compounds or compositions disclosed herein, or pharmaceutically acceptable derivatives thereof, with an anti-depressant.

Also provided is a combination therapy that treats or prevents the onset of the symptoms, or associated complications of high blood pressure and related diseases and disorders, comprising the administration to a subject in need thereof, of one of the compounds or compositions disclosed herein, or pharmaceutically acceptable derivatives thereof, with one or more of the following active agents selected from the group consisting of, ACE inhibitors, Angiotensin II blockers, anti-coagulants, anti-arrhythmics, beta blockers, calcium channel antagonists, lipid-modulating agents, cytokine antagonists, digitalis medicines, diuretics, endothelin blockers, and vasodilators.

Also provided is a combination therapy that treats or prevents the onset of the symptoms, or associated complications of heart disease and related diseases and disorders, comprising the administration to a subject in need thereof, of one of the compounds or compositions disclosed herein, or pharmaceutically acceptable derivatives thereof, with one or more of the following active agents selected from the group consisting of, ACE inhibitors, Angiotensin II blockers, anti-coagulants, anti-arrhythmics, beta blockers, calcium channel antagonists, lipid-modulating agents, cytokine antagonists, digitalis medicines, diuretics, endothelin blockers, and vasodilators.

Also provided is a combination therapy that treats, or prevents the onset of the symptoms, or associated complications of renal disease and related diseases and disorders, comprising the administration to a subject in need thereof, of one of the compounds or compositions disclosed herein, or pharmaceutically acceptable derivatives thereof, with one or more of the following active agents selected from the group consisting of, ACE inhibitors, Angiotensin II blockers, beta blockers, cytokine antagonists, glucose lowering agents, and erythropoietin.

Also provided is a combination therapy that treats, or prevents the onset of the symptoms, or associated complications of fibrosis, comprising the administration to a subject in need thereof, of one of the compounds or compositions disclosed herein, or pharmaceutically acceptable derivatives thereof, with one or more of the following active agents selected from the group consisting of, ACE inhibitors, cytokine antagonists, immune-suppressants and anti-inflammatory agents.

Also provided is a combination therapy that treats, or prevents the onset of the symptoms, or associated complications of epidermal dysfunction and related diseases and disorders, comprising the administration to a subject in need thereof of one of the compounds or compositions disclosed herein, or pharmaceutically acceptable derivatives thereof, with one or more of the following, a lipid-modulating agent, an antibiotic or an anti-inflammatory agent.

F. Preparation of the Compounds of the Invention

Starting materials in the synthesis examples provided herein are either available from commercial sources or via literature procedures (e.g., March *Advanced Organic Chemistry Reactions, Mechanisms, and Structure*, (1992) 4th Ed.; Wiley Interscience, New York). AU commercially available compounds were used without further purification unless otherwise indicated. CDCl$_3$ (99.8% D, Cambridge Isotope Laboratories) was used in all experiments as indicated. Proton ($^1$H) nuclear magnetic resonance (NMR) spectra were recorded on a Bruker Avance 400 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid). Flash chromatography was performed using Merck Silica Gel 60 (230-400 mesh) following standard protocol (Still et al. (1978) *J. Org. Chem.* 43:2923). It is understood that in the following description, combinations of substituents and/or variables of the depicted formulae are permissible only if such contributions result in stable compounds under standard conditions.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1991), 2nd Ed., Wiley-Interscience. One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that many of the products could exist as one or more isomers, that is E/Z isomers, enantiomers and/or diastereomers. Compounds of formula (I) may be prepared as depicted in Scheme 1. In general acylation of a primary or secondary amine, R$^6$R$^7$NH, with a pyrrole-3-carboxylic acid chloride under basic conditions and with heating can yield a pyrrole amide of formula (I). For example, a primary heteroaryl amine can be acylated with this acid chloride to afford the corresponding amide (I), wherein R$^6$ is hydrogen and R$^7$ is heteroaryl.

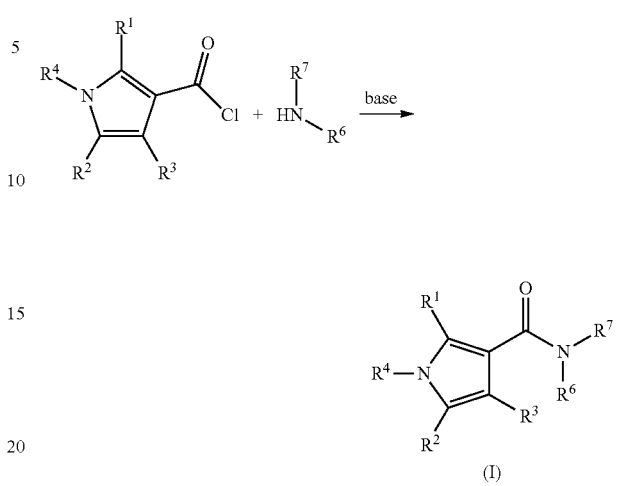

Scheme 1. General synthesis of compounds of formula (I).

Furthermore, a substituted aniline, such as [(R$^{26}$)(R$^{26}$)$_m$PhN(R$^6$)H], can react with a pyrrole-3-carboxylic acid chloride in a manner as described above to yield the corresponding pyrrole product of formula (Ib), equivalent to formula (I) wherein R$^7$ is a substituted phenyl.

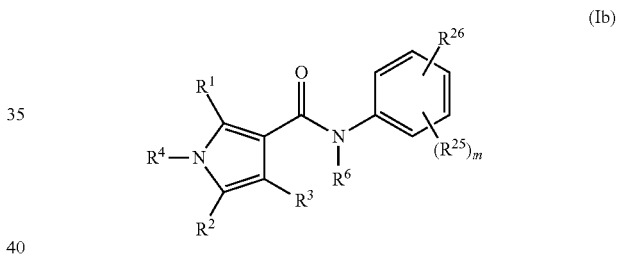

Compounds of formula (Ib) and analogous compounds of formula (I) in which R$^7$ is substituted aryl or heteroaryl also may be synthesized under alternate conditions as shown in Scheme 2.

Scheme 2. Preparation of compounds of formula (Ib).

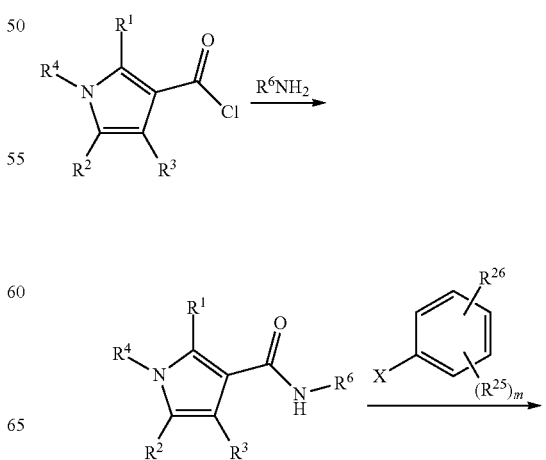

-continued

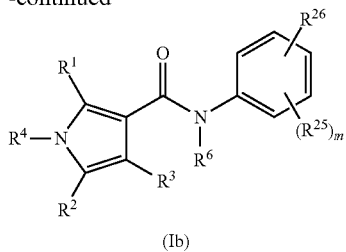

(Ib)

In general, an amine ($R^6NH_2$) can react with a pyrrole-3-carboxylic acid chloride under basic conditions to yield the corresponding carboxamide. This amide intermediate can then react with an aryl (or heteroaryl) bromide (chloride, iodide, triflate or tosylate) such as, for example, substituted bromobenzene under copper- or palladium-mediated conditions to give the corresponding product of formula (Ib), equivalent to formula (I) wherein $R^7$ is substituted phenyl. The synthetic methodology can be adapted from one of the highly general and robust conditions for transition metal-catalyzed amidations that have been reported by Buchwald (*J. Am. Chem. Soc.* 2002, 124, 7421-7428; *Org. Lett.* 2000, 2, 1101-1104).

In general, a pyrrole-3-carboxylic acid chloride may be prepared as depicted in Scheme 3.

Scheme 3. General synthesis of a pyrrole-3-carboxylic acid chloride.

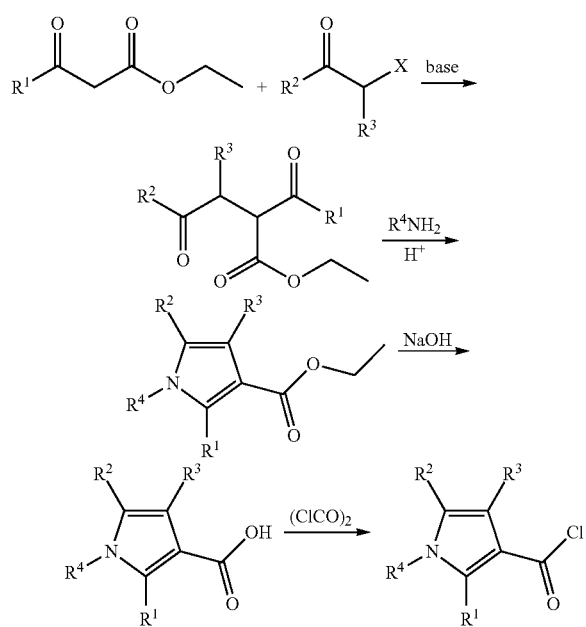

A haloketone (X=halo) can be reacted with a β-ketoester under basic conditions such as, for example, sodium hydride in THF, to yield the corresponding 1,4-diketone. This diketone intermediate can be condensed with a primary amine ($R^4NH_2$) such as, for example, where $R^4$ is aryl or heteroaryl, under acidic conditions and with heating to afford the respective pyrrole-3-carboxylic acid ester. This intermediate ester can then be converted into its corresponding acid chloride under typical conditions such as, for example, by first hydrolysis with 2N NaOH in methanol and followed by treatment with oxalyl chloride in DCM. Likewise, other types of primary amines such as, for example, benzyl amines (aralkyl) can be utilized in the reaction sequence to provide the corresponding pyrrole intermediates wherein $R^4$ is benzyl.

Other pyrrole-3-carboxylic acid chlorides, such as wherein $R^1=R^2$ and $R^3=H$, may be synthesized as shown in Scheme 4.

Scheme 4. Preparation of other pyrrole-3-carboxylic acid chlorides.

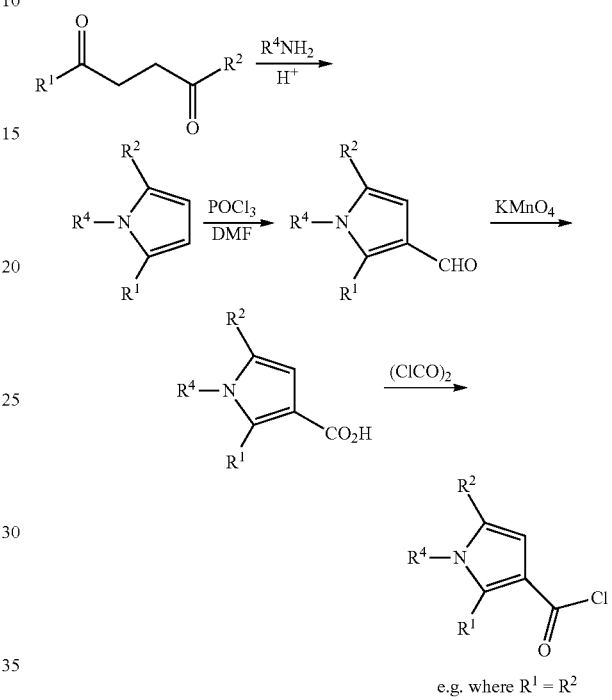

e.g. where $R^1 = R^2$

Thus, for example, a primary amine ($R^4NH_2$) and a symmetric 1,4-diketone can be condensed under Paal-Knorr conditions to yield the corresponding 2,5-disubstituted pyrrole, which can be converted to its pyrrole-3-carboxaldehyde under typical conditions such as, for example, Vilsmeier-Haack formulation. This intermediate aldehyde can then be oxidized to the corresponding carboxylic acid under conditions such as, for example, aqueous $KMnO_4$ in acetone. Next, the acid intermediate can be converted to its corresponding acid chloride under typical conditions.

Products of formula (I) in which $R^1$ is $NH_2$, equivalent to 2-aminopyrroles (Ic), may be prepared as depicted in Scheme 5. This reaction sequence has been described in previous literature (WO 03/027069). First, alkylation of a cyanoacetamide such as, for example, where $R^7$ is substituted phenyl, with a bromoketone in the presence of a base, e.g. NaOMe in methanol, can yield the corresponding diketone intermediate. A mixture of the diketone and a primary amine, $R^4NH_2$, can be heated under acidic conditions to afford the 2-aminopyrrole product of formula (Ic).

Scheme 5. Preparation of compounds of formula (Ic).

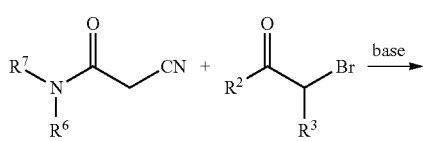

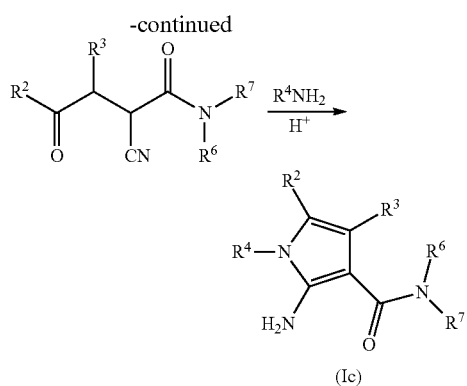

(Ic)

This 2-aminopyrrole (Ic) can be converted subsequently to other products, of which some sample reactions are depicted in Scheme 6.

Negishi, Suzuki and Sonogashira). For example, treatment with amines or alcohols under suitable conditions promoted by a palladium catalyst can yield aryl amines (Y=NR) or ethers (Y=O). Also the 2-halopyrrole may undergo carbonylation reactions to provide the corresponding pyrrole-2-carboxylic acid esters. These transformations represent a sampling of the many reactions that can be conceived for these 2-aminopyrroles.

Pyrrole compounds of formula (II) may be prepared as depicted in Scheme 7. First, an appropriate ketone can be alkylated with a halo-ketoester under basic conditions to give the corresponding 2,5-diketoester. This diketoester intermediate can react with an amine ($R^5NH_2$) under Paal-Knorr conditions to yield the corresponding pyrrole-2-carboxylic ester. Then this ester intermediate can be converted subsequently to the corresponding amide of formula (II) under conditions previously described.

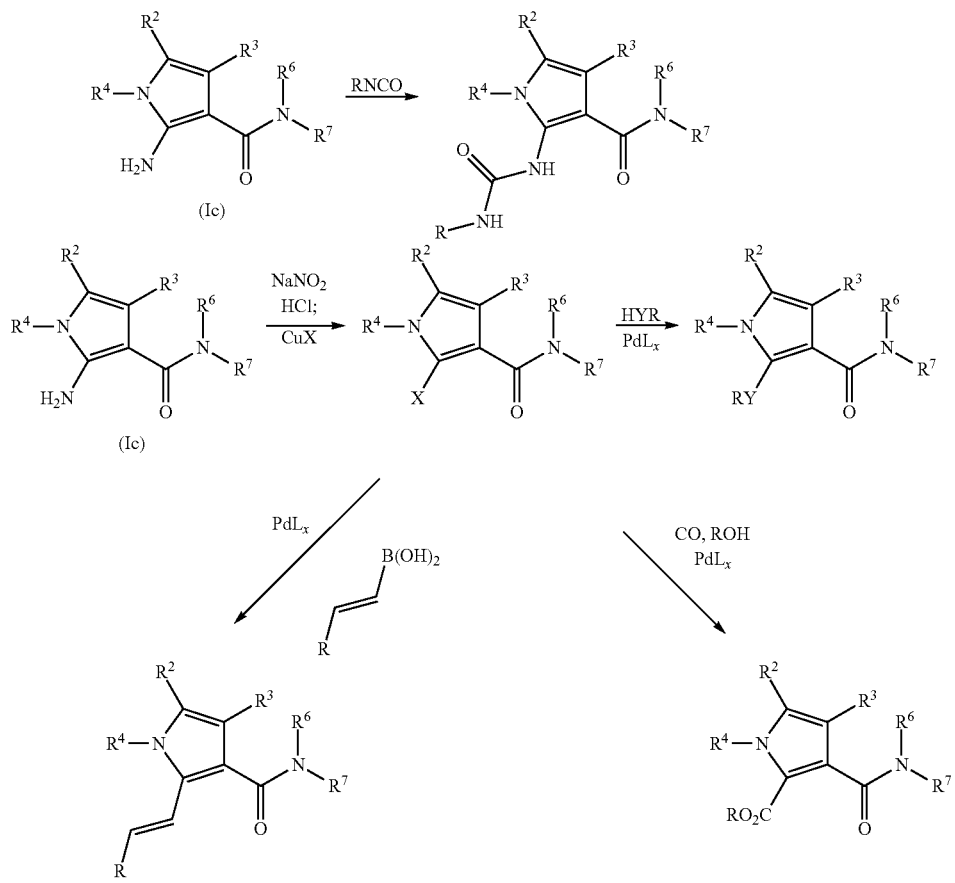

Scheme 6. Representative compounds derived from 2-aminopyrroles (Ic).

For example, treatment with an electrophile such as an acid chloride or isocyanate under basic conditions can yield the corresponding amide or urea, respectively. Alternatively, diazotization of the 2-aminopyrrole can provide the diazonium salt, which can be converted to its 2-halopyrrole or 2-cyanopyrrole under Sandmeyer conditions. Subsequently, the 2-halopyrrole can undergo other transition metal-catalyzed reactions such as aryl-aminations, aryl-amidations, Ullman ether syntheses and cross-coupling reactions (e.g. Heck, Scheme 7. Preparation of compounds of formula (II).

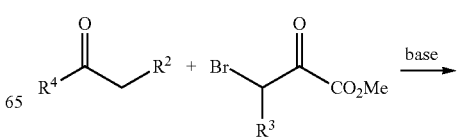

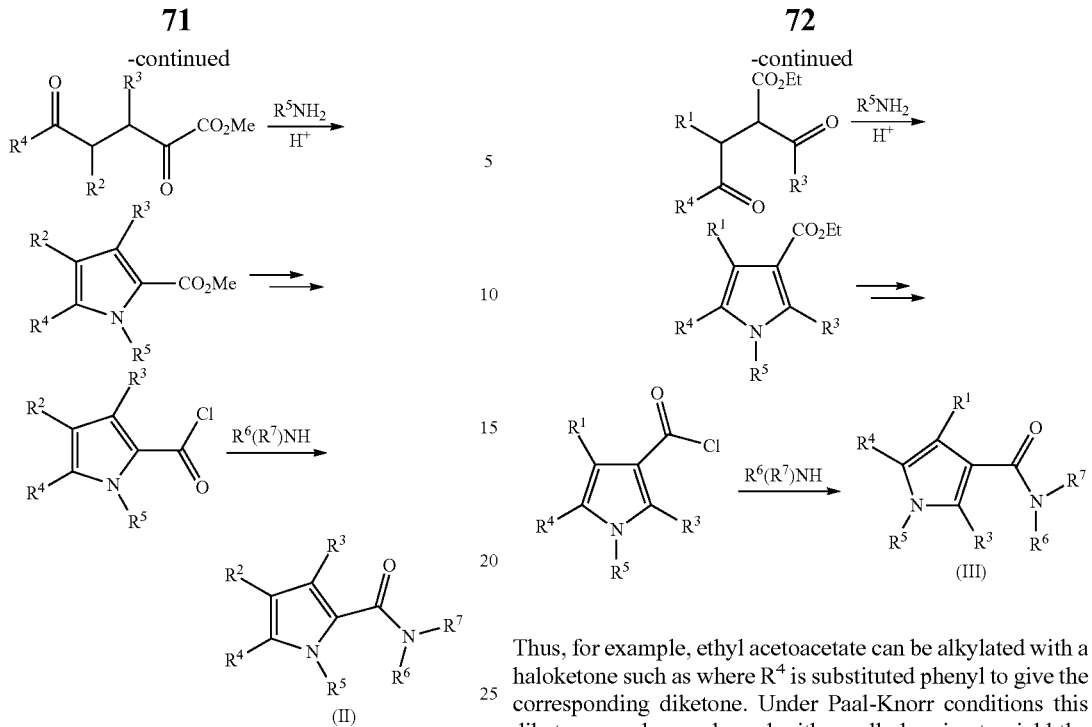

Thus, for example, a ketone wherein R⁴ is substituted phenyl can be alkylated with ethyl 3-bromo-2-ketopyruvate (R³=H) to yield the corresponding 2,5-diketoester. This diketoester intermediate can be condensed with an amine such as an alkyl amine to provide the corresponding pyrrole-2-carboxylic ester, in which R⁵ is alkyl. This ester intermediate can be converted to its acid chloride and then condensed with an amine, such as a heteroaryl amine, to afford the product of formula (IIb), equivalent to formula (II) wherein R⁴ is substituted phenyl and R⁷ is heteroaryl.

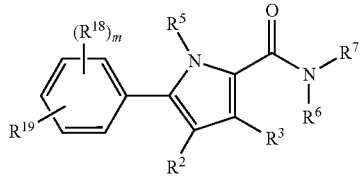

Compounds of formula (III) may be prepared as depicted in Scheme 8. Here, a haloketone can react with a β-ketoester under basic conditions to yield a 1,4-diketone. The diketone intermediate can be condensed as described previously with an amine, R⁵NH₂, to provide the corresponding pyrrole-3-carboxylic acid ester. Next this ester intermediate can be converted to its acid chloride and then condensed with an amine, R⁶(R⁷)NH, to afford the product of formula (III).

Scheme 8. General preparation of compounds of formula (III).

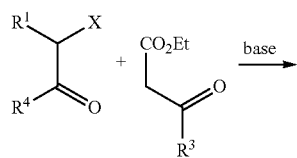

Thus, for example, ethyl acetoacetate can be alkylated with a haloketone such as where R⁴ is substituted phenyl to give the corresponding diketone. Under Paal-Knorr conditions this diketone can be condensed with an alkyl amine to yield the appropriate pyrrole-3-carboxylic acid ester, which can be converted to its acid chloride and then condensed with an amine, such as heteroaryl amine, to afford the product of formula (IIIb), equivalent to formula (III) wherein R⁴ is substituted phenyl and R⁷ is heteroaryl.

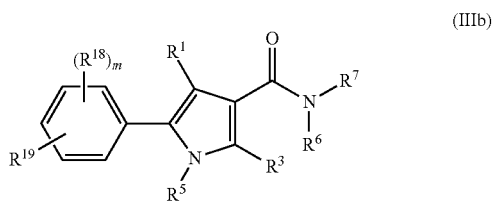

Other compounds of formula (III), such as where R³=H, may be prepared as depicted in Scheme 9. Here a haloketone can react with a cyanoacetate ester under basic conditions to yield the corresponding γ-ketoester. The ketoester intermediate can then be reductively cyclized under conditions such as with Raney-Ni and formic acid to provide the corresponding pyrroline-3-carboxylic acid ester. This ester intermediate can be oxidized under conditions such as via transfer hydrogenation with 10% Pd/C to give the corresponding pyrrole, which can be alkylated with a suitable electrophile, R⁵X. The resulting pyrrole-3-carboxylic acid ester can be converted to an amide of formula (IIIc) as previously described. For example, methyl cyanoacetate can be alkylated with a haloketone, e.g. R⁴ is substituted heteroaryl, to give the corresponding 2-cyano-4-ketoester. This ester intermediate can be converted to its pyrrole-3-carboxylic acid methyl ester as described previously and then alkylated by sequential treatment with a base, e.g. sodium hydride, and then a suitable electrophile, e.g. alkyl bromide. The resulting ester can be converted to its acid chloride and then treated with an amine, such as a substituted aniline, to yield the corresponding product of formula (IIIc), equivalent to formula (III) wherein R⁴ is substituted heteroaryl and R⁷ is substituted phenyl.

Scheme 9. Synthesis of other pyrrole compounds of formula (IIIc).

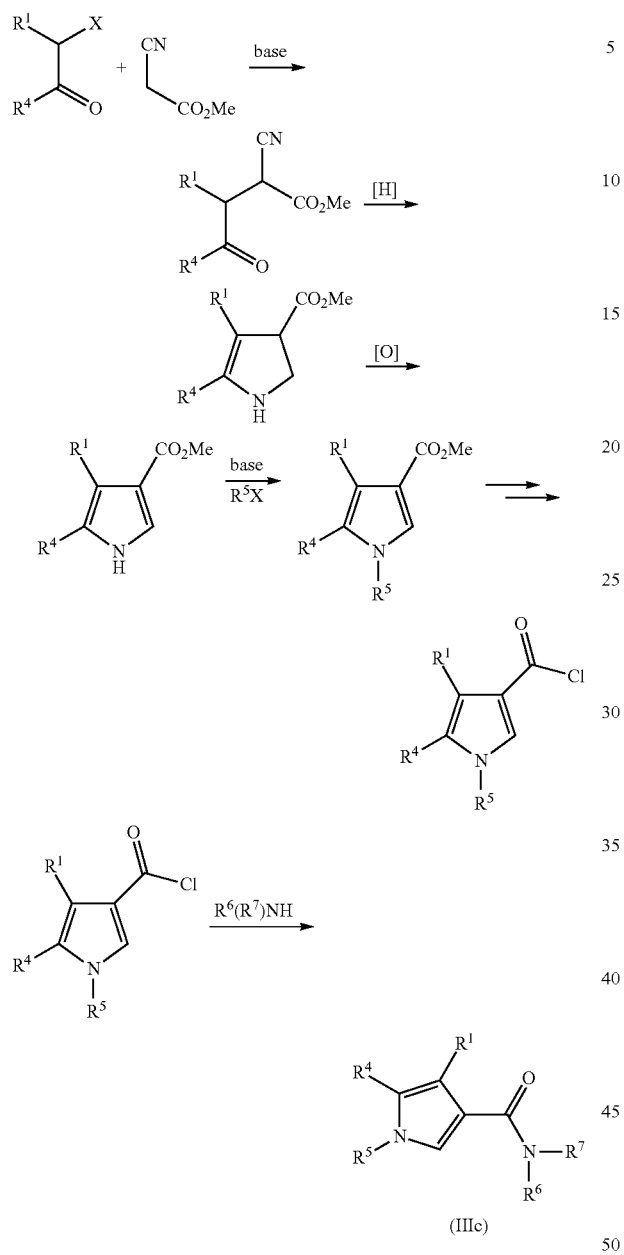

Alternatively these analogues (IIIc) may be prepared as depicted in Scheme 10. Here, a pyrrole-3-carboxylic acid ester can be brominated under typical conditions, such as with NBS, to afford the corresponding 5-bromopyrrole intermediate. Subsequent treatment with base followed by a suitable electrophile ($R^5X$) can then yield the N-substituted pyrrole intermediate. Next, a cross-coupling reaction of an appropriate boronic acid and this intermediate under typical Suzuki conditions can provide the corresponding pyrrole intermediate, analogous to that shown in Scheme 9. Likewise, the resulting pyrrole-3-carboxylic acid ester can be converted to amides of formula (IIIc) as previously described. In addition the list of suitable boronic acids is quite extensive and can consist of examples, where $R^4$ can be alkyl, alkenyl, aryl, heteroaryl and several others.

Scheme 10. Alternate preparation of pyrrole compounds (IIIc).

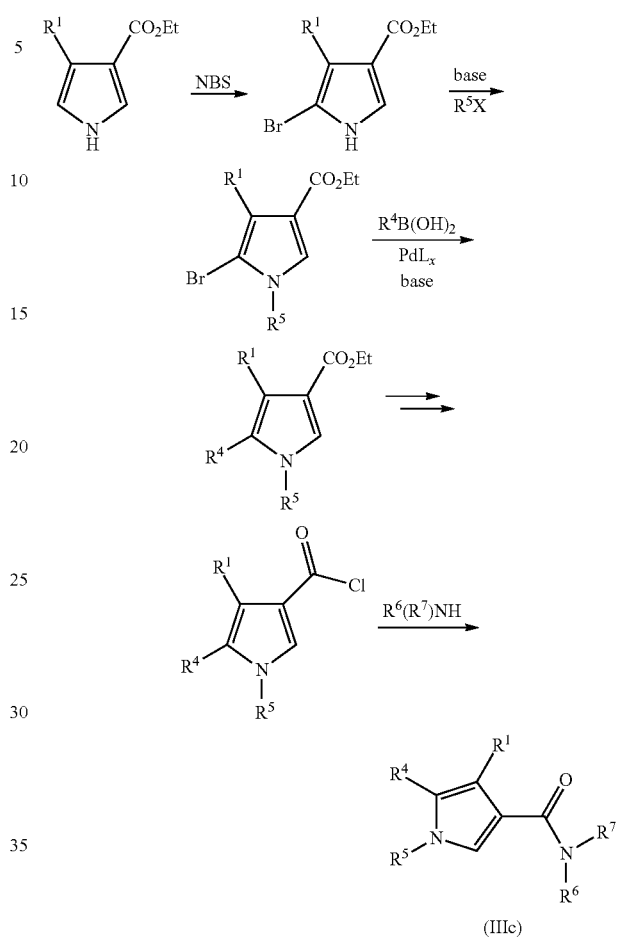

Compounds of formula (III) in which $R^3$ is $OR^9$, equivalent to 2-alkoxypyrroles (IIId), may be prepared as depicted in Scheme 11. Here, a malonate diester can be alkylated with a suitable bromoketone under basic conditions, e.g. NaH in THF, to yield a ketodiester, which can be condensed with an amine ($R^5NH_2$) under typical conditions to give the corresponding pyrrolinone-3-carboxylic acid ester. This pyrrolinone can be alkylated with a suitable electrophile under basic conditions and the resulting ester then can be converted to its amide of formula (IIId) under conditions previously described.

Scheme 11. Synthesis of pyrrole compounds of formula (IIId).

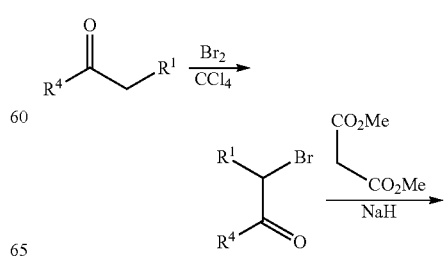

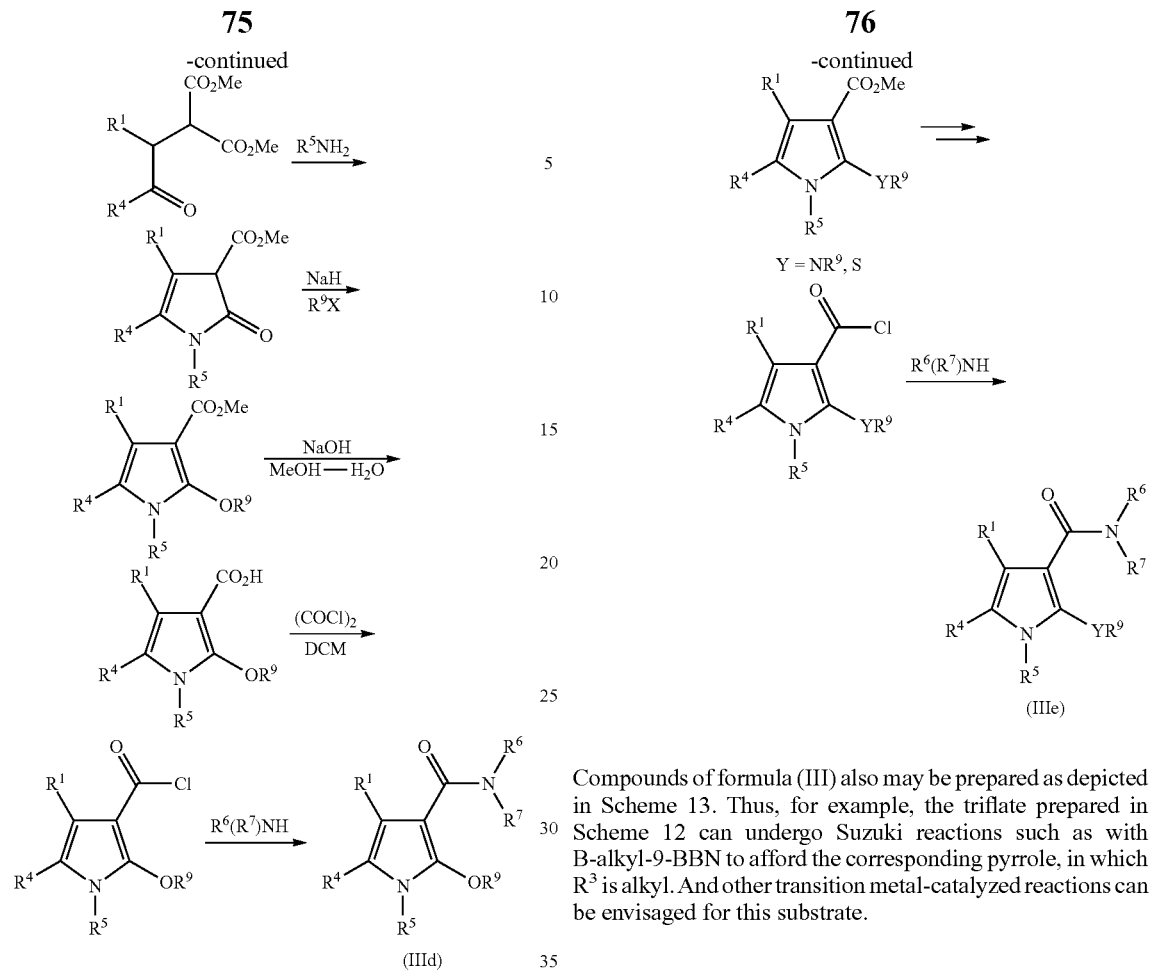

In addition, compounds of formula (III) in which $R^3$ is $YR^9$ may be prepared as depicted in Scheme 12. Here, the pyrrolinone-3-carboxylic acid ester, described previously in Scheme 11, can be converted to an activated sulfonate such as by sequential treatment with a suitable base, e.g. NaH in THF, and then trifluoromethane-sulfonic anhydride. This pyrrole intermediate can then undergo transition metal-catalyzed reactions such as couplings with amines or thiols under appropriate conditions to yield the respective aryl amines and sulfides. Likewise, these intermediates can be converted to amides of formula (IIIe), equivalent to formula (III) wherein $R^3$ is an amine ($Y=NR^9$) or a sulfide ($Y=S$).

Compounds of formula (III) also may be prepared as depicted in Scheme 13. Thus, for example, the triflate prepared in Scheme 12 can undergo Suzuki reactions such as with B-alkyl-9-BBN to afford the corresponding pyrrole, in which $R^3$ is alkyl. And other transition metal-catalyzed reactions can be envisaged for this substrate.

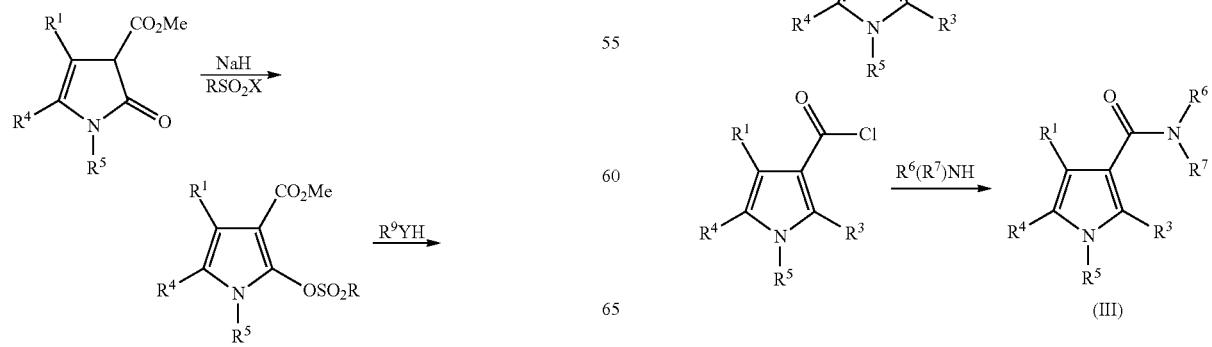

Similarly, compounds of formula (IV) may be prepared as depicted in Scheme 14. Here, a ketone can be alkylated with a halo-ketoester, e.g. ethyl bromopyruvate ($R^1$=H), under basic conditions to yield the corresponding 2,5-diketoester. This diketoester intermediate can be condensed as described previously with an amine, $R^{32}NH_2$, to provide the corresponding pyrrole-2-carboxylic ester. Next, this ester intermediate can be converted to its acid chloride and then condensed with an amine to afford the product of formula (IV).

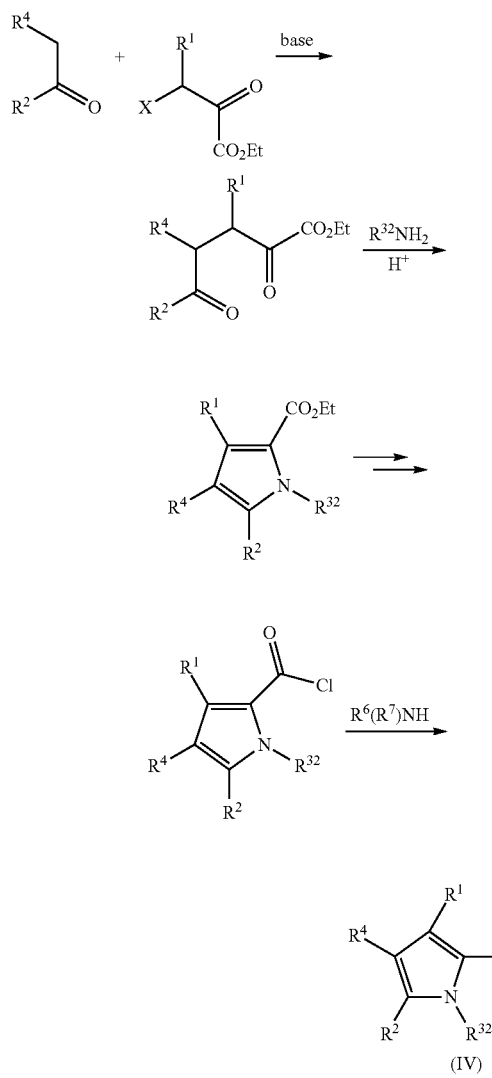

Also compounds of formula (IV) may be prepared as depicted in Scheme 15. Here, a pyrrole-2-carboxylic acid ester can undergo bromination under typical conditions such as with bromine in carbon tetrachloride to yield the corresponding 4-bromopyrrole ester. Next, this intermediate can undergo Suzuki cross-coupling reactions with boronic acids to provide the corresponding product esters, which can be converted to the final product amides as previously described. And other transition metal-catalyzed reactions can be envisaged for this substrate, such as Heck, Stifle, aryl amination and amidation.

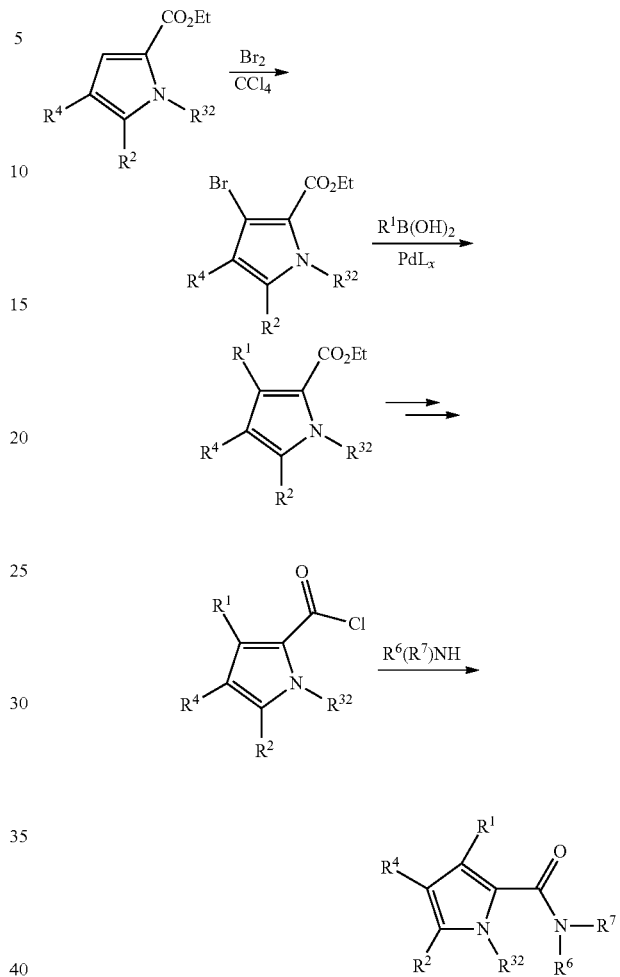

Schemes 1-15 depict the preparation of various pyrrole amide isomers (I-IV), many of which can be generated from commercially available amines, $R^6R^7NH$. In addition one skilled in the art of chemical synthesis should be familiar with numerous procedures reported for preparing amines in the literature. The following schemes focus on several reactions used for the synthesis of aryl and heteroaryl amines. In particular, the reaction schemes exemplify the preparation of amines bearing the following functional groups: ketone, sulfone, sulfonamide and ether. Multiple other modifications and syntheses can be envisaged for substituted aryl or heteroaryl amines. In general aliphatic amines are readily available from commercial sources. Also the preparation of aliphatic amines has been thoroughly documented in the literature and, thus, will not be elaborated herein.

As shown in Scheme 16, aminoaryl-ketones (V) can be prepared from acetanilides under Friedel-Crafts conditions [see J. Med. Chem. 1983, 26, 96-100]. Thus, acetanilides can be acylated, for example, with aryl chlorides to yield acetamido-benzophenones in which $R^{14}$ is substituted phenyl. Deprotection of the acetamides under typical conditions can provide the corresponding amino-benzophenones (V), which can be incorporated into amides of formulae (I-IV).

Scheme 16. Preparation of aminoaryl ketones (V).

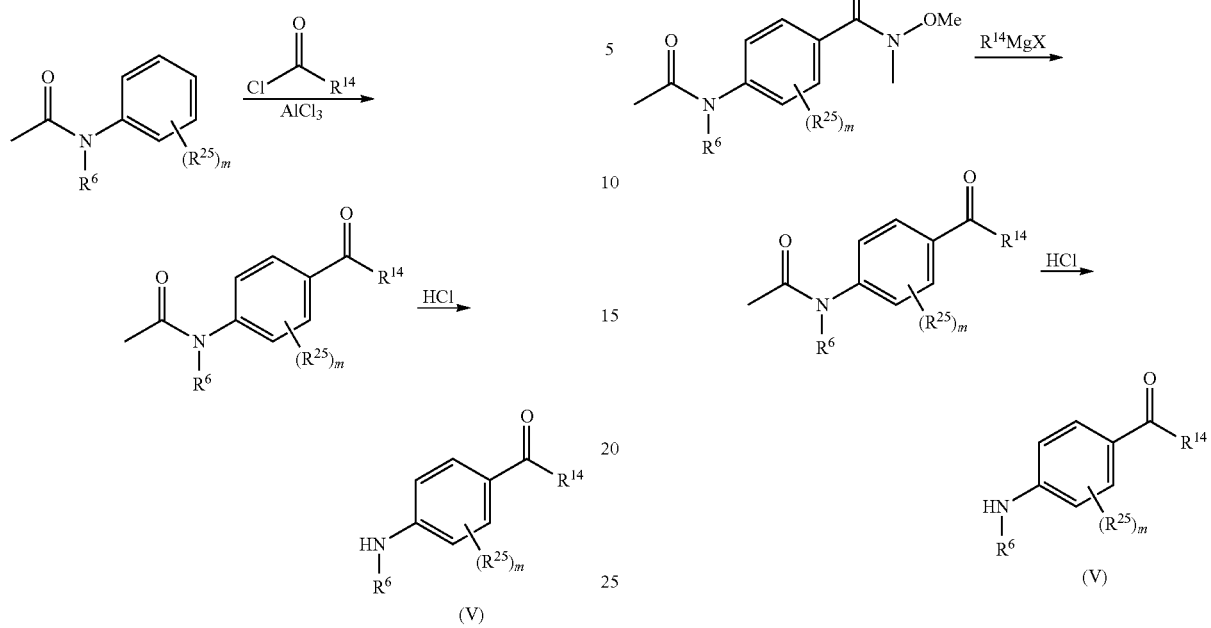

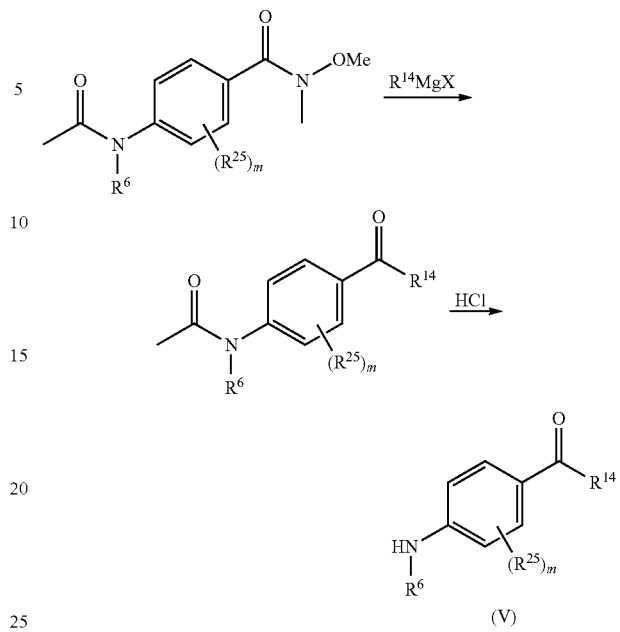

Aminoaryl ketones (V) can also be prepared via organometallic intermediates as depicted in Scheme 17. Thus, for example, an aryl-lithium species can be generated from a bromo-acetanilide and then added to an acid chloride to yield the corresponding ketone. Subsequent deprotection under typical conditions can then provide the desired aminoaryl ketone (V). Alternatively, a suitable Weinreb amide can be treated with a Grignard reagent to afford the corresponding ketone, which can be deprotected similarly. These reaction sequences also can be applied to appropriate starting materials for preparation of the ortho and meta isomers.

Aminoaryl sulfones may be prepared from appropriately substituted fluoro-nitrobenzenes and sulfinic acid metal salts as depicted in Scheme 18. Thus, a 4-fluoro-nitrobenzene species can react, for example, with sodium methanesulfinate to afford the corresponding 4-methanesulfonyl-nitrobenzene. Reduction of the nitro intermediate under typical conditions such as tin chloride then provide the desired 4-methanesulfonyl-aniline (VI), which can be incorporated into amides of formulae (I-IV). Similar chemistries can be pursued for isomeric species as well as heteroaryl analogues such as that represented by the pyridine species (VII).

Scheme 17. Alternative synthesis of aminoaryl ketones (V).

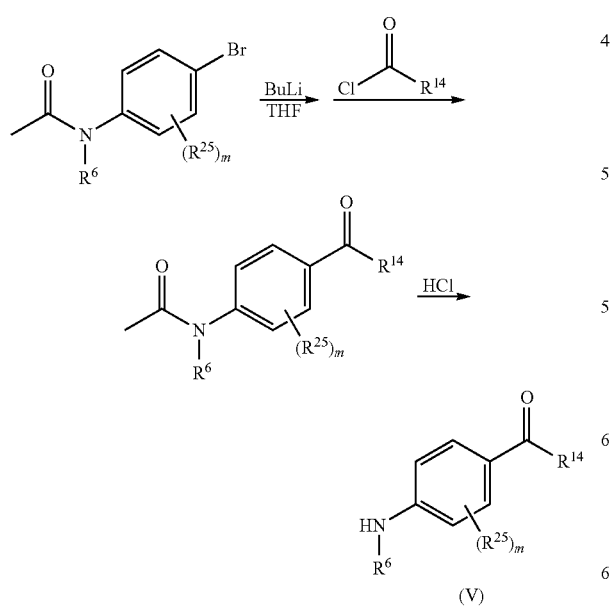

Scheme 18. Preparation of aminoary sulfones (VI) and pyridine analogues (VII).

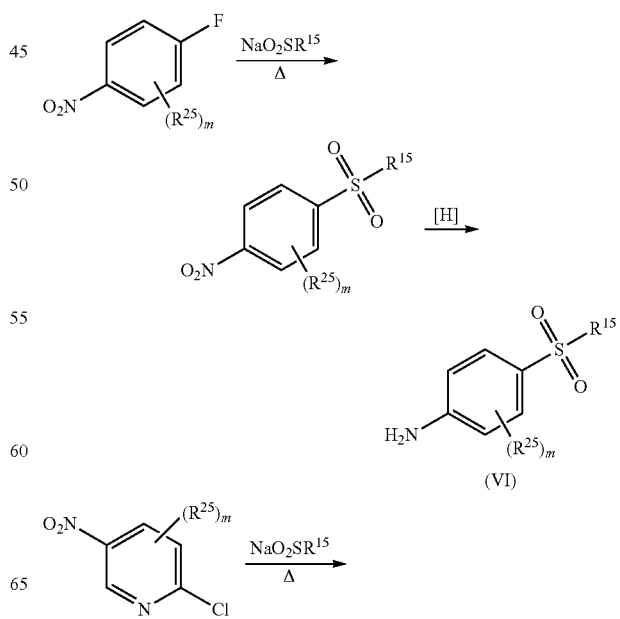

-continued

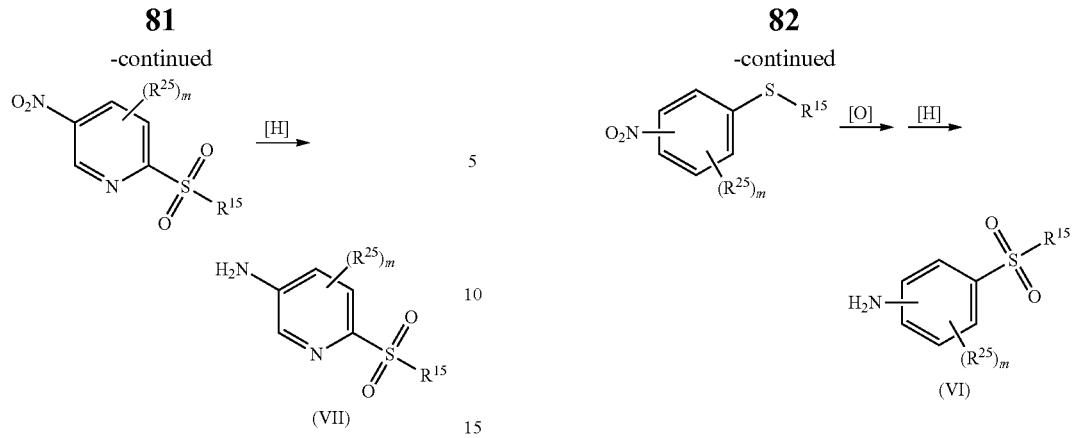

(VII)

(VI)

Similarly, aminoaryl sulfones (VI) may be prepared as depicted in Scheme 19. Here, thiols or thiolates can react with activated aryl halides or heteroaryl halides to give the corresponding sulfides, which can be oxidized under literature conditions such as with mCPBA to yield sulfone intermediates. Subsequent reduction of the nitro moiety under typical conditions, e.g. tin chloride, can provide the respective aryl or heteroaryl amine intermediate, which can be incorporated into amides of formulae (I-IV). Thus, for example, alkyl or aryl thiolates can undergo the reaction sequence with appropriately substituted fluoro-nitrobenzenes as described to yield the corresponding sulfones (VI), where $R^{15}$ is alkyl or aryl, respectively. Similar chemistries can be pursued for other aryl or heteroaryl isomers, such as those derived from an ortho-fluoro species.

Sulfonamides (VIII) may be prepared as depicted in Scheme 21. Here, various nitro-anilines can be diazotized under typical conditions and then converted directly to its corresponding sulfonyl chloride, for example, with sulfur dioxide and cuprous chloride under acidic conditions [U.S. Pat. No. 4,456,469; UK Pat. Applic. GB 2,246,352 A; *J. Med. Chem.* 2003, 46, 1811-1823]. Subsequent treatment of the isolated sulfonyl chloride with an amine, $(R^{14})_2NH$, followed by reduction under typical conditions can yield the corresponding aminoaryl sulfonamide (VIII), which can be incorporated into amides of formulae (I-IV). Similar chemistries can be pursued for heteroaryl analogues by starting with the appropriate nitro-heteroarylamines.

Scheme 19. Alternate synthesis of aminoaryl sulfones (VI).

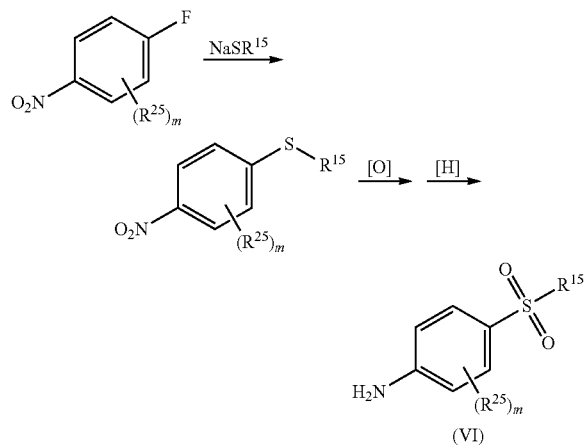

(VI)

Also, aryl and heteroaryl thiols may be substituted, e.g. alkylated with an alkyl bromide, and then converted to the corresponding sulfones (VI and VII) as shown in Scheme 20.

Scheme 20. Alternate synthesis of aminoaryl sulfones (VI).

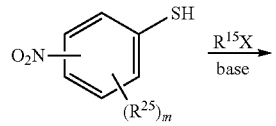

Scheme 21. Preparation of aminoaryl sulfonamides (VIII).

(VIII)

Alternatively, aminoaryl sulfonamides (VIII) may be synthesized as depicted in Scheme 22. Here, nitroaryl-sulfonyl chlorides can be prepared from nitroaryl-sulfides by reaction with a chlorinating agent, for example chlorine, in a suitable solvent such as chloroform in the presence of water [UK Pat. Applic. GB 2,246,352 A]. The sulfonyl chloride can then be converted its aminoaryl sulfonamide as described previously. Thus, for example, a nitroaryl halide can react with sodium benzylthiolate to afford the corresponding sulfide where $R^{15}$ is benzyl. Next, this sulfide can be converted to its sulfonyl chloride, condensed with an amine and then reduced to yield the corresponding sulfonamide (VIII), which can be incorporated into amides of formulae (I-IV).

Scheme 22. Alternate synthesis of aminoaryl sulfonamides (VIII).

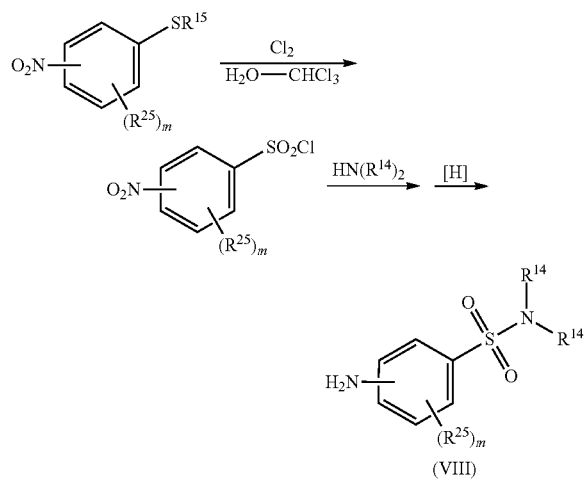

In addition, acetanilides can undergo chlorosulfonation under typical conditions, such as with chlorosulfonic acid [see, for example, *J. Med. Chem.* 2003, 46, 2187-2196], to yield chlorosulfonyl-acetanilides as shown in Scheme 23. Subsequently, the intermediate can be converted directly to the corresponding sulfonamides upon treatment with an amine, $HN(R^{14})_2$. The aminoaryl sulfonamide product (VIII) can then be obtained upon deprotection of the acetamide under typical conditions.

Scheme 23. Alternate synthesis of aminoaryl sulfonamides (VIII).

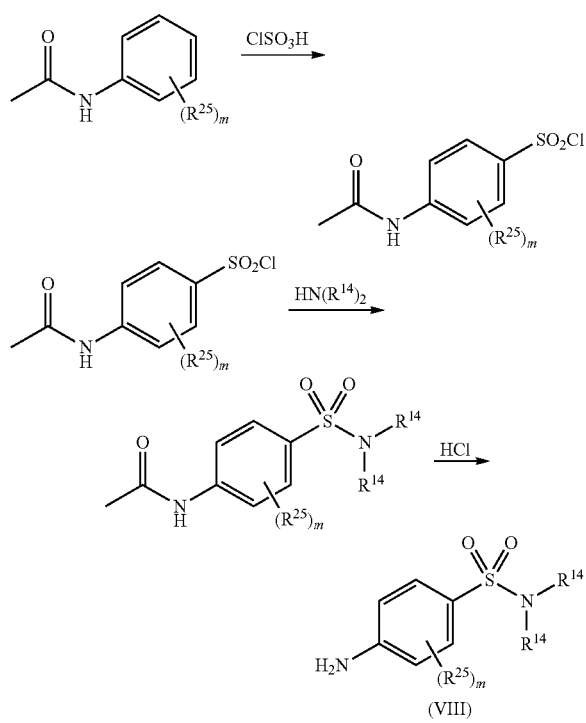

Aminoaryl ethers (IX) may be prepared by either of the methods depicted in Scheme 24. In the first, for example, an alkoxide can react with an activated nitroaryl species such as a 4-fluoro-nitrobenzene to yield the corresponding alkyl nitrophenyl ether. This intermediate ether can then be reduced, such as via catalytic hydrogenation, to give an aminoaryl ether product (IX). Similar chemistries can be envisaged wherein the alkoxide is replaced by a phenoxide or heterocyclic analogue. Also, the nitroaryl species can be replaced by a halo-nitroheteroaromatic analogue. In the second sequence, for example, a nitro-phenol species can be substituted, e.g. alkylated with an alkyl bromide, and then reduced as previously described to afford the corresponding aminoaryl ethers (IX). In addition, the nitro-phenol species can undergo substitution under Mitsunobu conditions with alcohols to yield similar alkyl nitrophenyl ethers, which can undergo reduction to give the corresponding ethers (IX). All of these aminoaryl ethers can subsequently be incorporated into amides of formulae (I-IV).

Scheme 24. Preparation of aminoaryl ethers (IX).

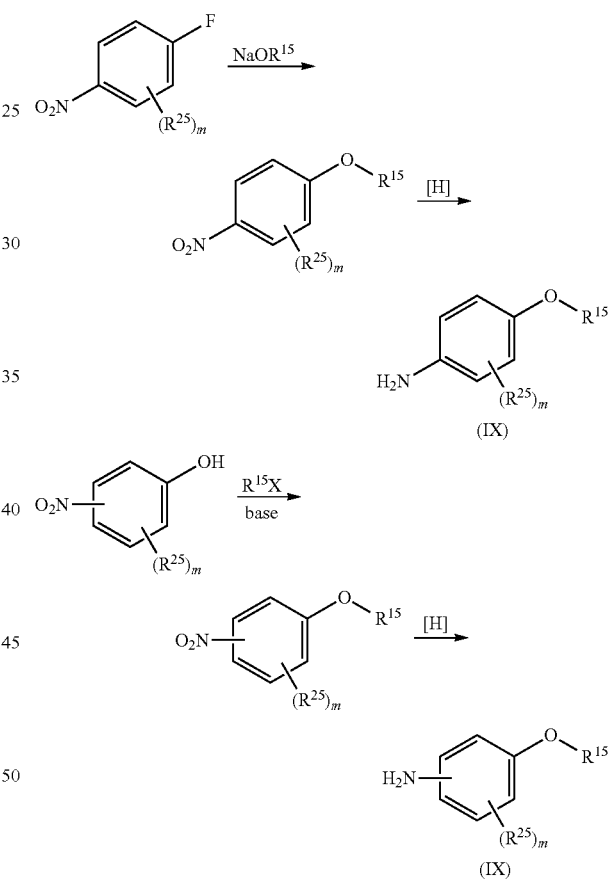

Alternatively, aminoaryl ethers (IX) wherein $R^{15}$ is aryl or heteroaryl may be prepared as depicted in Scheme 25. An acetamido-phenol can undergo copper-mediated reactions with aryl or heteroaryl boronic acids to yield the corresponding aryl ethers. These ether intermediates can then be deprotected under typical conditions to provide the desired diaryl ethers of formula (IX) wherein $R^{15}$ is aryl or heteroaryl. Thus, for example, reaction with a substituted phenyl-boronic acid can afford the corresponding diphenyl ether, which can be deprotected and then incorporated into amides of formulae (I-IV).

Scheme 25. Alternate synthesis of aminoaryl ethers (IX).

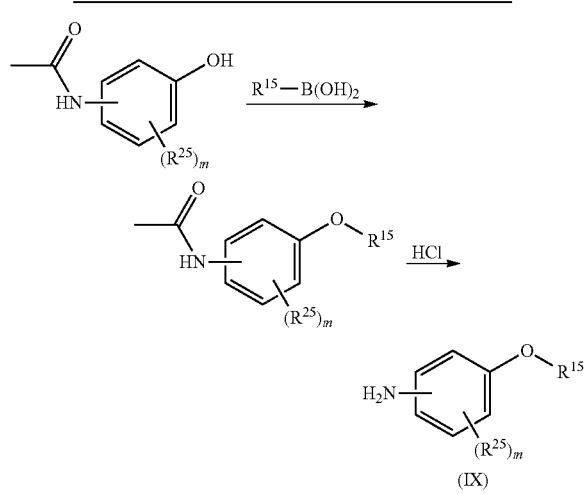

Compounds of formula (I) wherein $R^4$ is acyl or sulfonyl may be prepared as depicted in Scheme 26. Here, amides of formula (I) in which $R^4$ is benzyl can be converted to amides (I) in which $R^4$ is hydrogen under typical conditions such as via palladium-catalyzed hydrogenation. The resulting pyrroles can then undergo reactions with suitable electrophiles such as, for example, acid chlorides to yield the corresponding amides (Id), equivalent to formula (I) wherein $R^4$ is acyl. Likewise, the pyrrole intermediate can react with sulfonyl chlorides to afford various amides (i.e.), equivalent to formula (I) wherein $R^4$ is sulfonyl.

Scheme 26. Synthesis of compounds of formulae (Id) and (Ie).

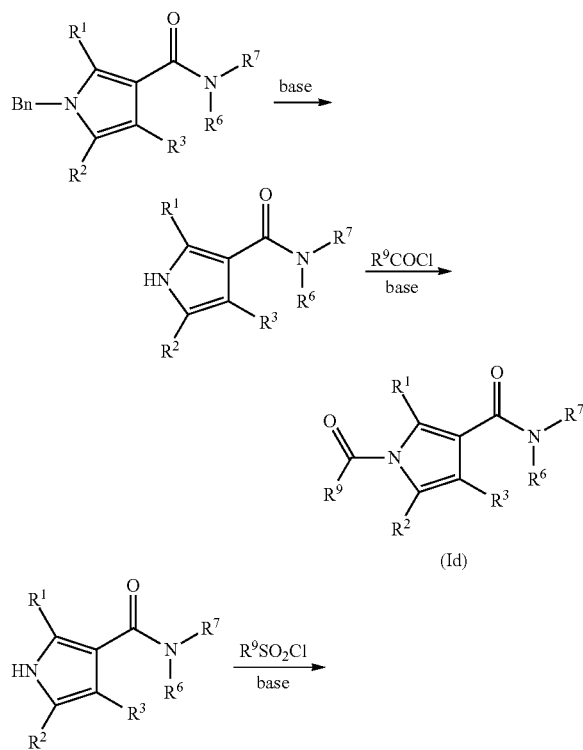

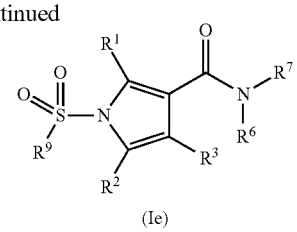

(Ie)

G. Examples

The foregoing examples are provided only to illustrate the present invention and are in no way intended to limit to the scope thereof. The skilled practitioner will understand that considerable variations in the practice of this invention are possible within the spirit and scope as claimed below.

Example 1

PREPARATION OF 1-(4-FLUORO-2-TRIFLUO-ROMETHYL-PHENYL)-2,5-DIMETHYL-1H-PYRROLE-3-CARBALDEHYDE

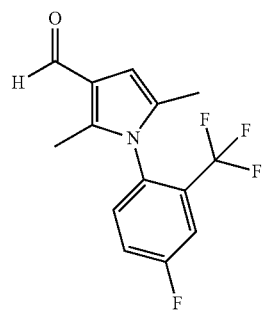 [SMILES: Cc1cc(C=O)c(C)n1-c1ccc(F)cc1C(F)(F)F]

A. A mixture of 4-fluoro-2-(trifluoromethyl)aniline (4.4 g, 24.6 mmol), 2,5-hexanedione (2.8 g, 24.5 mmol) and acetic acid (0.28 mL) was heated to 100° C. After 3 h the reaction mixture was cooled and partitioned between EtOAc and water. The organic layer was separated, dried (MgSO$_4$), and concentrated in vacuo. The residue was purified by flash chromatography (SiO$_2$), eluting with EtOAc/Hex (0:100 to 10:90) to afford 1-[4-fluoro-2-(trifluoromethyl)phenyl]-2,5-dimethyl-1H-pyrrole as a yellow oil (3.19 g, 50%); $^1$H NMR (CDCl$_3$): δ 7.52 (dd, J=8, 3 Hz, 1H), 7.35 (dt, J=3, 8 Hz, 1H), 7.25 (dd, J=5, 8 Hz, 1H), 5.90 (s, 2H), 1.91 (s, 6H); MS (ESI) m/z 258 [M+H]$^+$.

To anhyd DMF (10 mL) cooled under nitrogen to 0° C. was added phosphorous oxychloride (1.2 mL, 13.1 mmol). The resulting mixture was stirred at 0° C. for 30 min and then a solution of 1-[4-fluoro-2-(trifluoromethyl)phenyl]-2,5-dimethyl-1H-pyrrole (3.19 g, 12.4 mmol) in anhyd DMF (15 mL) was added portionwise. The reaction mixture was maintained at 0-3° C. for 10 min and then the reaction flask was heated on an oil bath at 95-100° C. After heating 1.5 h, the reaction mixture was cooled and poured onto 200 mL of ice cold 1 M NaOH. The resulting suspension was extracted twice with DCM. The combined extracts were dried (Na$_2$SO$_4$) and concentrated in vacuo. The residue was purified by flash chromatography (SiO$_2$), eluting with EtOAc/Hex (10:90 to 30:70) to afford the title compound as a light yellow solid (1.3 g, 37%);

¹H-NMR (CDCl₃): δ 9.90 (s, 1H), 7.58 (dd, J=8, 3 Hz, 1H), 7.43 (m, 1H), 7.29 (dd, J=5, 8 Hz, 1H), 6.39 (s, 1H), 2.20 (s, 3H), 1.91 (s, 3H); MS (ESI) m/z 286 [M+H]⁺.

PREPARATION OF 1-[4-FLUORO-2-(TRIFLUOROMETHYL)PHENYL]-2,5-DIMETHYL-1H-PYRROLE-3-CARBONYL CHLORIDE

B. To a solution of 1-[4-fluoro-2-(trifluoromethyl)phenyl]-2,5-dimethyl-1H-pyrrole-3-carbaldehyde (1.5 g, 5.3 mmol) in acetone (150 mL) was added a 0.3 M solution of KMnO₄ (150 mL). The reaction mixture was stirred 3 h at room temperature and then was charged with 10% H₂O₂ (5 mL). After 15 minutes the reaction mixture was filtered and the filtrate was concentrated in vacuo to remove acetone. The remaining aqueous suspension was acidified with acetic acid. The precipitates were recovered by filtration and dried under high vacuum to afford 1-(4-fluoro-2-(trifluoromethyl)phenyl]-2,5-dimethyl-1H-pyrrole-3-carboxylic acid (0.99 g, 62%) as a faintly yellow powder; ¹H NMR (CDCl₃): δ 7.56 (dd, J=8, 3 Hz, 1H), 7.41 (m, 1H), 7.27 (dd, J=5, 8 Hz, 1H), 6.42 (s, 1H), 2.21 (s, 3H), 1.90 (s, 3H); MS (ESI) m/z 302 [M+H]⁺.

To a suspension of 1-(4-fluoro-2-(trifluoromethyl)phenyl]-2,5-dimethyl-1H-pyrrole-3-carboxylic acid (0.65 g, 2.16 mmol) in anhyd toluene (5.0 mL) cooled to 0-3° C. were added thionyl chloride (0.25 mL) and DMF (20 µL). The reaction mixture was allowed to warm to room temperature where it remained for 3 h and then was concentrated in vacuo. The residue was evaporated twice from 5 mL of toluene to remove thionyl chloride and then was triturated in 3 mL of hexanes. The solids were removed by filtration and the filtrate was concentrated under reduced pressure and dried under high vacuum to afford the title compound (0.44 g, 64%) as a pale brown solid; ¹H NMR (CDCl₃): δ 7.59 (dd, J=8, 3 Hz, 1H), 7.44 (m, 1H), 7.27 (dd, J=5, 8 Hz, 1H), 6.51 (s, 1H), 2.17 (s, 3H), 1.89 (s, 3H); MS (ESI) m/z 320 [M+H]⁺.

PREPARATION OF 1-[4-FLUORO-2-(TRIFLUOROMETHYL)PHENYL]-2,5-DIMETHYL-1H-PYRROLE-3-CARBOXYLIC ACID [4-(SULFAMOYL)PHENYL]-AMIDE

C. Into an oven-dried 1 dram vial was added 2,5-dimethyl-1-[4-fluoro-2-(trifluoromethyl)phenyl]-1H-pyrrole-3-carboxylic acid chloride (106 mg, 332 µmol), sulfanilamide (62.0 mg, 360 µmol), anhyd THF (2.0 mL) and diisopropylethylamine (50 µL). The vial was sealed and heated at 80° C. overnight. The resulting residue was purified by flash chromatography (SiO₂), eluting with EtOAc/Hex (30:70 to 60:40) to afford the title compound as an off-white solid (99 mg, 66%); ¹H NMR (CDCl₃): δ 8.85 (s, 1H), 7.88 (d, J=7 Hz, 2H), 7.84 (d, J=7 Hz, 2H), 7.58 (dd, J=8, 3 Hz, 1H), 7.46 (m, 1H), 7.31 (dd, J=5, 8 Hz, 1H), 6.46 (s, 1H), 6.19 (s, 2H), 2.25 (s, 3H), 1.94 (s, 3H); MS (ESI) m/z 456 [M+H]⁺.

D. In a manner similar to that described in Examples 1A-1C, but replacing 4-fluoro-2-(trifluoromethyl)aniline with 2-(trifluoromethyl)aniline, the following compound was prepared:

2,5-Dimethyl-1-[2-(trifluoromethyl)phenyl]-1H-pyrrole-3-carboxylic acid (4-sulfamoyl-phenyl)-amide; ¹H NMR (DMSO-d₆): δ 9.5 (s, 1H), 7.77 (d, J=7 Hz, 2H), 7.68 (m, 3H), 7.57 (t, J=7 Hz, 1H), 7.51 (d, J=7 Hz, 2H), 7.26 (d, J=7 Hz, 1H), 6.98 (s, 2H), 6.42 (s, 1H), 3.08 (s, 3H), 1.90 (s, 3H); MS (ESI) m/z 438 [M+H]⁺.

E. In a manner similar to that described in Example 1C, but replacing sulfanilamide with the appropriate amine, the following compounds were prepared:

1-[4-Fluoro-2-(trifluoromethyl)phenyl]-2,5-dimethyl-1H-pyrrole-3-carboxylic acid [4-(benzoyl)phenyl]-amide; ¹H NMR (CDCl₃): δ 7.84 (d, J=8 Hz, 2H), 7.75-7.80 (m, 3H), 7.74 (d, J=8 Hz, 2H), 7.55-7.6 (m, 2H), 7.48 (t, J=7 Hz, 2H), 7.43 (dt, J=3, 8 Hz, 1H), 7.28 (dd, J=5, 8 Hz, 1H), 6.25 (s, 1H), 2.26 (s, 3H), 1.94 (s, 3H); MS (ESI) m/z 481 [M+H]⁺.

1-[4-Fluoro-2-(trifluoromethyl)phenyl]-2,5-dimethyl-1H-pyrrole-3-carboxylic acid [4-(methanesulfonyl)phenyl]-amide; ¹H NMR (CDCl₃): δ 7.90 (d, J=7 Hz, 2H), 7.83 (d, J=7 Hz, 2H), 7.72 (s, 1H), 7.58 (dd, J=8, 3 Hz, 1H), 7.44 (dt, J=8, 3 Hz, 1H), 7.29 (dd, J=5, 8 Hz, 1H), 6.23 (s, 1H), 3.06 (s, 3H), 2.26 (s, 3H), 1.95 (s, 3H); MS (ESI) m/z 455 [M+H]⁺.

F. In a manner similar to that described in Example I D, but replacing sulfanilamide with the appropriate amines, the following compounds were prepared:

1-[4-({2,5-Dimethyl-1-[2-(trifluoromethyl)phenyl]-1H-pyrrole-3-carbonyl}-amino)-phenyl]-3-methyl-1H-pyrazole-4-carboxylic acid ethyl ester; ¹H NMR (CDCl₃): δ 8.04 (s, 1H), 7.87 (d, J=8 Hz, 1H), 7.72-7.77 (m, 3H), 7.64-7.68 (m, 2H), 7.38 (d, J=7 Hz, 2H), 7.28 (d, J=8 Hz, 1H), 6.23 (s, 1H), 4.33 (q, J=6 Hz, 2H), 2.56 (s, 3H), 2.27 (s, 3H), 1.95 (s, 3H), 1.38 (t, J=6 Hz); MS (ESI) m/z 511 [M+H]⁺.

2,5-Dimethyl-1-[2-(trifluoromethyl)phenyl]-1H-pyrrole-3-carboxylic acid ([4-benzenesulfonyl)phenyl]-amide; ¹H NMR (CDCl₃): δ 7.89-7.95 (m, 4H), 7.87 (d, J=8 Hz, 1H), 7.71-7.76 (m, 3H), 7.66 (t, J=7 Hz, 2H), 7.47-7.57 (m, 3H), 7.26 (d, J=8 Hz, 1H), 6.19 (s, 1H), 2.23 (s, 3H), 1.93 (s, 3H); MS (ESI) m/z 499 [M+H]⁺.

2,5-Dimethyl-1-[2-(trifluoromethyl)phenyl]-1H-pyrrole-3-carboxylic acid (9-oxo-9H-fluoren-3-yl)-amide; ¹H NMR (CDCl₃): δ 8.13 (s, 1H), 7.81 (d, J=7 Hz, 1H), 7.55-7.68 (m, 5H), 7.49 (d, J=7 Hz, 1H), 7.40 (t, J=7 Hz, 1H), 7.19-7.24 (m, 2H), 7.14 (d, J=8 Hz, 1H), 6.16 (s, 1H), 2.21 (s, 3H), 1.88 (s, 3H); MS (ESI) m/z 461 [M+H]⁺.

2,5-Dimethyl-1-[2-(trifluoromethyl)phenyl]-1H-pyrrole-3-carboxylic acid [3-(sulfamoyl)phenyl]-amide; ¹H NMR (CD₃OD): δ 8.21 (s, 1H), 7.85 (d, J=8 Hz, 1H), 7.73 (m, 2H), 7.66 (t, J=8 Hz, 1H), 7.51 (d, J=8 Hz, 1H), 7.39 (t, J=8 Hz, 1H), 7.29 (d, J=8 Hz, 1H), 6.43 (s, 1H), 2.10 (s, 3H), 1.84 (s, 3H); MS (ESI) m/z 438 [M+H]⁺.

3-({2,5-Dimethyl-1-[2-(trifluoromethyl)phenyl]-1H-pyrrole-3-carbonyl}-amino)-benzoic acid ethyl ester; ¹H NMR (CDCl₃): δ 8.04-8.08 (m, 2H), 7.87 (d, J=8 Hz, 1H), 7.76 (d, J=8 Hz, 1H), 7.72 (t, J=8 Hz, 1H), 7.65 (t, J=8 Hz, 1H), 7.60 (s, 1H), 7.42 (t, J=8 Hz, 1H), 7.27 (d, J=8 Hz, 1H), 6.22 (s, 1H), 4.38 (q, J=7 Hz, 2H), 2.26 (s, 3H), 1.94 (s, 3H), 1.40 (t, J=7 Hz, 3H); MS (ESI) m/z 431 [M+H]⁺.

2,5-Dimethyl-1-[2-(trifluoromethyl)phenyl]-1H-pyrrole-3-carboxylic acid (1-oxo-indan-5-yl)-amide; ¹H NMR (CDCl₃): δ 8.12 (s, 1H), 7.88 (d, J=8 Hz, 1H), 7.64-7.76 (m, 4H), 7.26-7.31 (m, 2H), 6.22 (s, 1H), 3.13 (m, 2H), 2.69 (m, 2H), 2.27 (s, 3H), 1.95 (s, 3H); MS (ESI) m/z 413 [M+H]⁺.

1-[4-({2,5-Dimethyl-1-[2-(trifluoromethyl)phenyl]-1H-pyrrole-3-carbonyl}-amino)-phenyl]-3,5-dimethyl-1H-pyrazole-4-carboxylic acid ethyl ester; ¹H NMR (CDCl₃): δ 7.87 (d, J=8 Hz, 1H), 7.71-7.75 (m, 3H), 7.64-7.68 (m, 2H), 7.36 (d, J=8 Hz, 2H), 7.28 (d, J=8 Hz, 1H), 6.23 (s, 1H), 4.33 (q, J=7 Hz, 2H), 2.51 (s, 6H), 2.27 (s, 3H), 1.94 (s, 3H), 1.38 (t, J=7 Hz, 1H); MS (ESI) m/z 525 [M+H]⁺.

1-[4-Fluoro-2-(trifluoromethyl)phenyl]-2,5-dimethyl-1H-pyrrole-3-carboxylic acid [4-(benzoyl)phenyl]-amide; ¹H NMR (CDCl₃): δ 7.71-7.88 (m, 9H), 7.65 (t, J=8 Hz, 1H), 7.58 (t, J=7 Hz, 1H), 7.82 (t, J=7 Hz, 2H), 7.27 (d, J=7 Hz, 1H), 6.25 (s, 1H), 2.27 (s, 3H), 1.93 (s, 3H); MS (ESI) m/z 463 [M+H]$^+$.

2,5-Dimethyl-1-[2-(trifluoromethyl)phenyl]-1H-pyrrole-3-carboxylic acid [4-(methanesulfonyl)phenyl]-amide; $^1$H NMR (CDCl$_3$): δ 7.90 (t, J=9 Hz, 2H), 7.88 (d, J=8 Hz, 1H), 7.82 (d, J=9 Hz, 2H), 7.74 (t, J=8 Hz, 1H), 7.72 (s, 1H), 7.67 (t, J=8 Hz, 1H), 7.27 (d, J=8 Hz, 1H), 6.23 (s, 1H), 3.05 (s, 3H), 2.26 (s, 3H), 1.94 (s, 3H); MS (ESI) m/z 437 [M+H]$^+$.

2,5-Dimethyl-1-[2-(trifluoromethyl)phenyl]-1H-pyrrole-3-carboxylic acid [4-(trifluoromethanesulfonyl)phenyl]-amide; $^1$H NMR (CDCl$_3$): δ 7.98 (d, J=9 Hz, 2H), 7.93 (d, J=9 Hz, 2H), 7.88 (d, J=8 Hz, 1H), 7.83 (s, 1H), 7.75 (t, J=8 Hz, 1H), 7.68 (t, J=8 Hz, 1H), 7.28 (d, J=8 Hz, 1H), 6.23 (s, 1H), 2.26 (s, 3H), 1.94 (s, 3H); MS (ESI) m/z 491 [M+H]$^+$.

2,5-Dimethyl-1-[2-(trifluoromethyl)phenyl]-1H-pyrrole-3-carboxylic acid [4-(butyryl)phenyl]-amide; $^1$H NMR (CDCl$_3$): δ 8.06 (d, J=7 Hz, 2H), 7.96 (d, J=8 Hz, 1H), 7.75-7.85 (m, 4H), 7.36 (d, J=1Hz, 1H), 6.31 (s, 1H), 3.01 (t, J=7 Hz, 2H), 2.36 (s, 3H), 2.03 (s, 3H), 1.86 (sextet, J=7 Hz, 2H), 1.10 (t, J=3H); MS (ESI) m/z 429 [M+H]$^+$.

2,5-Dimethyl-1-[2-(trifluoromethyl)phenyl]-1H-pyrrole-3-carboxylic acid (5-oxo-5,6,7,8-tetrahydro-naphthalen-2-yl)-amide; $^1$H NMR (CDCl$_3$): δ 7.95 (d, J=8 Hz, 1H), 7.78-7.82 (m, 2H), 7.67 (t, J=8 Hz, 1H), 7.59 (t, J=8 Hz, 1H), 7.53 (s, 1H), 7.29 (s, 1H), 7.20 (d, J=8 Hz, 1H), 6.13 (s, 1H), 2.90 (m, 2H), 2.56 (m, 2H), 2.19 (s, 3H), 2.06 (m, 2H), 1.87 (s, 3H); MS (ESI) m/z 427 [M+H]$^+$.

4-({2,5-Dimethyl-1-[2-(trifluoromethyl)phenyl]-1H-pyrrole-3-carbonyl}-amino)-2-methoxy-benzoic acid methyl ester; $^1$H NMR (CDCl$_3$): δ 7.74-7.81 (m, 3H), 7.66 (t, J=8 Hz, 1H), 7.59 (t, J=8 Hz, 1H), 7.55 (s, 1H), 7.20 (d, J=8 Hz, 1H), 6.80 (d, J=9 Hz, 1H), 6.14 (s, 1H), 3.89 (s, 3H), 3.80 (s, 3H), 2.20 (s, 3H), 1.87 (s, 3H); MS (ESI) m/z 447 [M+H]$^+$.

2,5-Dimethyl-1-[2-(trifluoromethyl)phenyl]-1H-pyrrole-3-carboxylic acid (2-methyl-4-oxo-4H-chromen-7-yl)-amide; $^1$H NMR (CDCl$_3$): δ 8.20 (s, 1H), 8.04 (d, J=9 Hz, 1H), 7.81 (d, J=8 Hz, 1H), 7.76 (d, J=8 Hz, 1H), 7.67 (t, J=8 Hz, 1H), 7.59 (t, J=8 Hz, 1H), 7.20 (d, J=8 Hz, 1H), 7.16 (d, J=9 Hz, 1H), 6.18 (s, 1H), 6.11 (s, 1H), 2.31 (s, 3H), 2.20 (s, 3H), 1.87 (s, 3H); MS (ESI) m/z 441 [M+H]$^+$.

2,5-Dimethyl-1-[2-(trifluoromethyl)phenyl]-1H-pyrrole-3-carboxylic acid [(4-phenylsulfanyl)phenyl]-amide; $^1$H NMR (DMSO-d$_6$): δ 9.6 (s, 1H), 8.01 (d, J=7 Hz, 1H), 7.92 (t, J=8 Hz, 1H), 7.80-7.85 (m, 3H), 7.50 (t, J=8 Hz, 1H), 7.40 (d, J=7 Hz, 2H), 7.33 (t, J=7 Hz, 2H), 7.19-7.24 (m, 3H), 6.63 (s, 1H), 2.14 (s, 3H), 1.89 (s, 3H); MS (ESI) m/z 467 [M+H]$^+$.

2,5-Dimethyl-1-[2-(trifluoromethyl)phenyl]-1H-pyrrole-3-carboxylic acid [(4-dimethylsulfamoyl)phenyl]-amide; $^1$H NMR (CDCl$_3$): δ 7.87 (d, J=8 Hz, 1H), 7.80 (d, J=7 Hz, 2H), 7.7-7.8 (m, 4H), 7.66 (t, J=8 Hz, 1H), 7.27 (d, J=8 Hz, 1H), 6.24 (s, 1H), 2.70 (s, 6H), 2.26 (s, 3H), 1.94 (s, 3H); MS (ESI) m/z 466 [M+H]$^+$.

2,5-Dimethyl-1-[2-(trifluoromethyl)phenyl]-1H-pyrrole-3-carboxylic acid [4-(pyridine-4-carbonyl)phenyl]-amide; $^1$H NMR (CDCl$_3$): δ 8.75 (d, J=6 Hz, 2H), 7.81 (d, J=8 Hz, 1H), 7.78 (d, J=9 Hz, 2H), 7.71 (d, J=9 Hz, 2H), 7.61-7.68 (m, 4H), 7.57-7.60 (m, 3H), 7.21 (d, J=8 Hz, 1H), 6.16 (s, 1H), 2.21 (s, 3H), 1.88 (s, 3H); MS (ESI) m/z 464 [M+H]$^+$.

2,5-Dimethyl-1-[2-(trifluoromethyl)phenyl]-1H-pyrrole-3-carboxylic acid (4-guanidinosulfonyl-phenyl)-amide; $^1$H NMR (TFA salt-DMSO-d$_6$): δ 9.8 (s, 1H), 8.12 (d, J=7 Hz, 1H), 8 (d, J=8 Hz, 1H), 7.98 (d, J=7 Hz, 2H), 7.92 (t, J=8 Hz, 1H), 7.79 (d, J=7 Hz, 2H), 6.8 (br s, 4H), 6.76 (s, 1H), 2.25 (s, 3H), 2.00 (s, 3H); MS (ESI) m/z 480 [M+H]$^+$.

2,5-Dimethyl-1-[2-(trifluoromethyl)phenyl]-1H-pyrrole-3-carboxylic acid [4-(cyano-phenyl-methyl)-phenyl]-amide; $^1$H NMR (CDCl$_3$): δ 7.88 (d, J=8 Hz, 1H), 7.74-7.76 (m, 2H), 7.67 (t, J=8 Hz, 1H), 7.61 (d, J=7 Hz, 2H), 7.26-7.40 (m, 8H), 6.24 (s, 1H), 5.15 (s, 1H), 2.24 (s, 3H), 1.94 (s, 3H); MS (ESI) m/z 474 [M+H]$^+$.

2,5-Dimethyl-1-[2-(trifluoromethyl)phenyl]-1H-pyrrole-3-carboxylic acid [4-(piperidine-1-sulfonyl)-phenyl]-amide; $^1$H NMR (CDCl$_3$): δ 7.89 (d, J=8 Hz, 1H), 7.66-7.82 (m, 7H), 7.29 (d, J=8 Hz, 1H), 6.26 (s, 1H), 3.00 (m, 4H), 2.26 (s, 3H), 1.97 (s, 3H), 1.66 (m, 4H), 1.44 (m, 2H); MS (ESI) m/z 506 [M+H]$^+$.

2,5-Dimethyl-1-[2-(trifluoromethyl)phenyl]-1H-pyrrole-3-carboxylic acid [(4-methylsulfanyl)phenyl]-amide; $^1$H NMR (CDCl$_3$): δ 7.86 (d, J=8 Hz, 1H); 7.72 (t, J=8 Hz, 1H), 7.62 (t, J=8 Hz, 1H), 7.51 (d, J=9 Hz, 2H), 7.2-7.3 (m, 4H), 6.20 (s, 1H), 2.47 (s, 3H), 2.22 (s, 3H), 1.92 (s, 3H); MS (ESI) m/z 405 [M+H]$^+$.

2,5-Dimethyl-1-[2-(trifluoromethyl)phenyl]-1H-pyrrole-3-carboxylic acid (5-methyl-thiazol-2-yl)-amide; $^1$H NMR (CDCl$_3$): δ 7.87 (d, J=8 Hz, 1H), 7.74 (t, J=8 Hz, 1H), 7.66 (t, J=8 Hz, 1H), 7.25-7.28 (m, 2H), 7.09 (s, 1H), 6.75 (s, 1H), 2.42 (s, 3H), 2.29 (s, 3H), 1.94 (s, 3H); MS (ESI) m/z 380 [M+H]$^+$.

5-{[2,5-Dimethyl-1-[2-(trifluoromethyl)phenyl]-1H-pyrrole-3-carbonyl]-amino}-[1,3,4]thiadiazole-2-carboxylic acid ethyl ester; $^1$H NMR (CDCl$_3$): δ 7.85 (d, J=8 Hz, 1H), 7.71 (t, J=8 Hz, 1H), 7.63 (t, J=8 Hz, 1H), 7.23-7.27 (m, 2H), 6.38 (s, 1H), 4.28 (q, J=7 Hz, 2H), 2.19 (s, 3H), 1.89 (s, 3H), 1.35 (t, J=7 Hz, 3H); MS (ESI) m/z 439 [M+H]$^+$.

2,5-Dimethyl-1-[2-(trifluoromethyl)phenyl]-1H-pyrrole-3-carboxylic acid (4-benzoyl-phenyl)-amide; $^1$H NMR (CDCl$_3$): δ 7.71-7.88 (m, 9H), 7.65 (t, J=8 Hz, 1H), 7.58 (t, J=8 Hz, 2H), 7.48 (t, J=7 Hz, 2H), 7.27 (d, J=1Hz, 1H), 6.25 (s, 1H), 2.27 (s, 3H), 1.93 (s, 3H); MS (ESI) m/z 463 [M+H]$^+$.

2,5-Dimethyl-1-[2-(trifluoromethyl)phenyl]-1H-pyrrole-3-carboxylic acid indan-5-ylamide; $^1$H NMR (CDCl$_3$): δ 7.86 (d, J=8 Hz, 1H), 7.72 (t, J=8 Hz, 1H), 7.64 (t, J=8 Hz, 1H), 7.57 (s, 1H), 7.49 (br s, 1H), 7.27 (d, J=8 Hz, 1H), 7.15-7.23 (m, 2H), 6.19 (s, 1H), 2.89 (quintet, J=8 Hz, 4H), 2.24 (s, 3H), 2.09 (quintet, J=8 Hz, 2H), 1.93 (s, 3H); MS (ESI) m/z 399 [M+H]$^+$.

2,5-Dimethyl-1-[2-(trifluoromethyl)phenyl]-1H-pyrrole-3-carboxylic acid (3-benzoyl-phenyl)-amide; $^1$H NMR (CDCl$_3$): δ 8.11 (d, J=8 Hz, 1H), 7.81-7.89 (m, 4H), 7.74 (t, J=8 Hz, 1H), 7.66 (t, J=8 Hz, 1H), 7.60 (t, J=7 Hz, 2H), 7.45-7.52 (m, 4H), 7.27 (d, J=8 Hz, 1H), 6.27 (s, 1H), 2.26 (s, 3H), 1.94 (s, 3H); MS (ESI) m/z 463 [M+H]$^+$.

2,5-Dimethyl-1-[2-(trifluoromethyl)phenyl]-1H-pyrrole-3-carboxylic acid (3-methylsulfanyl-phenyl)-amide; $^1$H NMR (CDCl$_3$): δ 7.88 (d, J=8 Hz, 1H), 7.75 (t, J=8 Hz, 1H), 7.66 (t, J=8 Hz, 1H), 7.63 (s, 1H), 7.59 (s, 1H), 7.23-7.33 (m, 3H), 7.01 (d, J=8 Hz, 1H), 6.22 (s, 1H), 2.52 (s, 3H), 2.26 (s, 3H), 1.95 (s, 3H); MS (ESI) m/z 405 [M+H]$^+$.

2,5-Dimethyl-1-[2-(trifluoromethyl)phenyl]-1H-pyrrole-3-carboxylic acid (4-benzyloxy-phenyl)-amide; $^1$H NMR (CDCl$_3$): δ 7.84 (d, J=8 Hz, 1H), 7.70 (t, J=8 Hz, 1H), 7.62 (t, J=8 Hz, 1H), 7.54 (s, 1H), 7.40-7.48 (m, 4H), 7.37 (t, J=7 Hz, 2H), 7.31 (t, J=7 Hz, 1H), 7.24 (d, J=8 Hz, 1H), 6.96 (d, J=7 Hz, 2H), 6.19 (s, 1H), 5.04 (s, 2H), 2.23 (s, 3H), 1.91 (s, 3H); MS (ESI) m/z 465 [M+H]$^+$.

2,5-Dimethyl-1-[2-(trifluoromethyl)phenyl]-1H-pyrrole-3-carboxylic acid (4-phenoxy-phenyl)-amide; $^1$H NMR (CDCl$_3$): δ 7.86 (d, J=8 Hz, 1H), 7.72 (t, J=8 Hz, 1H), 7.64 (t, J=8 Hz, 1H), 7.57 (br s, 1H), 7.56 (d, J=7 Hz, 2H), 7.32 (t, J=7 Hz, 2H), 7.26 (d, J=8H, 1H), 7.07 (t, J=1H), 6.97-7.02 (m, 4H), 6.21 (s, 1H), 2.25 (s, 3H), 1.93 (s, 3H); MS (ESI) m/z 451 [M+H]$^+$.

2,5-Dimethyl-1-[2-(trifluoromethyl)phenyl]-1H-pyrrole-3-carboxylic acid benzo[1,3]dioxol-5-ylamide; $^1$H NMR (CDCl$_3$): δ 7.86 (d, J=8 Hz, 1H), 7.72 (t, J=8 Hz, 1H), 7.64 (t, J=3H), 7.39 (s, 1H), 7.35 (s, 1H), 7.26 (d, J=8 Hz, 1H), 6.85 (d, J=8 Hz, 1H), 6.76 (d, J=8 Hz, 1H), 6.17 (s, 1H), 5.95 (s, 2H), 2.25 (s, 3H), 1.93 (s, 1H); MS (ESI) m/z 403 [M+H]$^+$.

2,5-Dimethyl-1-[2-(trifluoromethyl)phenyl]-1H-pyrrole-3-carboxylic acid (3-acetyl-phenyl)-amide; $^1$H NMR (CDCl$_3$): δ 8.14 (s, 1H), 7.96 (d, J=8 Hz, 1H), 7.88 (t, J=8 Hz, 1H), 7.86 (s, 1H), 7.65-7.74 (m, 4H), 7.44 (t, J=8 Hz, 1H), 7.27 (d, J=8 Hz, 1H), 6.26 (s, 1H), 2.62 (s, 3H), 2.25 (s, 3H), 1.93 (s, 3H), MS (ESI) m/z 401 [M+H]$^+$.

2,5-Dimethyl-1-[2-(trifluoromethyl)phenyl]-1H-pyrrole-3-carboxylic acid (4-acetyl-phenyl)-amide; $^1$H NMR (CDCl$_3$): δ 7.96 (d, J=9 Hz, 2H), 7.87 (d, J=8 Hz, 1H), 7.83 (s, 1H), 7.71-7.55 (m, 3H), 7.66 (t, J=8 Hz, 1H), 7.27 (d, J=8 Hz, 1H), 6.25 (s, 1H), 2.58 (s, 3H), 2.26 (s, 3H), 1.93 (s, 1H); MS (ESI) m/z 401 [M+H]$^+$.

2,5-Dimethyl-1-[2-(trifluoromethyl)phenyl]-1H-pyrrole-3-carboxylic acid (5-methylsulfanyl-[1,3,4]thiadiazol-2-yl)-amide; $^1$H NMR (CDCl$_3$): δ 7.88 (d, J=8 Hz, 1H), 7.74 (t, J=8 Hz, 1H), 7.67 (t, J=8 Hz, 1H), 7.27 (d, J=8 Hz, 1H), 6.58 (s, 1H), 2.75 (s, 3H), 2.29 (s, 3H), 1.92 (s, 3H); MS (ESI) m/z 413 [M+H]$^+$.

2,5-Dimethyl-1-[2-(trifluoromethyl)phenyl]-1H-pyrrole-3-carboxylic acid (5-ethylsulfanyl-[1,3,4]thiadiazol-2-yl)-amide; $^1$H NMR (CDCl$_3$): δ 7.88 (d, J=8 Hz, 1H), 7.74 (t, J=8 Hz, 1H), 7.67 (t, J=8 Hz, 1H), 7.28 (d, J=8 Hz, 1H), 6.55 (s, 1H), 3.26 (q, J=7 Hz, 2H), 2.29 (s, 3H), 1.94 (s, 3H), 1.45 (t, J=7 Hz, 3H); MS (ESI) m/z 427 [M+H]$^+$.

2,5-Dimethyl-1-(2-trifluoromethyl-phenyl)-1H-pyrrole-3-carboxylic acid (pyridin-2-ylmethyl)-amide; MS (ES): 374 (MH+);

2,5-Dimethyl-1-(2-trifluoromethyl-phenyl)-1H-pyrrole-3-carboxylic acid 4-trifluoromethyl-benzylamide; MS (ES): 441 (MH+);

2,5-Dimethyl-1-(2-trifluoromethyl-phenyl)-1H-pyrrole-3-carboxylic acid 3-methyl-benzylamide; MS (ES): 387 (MH+);

2,5-Dimethyl-1-(2-trifluoromethyl-phenyl)-1H-pyrrole-3-carboxylic acid [2-(2,4-dichloro-phenyl)-ethyl]-amide; MS (ES): 455 (MH+);

2,5-Dimethyl-1-(2-trifluoromethyl-phenyl)-1H-pyrrole-3-carboxylic acid 2-ethoxy-benzylamide; MS (ES): 417 (MH+);

2,5-Dimethyl-1-(2-trifluoromethyl-phenyl)-1H-pyrrole-3-carboxylic acid methyl-phenethyl-amide; MS (ES): 401 (MH+);

(1,3-Dihydro-isoindol-2-yl)-[2,5-dimethyl-1-(2-trifluoromethyl-phenyl)-1H-pyrrol-3-yl]-methanone; MS (ES): 385 (MH+);

(3,4-Dihydro-1H-isoquinolin-2-yl)-[2,5-dimethyl-1-(2-trifluoromethyl-phenyl)-1H-pyrrol-3-yl]-methanone; MS (ES): 399 (MH+);

2,5-Dimethyl-1-(2-trifluoromethyl-phenyl)-1H-pyrrole-3-carboxylic acid 4-methyl-benzylamide; MS (ES): 387 (MH+);

2,5-Dimethyl-1-(2-trifluoromethyl-phenyl)-1H-pyrrole-3-carboxylic acid 3-chloro-benzylamide; MS (ES): 407 (MH+);

2,5-Dimethyl-1-(2-trifluoromethyl-phenyl)-1H-pyrrole-3-carboxylic acid (2-p-tolyl-ethyl)-amide; MS (ES): 401 (MH+);

2,5-Dimethyl-1-(2-trifluoromethyl-phenyl)-1H-pyrrole-3-carboxylic acid 3-methoxy-benzylamide; MS (ES): 403 (MH+);

2,5-Dimethyl-1-(2-trifluoromethyl-phenyl)-1H-pyrrole-3-carboxylic acid [2-(4-fluoro-phenyl)-ethyl]-amide; MS (ES): 405 (MH+);

2,5-Dimethyl-1-(2-trifluoromethyl-phenyl)-1H-pyrrole-3-carboxylic acid [2-(2-methoxy-phenyl)-ethyl]-amide; MS (ES): 417 (MH+);

2,5-Dimethyl-1-(2-trifluoromethyl-phenyl)-1H-pyrrole-3-carboxylic acid [2-(3-chloro-phenyl)-ethyl]-amide; MS (ES): 421 (MH+);

2,5-Dimethyl-1-(2-trifluoromethyl-phenyl)-1,1-pyrrole-3-carboxylic acid [2-(3-fluoro-phenyl)-ethyl]-amide; MS (ES): 405 (MH+);

2,5-Dimethyl-1-(2-trifluoromethyl-phenyl)-1H-pyrrole-3-carboxylic acid (1-phenyl-propyl)-amide; MS (ES): 401 (MH+);

2,5-Dimethyl-1-(2-trifluoromethyl-phenyl)-1H-pyrrole-3-carboxylic acid (1-methyl-3-phenyl-propyl)-amide; MS (ES): 415 (MH+);

2,5-Dimethyl-1-(2-trifluoromethyl-phenyl)-1H-pyrrole-3-carboxylic acid 3-trifluoromethyl-benzylamide; MS (ES): 441 (MH+);

2,5-Dimethyl-1-(2-trifluoromethyl-phenyl)-1H-pyrrole-3-carboxylic acid (thiophen-2-ylmethyl)-amide; MS (ES): 379 (MH+);

2,5-Dimethyl-1-(2-trifluoromethyl-phenyl)-1H-pyrrole-3-carboxylic acid 4-fluoro-benzylamide; MS (ES): 391 (MH+);

2,5-Dimethyl-1-(2-trifluoromethyl-phenyl)-1H-pyrrole-3-carboxylic acid (furan-2-ylmethyl)-amide; MS (ES): 363 (MH+);

2,5-Dimethyl-1-(2-trifluoromethyl-phenyl)-1H-pyrrole-3-carboxylic acid [2-(3,4-dimethoxy-phenyl)-ethyl]-amide; MS (ES): 447 (MH+);

2,5-Dimethyl-1-(2-trifluoromethyl-phenyl)-1H-pyrrole-3-carboxylic acid 2-fluoro-benzylamide; MS (ES): 391 (MH+);

2,5-Dimethyl-1-(2-trifluoromethyl-phenyl)-1H-pyrrole-3-carboxylic acid indan-1-ylamide; MS (ES): 399 (MH+);

2,5-Dimethyl-1-(2-trifluoromethyl-phenyl)-1H-pyrrole-3-carboxylic acid [2-(2-fluoro-phenyl)-ethyl]-amide; MS (ES): 405 (MH+);

2,5-Dimethyl-1-(2-trifluoromethyl-phenyl)-1H-pyrrole-3-carboxylic acid 2-trifluoromethyl-benzylamide; MS (ES): 441 (MH+);

3-{[2,5-Dimethyl-1-(2-trifluoromethyl-phenyl)-1H-pyrrole-3-carbonyl]-furan-2-ylmethyl-amino}-propionic acid ethyl ester; MS (ES): 463 (MH+);

2,5-Dimethyl-1-(2-trifluoromethyl-phenyl)-1H-pyrrole-3-carboxylic acid (2-thiophen-2-yl-ethyl)-amide; MS (ES): 393 (MH+);

2,5-Dimethyl-1-(2-trifluoromethyl-phenyl)-1H-pyrrole-3-carboxylic acid 2,4-difluoro-benzylamide; MS (ES): 409 (MH+);

2,5-Dimethyl-1-(2-trifluoromethyl-phenyl)-1H-pyrrole-3-carboxylic acid 4-chloro-benzylamide; MS (ES): 407 (MH+);

2,5-Dimethyl-1-(2-trifluoromethyl-phenyl)-1H-pyrrole-3-carboxylic acid [2-(4-chloro-phenyl)-ethyl]-amide; MS (ES): 421 (MH+);

2,5-Dimethyl-1-(2-trifluoromethyl-phenyl)-1H-pyrrole-3-carboxylic acid (3-phenyl-propyl)-amide; MS (ES): 401 (MH+);

2,5-Dimethyl-1-(2-trifluoromethyl-phenyl)-1H-pyrrole-3-carboxylic acid 2,4-dimethyl-benzylamide; MS (ES): 401 (MH+);

2,5-Dimethyl-1-(2-trifluoromethyl-phenyl)-1H-pyrrole-3-carboxylic acid [2-(3-methoxy-phenyl)-ethyl]-amide; MS (ES): 417 (MH+);

2,5-Dimethyl-1-(2-trifluoromethyl-phenyl)-1H-pyrrole-3-carboxylic acid 2,5-difluoro-benzylamide; MS (ES): 409 (MH+);

2,5-Dimethyl-1-(2-trifluoromethyl-phenyl)-1H-pyrrole-3-carboxylic acid [2-(4-bromo-phenyl)-ethyl]-amide; MS (ES): 465 (MH+);

2,5-Dimethyl-1-(2-trifluoromethyl-phenyl)-1H-pyrrole-3-carboxylic acid [2-(2-chloro-phenyl)-ethyl]-amide; MS (ES): 421 (MH+);

2,5-Dimethyl-1-(2-trifluoromethyl-phenyl)-1H-pyrrole-3-carboxylic acid 3-fluoro-benzylamide; MS (ES): 391 (MH+);

2,5-Dimethyl-1-(2-trifluoromethyl-phenyl)-1H-pyrrole-3-carboxylic acid phenethyl-amide; MS (ES): 387 (MH+);

2,5-Dimethyl-1-(2-trifluoromethyl-phenyl)-1H-pyrrole-3-carboxylic acid (5-methyl-furan-2-ylmethyl)-amide; MS (ES): 377 (MH+);

2,5-Dimethyl-1-(2-trifluoromethyl-phenyl)-1H-pyrrole-3-carboxylic acid 2-bromo-benzylamide; MS (ES): 451 (MH+);

2,5-Dimethyl-1-(2-trifluoromethyl-phenyl)-1H-pyrrole-3-carboxylic acid 4-phenoxy-benzylamide; MS (ES): 465 (MH+);

2,5-Dimethyl-1-(2-trifluoromethyl-phenyl)-1H-pyrrole-3-carboxylic acid 2,5-dimethyl-benzylamide; MS (ES): 401 (MH+);

2,5-Dimethyl-1-(2-trifluoromethyl-phenyl)-1H-pyrrole-3-carboxylic acid 3,4-dimethyl-benzylamide; MS (ES): 401 (MH+);

2,5-Dimethyl-1-(2-trifluoromethyl-phenyl)-1H-pyrrole-3-carboxylic acid (2-benzylsulfanyl-ethyl)-amide; MS (ES): 433 (MH+);

2,5-Dimethyl-1-(2-trifluoromethyl-phenyl)-1H-pyrrole-3-carboxylic acid benzyl-ethyl-amide; MS (ES): 401 (MH+);

2,5-Dimethyl-1-(2-trifluoromethyl-phenyl)-1H-pyrrole-3-carboxylic acid (2-phenyl-propyl)-amide; MS (ES): 401 (MH+);

2,5-Dimethyl-1-(2-trifluoromethyl-phenyl)-1H-pyrrole-3-carboxylic acid [2-(1H-indol-3-yl)-ethyl]-amide; MS (ES): 426 (MH+);

2,5-Dimethyl-1-(2-trifluoromethyl-phenyl)-1H-pyrrole-3-carboxylic acid (2,3-dihydro-benzo[1,4]dioxin-6-ylmethyl)-amide; MS (ES): 431 (MH+);

2,5-Dimethyl-1-(2-trifluoromethyl-phenyl)-1H-pyrrole-3-carboxylic acid (6-fluoro-4H-benzo[1,3]dioxin-8-ylmethyl)-amide; MS (ES): 449 (MH+);

2,5-Dimethyl-1-(2-trifluoromethyl-phenyl)-1H-pyrrole-3-carboxylic acid 4-fluoro-2-trifluoromethyl-benzylamide; MS (ES): 459 (MH+);

2,5-Dimethyl-1-(2-trifluoromethyl-phenyl)-1H-pyrrole-3-carboxylic acid 2-chloro-6-phenoxy-benzylamide; MS (ES): 499 (MH+);

2,5-Dimethyl-1-(2-trifluoromethyl-phenyl)-1H-pyrrole-3-carboxylic acid [(S)-1-(4-bromo-phenyl)-ethyl]-amide; MS (ES): 465 (MH+);

2,5-Dimethyl-1-(2-trifluoromethyl-phenyl)-1H-pyrrole-3-carboxylic acid ((R)-1-naphthalen-2-yl-ethyl)-amide; MS (ES): 437 (MH+);

2,5-Dimethyl-1-(2-trifluoromethyl-phenyl)-1H-pyrrole-3-carboxylic acid [bis-(4-methoxy-phenyl)-methyl]-amide; MS (ES): 509 (MH+);

2,5-Dimethyl-1-(2-trifluoromethyl-phenyl)-1H-pyrrole-3-carboxylic acid [(R)-1-(3-methoxy-phenyl)-ethyl]-amide; MS (ES): 417 (MH+);

2,5-Dimethyl-1-(2-trifluoromethyl-phenyl)-1H-pyrrole-3-carboxylic acid 2-methylsulfanyl-benzylamide; MS (ES): 419 (MH+);

2,5-Dimethyl-1-(2-trifluoromethyl-phenyl)-1H-pyrrole-3-carboxylic acid 4-methanesulfonyl-benzylamide; MS (ES): 451 (MH+);

2,5-Dimethyl-1-(2-trifluoromethyl-phenyl)-1H-pyrrole-3-carboxylic acid [1-(2-chloro-phenyl)-ethyl]-amide; MS (ES): 421 (MH+);

2,5-Dimethyl-1-(2-trifluoromethyl-phenyl)-1H-pyrrole-3-carboxylic acid 4-p-tolyloxy-benzylamide; MS (ES): 479 (MH+);

(S)-2-{[2,5-Dimethyl-1-(2-trifluoromethyl-phenyl)-1H-pyrrole-3-carbonyl]-amino}-3-(4-hydroxy-phenyl)-propionic acid tert-butyl ester; MS (ES): 503 (MH+);

2,5-Dimethyl-1-(2-trifluoromethyl-phenyl)-1H-pyrrole-3-carboxylic acid (2,2-diphenyl-propyl)-amide; MS (ES): 477 (MH+);

2,5-Dimethyl-1-(2-trifluoromethyl-phenyl)-1H-pyrrole-3-carboxylic acid [2-(3-ethoxy-4-methoxy-phenyl)-ethyl]-amide; MS (ES): 461 (MH+);

2,5-Dimethyl-1-(2-trifluoromethyl-phenyl)-1H-pyrrole-3-carboxylic acid (4'-fluoro-biphenyl-2-ylmethyl)-amide; MS (ES): 467 (MH+);

G. In a manner similar to that described in Examples 1A-1C, but replacing 4-fluoro-2-(trifluoromethyl)aniline with the appropriate amine and replacing sulfanilamide with 4-(methanesulfonyl)aniline, the following compounds were prepared:

1-[2,3-Dichloro-phenyl]-2,5-dimethyl-1H-pyrrole-3-carboxylic acid (4-methanesulfonyl-phenyl)-amide; MS (ESI) m/z 437 [M+H]$^+$.

1-(2-Bromophenyl)-2,5-dimethyl-1H-pyrrole-3-carboxylic acid (4-methanesulfonyl-phenyl)-amide; MS (ESI) m/z 447, 449 each [M+H]$^+$.

1-(2-Isopropyl-phenyl)-2,5-dimethyl-1H-pyrrole-3-carboxylic acid (4-methanesulfonyl-phenyl)-amide; MS (ESI) m/z 411 [M+H]$^+$.

1-(2-Tert-butyl-phenyl)-2,5-dimethyl-1H-pyrrole-3-carboxylic acid (4-methanesulfonyl-phenyl)-amide; MS (ESI) m/z 425 [M+H]$^+$.

2,5-Dimethyl-1-naphthalen-1-yl-1H-pyrrole-3-carboxylic acid (4-methanesulfonyl-phenyl)-amide; MS (ESI) m/z 419 [M+H]$^+$.

1-(2-Tert-butyl-phenyl)-2,5-dimethyl-1H-pyrrole-3-carboxylic acid (4-methanesulfonyl-phenyl)-amide; MS (ESI) m/z 425 [M+H]$^+$.

Example 2

PREPARATION OF 2,5-DIMETHYL-1-[2-(TRIFLUOROMETHYL)PHENYL]-1H-PYRROLE-3-CARBOXYLIC ACID PHENYLAMIDE AND VARIATIONS

A. A 0.125 M stock solution of 1-[2-(trifluoromethyl)phenyl]-2,5-dimethyl-1H-pyrrole-3-carboxylic acid chloride was prepared in THF. Anilines and other heterocyclic amines were individually weighed and were dissolved to 0.125 M using a Tecan Genesis workstation and a 1.0 M diisopropylethylamine in THF solution. The Tecan was used to dispense 200 µL of 0.125 M 1-[2-(trifluoromethyl)phenyl]-2,5-dimethyl-1H-pyrrole-3-carboxylic acid chloride to each reaction vessel and then was used to dispense 200 µL of amine stock solutions to individual reaction vessels. The reaction vessels were sealed and were allowed to react, at room temperature with agitation, for 18 h. The reaction vessels were then unsealed and THF (0.90 mL) was added. The THF was removed by filtration and the reaction vessels were washed with 2×500 μL of THF. Sample solutions were dried in vacuo.

B. Samples were dissolved in 500 μL of DMSO and 500 μL of methanol. Purity was determined by LC-MS using a combination of $UV_{254}$, $UV_{220}$, and ELSD detection [purity=$(UV_{254}+UV_{220}/2)$]. The HPLC conditions were: 4.6 mm×50 mm C18 column, 10-90% acetonitrile gradient over 5 minutes (mobile phases were $H_2O$ with 0.05% TFA and acetonitrile with 0.035% TFA), with a flow rate of 3.5 ml/min. Samples below 80% purity were purified using a mass-directed LC-MS purification. Purified samples were concentrated in vacuo, were dissolved in DMSO and were reformatted into 96 well microtiter plates. Samples were tested for purity using LC-MS and quantity was estimated by correlating ELSD response to a standard concentration-ELSD response curve. Samples then were concentrated to dryness and were dissolved in DMSO to a final concentration of 10 μM, based on ELSD quantification.

C. The following compounds were prepared in a manner similar to that described in Examples 2A-2B using the appropriate amines:

2,5-Dimethyl-1-(2-trifluoromethyl-phenyl)-1H-pyrrole-3-carboxylic acid (2-methoxy-6-methyl-phenyl)-amide; MS (ESI) m/z 403 [M+H]$^+$;

2,5-Dimethyl-1-(2-trifluoromethyl-phenyl)-1H-pyrrole-3-carboxylic acid benzothiazol-2-ylamide; MS (ESI) m/z 416 [M+H]$^+$;

2,5-Dimethyl-1-(2-trifluoromethyl-phenyl)-1H-pyrrole-3-carboxylic acid (2,5-dichloro-phenyl)-amide; MS (ESI) m/z 427 [M+H]$^+$;

2,5-Dimethyl-1-(2-trifluoromethyl-phenyl)-1H-pyrrole-3-carboxylic acid (4-methylsulfanyl-phenyl)-amide; MS (ESI) m/z 405 [M+H]$^+$;

2,5-Dimethyl-1-(2-trifluoromethyl-phenyl)-1H-pyrrole-3-carboxylic acid (2,4-dichloro-phenyl)-amide; MS (ESI) m/z 427 [M+H]$^+$;

2,5-Dimethyl-1-(2-trifluoromethyl-phenyl)-1H-pyrrole-3-carboxylic acid (5-methyl-[1,3,4]thiadiazol-2-yl)-amide; MS (ESI) m/z 381 [M+H]$^+$;

2,5-Dimethyl-1-(2-trifluoromethyl-phenyl)-1H-pyrrole-3-carboxylic acid (5,6,7,8-tetrahydro-naphthalen-1-yl)-amide; MS (ESI) m/z 413 [M+H]$^+$;

2,5-Dimethyl-1-(2-trifluoromethyl-phenyl)-1H-pyrrole-3-carboxylic acid (2-chloro-4-fluoro-phenyl)-amide; MS (ESI) m/z 411 [M+H]$^+$;

2,5-Dimethyl-1-(2-trifluoromethyl-phenyl)-1H-pyrrole-3-carboxylic acid (4-chloro-2-fluoro-phenyl)-amide; MS (ESI) m/z 411 [M+H]$^+$;

2,5-Dimethyl-1-(2-trifluoromethyl-phenyl)-1H-pyrrole-3-carboxylic acid (3-fluoro-4-methyl-phenyl)-amide; MS (ESI) m/z 391 [M+H]$^+$;

2,5-Dimethyl-1-(2-trifluoromethyl-phenyl)-1H-pyrrole-3-carboxylic acid (4-methoxy-2-methyl-phenyl)-amide; MS (ESI) m/z 403 [M+H]$^+$;

2,5-Dimethyl-1-(2-trifluoromethyl-phenyl)-1H-pyrrole-3-carboxylic acid (3-chloro-4-methyl-phenyl)-amide; MS (ESI) m/z 407 [M+H]$^+$;

2,5-Dimethyl-1-(2-trifluoromethyl-phenyl)-1H-pyrrole-3-carboxylic acid (3,4-difluoro-phenyl)-amide; MS (ESI) m/z 395 [M+H];

2,5-Dimethyl-1-(2-trifluoromethyl-phenyl)-1H-pyrrole-3-carboxylic acid (2-methylsulfanyl-phenyl)-amide; MS (ESI) m/z 405 [M+H]$^+$;

2,5-Dimethyl-1-(2-trifluoromethyl-phenyl)-1H-pyrrole-3-carboxylic acid (2,6-diethyl-phenyl)-amide; MS (ESI) m/z 415 [M+H]$^+$;

2,5-Dimethyl-1-(2-trifluoromethyl-phenyl)-1H-pyrrole-3-carboxylic acid (4-propyl-phenyl)-amide; MS (ESI) m/z 401 [M+H]$^+$;

2,5-Dimethyl-1-(2-trifluoromethyl-phenyl)-1H-pyrrole-3-carboxylic acid (4-fluoro-2-methyl-phenyl)-amide; MS (ESI) m/z 391 [M+H]$^+$;

2,5-Dimethyl-1-(2-trifluoromethyl-phenyl)-1H-pyrrole-3-carboxylic acid (2,3-difluoro-phenyl)-amide; MS (ESI) m/z 395 [M+H]$^+$;

2,5-Dimethyl-1-(2-trifluoromethyl-phenyl)-1H-pyrrole-3-carboxylic acid (2,5-dimethoxy-phenyl)-amide; MS (ESI) m/z 419 [M+H]$^+$;

2,5-Dimethyl-1-(2-trifluoromethyl-phenyl)-1H-pyrrole-3-carboxylic acid (2-bromo-4-fluoro-phenyl)-amide; MS (ESI) m/z 455 [M+H]$^+$;

2,5-Dimethyl-1-(2-trifluoromethyl-phenyl)-1H-pyrrole-3-carboxylic acid (2-fluoro-5-trifluoromethyl-phenyl)-amide; MS (ESI) m/z 445 [M+H]$^+$;

2,5-Dimethyl-1-(2-trifluoromethyl-phenyl)-1H-pyrrole-3-carboxylic acid (4-difluoromethoxy-phenyl)-amide; MS (ESI) m/z 425 [M+H]$^+$;

2,5-Dimethyl-1-(2-trifluoromethyl-phenyl)-1H-pyrrole-3-carboxylic acid (2,6-diisopropyl-phenyl)-amide; MS (ESI) m/z 443 [M+H]$^+$;

2,5-Dimethyl-1-(2-trifluoromethyl-phenyl)-1H-pyrrole-3-carboxylic acid (2-ethyl-6-methyl-phenyl)-amide; MS (ESI) m/z 401 [M+H]$^+$;

2,5-Dimethyl-1-(2-trifluoromethyl-phenyl)-1H-pyrrole-3-carboxylic acid (3-ethoxy-phenyl)-amide; MS (ESI) m/z 403 [M+H]$^+$;

2,5-Dimethyl-1-(2-trifluoromethyl-phenyl)-1H-pyrrole-3-carboxylic acid (3-bromo-phenyl)-amide; MS (ESI) m/z 437 [M+H]$^+$;

2,5-Dimethyl-1-(2-trifluoromethyl-phenyl)-1H-pyrrole-3-carboxylic acid (3-fluoro-2-methyl-phenyl)-amide; MS (ESI) m/z 391 [M+H]$^+$;

2,5-Dimethyl-1-(2-trifluoromethyl-phenyl)-1H-pyrrole-3-carboxylic acid (2-fluoro-5-methyl-phenyl)-amide; MS (ESI) m/z 391 [M+H]$^+$;

2,5-Dimethyl-1-(2-trifluoromethyl-phenyl)-1H-pyrrole-3-carboxylic acid indan-5-ylamide; MS (ESI) m/z 399 [M+H]$^+$;

2,5-Dimethyl-1-(2-trifluoromethyl-phenyl)-1H-pyrrole-3-carboxylic acid (2-ethyl-phenyl)-amide; MS (ESI) m/z 387 [M+H]$^+$;

2,5-Dimethyl-1-(2-trifluoromethyl-phenyl)-1H-pyrrole-3-carboxylic acid (2,6-dimethyl-phenyl)-amide; MS (ESI) m/z 387 [M+H]$^+$;

2,5-Dimethyl-1-(2-trifluoromethyl-phenyl)-1H-pyrrole-3-carboxylic acid (2,5-difluoro-phenyl)-amide; MS (ESI) m/z 395 [M+H]$^+$;

2,5-Dimethyl-1-(2-trifluoromethyl-phenyl)-1H-pyrrole-3-carboxylic acid (3-ethyl-phenyl)-amide; MS (ESI) m/z 387 [M+H]$^+$;

2,5-Dimethyl-1-(2-trifluoromethyl-phenyl)-1H-pyrrole-3-carboxylic acid (3-chloro-2-methyl-phenyl)-amide; MS (ESI) m/z 407 [M+H]$^+$;

2,5-Dimethyl-1-(2-trifluoromethyl-phenyl)-1H-pyrrole-3-carboxylic acid (4-ethyl-phenyl)-amide; MS (ESI) m/z 387 [M+H]$^+$;

2,5-Dimethyl-1-(2-trifluoromethyl-phenyl)-1H-pyrrole-3-carboxylic acid (3-bromo-4-methyl-phenyl)-amide; MS (ESI) m/z 451 [M+H]$^+$;

2,5-Dimethyl-1-(2-trifluoromethyl-phenyl)-1H-pyrrole-3-carboxylic acid (5-bromo-2-methyl-phenyl)-amide; MS (ESI) m/z 451 [M+H]$^+$;

2,5-Dimethyl-1-(2-trifluoromethyl-phenyl)-1H-pyrrole-3-carboxylic acid (2,4,6-trimethyl-phenyl)-amide; MS (ESI) m/z 401 [M+H]$^+$;

2,5-Dimethyl-1-(2-trifluoromethyl-phenyl)-1H-pyrrole-3-carboxylic acid (4-chloro-naphthalen-1-yl)-amide; MS (ESI) m/z 443 [M+H]$^+$;

2,5-Dimethyl-1-(2-trifluoromethyl-phenyl)-1H-pyrrole-3-carboxylic acid (3-benzoyl-phenyl)-amide; MS (ESI) m/z 463 [M+H]$^+$;

2,5-Dimethyl-1-(2-trifluoromethyl-phenyl)-1H-pyrrole-3-carboxylic acid (3-benzyloxy-phenyl)-amide; MS (ESI) m/z 465 [M+H]$^+$;

2,5-Dimethyl-1-(2-trifluoromethyl-phenyl)-1H-pyrrole-3-carboxylic acid (2,6-dichloro-3-methyl-phenyl)-amide; MS (ESI) m/z 441 [M+H]$^+$;

2,5-Dimethyl-1-(2-trifluoromethyl-phenyl)-1H-pyrrole-3-carboxylic acid (4-chloro-3-trifluoromethyl-phenyl)-amide; MS (ESI) m/z 461 [M+H]$^+$;

2,5-Dimethyl-1-(2-trifluoromethyl-phenyl)-1H-pyrrole-3-carboxylic acid (4-benzoyl-phenyl)-amide; MS (ESI) m/z 463 [M+H]$^+$;

2,5-Dimethyl-1-(2-trifluoromethyl-phenyl)-1H-pyrrole-3-carboxylic acid (9H-fluoren-2-yl)-amide; MS (ESI) m/z 447 [M+H]$^+$;

2,5-Dimethyl-1-(2-trifluoromethyl-phenyl)-1H-pyrrole-3-carboxylic acid (2-chloro-pyridin-3-yl)-amide; MS (ESI) m/z 394 [M+H]$^+$;

2,5-Dimethyl-1-(2-trifluoromethyl-phenyl)-1H-pyrrole-3-carboxylic acid (2,6-dichloro-phenyl)-amide; MS (ESI) m/z 427 [M+H]$^+$;

2,5-Dimethyl-1-(2-trifluoromethyl-phenyl)-1H-pyrrole-3-carboxylic acid (2-phenoxy-phenyl)-amide; MS (ESI) m/z 451 [M+H]$^+$;

2,5-Dimethyl-1-(2-trifluoromethyl-phenyl)-1H-pyrrole-3-carboxylic acid (4-bromo-3-methyl-phenyl)-amide; MS (ESI) m/z 451 [M+H]$^+$;

2,5-Dimethyl-1-(2-trifluoromethyl-phenyl)-1H-pyrrole-3-carboxylic acid (5-methyl-pyridin-2-yl)-amide; MS (ESI) m/z 374 [M+H]$^+$;

2,5-Dimethyl-1-(2-trifluoromethyl-phenyl)-1H-pyrrole-3-carboxylic acid (3-fluoro-4-methoxy-phenyl)-amide; MS (ESI) m/z 407 [M+H]$^+$;

2,5-Dimethyl-1-(2-trifluoromethyl-phenyl)-1H-pyrrole-3-carboxylic acid (2-sec-butyl-phenyl)-amide; MS (ESI) m/z 415 [M+H]$^+$;

2,5-Dimethyl-1-(2-trifluoromethyl-phenyl)-1H-pyrrole-3-carboxylic acid (2-methoxy-5-methyl-phenyl)-amide; MS (ESI) m/z 403 [M+H]$^+$;

2,5-Dimethyl-1-(2-trifluoromethyl-phenyl)-1H-pyrrole-3-carboxylic acid (2,4,6-trichloro-phenyl)-amide; MS (ESI) m/z 461 [M+H]$^+$;

2,5-Dimethyl-1-(2-trifluoromethyl-phenyl)-1H-pyrrole-3-carboxylic acid (4-chloro-phenyl)-amide; MS (ESI) m/z 393 [M+H]$^+$;

2,5-Dimethyl-1-(2-trifluoromethyl-phenyl)-1H-pyrrole-3-carboxylic acid (3,5-difluoro-phenyl)-amide; MS (ESI) m/z 395 [M+H]$^+$;

2,5-Dimethyl-1-(2-trifluoromethyl-phenyl)-1H-pyrrole-3-carboxylic acid (4-bromo-2-fluoro-phenyl)-amide; MS (ESI) m/z 455 [M+H]$^+$;

2,5-Dimethyl-1-(2-trifluoromethyl-phenyl)-1H-pyrrole-3-carboxylic acid (2-chloro-5-methyl-phenyl)-amide; MS (ESI) m/z 407 [M+H]$^+$;

2,5-Dimethyl-1-(2-trifluoromethyl-phenyl)-1H-pyrrole-3-carboxylic acid (2,4,6-trifluoro-phenyl)-amide; MS (ESI) m/z 413 [M+H]$^+$;

2,5-Dimethyl-1-(2-trifluoromethyl-phenyl)-1H-pyrrole-3-carboxylic acid (2-isopropyl-6-methyl-phenyl)-amide; MS (ESI) m/z 415 [M+H]$^+$;

2,5-Dimethyl-1-(2-trifluoromethyl-phenyl)-1H-pyrrole-3-carboxylic acid (3,5-dichloro-phenyl)-amide; MS (ESI) m/z 427 [M+H]$^+$;

2,5-Dimethyl-1-(2-trifluoromethyl-phenyl)-1H-pyrrole-3-carboxylic acid (5-methyl-thiazol-2-yl)-amide; MS (ESI) m/z 380 [M+H]$^+$;

2,5-Dimethyl-1-(2-trifluoromethyl-phenyl)-1H-pyrrole-3-carboxylic acid (2-bromo-phenyl)-amide; MS (ESI) m/z 437 [M+H]$^+$;

2,5-Dimethyl-1-(2-trifluoromethyl-phenyl)-1H-pyrrole-3-carboxylic acid (6-methyl-pyridin-2-yl)-amide; MS (ESI) m/z 374 [M+H]$^+$;

2,5-Dimethyl-1-(2-trifluoromethyl-phenyl)-1H-pyrrole-3-carboxylic acid (4-chloro-2-methoxy-5-methyl-phenyl)-amide; MS (ESI) m/z 437 [M+H]$^+$;

2,5-Dimethyl-1-(2-trifluoromethyl-phenyl)-1H-pyrrole-3-carboxylic acid (2,4-difluoro-phenyl)-amide; MS (ESI) m/z 395 [M+H]$^+$;

2,5-Dimethyl-1-(2-trifluoromethyl-phenyl)-1H-pyrrole-3-carboxylic acid (2,4,5-trichloro-phenyl)-amide; MS (ESI) m/z 461 [M+H]$^+$;

2,5-Dimethyl-1-(2-trifluoromethyl-phenyl)-1H-pyrrole-3-carboxylic acid (2-benzoyl-phenyl)-amide; MS (ESI) m/z 463 [M+H]$^+$;

2,5-Dimethyl-1-(2-trifluoromethyl-phenyl)-1H-pyrrole-3-carboxylic acid (2-difluoromethoxy-phenyl)-amide; MS (ESI) m/z 425 [M+H]$^+$;

2,5-Dimethyl-1-(2-trifluoromethyl-phenyl)-1H-pyrrole-3-carboxylic acid (2-chloro-5-methyl-phenyl)-amide; MS (ESI) m/z 407 [M+H]$^+$;

2,5-Dimethyl-1-(2-trifluoromethyl-phenyl)-1H-pyrrole-3-carboxylic acid (3-methylsulfanyl-phenyl)-amide; MS (ESI) m/z 405 [M+H]$^+$;

2,5-Dimethyl-1-(2-trifluoromethyl-phenyl)-1H-pyrrole-3-carboxylic acid (2-isopropyl-phenyl)-amide; MS (ESI) m/z 401 [M+H]$^+$;

2,5-Dimethyl-1-(2-trifluoromethyl-phenyl)-1H-pyrrole-3-carboxylic acid (4-chloro-3-nitro-phenyl)-amide; MS (ESI) m/z 438 [M+H]$^+$;

3-Chloro-2-{[2,5-dimethyl-1-(2-trifluoromethyl-phenyl)-1H-pyrrole-3-carbonyl]-amino}-benzoic acid; MS (ESI) m/z 437 [M+H]$^+$;

2,5-Dimethyl-1-(2-trifluoromethyl-phenyl)-1H-pyrrole-3-carboxylic acid (3-nitro-phenyl)-amide; MS (ESI) m/z 404 [M+H]$^+$;

2,5-Dimethyl-1-(2-trifluoromethyl-phenyl)-1H-pyrrole-3-carboxylic acid (4-benzyloxy-phenyl)-amide; MS (ESI) m/z 465 [M+H]$^+$;

2,5-Dimethyl-1-(2-trifluoromethyl-phenyl)-1H-pyrrole-3-carboxylic acid (5-tert-butyl-[1,3,4]thiadiazol-2-yl)-amide; MS (ESI) m/z 423 [M+H]$^+$;

2-{[2,5-Dimethyl-1-(2-trifluoromethyl-phenyl)-1H-pyrrole-3-carbonyl]-amino}-benzoic acid; MS (ESI) m/z 403 [M+H]$^+$;

2-{[2,5-Dimethyl-1-(2-trifluoromethyl-phenyl)-1H-pyrrole-3-carbonyl]-amino}-benzoic acid methyl ester; MS (ESI) m/z 417 [M+H]$^+$;

2,5-Dimethyl-1-(2-trifluoromethyl-phenyl)-1H-pyrrole-3-carboxylic acid (4-cyclohexyl-phenyl)-amide; MS (ESI) m/z 441 [M+H]$^+$;

2,5-Dimethyl-1-(2-trifluoromethyl-phenyl)-1H-pyrrole-3-carboxylic acid (1H-indazol-5-yl)-amide; MS (ESI) m/z 399 [M+H]$^+$;

2,5-Dimethyl-1-(2-trifluoromethyl-phenyl)-1H-pyrrole-3-carboxylic acid (2-methoxy-biphenyl-4-yl)-amide; MS (ESI) m/z 465 [M+H]$^+$;

2,5-Dimethyl-1-(2-trifluoromethyl-phenyl)-1H-pyrrole-3-carboxylic acid naphthalen-2-ylamide; MS (ESI) m/z 409 [M+H]$^+$;

2,5-Dimethyl-1-(2-trifluoromethyl-phenyl)-1H-pyrrole-3-carboxylic acid (2-ethoxy-phenyl)-amide; MS (ESI) m/z 403 [M+H]$^+$;

4-{[2,5-Dimethyl-1-(2-trifluoromethyl-phenyl)-1H-pyrrole-3-carbonyl]-amino}-benzoic acid methyl ester; MS (ESI) m/z 417 [M+H]$^+$;

2,5-Dimethyl-1-(2-trifluoromethyl-phenyl)-1H-pyrrole-3-carboxylic acid (4-fluoro-phenyl)-amide; MS (ESI) m/z 377 [M+H]$^+$;

2,5-Dimethyl-1-(2-trifluoromethyl-phenyl)-1H-pyrrole-3-carboxylic acid (2-fluoro-phenyl)-amide; MS (ESI) m/z 377 [M+H]$^+$;

2,5-Dimethyl-1-(2-trifluoromethyl-phenyl)-1H-pyrrole-3-carboxylic acid (4-phenoxy-phenyl)-amide; MS (ESI) m/z 451 [M+H]$^+$;

2,5-Dimethyl-1-(2-trifluoromethyl-phenyl)-1H-pyrrole-3-carboxylic acid biphenyl-2-ylamide; MS (ESI) m/z 435 [M+H]$^+$;

2,5-Dimethyl-1-(2-trifluoromethyl-phenyl)-1H-pyrrole-3-carboxylic acid (2-hydroxy-naphthalen-1-yl)-amide; MS (ESI) m/z 425 [M+H]$^+$;

2,5-Dimethyl-1-(2-trifluoromethyl-phenyl)-1H-pyrrole-3-carboxylic acid (2,3-dihydro-benzo[1,4]dioxin-6-yl)-amide; MS (ESI) m/z 417 [M+H]$^+$;

2,5-Dimethyl-1-(2-trifluoromethyl-phenyl)-1H-pyrrole-3-carboxylic acid quinolin-6-ylamide; MS (ESI) m/z 410 [M+H]$^+$;

2,5-Dimethyl-1-(2-trifluoromethyl-phenyl)-1H-pyrrole-3-carboxylic acid isoquinolin-5-ylamide; MS (ESI) m/z 410 [M+H]$^+$;

2,5-Dimethyl-1-(2-trifluoromethyl-phenyl)-1H-pyrrole-3-carboxylic acid (4-isopropoxy-phenyl)-amide; MS (ESI) m/z 417 [M+H]$^+$;

2,5-Dimethyl-1-(2-trifluoromethyl-phenyl)-1H-pyrrole-3-carboxylic acid [3-chloro-2-(2-hydroxy-ethyl)-phenyl]-amide; MS (ESI) m/z 437 [M+H]$^+$;

(4-{[2,5-Dimethyl-1-(2-trifluoromethyl-phenyl)-1H-pyrrole-3-carbonyl]-amino}-phenyl)-acetic acid ethyl ester; MS (ESI) m/z 445 [M+H]$^+$;

2,5-Dimethyl-1-(2-trifluoromethyl-phenyl)-1H-pyrrole-3-carboxylic acid (3-hydroxymethyl-2-methyl-phenyl)-amide; MS (ESI) m/z 403 [M+H]$^+$;

2,5-Dimethyl-1-(2-trifluoromethyl-phenyl)-1H-pyrrole-3-carboxylic acid (2,5-diethoxy-4-morpholin-4-yl-phenyl)-amide; MS (ESI) m/z 532 [M+H]$^+$;

2,5-Dimethyl-1-(2-trifluoromethyl-phenyl)-1H-pyrrole-3-carboxylic acid (4-methyl-3-nitro-phenyl)-amide; MS (ESI) m/z 418 [M+H]$^+$;

2,5-Dimethyl-1-(2-trifluoromethyl-phenyl)-1H-pyrrole-3-carboxylic acid (5-hydroxymethyl-2-methyl-phenyl)-amide; MS (ESI) m/z 403 [M+H]$^+$;

2,5-Dimethyl-1-(2-trifluoromethyl-phenyl)-1H-pyrrole-3-carboxylic acid (2-methyl-5-nitro-phenyl)-amide; MS (ESI) m/z 418 [M+H]$^+$;

2,5-Dimethyl-1-(2-trifluoromethyl-phenyl)-1H-pyrrole-3-carboxylic acid (3-hydroxy-phenyl)-amide; MS (ESI) m/z 375 [M+H]$^+$;

2,5-Dimethyl-1-(2-trifluoromethyl-phenyl)-1H-pyrrole-3-carboxylic acid [4-(acetyl-methyl-amino)-phenyl]-amide; MS (ESI) m/z 430 [M+H]$^+$;

2-{[2,5-Dimethyl-1-(2-trifluoromethyl-phenyl)-1H-pyrrole-3-carbonyl]-amino}-benzoic acid isopropyl ester; MS (ESI) m/z 445 [M+H]$^+$;

2,5-Dimethyl-1-(2-trifluoromethyl-phenyl)-1H-pyrrole-3-carboxylic acid (2-methyl-1H-indol-5-yl)-amide; MS (ESI) m/z 412 [M+H]$^+$;

2,5-Dimethyl-1-(2-trifluoromethyl-phenyl)-1H-pyrrole-3-carboxylic acid (2-hydroxymethyl-4-methyl-phenyl)-amide; MS (ESI) m/z 403 [M+H]$^+$;

3,5-Dichloro-4-{[2,5-dimethyl-1-(2-trifluoromethyl-phenyl)-1H-pyrrole-3-carbonyl]-amino}-benzoic acid ethyl ester; MS (ESI) m/z 499 [M+H]$^+$;

2,5-Dimethyl-1-(2-trifluoromethyl-phenyl)-1H-pyrrole-3-carboxylic acid (2,5-dichloro-4-pyrrol-1-yl-phenyl)-amide; MS (ESI) m/z 492 [M+H]$^+$;

2,5-Dimethyl-1-(2-trifluoromethyl-phenyl)-1H-pyrrole-3-carboxylic acid (3-isopropoxy-phenyl)-amide; MS (ESI) m/z 417 [M+H]$^+$;

2-{[2,5-Dimethyl-1-(2-trifluoromethyl-phenyl)-1H-pyrrole-3-carbonyl]-amino}-benzoic acid phenyl ester; MS (ESI) m/z 479 [M+H]$^+$;

2,5-Dimethyl-1-(2-trifluoromethyl-phenyl)-1H-pyrrole-3-carboxylic acid (2-chloro-5-fluoro-phenyl)-amide; MS (ESI) m/z 411 [M+H]$^+$;

2,5-Dimethyl-1-(2-trifluoromethyl-phenyl)-1H-pyrmmole-3-carboxylic acid (2-bromo-5-nitro-phenyl)-amide; MS (ESI) m/z 482 [M+H]$^+$;

2,5-Dimethyl-1-(2-trifluoromethyl-phenyl)-1H-pyrrole-3-carboxylic acid (3-hydroxy-2-methyl-phenyl)-amide; MS (ESI) m/z 389 [M+H]$^+$;

2,5-Dimethyl-1-(2-trifluoromethyl-phenyl)-1H-pyrrole-3-carboxylic acid (2-methoxy-5-nitro-phenyl)-amide; MS (ESI) m/z 434 [M+H]$^+$;

[2,5-Dimethyl-1-(2-trifluoromethyl-phenyl)-1H-pyrrol-3-yl]-(2-methyl-3,4-dihydro-2H-quinolin-1-yl)-methanone; MS (ESI) m/z 413 [M+H]$^+$;

5-(4-{[2,5-Dimethyl-1-(2-trifluoromethyl-phenyl)-1H-pyrrole-3-carbonyl]-amino}-phenyl)-2-methyl-furan-3-carboxylic acid ethyl ester; MS (ESI) m/z 511 [M+H]$^+$;

2,5-Dimethyl-1-(2-trifluoromethyl-phenyl)-1H-pyrrole-3-carboxylic acid (5-chloro-2-fluoro-phenyl)-amide; MS (ESI) m/z 411 [M+H]$^+$;

2,5-Dimethyl-1-(2-trifluoromethyl-phenyl)-1H-pyrrole-3-carboxylic acid (5-chloro-2,4-dimethoxy-phenyl)-amide; MS (ESI) m/z 453 [M+H]$^+$;

2,5-Dimethyl-1-(2-trifluoromethyl-phenyl)-1H-pyrrole-3-carboxylic acid [2-(5-methyl-thieno[2,3-d]pyrimidin-4-ylsulfanyl)-phenyl]-amide; MS (ESI) m/z 539 [M+H]$^+$;

[[2,5-Dimethyl-1-(2-trifluoromethyl-phenyl)-1H-pyrrole-3-carbonyl]-(4-trifluoromethoxy-phenyl)-amino]-acetic acid ethyl ester; MS (ESI) m/z 529 [M+H]$^+$;

2,5-Dimethyl-1-(2-trifluoromethyl-phenyl)-1H-pyrrole-3-carboxylic acid (4-chloro-2-trifluoromethoxy-phenyl)-amide; MS (ESI) m/z 477 [M+H]$^+$;

2,5-Dimethyl-1-(2-trifluoromethyl-phenyl)-1H-pyrrole-3-carboxylic acid (3-bromo-4-trifluoromethoxy-phenyl)-amide; MS (ESI) m/z 521 [M+H]$^+$;

2,5-Dimethyl-1-(2-trifluoromethyl-phenyl)-1H-pyrrole-3-carboxylic acid (2-tert-butylcarbamoyl-phenyl)-amide; MS (ESI) m/z 458 [M+H]$^+$;

2,5-Dimethyl-1-(2-trifluoromethyl-phenyl)-1H-pyrrole-3-carboxylic acid (2-methyl-benzothiazol-6-yl)-amide; MS (ESI) m/z 430 [M+H]$^+$;

2,5-Dimethyl-1-(2-trifluoromethyl-phenyl)-1H-pyrrole-3-carboxylic acid (3-chloro-2-fluoro-phenyl)-amide; MS (ESI) m/z 411 [M+H]$^+$;

2,5-Dimethyl-1-(2-trifluoromethyl-phenyl)-1H-pyrrole-3-carboxylic acid (2-chloro-4,6-dimethoxy-phenyl)-amide; MS (ESI) m/z 453 [M+H]$^+$;

2,5-Dimethyl-1-(2-trifluoromethyl-phenyl)-1H-pyrrole-3-carboxylic acid (2,4,5-trimethyl-phenyl)-amide; MS (ESI) m/z 401 [M+H]$^+$;

2,5-Dimethyl-1-(2-trifluoromethyl-phenyl)-1H-pyrrole-3-carboxylic acid (4-fluoro-3-methoxy-phenyl)-amide; MS (ESI) m/z 407 [M+H]$^+$;

2,5-Dimethyl-1-(2-trifluoromethyl-phenyl)-1H-pyrrole-3-carboxylic acid [2-(4-methyl-benzoyl)-phenyl]-amide; MS (ESI) m/z 477 [M+H]$^+$;

2,5-Dimethyl-1-(2-trifluoromethyl-phenyl)-1H-pyrrole-3-carboxylic acid (2-benzoyl-5-methyl-phenyl)-amide; MS (ESI) m/z 477 [M+H]$^+$;

2,5-Dimethyl-1-(2-trifluoromethyl-phenyl)-1H-pyrrole-3-carboxylic acid [2-(2,2,2-trifluoro-ethoxy)-5-trifluoromethyl-phenyl]-amide; MS (ESI) m/z 525 [M+H]$^+$;

2,5-Dimethyl-1-(2-trifluoromethyl-phenyl)-1H-pyrrole-3-carboxylic acid (2-piperidin-1-yl-5-trifluoromethyl-phenyl)-amide; MS (ESI) m/z 510 [M+H]$^+$;

2,5-Dimethyl-1-(2-trifluoromethyl-phenyl)-1H-pyrrole-3-carboxylic acid (2-benzoyl-4-chloro-phenyl)-amide; MS (ESI) m/z 497 [M+H]$^+$;

2,5-Dimethyl-1-(2-trifluoromethyl-phenyl)-1H-pyrrole-3-carboxylic acid [2-(4-chloro-benzoyl)-phenyl]-amide; MS (ESI) m/z 497 [M+H]$^+$;

2,5-Dimethyl-1-(2-trifluoromethyl-phenyl)-1H-pyrrole-3-carboxylic acid (5-cyclohexyl-2-methoxy-phenyl)-amide; MS (ESI) m/z 471 [M+H]$^+$;

2,5-Dimethyl-1-(2-trifluoromethyl-phenyl)-1H-pyrrole-3-carboxylic acid [2-(2-methoxy-phenoxy)-5-trifluoromethyl-phenyl]-amide; MS (ESI) m/z 549 [M+H]$^+$;

2,5-Dimethyl-1-(2-trifluoromethyl-phenyl)-1H-pyrrole-3-carboxylic acid [2-(4-methoxy-phenoxy)-5-trifluoromethyl-phenyl]-amide; MS (ESI) m/z 549 [M+H]$^+$;

2,5-Dimethyl-1-(2-trifluoromethyl-phenyl)-1H-pyrrole-3-carboxylic acid (4-chloro-2,6-dimethyl-phenyl)-amide; MS (ESI) m/z 421 [M+H]$^+$;

2,5-Dimethyl-1-(2-trifluoromethyl-phenyl)-1H-pyrrole-3-carboxylic acid (2-chloro-4,6-dimethyl-phenyl)-amide; MS (ESI) m/z 421 [M+H]$^+$;

2,5-Dimethyl-1-(2-trifluoromethyl-phenyl)-1H-pyrrole-3-carboxylic acid (5-tert-butyl-2-methoxy-phenyl)-amide; MS (ESI) m/z 445 [M+H]$^+$;

2,5-Dimethyl-1-(2-trifluoromethyl-phenyl)-1H-pyrrole-3-carboxylic acid (4-methoxy-biphenyl-3-yl)-amide; MS (ESI) m/z 465 [M+H]$^+$;

2,5-Dimethyl-1-(2-trifluoromethyl-phenyl)-1H-pyrrole-3-carboxylic acid (2-pyrrol-1-yl-phenyl)-amide; MS (ESI) m/z 424 [M+H]$^+$;

2,5-Dimethyl-1-(2-trifluoromethyl-phenyl)-1H-pyrrole-3-carboxylic acid (2-methoxy-5-trifluoromethyl-phenyl)-amide; MS (ESI) m/z 457 [M+H]$^+$;

2,5-Dimethyl-1-(2-trifluoromethyl-phenyl)-1H-pyrrole-3-carboxylic acid (2-trifluoromethyl-phenyl)-amide; MS (ESI) m/z 427 [M+H]$^+$;

2,5-Dimethyl-1-(2-trifluoromethyl-phenyl)-1H-pyrrole-3-carboxylic acid (5-methoxy-2-methyl-phenyl)-amide; MS (ESI) m/z 403 [M+H]$^+$;

2,5-Dimethyl-1-(2-trifluoromethyl-phenyl)-1H-pyrrole-3-carboxylic acid (4-sec-butyl-phenyl)-amide; MS (ESI) m/z 415 [M+H]$^+$;

2,5-Dimethyl-1-(2-trifluoromethyl-phenyl)-1H-pyrrole-3-carboxylic acid (3-chloro-2,6-diethyl-phenyl)-amide; MS (ESI) m/z 449 [M+H]$^+$;

2,5-Dimethyl-1-(2-trifluoromethyl-phenyl)-1H-pyrrole-3-carboxylic acid (2-chloro-phenyl)-amide; MS (ESI) m/z 393 [M+H]$^+$;

2,5-Dimethyl-1-(2-trifluoromethyl-phenyl)-1H-pyrrole-3-carboxylic acid (2,3,4-trifluoro-phenyl)-amide; MS (ESI) m/z 413 [M+H]$^+$;

2,5-Dimethyl-1-(2-trifluoromethyl-phenyl)-1H-pyrrole-3-carboxylic acid (4-isopropyl-phenyl)-amide; MS (ESI) m/z 401 [M+H]$^+$;

2,5-Dimethyl-1-(2-trifluoromethyl-phenyl)-1H-pyrrole-3-carboxylic acid (4-tert-butyl-phenyl)-amide; MS (ESI) m/z 415 [M+H]$^+$;

2,5-Dimethyl-1-(2-trifluoromethyl-phenyl)-1H-pyrrole-3-carboxylic acid (2-propyl-phenyl)-amide; MS (ESI) m/z 401 [M+H]$^+$;

2-{[2,5-Dimethyl-1-(2-trifluoromethyl-phenyl)-1H-pyrrole-3-carbonyl]-amino}-4-methyl-benzoic acid; MS (ESI) m/z 417 [M+H]$^+$;

2,5-Dimethyl-1-(2-trifluoromethyl-phenyl)-1H-pyrrole-3-carboxylic acid quinolin-5-ylamide; MS (ESI) m/z 410 [M+H]$^+$;

2,5-Dimethyl-1-(2-trifluoromethyl-phenyl)-1H-pyrrole-3-carboxylic acid (4-hydroxy-3-methyl-phenyl)-amide; MS (ESI) m/z 389 [M+H]$^+$;

2,5-Dimethyl-1-(2-trifluoromethyl-phenyl)-1H-pyrrole-3-carboxylic acid (4-bromo-2-ethyl-phenyl)-amide; MS (ESI) m/z 465 [M+H]$^+$;

2,5-Dimethyl-1-(2-trifluoromethyl-phenyl)-1H-pyrrole-3-carboxylic acid (8-hydroxy-quinolin-5-yl)-amide; MS (ESI) m/z 426 [M+H]$^+$;

2,5-Dimethyl-1-(2-trifluoromethyl-phenyl)-1H-pyrrole-3-carboxylic acid (4-sulfamoyl-phenyl)-amide; MS (ESI) m/z 438 [M+H]$^+$;

2,5-Dimethyl-1-(2-trifluoromethyl-phenyl)-1H-pyrrole-3-carboxylic acid (4-imidazol-1-yl-phenyl)-amide; MS (ESI) m/z 425 [M+H]$^+$;

2-{[2,5-Dimethyl-1-(2-trifluoromethyl-phenyl)-1H-pyrrole-3-carbonyl]-amino}-nicotinic acid; MS (ESI) m/z 404 [M+H]$^+$;

2,5-Dimethyl-1-(2-trifluoromethyl-phenyl)-1H-pyrrole-3-carboxylic acid {4-[2-(2-chloro-phenylcarbamoyl)-acetyl]-phenyl}-amide; MS (ESI) m/z 554 [M+H]$^+$;

2,5-Dimethyl-1-(2-trifluoromethyl-phenyl)-1H-pyrrole-3-carboxylic acid [3-(3-methyl-2-oxo-imidazolidin-1-yl)-phenyl]-amide; MS (ESI) m/z 457 [M+H]$^+$;

2,5-Dimethyl-1-(2-trifluoromethyl-phenyl)-1H-pyrrole-3-carboxylic acid [4-(pyrimidin-2-ylsulfamoyl)-phenyl]-amide; MS (ESI) m/z 516 [M+H]$^+$;

2,5-Dimethyl-1-(2-trifluoromethyl-phenyl)-1H-pyrrole-3-carboxylic acid [4-(3,5-dimethyl-pyrazol-1-yl)-phenyl]-amide; MS (ESI) m/z 453 [M+H]$^+$; 5-Chloro-4-{[2,5-dimethyl-1-(2-trifluoromethyl-phenyl)-1H-pyrrole-3-carbonyl]-amino}-2-methoxy-benzoic acid; MS (ESI) m/z 467 [M+H]$^+$;

2,5-Dimethyl-1-(2-trifluoromethyl-phenyl)-1H-pyrrole-3-carboxylic acid [4-((E)-2-pyridin-2-yl-vinyl)-phenyl]-amide; MS (ESI) m/z 462 [M+H]$^+$;

2,5-Dimethyl-1-(2-trifluoromethyl-phenyl)-1H-pyrrole-3-carboxylic acid [4-(thiazol-2-ylsulfamoyl)-phenyl]-amide; MS (ESI) m/z 521 [M+H]$^+$;

2,5-Dimethyl-1-(2-trifluoromethyl-phenyl)-1H-pyrrole-3-carboxylic acid [4-(morpholine-4-sulfonyl)-phenyl]-amide; MS (ESI) m/z 508 [M+H]$^+$;

2,5-Dimethyl-1-(2-trifluoromethyl-phenyl)-1H-pyrrole-3-carboxylic acid (4-ethoxy-phenyl)-amide; MS (ESI) m/z 403 [M+H]$^+$;

2,5-Dimethyl-1-(2-trifluoromethyl-phenyl)-1H-pyrrole-3-carboxylic acid (2-methoxy-phenyl)-amide; MS (ESI) m/z 389 [M+H]⁺;

2,5-Dimethyl-1-(2-trifluoromethyl-phenyl)-1H-pyrrole-3-carboxylic acid (4-trifluoromethoxy-phenyl)-amide; MS (ESI) m/z 443 [M+H]⁺;

2,5-Dimethyl-1-(2-trifluoromethyl-phenyl)-1H-pyrrole-3-carboxylic acid (2,4-dimethyl-phenyl)-amide; MS (ESI) m/z 387 [M+H]⁺;

2,5-Dimethyl-1-(2-trifluoromethyl-phenyl)-1H-pyrrole-3-carboxylic acid (4-chloro-2-methyl-phenyl)-amide; MS (ESI) m/z 407 [M+H]⁺;

2,5-Dimethyl-1-(2-trifluoromethyl-pheny)-1H-pyrrole-3-carboxylic acid (3-fluoro-phenyl)-amide; MS (ESI) m/z 377 [M+H]⁺;

2,5-Dimethyl-1-(2-trifluoromethyl-phenyl)-1H-pyrrole-3-carboxylic acid (3-methoxy-phenyl)-amide; MS (ESI) m/z 389 [M+H]⁺;

2,5-Dimethyl-1-(2-trifluoromethyl-phenyl)-1H-pyrrole-3-carboxylic acid (3,5-dimethyl-phenyl)-amide; MS (ESI) m/z 387 [M+H]⁺;

2,5-Dimethyl-1-(2-trifluoromethyl-phenyl)-1H-pyrrole-3-carboxylic acid (2-fluoro-3-trifluoromethyl-phenyl)-amide; MS (ESI) m/z 445 [M+H]*;

2,5-Dimethyl-1-(2-trifluoromethyl-phenyl)-1H-pyrrole-3-carboxylic acid (2-chloro-5-trifluoromethyl-phenyl)-amide; MS (ESI) m/z 461 [M+H]⁺;

2,5-Dimethyl-1-(2-trifluoromethyl-phenyl)-1H-pyrrole-3-carboxylic acid isoxazol-3-ylamide; MS (ESI) m/z 350 [M+H]⁺;

2,5-Dimethyl-1-(2-trifluoromethyl-phenyl)-1H-pyrrole-3-carboxylic acid (5-chloro-2-methyl-phenyl)-amide; MS (ESI) m/z 407 [M+H]⁺;

2,5-Dimethyl-1-(2-trifluoromethyl-phenyl)-1H-pyrrole-3-carboxylic acid (4-bromo-phenyl)-amide; MS (ESI) m/z 437 [M+H]⁺;

2,5-Dimethyl-1-(2-trifluoromethyl-phenyl)-1H-pyrrole-3-carboxylic acid (3-phenoxy-phenyl)-amide; MS (ESI) m/z 451 [M+H]⁺;

2,5-Dimethyl-1-(2-trifluoromethyl-phenyl)-1H-pyrrole-3-carboxylic acid (3-chloro-4-fluoro-phenyl)-amide; MS (ESI) m/z 411 [M+H]⁺;

2,5-Dimethyl-1-(2-trifluoromethyl-phenyl)-1H-pyrrole-3-carboxylic acid (2,3,5,6-tetrafluoro-phenyl)-amide; MS (ESI) m/z 431 [M+H]⁺;

2,5-Dimethyl-1-(2-trifluoromethyl-phenyl)-1H-pyrrole-3-carboxylic acid (3,4-dimethyl-phenyl)-amide; MS (ESI) m/z 387 [M+H]⁺;

2,5-Dimethyl-1-(2-trifluoromethyl-phenyl)-1H-pyrrole-3-carboxylic acid (3-chloro-4-methoxy-phenyl)-amide; MS (ESI) m/z 423 [M+H]⁺;

2,5-Dimethyl-1-(2-trifluoromethyl-phenyl)-1H-pyrrole-3-carboxylic acid (5-chloro-2-methoxy-phenyl)-amide; MS (ESI) m/z 423 [M+H]⁺;

2,5-Dimethyl-1-(2-trifluoromethyl-phenyl)-1H-pyrrole-3-carboxylic acid (4-methoxy-phenyl)-amide; MS (ESI) m/z 389 [M+H]⁺;

2,5-Dimethyl-1-(2-trifluoromethyl-phenyl)-1H-pyrrole-3-carboxylic acid (3,4,5-trimethoxy-phenyl)-amide; MS (ESI) m/z 449 [M+H]⁺;

2,5-Dimethyl-1-(2-trifluoromethyl-phenyl)-1H-pyrrole-3-carboxylic acid (2-chloro-5-methoxy-phenyl)-amide; MS (ESI) m/z 423 [M+H]⁺;

2,5-Dimethyl-1-(2-trifluoromethyl-phenyl)-1H-pyrrole-3-carboxylic acid (3,4-dichloro-phenyl)-amide; MS (ESI) m/z 427 [M+H]⁺;

2,5-Dimethyl-1-(2-trifluoromethyl-phenyl)-1H-pyrrole-3-carboxylic acid (5-chloro-pyridin-2-yl)-amide; MS (ESI) m/z 394 [M+H]⁺;

2,5-Dimethyl-1-(2-trifluoromethyl-phenyl)-1H-pyrrole-3-carboxylic acid benzo[1,3]dioxol-5-ylamide; MS (ESI) m/z 403 [M+H]⁺;

2-{[2,5-Dimethyl-1-(2-trifluoromethyl-phenyl)-1H-pyrrole-3-carbonyl]-amino}-benzoic acid ethyl ester; MS (ESI) m/z 431 [M+H]⁺;

2,5-Dimethyl-1-(2-trifluoromethyl-phenyl)-1H-pyrrole-3-carboxylic acid quinolin-8-ylamide; MS (ESI) m/z 410 [M+H]⁺;

2,5-Dimethyl-1-(2-trifluoromethyl-phenyl)-1H-pyrrole-3-carboxylic acid (2,5-dimethyl-phenyl)-amide; MS (ESI) m/z 387 [M+H]⁺;

2,5-Dimethyl-1-(2-trifluoromethyl-phenyl)-1H-pyrrole-3-carboxylic acid (3,4-dimethoxy-phenyl)-amide; MS (ESI) m/z 419 [M+H]⁺;

2,5-Dimethyl-1-(2-trifluoromethyl-phenyl)-1H-pyrrole-3-carboxylic acid (4-bromo-2-methyl-phenyl)-amide; MS (ESI) m/z 451 [M+H]⁺;

2,5-Dimethyl-1-(2-trifluoromethyl-phenyl)-1H-pyrrole-3-carboxylic acid naphthalen-1-ylamide; MS (ESI) m/z 409 [M+H]⁺;

2,5-Dimethyl-1-(2-trifluoromethyl-phenyl)-1H-pyrrole-3-carboxylic acid (3,5-dimethoxy-phenyl)-amide; MS (ESI) m/z 419 [M+H]⁺;

2,5-Dimethyl-1-(2-trifluoromethyl-phenyl)-1H-pyrrole-3-carboxylic acid (4-fluoro-2-trifluoromethyl-phenyl)-amide; MS (ESI) m/z 445 [M+H]⁺;

2,5-Dimethyl-1-(2-trifluoromethyl-phenyl)-1H-pyrrole-3-carboxylic acid (5-methyl-isoxazol-3-yl)-amide; MS (ESI) m/z 364 [M+H]⁺;

2-{[2,5-Dimethyl-1-(2-trifluoromethyl-phenyl)-1H-pyrrole-3-carbonyl]-amino}-3-methyl-benzoic acid; MS (ESI) m/z 417 [M+H]⁺;

2,5-Dimethyl-1-(2-trifluoromethyl-phenyl)-1H-pyrrole-3-carboxylic acid (1H-indol-5-yl)-amide; MS (ESI) m/z 398 [M+H]⁺;

2,5-Dimethyl-1-(2-trifluoromethyl-phenyl)-1H-pyrrole-3-carboxylic acid (4-fluoro-3-nitro-phenyl)-amide; MS (ESI) m/z 422 [M+H]⁺;

4-{[2,5-Dimethyl-1-(2-trifluoromethyl-phenyl)-1H-pyrrole-3-carbonyl]-amino}-benzoic acid pentyl ester; MS (ESI) m/z 473 [M+H]⁺;

2,5-Dimethyl-1-(2-trifluoromethyl-phenyl)-1H-pyrrole-3-carboxylic acid (2,4,5-trifluoro-phenyl)-amide; MS (ESI) m/z 413 [M+H]⁺;

2,5-Dimethyl-1-(2-trifluoromethyl-phenyl)-1H-pyrrole-3-carboxylic acid (4-bromo-2-chloro-phenyl)-amide; MS (ESI) m/z 471 [M+H]⁺;

2,5-Dimethyl-1-(2-trifluoromethyl-phenyl)-1H-pyrrole-3-carboxylic acid (3-acetyl-phenyl)-amide; MS (ESI) m/z 401 [M+H]⁺;

2,5-Dimethyl-1-(2-trifluoromethyl-phenyl)-1H-pyrrole-3-carboxylic acid (4-acetyl-phenyl)-amide; MS (ESI) m/z 401 [M+H]⁺;

2-{[2,5-Dimethyl-1-(2-trifluoromethyl-phenyl)-1H-pyrrole-3-carbonyl]-amino}-5-methyl-benzoic acid; MS (ESI) m/z 417 [M+H]⁺;

2,5-Dimethyl-1-(2-trifluoromethyl-phenyl)-1H-pyrrole-3-carboxylic acid (6-methyl-benzothiazol-2-yl)-amide; MS (ESI) m/z 430 [M+H]⁺;

2,5-Dimethyl-1-(2-trifluoromethyl-phenyl)-1H-pyrrole-3-carboxylic acid (4-hydroxy-5-isopropyl-2-methyl-phenyl)-amide; MS (ESI) m/z 431 [M+H]⁺;

2,5-Dimethyl-1-(2-trifluoromethyl-phenyl)-1H-pyrrole-3-carboxylic acid (2-acetyl-phenyl)-amide; MS (ESI) m/z 401 [M+H]+;

2,5-Dimethyl-1-(2-trifluoromethyl-phenyl)-1H-pyrrole-3-carboxylic acid (4-fluoro-3-trifluoromethyl-phenyl)-amide; MS (ESI) m/z 445 [M+H]+;

2,5-Dimethyl-1-(2-trifluoromethyl-phenyl)-1H-pyrrole-3-carboxylic acid (4-nitro-phenyl)-amide; MS (ESI) m/z 404 [M+H]+;

2,5-Dimethyl-1-(2-trifluoromethyl-phenyl)-1H-pyrrole-3-carboxylic acid (2-trifluoromethoxy-phenyl)-amide; MS (ESI) m/z 443 [M+H]+;

2,5-Dimethyl-1-(2-trifluoromethyl-phenyl)-1H-pyrrole-3-carboxylic acid (2,3-dimethyl-phenyl)-amide; MS (ESI) m/z 387 [M+H]+;

2,5-Dimethyl-1-(2-trifluoromethyl-phenyl)-1H-pyrrole-3-carboxylic acid (5-methylsulfanyl-[1,3,4]thiadiazol-2-yl)-amide; MS (ESI) m/z 413 [M+H]+;

2,5-Dimethyl-1-(2-trifluoromethyl-phenyl)-1H-pyrrole-3-carboxylic acid (3-methyl-isothiazol-5-yl)-amide; MS (ESI) m/z 380 [M+H]+;

2,5-Dimethyl-1-(2-trifluoromethyl-phenyl)-1H-pyrrole-3-carboxylic acid (6-acetyl-benzo[1,3]dioxol-5-yl)-amide; MS (ESI) m/z 445 [M+H]+;

2,5-Dimethyl-1-(2-trifluoromethyl-phenyl)-1H-pyrrole-3-carboxylic acid thiazol-2-ylamide; MS (ESI) m/z 366 [M+H]+;

2,5-Dimethyl-1-(2-trifluoromethyl-phenyl)-1H-pyrrole-3-carboxylic acid pyridin-4-ylamide; MS (ESI) m/z 360 [M+H]+;

2,5-Dimethyl-1-(2-trifluoromethyl-phenyl)-1H-pyrrole-3-carboxylic acid (4-chloro-benzothiazol-2-yl)-amide; MS (ESI) m/z 450 [M+H]+;

2,5-Dimethyl-1-(2-trifluoromethyl-phenyl)-1H-pyrrole-3-carboxylic acid (2,3-dichloro-phenyl)-amide; MS (ESI) m/z 427 [M+H]+;

2,5-Dimethyl-1-(2-trifluoromethyl-phenyl)-1H-pyrrole-3-carboxylic acid (4-methyl-thiazol-2-yl)-amide; MS (ESI) m/z 380 [M+H]+;

2,5-Dimethyl-1-(2-trifluoromethyl-phenyl)-1H-pyrrole-3-carboxylic acid (5-ethylsulfanyl-[1,3,4]thiadiazol-2-yl)-amide; MS (ESI) m/z 427 [M+H]+;

2,5-Dimethyl-1-(2-trifluoromethyl-phenyl)-1H-pyrrole-3-carboxylic acid (2-methyl-benzothiazol-5-yl)-amide; MS (ESI) m/z 430 [M+H]+;

2,5-Dimethyl-1-(2-trifluoromethyl-phenyl)-1H-pyrrole-3-carboxylic acid [1,3,4]thiadiazol-2-ylamide; MS (ESI) m/z 367 [M+H]+;

5-{[2,5-Dimethyl-1-(2-trifluoromethyl-phenyl)-1H-pyrrole-3-carbonyl]-amino}-[1,3,4]thiadiazole-2-carboxylic acid ethyl ester; MS (ESI) m/z 439 [M+H]+;

2,5-Dimethyl-1-(2-trifluoromethyl-phenyl)-1H-pyrrole-3-carboxylic acid (1-methyl-1H-benzoimidazol-2-yl)-amide; MS (ESI) m/z 413 [M+H]+;

2,5-Dimethyl-1-(2-trifluoromethyl-phenyl)-1H-pyrrole-3-carboxylic acid (4-benzoylamino-2-methoxy-5-methyl-phenyl)-amide; MS (ESI) m/z 522 [M+H]+;

2,5-Dimethyl-1-(2-trifluoromethyl-phenyl)-1H-pyrrole-3-carboxylic acid (5-tert-butyl-isoxazol-3-yl)-amide; MS (ESI) m/z 406 [M+H]+;

2,5-Dimethyl-1-(2-trifluoromethyl-phenyl)-1H-pyrrole-3-carboxylic acid quinolin-2-ylamide; MS (ESI) m/z 410 [M+H]+;

2,5-Dimethyl-1-(2-trifluoromethyl-phenyl)-1H-pyrrole-3-carboxylic acid isoquinolin-3-ylamide; MS (ESI) m/z 410 [M+H]+;

2,5-Dimethyl-1-(2-trifluoromethyl-phenyl)-1H-pyrrole-3-carboxylic acid (2-acetyl-5-phenyl-thiophen-3-yl)-amide; MS (ESI) m/z 483 [M+H]+;

3-{[2,5-Dimethyl-1-(2-trifluoromethyl-phenyl)-1H-pyrrole-3-carbonyl]-amino}-5-(4-fluoro-phenyl)-thiophene-2-carboxylic acid methyl ester; MS (ESI) m/z 517 [M+H]+;

(2-{[2,5-Dimethyl-1-(2-trifluoromethyl-phenyl)-1H-pyrrole-3-carbonyl]-amino}-thiazol-4-yl)-acetic acid ethyl ester; MS (ESI) m/z 452 [M+H]+;

2-{[2,5-Dimethyl-1-(2-trifluoromethyl-phenyl)-1H-pyrrole-3-carbonyl]-amino}-4,5,6,7-tetrahydro-benzo[b]thiophene-3-carboxylic acid ethyl ester; MS (ESI) m/z 491 [M+H]+;

2,5-Dimethyl-1-(2-trifluoromethyl-phenyl)-1H-pyrrole-3-carboxylic acid (2-oxo-4-trifluoromethyl-2H-chromen-7-yl)-amide; MS (ESI) m/z 495 [M+H]+;

2,5-Dimethyl-1-(2-trifluoromethyl-phenyl)-1H-pyrrole-3-carboxylic acid (3-chloro-4-hydroxy-phenyl)-amide; MS (ESI) m/z 409 [M+H]+;

2,5-Dimethyl-1-(2-trifluoromethyl-phenyl)-1H-pyrrole-3-carboxylic acid (5-chloro-2-hydroxy-phenyl)-amide; MS (ESI) m/z 409 [M+H]+;

2,5-Dimethyl-1-(2-trifluoromethyl-phenyl)-1H-pyrrole-3-carboxylic acid methyl-phenyl-amide; MS (ESI) m/z 373 [M+H]+;

2,5-Dimethyl-1-(2-trifluoromethyl-phenyl)-1H-pyrrole-3-carboxylic acid biphenyl-4-ylamide; MS (ESI) m/z 435 [M+H]+;

(2,3-Dihydro-indol-1-yl)-[2,5-dimethyl-1-(2-trifluoromethyl-phenyl)-1H-pyrrol-3-yl]-methanone; MS (ESI) m/z 385 [M+H]+;

2,5-Dimethyl-1-(2-trifluoromethyl-phenyl)-1H-pyrrole-3-carboxylic acid (2,4-dimethoxy-phenyl)-amide; MS (ESI) m/z 419 [M+H]+;

2,5-Dimethyl-1-(2-trifluoromethyl-phenyl)-1H-pyrrole-3-carboxylic acid ethyl-(2-trifluoromethoxy-phenyl)-amide; MS (ESI) m/z 471 [M+H]+;

2,5-Dimethyl-1-(2-trifluoromethyl-phenyl)-1H-pyrrole-3-carboxylic acid (3-carbamoyl-phenyl)-amide; MS (ESI) m/z 402 [M+H]+;

2,5-Dimethyl-1-(2-trifluoromethyl-phenyl)-1H-pyrrole-3-carboxylic acid (4-cyanomethyl-phenyl)-amide; MS (ESI) m/z 398 [M+H]+;

5-Bromo-2-=[2,5-dimethyl-1-(2-trifluoromethyl-phenyl)-1H-pyrrole-3-carbonyl]-amino)-benzoic acid methyl ester; MS (ESI) m/z 495 [M+H]+;

2,5-Dimethyl-1-(2-trifluoromethyl-phenyl)-1H-pyrrole-3-carboxylic acid ethyl-m-tolyl-amide; MS (ESI) m/z 401 [M+H]+;

2,5-Dimethyl-1-(2-trifluoromethyl-phenyl)-1H-pyrrole-3-carboxylic acid (4-cyano-phenyl)-amide; MS (ESI) m/z 384 [M+H]+;

2,5-Dimethyl-1-(2-trifluoromethyl-phenyl)-1H-pyrrole-3-carboxylic acid (2-sulfamoyl-phenyl)-amide; MS (ESI) m/z 438 [M+H]+;

2,5-Dimethyl-1-(2-trifluoromethyl-phenyl)-1H-pyrrole-3-carboxylic acid (2-cyano-phenyl)-amide; MS (ESI) m/z 384 [M+H]+;

(3,4-Dihydro-2H-quinolin-1-yl)-[2,5-dimethyl-1-(2-trifluoromethyl-phenyl)-1H-pyrrol-3-yl]-methanone; MS (ESI) m/z 399 [M+H]+;

2,5-Dimethyl-1-(2-trifluoromethyl-phenyl)-1H-pyrrole-3-carboxylic acid o-tolylamide; MS (ESI) m/z 373 [M+H]+;

2,5-Dimethyl-1-(2-trifluoromethyl-phenyl)-1H-pyrrole-3-carboxylic acid (4-trifluoromethyl-phenyl)-amide; MS (ESI) m/z 427 [M+H]+;

2,5-Dimethyl-1-(2-trifluoromethyl-phenyl)-1H-pyrrole-3-carboxylic acid propyl-m-tolyl-amide; MS (ESI) m/z 415 [M+H]+;

2,5-Dimethyl-1-(2-trifluoromethyl-phenyl)-1H-pyrrole-3-carboxylic acid ethyl-(5-hydroxy-2-methyl-phenyl)-amide; MS (ESI) m/z 417 [M+H]+;

2,5-Dimethyl-1-(2-trifluoromethyl-phenyl)-1H-pyrrole-3-carboxylic acid acetyl-(3-ethylamino-4-methyl-phenyl)-amide; MS (ESI) m/z 458 [M+H]+;

(5-Bromo-2,3-dihydro-indol-1-yl)-[2,5-dimethyl-1-(2-trifluoromethyl-phenyl)-1H-pyrrol-3-yl]-methanone; MS (ESI) m/z 463 [M+H]+;

2,5-Dimethyl-1-(2-trifluoromethyl-phenyl)-1H-pyrrole-3-carboxylic acid ethyl-o-tolyl-amide; MS (ESI) m/z 401 [M+H]+;

4-{Butyl-[2,5-dimethyl-1-(2-trifluoromethyl-phenyl)-1H-pyrrole-3-carbonyl]-amino}-benzoic acid ethyl ester; MS (ESI) m/z 487 [M+H]+;

2,5-Dimethyl-1-(2-trifluoromethyl-phenyl)-1H-pyrrole-3-carboxylic acid (2-chloro-pyridin-4-yl)-amide; MS (ESI) m/z 394 [M+H]+;

2,5-Dimethyl-1-(2-trifluoromethyl-phenyl)-1H-pyrrole-3-carboxylic acid pyrimidin-4-ylamide; MS (ESI) m/z 361 [M+H]+;

2,5-Dimethyl-1-(2-trifluoromethyl-phenyl)-1H-pyrrole-3-carboxylic acid (3,4-dimethyl-isoxazol-5-yl)-amide; MS (ESI) m/z 378 [M+H]+;

2,5-Dimethyl-1-(2-trifluoromethyl-phenyl)-1H-pyrrole-3-carboxylic acid (2,5-dimethyl-2H-pyrazol-3-yl)-amide; MS (ESI) m/z 377 [M+H]+;

3-{[2,5-Dimethyl-1-(2-trifluoromethyl-phenyl)-1H-pyrrole-3-carbonyl]-amino}-thiophene-2-carboxylic acid methyl ester; MS (ESI) m/z 423 [M+H]+;

2,5-Dimethyl-1-(2-trifluoromethyl-phenyl)-1H-pyrrole-3-carboxylic acid (3-methyl-isoxazol-5-yl)-amide; MS (ESI) m/z 364 [M+H]+;

2,5-Dimethyl-1-(2-trifluoromethyl-phenyl)-1H-pyrrole-3-carboxylic acid (3-chloro-4-cyano-phenyl)-amide; MS (ESI) m/z 418 [M+H]+;

2,5-Dimethyl-1-(2-trifluoromethyl-phenyl)-1H-pyrrole-3-carboxylic acid (1H-indazol-6-yl)-amide; MS (ESI) m/z 399 [M+H]+;

2,5-Dimethyl-1-(2-trifluoromethyl-phenyl)-1H-pyrrole-3-carboxylic acid (4-carbazol-9-yl-phenyl)-amide; MS (ESI) m/z 524 [M+H]+;

2,5-Dimethyl-1-(2-trifluoromethyl-phenyl)-1H-pyrrole-3-carboxylic acid (4-acetylsulfamoyl-phenyl)-amide; MS (ESI) m/z 480 [M+H]+;

2,5-Dimethyl-1-(2-trifluoromethyl-phenyl)-1H-pyrrole-3-carboxylic acid (4-ureidosulfonyl-phenyl)-amide; MS (ESI) m/z 481 [M+H]+;

2,5-Dimethyl-1-(2-trifluoromethyl-phenyl)-1H-pyrrole-3-carboxylic acid (4-phenyl-thiazol-2-yl)-amide; MS (ESI) m/z 442 [M+H]+;

2,5-Dimethyl-1-(2-trifluoromethyl-phenyl)-1H-pyrrole-3-carboxylic acid (4-carbamoyl-phenyl)-amide; MS (ESI) m/z 402 [M+H]+;

2,5-Dimethyl-1-(2-trifluoromethyl-phenyl)-1H-pyrrole-3-carboxylic acid (2-mercapto-benzothiazol-6-yl)-amide; MS (ESI) m/z 448 [M+H]+;

2,5-Dimethyl-1-(2-trifluoromethyl-phenyl)-1H-pyrrole-3-carboxylic acid (4-bromo-3-fluoro-phenyl)-amide; MS (ESI) m/z 455 [M+H]+;

2,5-Dimethyl-1-(2-trifluoromethyl-phenyl)-1H-pyrrole-3-carboxylic acid (2-methoxy-pyridin-3-yl)-amide; MS (ESI) m/z 390 [M+H]+;

2,5-Dimethyl-1-(2-trifluoromethyl-phenyl)-1H-pyrrole-3-carboxylic acid (6-ethyl-pyridin-2-yl)-amide; MS (ESI) m/z 388 [M+H]+;

2,5-Dimethyl-1-(2-trifluoromethyl-phenyl)-1H-pyrrole-3-carboxylic acid (1-bromo-isoquinolin-3-yl)-amide; MS (ESI) m/z 488 [M+H]+;

2,5-Dimethyl-1-(2-trifluoromethyl-phenyl)-1H-pyrrole-3-carboxylic acid (2-cyano-5-methyl-phenyl)-amide; MS (ESI) m/z 398 [M+H]+;

2,5-Dimethyl-1-(2-trifluoromethyl-phenyl)-1H-pyrrole-3-carboxylic acid (6-trifluoromethyl-pyridin-3-yl)-amide; MS (ESI) m/z 428 [M+H]+;

2,5-Dimethyl-1-(2-trifluoromethyl-phenyl)-1H-pyrrole-3-carboxylic acid (4'-fluoro-biphenyl-3-yl)-amide; MS (ESI) m/z 453 [M+H]+;

2,5-Dimethyl-1-(2-trifluoromethyl-phenyl)-1H-pyrrole-3-carboxylic acid (3'-fluoro-biphenyl-4-yl)-amide; MS (ESI) m/z 453 [M+H]+;

2,5-Dimethyl-1-(2-trifluoromethyl-phenyl)-1H-pyrrole-3-carboxylic acid [4-(4-fluoro-phenyl)-thiazol-2-yl]-amide; MS (ESI) m/z 460 [M+H]+;

2,5-Dimethyl-1-(2-trifluoromethyl-phenyl)-1H-pyrrole-3-carboxylic acid (1,3-dihydro-isobenzofuran-5-yl)-amide; MS (ESI) m/z 401 [M+H]+;

2,5-Dimethyl-1-(2-trifluoromethyl-phenyl)-1H-pyrrole-3-carboxylic acid [5-(4-fluoro-phenyl)-2H-pyrazol-3-yl]-amide; MS (ESI) m/z 443 [M+H]+;

2,5-Dimethyl-1-(2-trifluoromethyl-phenyl)-1H-pyrrole-3-carboxylic acid (3-benzyl-phenyl)-amide; MS (ESI) m/z 449 [M+H]+;

2-{[2,5-Dimethyl-1-(2-trifluoromethyl-phenyl)-1H-pyrrole-3-carbonyl]-amino}-5-methyl-4-phenyl-thiophene-3-carboxylic acid ethyl ester; MS (ESI) m/z 527 [M+H]+;

2,5-Dimethyl-1-(2-trifluoromethyl-phenyl)-1H-pyrrole-3-carboxylic acid (9-ethyl-9H-carbazol-3-yl)-amide; MS (ESI) m/z 476 [M+H]+;

2,5-Dimethyl-1-(2-trifluoromethyl-phenyl)-1H-pyrrole-3-carboxylic acid (4-methyl-5-phenyl-2H-pyrazol-3-yl)-amide; MS (ESI) m/z 439 [M+H]+;

2,5-Dimethyl-1-(2-trifluoromethyl-phenyl)-1H-pyrrole-3-carboxylic acid (1-methyl-1H-[1,2,4]triazol-3-yl)-amide; MS (ESI) m/z 364 [M+H]+;

2,5-Dimethyl-1-(2-trifluoromethyl-phenyl)-1H-pyrrole-3-carboxylic acid [4-(4-chloro-phenoxy)-phenyl]-amide; MS (ESI) m/z 485 [M+H]+;

2,5-Dimethyl-1-(2-trifluoromethyl-phenyl)-1H-pyrrole-3-carboxylic acid (4-bromo-5-methyl-isoxazol-3-yl)-amide; MS (ESI) m/z 442 [M+H]+;

2,5-Dimethyl-1-(2-trifluoromethyl-phenyl)-1H-pyrrole-3-carboxylic acid [6-(4-tert-butyl-phenoxy)-pyridin-3-0]-amide; MS (ESI) m/z 508 [M+H]+;

3-{[2,5-Dimethyl-1-(2-trifluoromethyl-phenyl)-1H-pyrrole-3-carbonyl]-amino}-5-phenyl-thiophene-2-carboxylic acid methyl ester; MS (ESI) m/z 499 [M+H]+;

2-{[2,5-Dimethyl-1-(2-trifluoromethyl-phenyl)-1H-pyrrole-3-carbonyl]-amino}-4-furan-2-yl-thiophene-3-carboxylic acid ethyl ester; MS (ESI) m/z 503 [M+H]+;

2,5-Dimethyl-1-(2-trifluoromethyl-phenyl)-1H-pyrrole-3-carboxylic acid (4-butyl-2-methyl-phenyl)-amide; MS (ESI) m/z 429 [M+H]+;

2,5-Dimethyl-1-(2-trifluoromethyl-phenyl)-1H-pyrrole-3-carboxylic acid (4-chloro-3-methyl-phenyl)-amide; MS (ESI) m/z 407 [M+H]+;

2,5-Dimethyl-1-(2-trifluoromethyl-phenyl)-1H-pyrrole-3-carboxylic acid (4-bromo-3-chloro-phenyl)-amide; MS (ESI) m/z 471 [M+H]+;

2,5-Dimethyl-1-(2-trifluoromethyl-phenyl)-1H-pyrrole-3-carboxylic acid (5-methyl-1H-pyrazol-3-yl)-amide; MS (ESI) m/z 363 [M+H]+;

2,5-Dimethyl-1-(2-trifluoromethyl-phenyl)-1H-pyrrole-3-carboxylic acid (6-methoxy-benzothiazol-2-yl)-amide; MS (ESI) m/z 446 [M+H]+;

2,5-Dimethyl-1-(2-trifluoromethyl-phenyl)-1H-pyrrole-3-carboxylic acid (6-chloro-pyridin-3-yl)-amide; MS (ESI) m/z 394 [M+H]+;

2,5-Dimethyl-1-(2-trifluoromethyl-phenyl)-1H-pyrrole-3-carboxylic acid quinolin-3-ylamide; MS (ESI) m/z 410 [M+H]+;

2,5-Dimethyl-1-(2-trifluoromethyl-phenyl)-1H-pyrrole-3-carboxylic acid (4,6-dimethyl-pyridin-2-yl)-amide; MS (ESI) m/z 388 [M+H]+;

2,5-Dimethyl-1-(2-trifluoromethyl-phenyl)-1H-pyrrole-3-carboxylic acid (6-ethoxy-benzothiazol-2-yl)-amide; MS (ESI) m/z 460 [M+H]+;

2,5-Dimethyl-1-(2-trifluoromethyl-phenyl)-1H-pyrrole-3-carboxylic acid (6-methoxy-pyridin-3-yl)-amide; MS (ESI) m/z 390 [M+H]+;

2,5-Dimethyl-1-(2-trifluoromethyl-phenyl)-1H-pyrrole-3-carboxylic acid (3-trifluoromethoxy-phenyl)-amide; MS (ESI) m/z 443 [M+H]+;

2,5-Dimethyl-1-(2-trifluoromethyl-phenyl)-1H-pyrrole-3-carboxylic acid (2-methoxy-4-nitro-phenyl)-amide; MS (ESI) m/z 434 [M+H]+;

2,5-Dimethyl-1-(2-trifluoromethyl-phenyl)-1H-pyrrole-3-carboxylic acid (2-hydroxy-5-nitro-phenyl)-amide; MS (ESI) m/z 420 [M+H]+;

2,5-Dimethyl-1-(2-trifluoromethyl-phenyl)-1H-pyrrole-3-carboxylic acid (5-tert-butyl-2-hydroxy-phenyl)-amide; MS (ESI) m/z 431 [M+H]+;

2,5-Dimethyl-1-(2-trifluoromethyl-phenyl)-1H-pyrrole-3-carboxylic acid (3-mercapto-phenyl)-amide; MS (ESI) m/z 391 [M+H]+;

2,5-Dimethyl-1-(2-trifluoromethyl-phenyl)-1H-pyrrole-3-carboxylic acid [4-(4-nitro-phenylsulfanyl)-phenyl]-amide; MS (ESI) m/z 512 [M+H]+;

2,5-Dimethyl-1-(2-trifluoromethyl-phenyl)-1H-pyrrole-3-carboxylic acid (4-nitro-3-trifluoromethyl-phenyl)-amide; MS (ESI) m/z 472 [M+H]+;

2,5-Dimethyl-1-(2-trifluoromethyl-phenyl)-1H-pyrrole-3-carboxylic acid (2-methyl-5-phenyl-2H-pyrazol-3-yl)-amide; MS (ESI) m/z 439 [M+H]+;

2,5-Dimethyl-1-(2-trifluoromethyl-phenyl)-1H-pyrrole-3-carboxylic acid (1,3,5-trimethyl-1H-pyrazol-4-yl)-amide; MS (ESI) m/z 391 [M+H]+;

2,5-Dimethyl-1-(2-trifluoromethyl-phenyl)-1H-pyrrole-3-carboxylic acid (4-pyrazol-1-yl-phenyl)-amide; MS (ESI) m/z 425 [M+H]+;

2,5-Dimethyl-1-(2-trifluoromethyl-phenyl)-1H-pyrrole-3-carboxylic acid (3,4-dicyano-phenyl)-amide; MS (ESI) m/z 409 [M+H]+;

2,5-Dimethyl-1-(2-trifluoromethyl-phenyl)-1H-pyrrole-3-carboxylic acid (5-methoxy-2-methyl-4-nitro-phenyl)-amide; MS (ESI) m/z 448 [M+H]+; and 2,5-Dimethyl-1-(2-trifluoromethyl-phenyl)-1H-pyrrole-3-carboxylic acid [2-methoxy-5-(1-methyl-1-phenyl-ethyl)-phenyl]-amide; MS (ESI) m/z 507 [M+H]+.

Example 3

PREPARATION OF 2,5-DIMETHYL-1-(2-TRIFLUOROMETHYL-PHENYL)-1H-PYRROLE-3-CARBOXYLIC ACID [4-(4-FLUOROBENZOYL)-PHENYL]-AMIDE

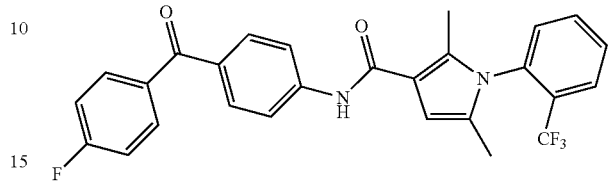

A. A solution of tin (II) chloride dihydrate (1.05 g, 4.7 mmol) in conc hydrochloric acid (4.2 mL) was added to 4-fluoro-4'-nitrobenzophenone (0.37 g, 1.5 mmol) in a mixture of DME (4 mL) and EtOH (5 mL) at such a rate that the internal temperature remained under 35° C. After 5 h the reaction mixture was quenched by addition to ice-water (40 mL). The mixture was diluted with DCM (25 mL), made basic (pH=11) by addition of 10% NaOH, and then extracted with DCM (2×25 mL). The combined extracts were washed with water and brine, dried (anhyd $Na_2SO_4$) and concentrated under reduced pressure. The crude material was chromatographed (silica, EtOAc/Hex, 0:100 to 40:60) to afford 4'-amino-4-fluorobenzophenone (0.27 g, 83%) as a white solid. $^1$H-NMR (DMSO-$d_6$) δ 7.68 (2H, dd, J=5.6, 8.8), 7.51 (2H, d, J=8.8), 7.32 (2H, app t, J=8.8), 6.61 (2H, d, J=8.8), 6.18 (2H, br s). A solution of tin (II) chloride dihydrate (1.05 g, 4.7 mmol) in conc hydrochloric acid (4.2 mL) was added to 4-fluoro-4'-nitrobenzophenone (0.37 g, 1.5 mmol) in a mixture of DME (4

The title compound was prepared from 4'amino-4-fluorobenzophenone in a manner similar to that described in Example 1D: $^1$H-NMR (DMSO-$d_6$) δ 9.82 (1H, s), 8.01 (1H, d, J=7.8), 7.97 (2H, d, J=8.8), 7.92 (1H, app t, J=7.6), 7.78-7.84 (3H, m), 7.74 (2H, d, J=8.8), 7.51 (1H, d, J=7.6), 7.39 (2H, app t, J=8.8), 6.68 (1H, s), 2.15 (3H, s), 1.89 (3H, s); MS (ESI): 481 (MH+).

B. In a manner similar to that described for Example 3A, the following compounds were prepared from the appropriate benzophenones: 2,5-dimethyl-1-(2-trifluoromethyl-phenyl)-1H-pyrrole-3-carboxylic acid [4-(3-fluorobenzoyl)-phenyl]-amide; MS (ESI): 481 (MH+);

2,5-dimethyl-1-(2-trifluoromethyl-phenyl)-1H-pyrrole-3-carboxylic acid [4-(2-fluorobenzoyl)-phenyl]-amide; MS (ESI): 481 (MH+).

Example 4

PREPARATION OF 2,5-DIMETHYL-1-(2-TRIFLUOROMETHYL-PHENYL)-1H-PYRROLE-3-CARBOXYLIC ACID (4-ETHYLTHIO-PHENYL)-AMIDE

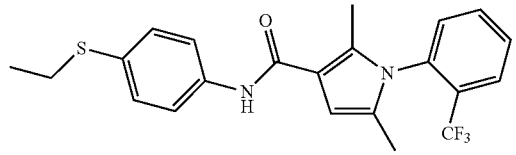 [SMILES: CCSc1ccc(NC(=O)c2cc(C)n(-c3ccccc3C(F)(F)F)c2C)cc1]

A. To a solution of NaOH (0.13 g, 3.2 mmol) in EtOH (10 mL) was added 4-nitrothiophenol (0.50 g, 3.2 mmol) and iodoethane (0.26 mL, 3.2 mmol). After stirring 2 h the reaction mixture was added to water (30 mL) and extracted with Et$_2$O (3×25 mL). The combined extracts were washed with satd NH$_4$Cl (3×25 mL) and brine, dried (MgSO$_4$) and concentrated under reduced pressure. The crude material was chromatographed (silica, EtOAc/Hex 0:100 to 30:70) to yield 1-ethylthio-4-nitrobenzene (0.35 g, 59%) as a yellow crystalline solid. $^1$H-NMR (CDCl$_3$) δ 8.13 (2H, d, J=8.8), 7.32 (2H, d, J=8.8), 3.06 (2H, q, J=7.3), 1.41 (3H, t, J=7.3).
The title compound was prepared from 1-ethylthio-4-nitrobenzene in a manner similar to that described in Example 3A: MS (ESI): 419 (MH$^+$).

PREPARATION OF 2,5-DIMETHYL-1-(2-TRIFLUOROMETHYL-PHENYL)-1H-PYRROLE-3-CARBOXYLIC ACID (4-ETHANESULFONYL-PHENYL)-AMIDE

B. To a solution of 2,5-dimethyl-1-(2-trifluoromethyl-phenyl)-1H-pyrrole-3-carboxylic acid (4-ethylthio-phenyl)-amide (0.13 g, 0.30 mmol) in DCM (3 mL) was added 3-chloroperoxybenzoic acid (77%, 0.17 g, 0.75 mmol). After stirring 1.5 h the reaction mixture was diluted with DCM (50 mL), washed with satd NaHCO$_3$ (2×20 mL) and brine (20 mL), then dried (anhyd Na$_2$SO$_4$) and concentrated under reduced pressure. The crude material was purified by reverse-phase chromatography (C18 column), eluting with 0.05% TFA in MeCN/H$_2$O (30:70 to 90:10) to yield the title compound (30 mg) as a white solid. $^1$H-NMR (DMSO-d$_6$) δ 9.87 (1H, s), 7.99-8.06 (3H, m), 7.92 (1H, app t, J=7.6), 7.77-7.85 (3H, m), 7.51 (1H, d, J=7.6), 6.67 (1H, s), 3.24 (2H, q, J=7.3), 2.14 (3H, s), 1.89 (3H, s), 1.10 (3H, t, J=7.3); MS (ESI): 451 (MH$^+$).
C. In a manner similar to that described for Examples 4A-B, the following was prepared by replacing iodoethane with 2-bromopropane:
2,5-dimethyl-1-(2-trifluoromethyl-phenyl)-1H-pyrrole-3-carboxylic acid [4-(propane-2-sulfonyl)-phenyl]-amide. $^1$H-NMR (DMSO-d$_6$) δ 9.88 (1H, s), 8.04 (2H, d, J=8.8), 8.01 (1H, d, J=7.8), 7.92 (1H, app t, J=7.8), 7.83 (1H, app t, J=7.8), 7.77 (2H, d, J=8.8), 6.66 (1H, s), 3.34 (H, sept, J=6.8), 2.14 (3H, s), 1.89 (3H, s), 1.16 (6H, d, J=6.8); MS (ESI): 465 (MH$^+$).

Example 5

PREPARATION OF 2,5-DIMETHYL-1-(2-TRIFLUOROMETHYL-PHENYL)-1H-PYRROLE-3-CARBOXYLIC ACID (4-METHANESULFONYL-3-TRIFLUOROMETHYL-PHENYL)-AMIDE

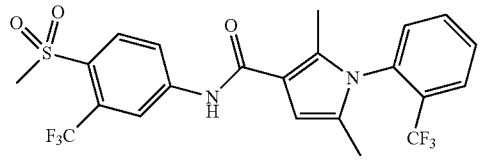 [SMILES: Cc1cc(C(=O)Nc2ccc(S(C)(=O)=O)c(C(F)(F)F)c2)c(C)n1-c1ccccc1C(F)(F)F]

A. A mixture of 2-fluoro-5-nitro-benzotrifluoride (0.50 g, 2.4 mmol) and sodium methanesulfinate (0.25 g, 2.4 mmol) in anhyd DMF (1.0 mL) was heated at 120° C. with stirring. After 18 h the reaction mixture was cooled, concentrated and chromatographed (silica, EtOAc/Hex, 0:100 to 40:60) to give 2-methanesulfonyl-5-nitro-benzotrifluoride (0.41 g, 64%) as a white solid: $^1$H-NMR (CDCl$_3$) δ 8.76 (1H, d, J=2.0), 8.62 (1H, dd, J=2.0, 8.8), 8.57 (1H, d, J=8.8), 3.26 (3H, s).

The title compound was prepared from 2-methanesulfonyl-5-nitro-benzotrifluoride in a manner similar to that described in Example 3A: $^1$H-NMR (DMSO-d$_6$) δ 10.14 (1H, s), 8.50 (1H, d, J=2.0), 8.35 (1H, dd, J=2.0, 8.6), 8.16 (1H, d, J=8.8), 8.02 (1H, d, J=7.8), 7.92 (1H, app t, J=7.8), 7.82 (1H, app t, J=7.8), 7.52 (1H, d, J=7.8), 6.69 (1H, s), 3.26 (3H, s), 2.15 (3H, s), 1.89 (3H, s); MS (ESI): 505 (MH$^+$).
B. In a manner similar to that described for Example 5A, the following compound was prepared by replacing 2-fluoro-5-nitro-benzotrifluoride with 3-chloro-4-fluoro-nitrobenzene:
2,5-dimethyl-1-(2-trifluoromethyl-phenyl)-1H-pyrrole-3-carboxylic acid (3-chloro-4-methanesulfonyl-phenyl)-amide: $^1$H-NMR (CD$_2$Cl$_2$) δ 8.12 (1H, d, J=2.3), 8.03 (1H, d, J=8.6), 7.89 (1H, d, J=7.8), 7.77 (1H, app t), 7.73 (1H, s), 7.69 (1H, app t), 7.57 (1H, dd, J=2.3, 8.6), 7.30 (1H, d, J=7.8), 6.24 (1H, s), 3.22 (3H, s), 2.23 (3H, s), 1.94 (3H, s); MS (ESI): 471 (MH$^+$).
C. In a manner similar to that described for Example 5A, the following compound was prepared by replacing 2-fluoro-5-nitro-benzotrifluoride with 2-chloro-5-nitropyridine:
2,5-dimethyl-1-(2-trifluoromethyl-phenyl)-1H-pyrrole-3-carboxylic acid (6-methanesulfonyl-pyridin-3-yl)-amide: $^1$H-NMR (DMSO-d$_6$) δ 10.08 (1, s), 9.09 (1H, d, J=2.3), 8.51 (1H, dd, J=2.3, 8.6), 8.02 (2H, d, J=8.6), 7.93 (1H, app t), 7.82 (1H, app t), 7.52 (1H, d, J=7.6), 6.68 (1H, s), 3.24 (3H, s), 2.15 (3H, s), 1.90 (3H, s); MS (ESI): 438 (MH$^+$).
D. In a manner similar to that described for Example 1C, the following compounds were prepared from the appropriate amines generated for Examples 5B-C:
1-(4-fluoro-2-trifluoromethyl-phenyl)-2,5-dimethyl-1H-pyrrole-3-carboxylic acid (3-chloro-4-methanesulfonyl-phenyl)-amide: $^1$H-NMR (CD$_2$Cl$_2$) δ 8.12 (1H, d, J=2.0), 8.03 (1H, d, J=8.6), 7.73 (1H, s), 7.60 (1H, dd, J=2.8, 8.6), 7.57 (1H, dd, J=2.0, 8.6), 7.47 (1H, m), 7.32 (1H, dd, J=5.0, 8.6), 6.24 (1H, s), 3.22 (3H, s), 2.24 (3H, s), 1.94 (3H, s); MS (ESI): 489 (MH$^+$).
1-(4-fluoro-2-trifluoromethyl-phenyl)-2,5-dimethyl-1H-pyrrole-3-carboxylic acid (6-methanesulfonyl-pyridin-3-yl)-amide: $^1$H-NMR (DMSO-d$_6$) δ 10.08 (1, s), 9.08 (1H, d, J=2.3), 8.51 (1H, dd, J=2.3, 8.6), 8.02 (1H, d, J=8.6), 7.97 (1H, dd, J=2.8, 8.8), 7.81 (1H, m), 7.62 (1H, dd, J=5.1, 8.8), 6.68 (1H, s), 3.24 (3H, s), 2.16 (3H, s), 1.90 (3H, s); MS (ESI): 456 (MH$^+$).
E. In a manner similar to that described for Example 1D, the following compound was prepared from 2-chloro-4-methanesulfonyl-aniline: In a manner similar to that described for Example 1D, the following compound was prepared from 2-chloro-4-methanesulfonyl-aniline:
2,5-dimethyl-1-(2-trifluoromethyl-phenyl)-1H-pyrrole-3-carboxylic acid (2-chloro-4-methanesulfonyl-phenyl)-amide; MS (ES): 471 (MH$^+$);

Example 6

PREPARATION OF 2,5-DIMETHYL-1-(2-TRIFLUOROMETHYL-PHENYL)-1H-PYRROLE-3-CARBOXYLIC ACID (3-METHOXY-4-SULFAMOYL-PHENYL)-AMIDE

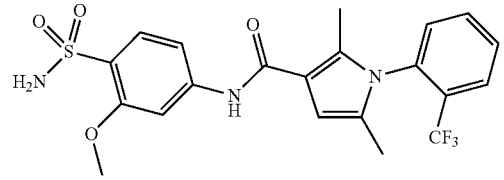 [SMILES: COc1cc(NC(=O)c2cc(C)n(-c3ccccc3C(F)(F)F)c2C)ccc1S(N)(=O)=O]

A. To a concentrated solution of ammonium hydroxide (28%, 2.5 mL, 20 mmol) was added cautiously 2-methoxy-4-nitrobenzenesulfonyl chloride (0.25 g, 1.0 mmol). After stirring 24 h the reaction mixture was added to satd $NH_4Cl$ (50 mL) and extracted with DCM (2×50 mL). The combined extracts were washed with brine, dried (anhyd $Na_2SO_4$) and concentrated under reduced pressure. The crude residue was chromatographed (silica, MeOH/DCM, 0:100 to 10:90) to yield 2-methoxy-4-nitrobenzenesulfonamide (0.16 g, 68%) as a pale brown solid. $^1$H-NMR (DMSO-$d_6$) δ 7.99 (1H, d), 7.90-7.95 (2H, m), 7.47 (2H, br s), 4.04 (3H, s).

The title compound was prepared from 2-methoxy-4-nitrobenzenesulfonamide in a manner similar to that described for Example 3A. $^1$H-NMR (DMSO-$d_6$) δ 9.69 (1H, s), 8.01 (1H, d, J=8.1), 7.92 (1H, app t, J=7.6), 7.81 (1H, app t, J=7.6), 7.74 (1H, d, J=1.8), 7.63 (1H, d, J=8.6), 7.50 (1H, d, J=7.6), 7.47 (1H, dd, J=1.8, 8.6), 6.93 (2H, s), 6.66 (1H, s), 3.88 (3H, s), 2.14 (3H, s), 1.89 (3H, s); MS (ESI): 468 (MH$^+$).

B. In a similar manner as that described for Example 6A, the following was prepared by replacing ammonium hydroxide with dimethylamine:

2,5-dimethyl-1-(2-trifluoromethyl-phenyl)-1H-pyrrole-3-carboxylic acid (4-dimethylsulfamoyl-3-methoxy-phenyl)-amide. $^1$H-NMR (DMSO-$d_6$) δ 9.76 (1H, s), 8.01 (1H, d, J=7.8), 7.92 (1H, app t, J=7.8), 7.81 (1H, app t, J=7.8), 7.78 (1H, d, J=1.8), 7.64 (1H, d, J=8.6), 7.48-7.54 (2H, m), 6.65 (1H, s), 3.86 (3H, s), 2.70 (6H, s), 2.14 (3H, s), 1.89 (3H, s); MS (ESI): 496 (MH$^+$).

C. In a manner similar to that described for Example 1C, the following compound was prepared from the amine generated for Example 6A:

1-(4-fluoro-2-trifluoromethyl-phenyl)-2,5-dimethyl-1H-pyrrole-3-carboxylic acid (3-methoxy-4-sulfamoyl-phenyl)-amide: $^1$H-NMR (DMSO-$d_6$) δ 9.69 (1H, s), 7.96 (1H, dd, J=3.0, 8.8), 7.80 (1H, ddd, J=3.0, 8.3, 8.3), 7.74 (1H, d, J=2.0), 7.63 (1H, d, J=8.6), 7.61 (1H, dd, J=5.0, 8.6), 7.47 (1H, dd, J=2.0, 8.6), 6.93 (2H, s), 6.66 (1H, s), 3.88 (3H, s), 2.15 (3H, s), 1.89 (3H, s); MS (ESI): 486 (MH$^+$).

Example 7

PREPARATION OF 2,5-DIMETHYL-1-(2-TRIFLUOROMETHYL-PHENYL)-1H-PYRROLE-3-CARBOXYLIC ACID (3-CHLORO-4-SULFAMOYL-PHENYL)-AMIDE

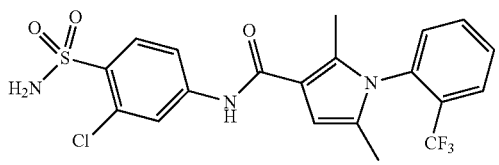 [SMILES: Cc1cc(C(=O)Nc2ccc(S(N)(=O)=O)c(Cl)c2)c(C)n1-c1ccccc1C(F)(F)F]

A. To a solution of 2-chloro-4-nitroaniline (2.10 g, 12.1 mmol) in TFA (40 mL) was added conc HCl (4 mL). The reaction mixture was chilled to 0° C. and then charged with a solution of sodium nitrite (1.06 g, 15.4 mmol) in 3 mL of water over a 20 min period while maintaining an internal temperature of 0° C. After another 20 min the reaction mixture was poured into a solution of CuCl (80 mg), $CuCl_2$ (0.826 g, 6.2 mmol) and sulfurous acid (40 mL) in acetic acid (40 mL) chilled to 0° C. After the initial effervescence ceased, the reaction mixture was allowed to stir at ambient temperature. After 30 min the reaction mixture was diluted with water (200 mL) and extracted with hexanes (2×100 mL). The combined extracts were concentrated under reduced pressure to yield the crude sulfonyl chloride (1.8 g) as an amber oil. This intermediate was dissolved in acetone (25 mL) and treated with conc ammonium hydroxide (5 mL). After 1 h the reaction mixture was diluted with satd ammonium chloride (25 mL) and water (100 mL), then extracted with DCM (2×75 mL). The combined extracts were washed with brine, dried ($Na_2SO_4$), concentrated under reduced pressure and chromatographed (silica, EtOAc/Hex, 0:100 to 50:50) to afford 2-chloro-4-nitro-benzenesulfonamide (1.1 g, 38%) as a pale yellow solid. $^1$H-NMR (DMSO-$d_6$) δ 8.44 (1H, d, J=2.3), 8.35 (1H, dd, J=2.3, 8.6), 8.22 (1H, d, J=8.6), 7.99 (2H, s).

The title compound was prepared from 2-chloro-4-nitrobenzenesulfonamide in a manner similar to that described for Example 3A. $^1$H-NMR (DMSO-$d_6$) δ 9.86 (1H, s), 8.13 (1H, d, J=1.8), 8.01 (1H, d, J=7.6), 7.87-7.95 (2H, m), 7.78-7.86 (2H, m), 7.51 (1H, d, J=7.6), 7.47 (2H, s), 6.66 (1H, s), 2.14 (3H, s), 1.88 (3H, s); MS (ESI): 472 (MH$^+$).

B. In a manner similar to that described in Example 7A, the following compound was prepared by replacing 2-chloro-4-nitroaniline with 4-nitro-2-trifluoromethyl-aniline:

2,5-dimethyl-1-(2-trifluoromethyl-phenyl)-1H-pyrrole-3-carboxylic acid (4-sulfamoyl-3-trifluoromethyl-phenyl)-amide. $^1$H-NMR (DMSO-$d_6$) δ 0.01 (1H, s), 8.40 (1H, d, J=2.0), 8.24 (1H, dd, J=2.0, 8.8), 8.09 (1H, d, J=8.8), 8.02 (1H, d, J=7.8), 7.92 (1H, app t), 7.82 (1H, app t), 7.56 (2H, s), 7.52 (1H, s), 6.68 (1H, s), 2.15 (3H, s), 1.89 (3H, s); MS (ESI): 506 (MH$^+$).

C. In a manner similar to that described in Example 1C, the following compounds were prepared from the appropriate anilines generated in Examples 7A-B:

1-(4-fluoro-2-trifluoromethyl-phenyl)-2,5-dimethyl-1H-pyrrole-3-carboxylic acid (3-chloro-4-sulfamoyl-phenyl)-amide; $^1$H-NMR (DMSO-$d_6$) δ 9.86 (1H, s), 8.13 (1H, d, J=1.8), 7.96 (1H, dd, J=2.8, 8.8), 7.90 (1H, d, J=8.8), 7.84 (1H, dd, J=1.8, 8.8), 7.77-7.82 (1H, m), 7.61 (1H, dd, J=5.1, 8.8), 7.47 (2H, s), 6.65 (1H, s), 2.15 (3H, s), 1.89 (3H, s); MS (ESI): 490 (MH$^+$).

1-(4-fluoro-2-trifluoromethyl-phenyl)-2,5-dimethyl-1H-pyrrole-3-carboxylic acid (4-sulfamoyl-3-trifluoromethyl-phenyl)-amide: $^1$H-NMR (DMSO-$d_6$) δ 10.02 (1H, s), 8.39 (1H, d, J=2.0), 8.24 (1H, dd, J=2.0, 8.8), 8.09 (1H, d, J=8.8), 7.96 (1H, dd, J=2.8, 8.8), 7.80 (1H, ddd, J=2.8, 8.3, 8.3), 7.62 (1H, dd, J=5.1, 8.6), 7.56 (2H, s), 6.68 (1H, s), 2.16 (3H, s), 1.90 (3H, s); MS (ESI): 524 (MH$^+$).

D. In a manner similar to that described for Example 1C, the following compound was prepared from 2,5-dimethyl-1-naphthalen-1-yl-1H-pyrrole-3-carboxylic acid chloride (used in Example 1G) and 4-amino-2-chloro-benzenesulfonamide (see Example 7A):

2,5-Dimethyl-1-naphthalen-1-yl-1H-pyrrole-3-carboxylic acid (3-chloro-4-sulfamoyl-phenyl)-amide; MS (ESI): 454 (MH$^+$).

Example 8

PREPARATION OF 4-({2,5-DIMETHYL-1-[2-(TRIFLUOROMETHYL)PHENYL]-1H-PYRROLE-3-CARBONYL}-AMINO)-BENZOIC ACID

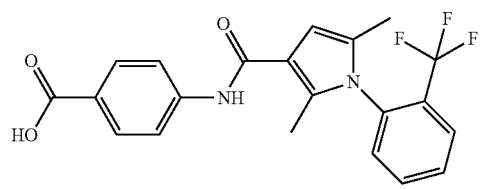 [SMILES: Cc1cc(C(=O)Nc2ccc(C(=O)O)cc2)c(C)n1-c1ccccc1C(F)(F)F]

In a manner similar to that described in Example 1F, 4-({2,5-dimethyl-1-[2-(trifluoromethyl)phenyl]-1H-pyrrole-3-carbonyl}-amino)-benzoic acid ethyl ester was prepared from ethyl 4-aminobenzoate; MS (ESI) m/z 431 [M+H]$^+$.

A mixture of 4-({2,5-dimethyl-1-[2-(trifluoromethyl)phenyl]-1H-pyrrole-3-carbonyl}-amino)-benzoic acid ethyl ester (0.46 g, 1.1 mmol), lithium hydroxide monohydrate (0.15 g, 3.5 mmol, 3.3 eq), 2 mL of water, 2 mL of THF, and 3 mL of MeOH was stirred 17 h and then was concentrated under reduced pressure. The resulting suspension was treated with 200 µL of TFA and was washed into a separatory funnel with DCM and water. The water was separated and extracted with DCM. The combined extracts were dried (Na$_2$SO$_4$) and concentrated in vacuo. The crude acid was purified by reverse-phase HPLC to afford the title compound (65 mg, 15%) as a colorless solid; $^1$H NMR (DMSO-d$_6$): δ 12.7-12.8 (br s, 1H), 9.84 (s, 1H), 8.12 (d, J=8 Hz, 1H), 8.03 (t, J=8 Hz, 1H), 8.00 (s, 4H), 7.93 (t, J=8 Hz, 1H), 7.61 (d, J=2H), 6.77 (s, 1H), 2.26 (s, 3H), 2.00 (s, 3H); MS (ESI) m/z 403 [M+H]$^+$.

Example 9

PREPARATION OF 1-(2-BROMOPHENYL)-2,5-DIMETHYL-1H-PYRROLE-3-CARBOXYLIC ACID [4-(METHANESULFINYL)PHENYL]-AMIDE

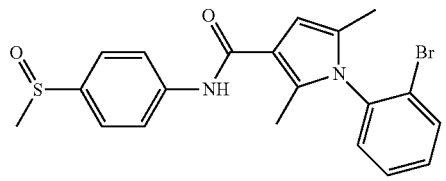 [SMILES: Cc1cc(C(=O)Nc2ccc(S(C)=O)cc2)c(C)n1-c1ccccc1Br]

In a manner similar to that described in Examples 1A-1C, but replacing 4-fluoro-2-(trifluoromethyl)aniline with 2-bromoaniline and replacing sulfanilamide with 4-methylthio-aniline, the following compound was prepared:

1-(2-Bromo-phenyl)-2,5-dimethyl-1H-pyrrole-3-carboxylic acid (4-methylthio-phenyl)-amide; $^1$H NMR (CDCl$_3$): δ 7.68 (d, J=8 Hz, 1H), 7.47 (d, J=9 Hz, 2H), 7.40 (t, J=8 Hz, 1H), 7.30 (t, J=8 Hz, 1H), 7.19-7.23 (m, 3H), 6.12 (s, 1H), 2.43 (s, 3H), 2.24 (s, 3H), 1.90 (s, 3H); MS (ESI) m/z 415 and 417, both [M+H]$^+$.

A suspension of 1-(2-bromo-phenyl)-2,5-dimethyl-1H-pyrrole-3-carboxylic acid (4-methylthio-phenyl)-amide (2.4 g, 5.8 mmol) in MeOH (5 mL) was prepared and then cooled to −10° C. To this suspension was added a solution of Oxone (3.92 g, 6.4 mmol) in water (10 mL) dropwise over 15 min. Next a solution of satd sodium sulfite (40 mL) was added and the reaction mixture was washed into a separatory funnel with DCM (200 mL). The aqueous phase was separated and extracted with DCM. The combined extracts were dried (anhyd Na$_2$SO$_4$) and concentrated in vacuo to yield the title compound (2.5 g, 100%); $^1$H NMR (CDCl$_3$): δ 9.5 (s, 1H), 7.75 (d, J=9 Hz, 2H), 7.69 (d, J=8 Hz, 1H), 7.37-7.43 (m, 3H), 7.26-7.32 (m, 2H), 6.44 (s, 1H), 2.50 (s, 3H), 1.96 (s, 3H), 1.70 (s, 3H); MS (ESI) m/z 431 and 433, both [M+H]$^+$.

Example 10

PREPARATION OF 2,5-DIMETHYL-1-[2-(TRIFLUOROMETHYL)PHENYL]-1H-PYRROLE-3-CARBOXYLIC ACID (4-ETHYLSULFAMOYL-PHENYL)-AMIDE AND 2,5-DIMETHYL-1-[2-(TRIFLUOROMETHYL)PHENYL]-1H-PYRROLE-3-CARBOXYLIC ACID (4-DIETHYLSULFAMOYL-PHENYL)-AMIDE

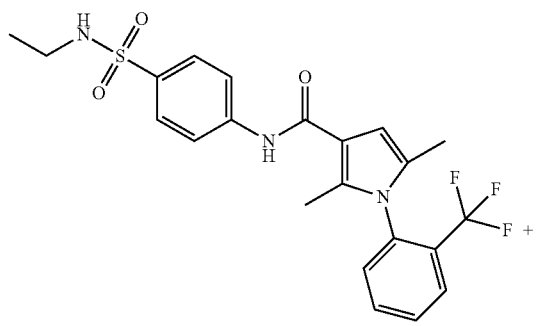

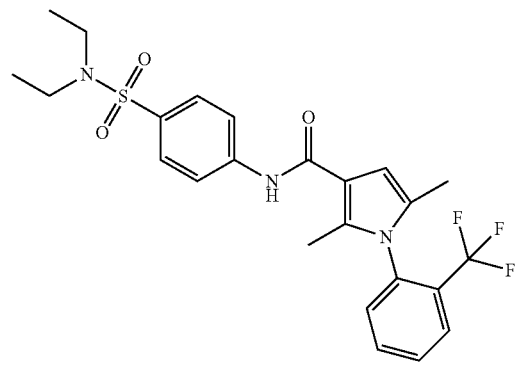

To a suspension of 2,5-dimethyl-1-[2-(trifluoromethyl)phenyl]-1H-pyrrole-3-carboxylic acid (4-sulfamoyl-phenyl)-amide (83 mg, 0.19 mmol) and K$_2$CO$_3$ (34 mg) in anhyd DMF (0.5 mL) was added ethyl iodide (15 µL, 0.19 mmol). After 19 h additional ethyl iodide (10 µL) was added. After 23 h total the reaction mixture was concentrated to dryness in vacuo. The residue was purified by reverse-phase HPLC to yield 2,5-dimethyl-1-[2-(trifluoromethyl)phenyl]-1H-pyrrole-3-carboxylic acid (4-ethylsulfamoyl-phenyl)-amide (17 mg, 19%) as a colorless powder; $^1$H NMR (DMSO-d$_6$): δ 9.7 (s, 1H), 7.90 (d, J=8 Hz, 1H), 7.85 (d, J=8 Hz, 2H), 7.81 (t, J=8 Hz, 1H), 7.70 (t, J=8 Hz, 1H), 7.60 (d, J=8 Hz, 2H), 7.39 (d, J=8 Hz, 1H), 7.28 (d, J=8 Hz, 1H), 6.54 (s, 1H), 2.66 (quintet, J=7 Hz, 2H), 2.03 (s, 3H), 1.77 (s, 3H), 0.86 (t, J=7 Hz, 3H); MS (ESI) m/z 466 [M+H]$^+$. Also recovered from the reaction was dimethyl-1-[2-(trifluoromethyl)phenyl]-1H-pyrrole-3-carboxylic acid (4-diethylsulfamoyl-phenyl)-amide (12 mg, 13%) as a colorless solid; $^1$H NMR (DMSO-d$_6$): δ 9.9 (s, 1H), 8.11 (d, J=8 Hz, 1H), 8.08 (d, J=7 Hz, 2H), J=8 Hz, 1H), 7.92 (t, J=8 Hz, 1H), 7.82 (d, J=7 Hz, 2H), 7.60 (d, J=8 Hz, 1H), 6.77 (s, 1H), 3.25 (q, J=7 Hz, 4H), 2.24 (s, 3H), 1.99 (s, 3H), 1.45 (t, J=7 Hz, 6H); MS (ESI) m/z 494 [M+H]+.

Example 11

PREPARATION OF 2,5-DIMETHYL-1-[4-((E)-STYRYL)-2-(TRIFLUOROMETHYL)PHENYL]-1H-PYRROLE-3-CARBOXYLIC ACID (4-METHANESULFONYL-PHENYL)-AMIDE

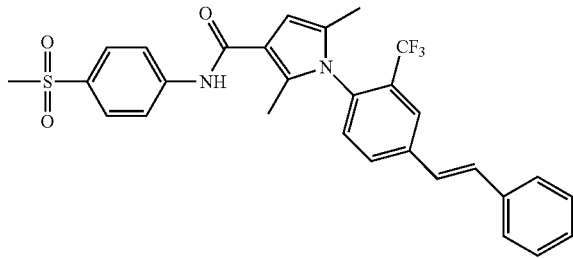 [SMILES: Cc1cc(C(=O)Nc2ccc(S(C)(=O)=O)cc2)c(C)n1-c1ccc(/C=C/c2ccccc2)cc1C(F)(F)F]

A. 1-[4-Bromo-2-(trifluoromethyl)phenyl]-2,5-dimethyl-1H-pyrrole-3-carboxylic acid [4-(methanesulfonyl)phenyl]-amide was prepared as described in Example 1G. A stock solution was prepared 0.25 M in DMF. A stock solution of trans-β-styreneboronic acid was prepared 0.25 M in DMF, a stock solution of sodium carbonate was prepared 1.0 M in water, and a stock solution of dihydrogen di-μ-chlorobis(di-tert-butylphosphino-κP) dipalladate (2-) (POPd₂) was prepared 0.025 M in DMF. Into a 1 dram reaction vial was placed 300 μL of bromide stock, 600 μL of boronic acid stock, and 150 μL of POPd₂ stock solutions. The solution was heated to 60-70° C. and 150 μL of sodium carbonate stock solution was dispensed. After heating for 18 h with agitation, the reaction vial was cooled and unsealed. Additional aliquots from stock solutions of the boronic acid (300 μL) and POPd₂ (150 μL) were dispensed into the vial, which was sealed and heated 1 h. The reaction mixture was cooled, filtered to remove solids, and concentrated in vacuo. The residue was purified by reverse-phase HPLC to afford the product as an off-white solid, yield: 22 mg (54%); ¹H NMR (CDCl₃): δ 7.96 (s, 1H), 7.90 (d, J=8 Hz, 2H), 7.8-7.85 (m, 3H), 7.76 (s, 1H), 7.57 (d, J=7 Hz, 2H), 7.42 (t, J=8 Hz, 2H), 7.35 (m, 1H), 7.25 (d, J=8 Hz, 1H), 7.19 (s, 1H), 6.25 (s, 1H), 3.06 (s, 3H), 2.28 (s, 3H), 1.97 (s, 3H); MS (ESI) m/z 539 [M+H]+.

B. In a similar manner as that described for Example 11A, the following was prepared by replacing trans-β-styreneboronic acid with the appropriate boronic acid:

1-(4'-Carbamoyl-3-trifluoromethyl-biphenyl-4-yl)-2,5-dimethyl-1H-pyrrole-3-carboxylic acid (4-methanesulfonyl-phenyl)-amide; ¹H NMR (DMSO-d₆): δ 9.89 (s, 1H), 8.26 (d, J=9 Hz, 2H), 8.12 (s, 1H), 8.05 (d, J=8 Hz, 4H), 7.97 (d, J=9 Hz, 2H), 7.86 (d, J=9 Hz, 2H), 7.63 (d, J=8 Hz, 1H), 7.49 (s, 1H), 6.71 (s, 1H), 3.18 (s, 3H), 2.21 (s, 3H), 1.95 (s, 3H); MS (ESI) m/z 556 [M+H]+.

1-(4'-Dimethylcarbamoyl-3-trifluoromethyl-biphenyl-4-yl)-2,5-dimethyl-1H-pyrrole-3-carboxylic acid (4-methane-sulfonyl-phenyl)-amide; ¹H NMR (DMSO-d₆): δ 9.89 (s, 1H), 8.24 (d, J=8 Hz, 2H), 8.04 (d, 2H), 7.95 (d, J=8 Hz, 4H), 7.86 (d, J=9 Hz, 2H), 7.62 (d, J=8 Hz, 1H), 7.58 (d, J=9 Hz, 2H), 6.70 (s, 1H), 3.18 (s, 3H), 3.02 (s, 3H), 2.97 (s, 3H), 2.20 (s, 3H), 1.95 (s, 3H); MS (ESI) m/z 584 [M+H]+.

1-[4-(1H-Indol-5-yl)-2-trifluoromethyl-phenyl]-2,5-dimethyl-1H-pyrrole-3-carboxylic acid (4-methanesulfonyl-phenyl)-amide; ¹H NMR (DMSO-d₆): δ 11.49 (s, 1H), 10.07 (s, 1H), 8.38 (d, J=7 Hz 2H), 8.24 (d, J=9 Hz, 3H), 8.06 (d, J=9 Hz, 2H), 7.75 (m, 3H), 7.64 (m, 1H), 6.89 (s, 1H), 6.75 (m, 1H), 3.38 (s, 3H), 2.42 (s, 3H), 2.16 (s, 3H); MS (ESI) m/z 552 [M+H]+.

PREPARATION OF 1-(3-TRIFLUOROMETHYL-BIPHENYL-4-YL)-2,5-DIMETHYL-1H-PYRROLE-3-CARBOXYLIC ACID (4-METHANESULFONYL-PHENYL)-AMIDES AND VARIATIONS

C. A 0.25 M stock solution of 1-[4-bromo-2-(trifluoromethyl)phenyl]-2,5-dimethyl-1H-pyrrole-3-carboxylic acid [4-(methanesulfonyl)phenyl]-amide (Example 1G) in anhyd DMF was prepared. Boronic acids (or boronate esters) were individually weighed and were dissolved in DMF to give 0.25 M stock solutions using a Tecan Genesis workstation. Also stock solutions of 1.0 M Na₂CO₃ (aq) and 0.025 M dihydrogen di-μ-chlorobis(di-tert-butylphosphino-κP) dipalladate (2-) (POPd₂) in anhyd DMF were prepared. The Tecan was used to dispense 200 μL of boronic acids, 100 μL of bromide, and 50 μL of POPd₂ stock solutions into individual reaction vials. The set of vials were heated to 60-70° C. and then each vial was treated with 50 μL of 1 M Na₂CO₃. The vials were sealed and shaken at 60-70° C. After heating overnight the vials were unsealed and an additional 100 μL of each boronic acid and 50 μL of POPd₂ stock solutions were dispensed into respective vials. After heating another 1 h the samples were cooled, filtered and concentrated in vacuo. A 0.25 M stock solution of 1-[4-bromo-2-(trifluoromethyl)phenyl]-2,5-dimethyl-1H-pyrrole-3-carboxylic acid [4-(methanesulfonyl)phenyl]-amide (Example 1G) in anhyd DMF was prep D. Library samples were processed as described in Example 2C. The following compounds were prepared in the manner described above in Examples 11A and C using the appropriate boronic acids:

1-(3'-Hydroxy-3-trifluoromethyl-biphenyl-4-yl)-2,5-dimethyl-1H-pyrrole-3-carboxylic acid (4-methanesulfonyl-phenyl)-amide; MS (ESI) m/z 529 [M+H]+.

1-(4'-Butyl-3-trifluoromethyl-biphenyl-4-yl)-2,5-dimethyl-1H-pyrrole-3-carboxylic acid (4-methanesulfonyl-phenyl)-amide; MS (ESI) m/z 569 [M+H]+.

1-(4'-Ethyl-3-trifluoromethyl-biphenyl-4-yl)-2,5-dimethyl-1H-pyrrole-3-carboxylic acid (4-methanesulfonyl-phenyl)-amide; MS (ESI) m/z 541 [M+H]+.

1-(2',6'-Difluoro-3-trifluoromethyl-biphenyl-4-yl)-2,5-dimethyl-1H-pyrrole-3-carboxylic acid (4-methanesulfonyl-phenyl)-amide; MS (ESI) m/z 549 [M+H]+.

1-(2'-Methoxy-5'-methyl-3-trifluoromethyl-biphenyl-4-yl)-2,5-dimethyl-1H-pyrrole-3-carboxylic acid (4-methanesulfonyl-phenyl)-amide; MS (ESI) m/z 557 [M+H]+.

1-(2'-Ethoxy-3-trifluoromethyl-biphenyl-4-yl)-2,5-dimethyl-1H-pyrrole-3-carboxylic acid (4-methanesulfonyl-phenyl)-amide; MS (ESI) m/z 557 [M+H]+.

1-(4'-Acetylamino-3-trifluoromethyl-biphenyl-4-yl)-2,5-dimethyl-1H-pyrrole-3-carboxylic acid (4-methanesulfonyl-phenyl)-amide; MS (ESI) m/z 570 [M+H]+.

1-(2'-Isopropyl-3-trifluoromethyl-biphenyl-4-yl)-2,5-dimethyl-1H-pyrrole-3-carboxylic acid (4-methanesulfonyl-phenyl)-amide; MS (ESI) m/z 555 [M+H]+.

1-(3'-Amino-3-trifluoromethyl-biphenyl-4-yl)-2,5-dimethyl-1H-pyrrole-3-carboxylic acid (4-methanesulfonyl-phenyl)-amide; MS (ESI) m/z 528 [M+H]+.

1-(4-Benzo[b]thiophen-2-yl-2-trifluoromethyl-phenyl)-2,5-dimethyl-1H-pyrrole-3-carboxylic acid (4-methanesulfonyl-phenyl)-amide; MS (ESI) m/z 569 [M+H]+.

4'-[3-(4-Methanesulfonyl-phenylcarbamoyl)-2,5-dimethyl-pyrrol-1-yl]-3'-trifluoromethyl-biphenyl-3-carboxylic acid; MS (ESI) m/z 557 [M+H]$^+$.

1-(2'-Fluoro-3-trifluoromethyl-biphenyl-4-yl)-2,5-dimethyl-1H-pyrrole-3-carboxylic acid (4-methanesulfonyl-phenyl)-amide; MS (ESI) m/z 531 [M+H]$^+$.

1-(3'-Fluoro-4'-methoxy-3-trifluoromethyl-biphenyl-4-yl)-2,5-dimethyl-1H-pyrrole-3-carboxylic acid (4-methanesulfonyl-phenyl)-amide; MS (ESI) m/z 561 [M+H]$^+$.

1-(2'-Fluoro-6'-methoxy-3-trifluoromethyl-biphenyl-4-yl)-2,5-dimethyl-1H-pyrrole-3-carboxylic acid (4-methanesulfonyl-phenyl)-amide; MS (ESI) m/z 561 [M+H]$^+$.

1-[4-(5-Cyano-thiophen-2-yl)-2-trifluoromethyl-phenyl]-2,5-dimethyl-1H-pyrrole-3-carboxylic acid (4-methanesulfonyl-phenyl)-amide; MS (ESI) m/z 544 [M+H]$^+$.

2,5-Dimethyl-1-(4'-methylcarbamoyl-3-trifluoromethyl-biphenyl-4-yl)-1H-pyrrole-3-carboxylic acid (4-methanesulfonyl-phenyl)-amide; MS (ESI) m/z 570 [M+H]$^+$.

1-(3',4'-Dimethyl-3-trifluoromethyl-biphenyl-4-yl)-2,5-dimethyl-1H-pyrrole-3-carboxylic acid (4-methanesulfonyl-phenyl)-amide; MS (ESI) m/z 541 [M+H]$^+$.

2,5-Dimethyl-1-(4-naphthalen-2-yl-2-trifluoromethyl-phenyl)-1H-pyrrole-3-carboxylic acid (4-methanesulfonyl-phenyl)-amide; MS (ESI) m/z 563 [M+H]$^+$.

1-(4'-Hydroxymethyl-3-trifluoromethyl-biphenyl-4-yl)-2,5-dimethyl-1H-pyrrole-3-carboxylic acid (4-methanesulfonyl-phenyl)-amide; MS (ESI) m/z 543 [M+H]$^+$.

1-[4-(2,3-Dihydro-benzofuran-5-yl)-2-trifluoromethyl-phenyl]-2,5-dimethyl-1H-pyrrole-3-carboxylic acid (4-methanesulfonyl-phenyl)-amide; MS (ESI) m/z 555 [M+H]$^+$.

2,5-Dimethyl-1-(4-quinolin-8-yl-2-trifluoromethyl-phenyl)-1H-pyrrole-3-carboxylic acid (4-methanesulfonyl-phenyl)-amide; MS (ESI) m/z 564 [M+H]$^+$.

2,5-Dimethyl-1-[4-(1-methyl-1H-indol-5-yl)-2-trifluoromethyl-phenyl]-1H-pyrrole-3-carboxylic acid (4-methanesulfonyl-phenyl)-amide; MS (ESI) m/z 566 [M+H]$^+$.

1-(4'-Methoxy-2'-methyl-3-trifluoromethyl-biphenyl-4-yl)-2,5-dimethyl-1H-pyrrole-3-carboxylic acid (4-methanesulfonyl-phenyl)-amide; MS (ESI) m/z 557 [M+H]$^+$.

Example 12

PREPARATION OF 2,5-DI METHYL-1-(2-TRIFLUOROMETHYL-PHENYL)-1H-PYRROLE-3-CARBOXAMIDE

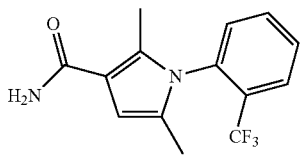 [SMILES: Cc1cc(C(N)=O)c(C)n1-c1ccccc1C(F)(F)F]

A. To conc ammonium hydroxide (28%, 9.8 mL, 70 mmol) at 0° C. was added cautiously a solution of 2,5-dimethyl-1-(2-trifluoromethyl-phenyl)-1H-pyrrole-3-carbonyl chloride (2.1 g, 7.0 mmol) in THF (10 mL). After 10 min the reaction mixture was removed from the ice-bath and allowed to stir at ambient temperature. After 1 h the mixture was added to satd NH$_4$Cl (30 mL) and extracted with DCM (3×30 mL). The combined extracts were washed with water (2×50 mL) and brine (50 mL), dried (anhyd Na$_2$SO$_4$) and concentrated under reduced pressure to afford the title compound (1.9 g, 96%) as a pale brown solid, which was used without purification in the next step. $^1$H-NMR (DMSO-d$_6$) δ 7.98 (1H, d, J=7.8), 7.88 (1H, app t, J=7.8), 7.78 (1H, app t, J=7.8), 7.44 (1H, d, J=7.8), 7.17 (1H, br s), 6.66 (1H, br s), 6.35 (1H, s), 2.07 (3H, s), 1.81 (3H, s).

PREPARATION OF 4-BROMO-2,N,N-TRIMETHYL-BENZENESULFONAMIDE

B. To a mixture of 40% dimethylamine (aqueous, 2.5 mL, 20 mmol) in THF (2.5 mL) added 4-bromo-2-methylbenzenesulfonyl chloride (0.27 g, 1.0 mmol) with stirring. After 5 h the reaction mixture was partitioned between DCM (50 mL) and water (50 mL), washed with water (2×50 mL) and brine (50 mL), dried (anhyd Na$_2$SO$_4$) and concentrated under reduced pressure to provide the title compound (0.28 g, quant) as a colorless liquid, which was used without purification in the next step. $^1$H-NMR (CDCl$_3$) δ 7.74 (1H, d, J=8.3), 7.49 (1H, d, J=1.8), 7.46 (1H, dd, J=1.8, 8.3), 2.80 (6H, s), 2.60 (3H, s); R$_f$=0.38 (silica, 1:4 EtOAc/Hex).

PREPARATION OF 2,5-DIMETHYL-1-(2-TRIFLUOROMETHYL-PHENYL)-1H-PYRROLE-3-CARBOXYLIC ACID (4-DIMETHYLSULFAMOYL-3-METHYL-PHENYL)-AMIDE

C. An oven-dried, argon-sparged vial was charged with 4-bromo-2,N,N-trimethyl-benzenesulfonamide (70 mg, 0.25 mmol), 2,5-dimethyl-1-(2-trifluoromethyl-phenyl)-1H-pyrrole-3-carboxamide (85 mg, 0.30 mmol), anhyd K$_2$CO$_3$ (69 mg, 0.50 mmol), and copper (I) iodide (10 mg, 0.05 mmol), and then briefly sparged with argon. To the vial under argon was added anhyd toluene (0.5 mL) and N,N'-dimethyl-ethylenediamine (11 μL, 0.10 mmol), then capped and heated at 120° C. After 24 h the reaction mixture was cooled, diluted with EtOAc, filtered through Celite and concentrated under reduced pressure. The crude material was chromatographed (silica, EtOAc/Hex, 0:100 to 50:50) to afford the title compound (95 g, 79%) as a white solid. $^1$H-NMR (DMSO-d$_6$) δ 9.74 (1H, s), 8.01 (1H, d, J=7.8), 7.92 (1H, app t, J=7.8), 7.78-7.86 (3H, m), 7.71 (1H, d, J=8.3), 7.51 (1H, d, J=7.8), 6.65 (1H, s), 2.69 (6H, s), 2.53 (3H, s), 2.14 (3H, s), 1.88 (3H, s); MS(ESI): 480 (MH$^+$).

D. In a manner similar to that described for Examples 12B-C, the following compounds were prepared from the appropriate aryl bromides:

2,5-dimethyl-1-(2-trifluoromethyl-phenyl)-1H-pyrrole-3-carboxylic acid (4-dimethylsulfamoyl-3-ethyl-phenyl)-amide; MS (ESI): 494 (MH$^+$);

2,5-dimethyl-1-(2-trifluoromethyl-phenyl)-1H-pyrrole-3-carboxylic acid (4-dimethylsulfamoyl-3-trifluoromethyl-phenyl)-amide; MS (ESI): 534 (MH$^+$);

2,5-dimethyl-1-(2-trifluoromethyl-phenyl)-1H-pyrrole-3-carboxylic acid (3-acetylamino-phenyl)-amide; MS (ESI): 416 (MH$^+$);

2,5-dimethyl-1-(2-trifluoromethyl-phenyl)-1H-pyrrole-3-carboxylic acid (3-methanesulfonylamino-phenyl)-amide; MS (ESI): 452 (MH$^+$).

2,5-dimethyl-1-(2-trifluoromethyl-phenyl)-1H-pyrrole-3-carboxylic acid (3-chloro-4-dimethylsulfamoyl-phenyl)-amide; MS (ESI): 500 (MH$^+$);

2,5-dimethyl-1-(2-trifluoromethyl-phenyl)-1H-pyrrole-3-carboxylic acid (3-dimethylamino-4-dimethylsulfamoyl-phenyl)-amide; MS (ESI): 509 (MH$^+$);

2,5-dimethyl-1-(2-trifluoromethyl-phenyl)-1H-pyrrole-3-carboxylic acid (4-methanesulfonyl-3-trifluoromethoxy-phenyl)-amide; MS (ESI): 521 (MH$^+$);

2,5-dimethyl-1-(2-trifluoromethyl-phenyl)-1H-pyrrole-3-carboxylic acid (5-dimethylsulfamoyl-thiophen-2-0)-amide; MS (ESI): 472 (MH$^+$);

2,5-dimethyl-1-(2-trifluoromethyl-phenyl)-1H-pyrrole-3-carboxylic acid (3-acetylamino-phenyl)-amide; MS (ESI): 416 (MH$^+$);

2,5-dimethyl-1-(2-trifluoromethyl-phenyl)-1H-pyrrole-3-carboxylic acid (3-methanesulfonylamino-phenyl)-amide; MS (ESI): 452 (MH$^+$);

2,5-dimethyl-1-(2-trifluoromethyl-phenyl)-1H-pyrrole-3-carboxylic acid (4-methanesulfonylamino-phenyl)-amide; MS (ESI): 452 (MH$^+$);

1-(2,3-dichloro-phenyl)-2,5-dimethyl-1H-pyrrole-3-carboxylic acid (4-dimethylsulfamoyl-phenyl)-amide; MS (ESI): 466 (MH$^+$).

PREPARATION OF 2,5-DIMETHYL-1-[2-(TRIFLUOROMETHYL)PHENYL]-1H-PYRROLE-3-CARBOXYLIC ACID (4-METHANESULFONYL-METHYL-PHENYL)-AMIDE

E. Sodium thiomethoxide (1.0 g, 14.3 mmol) and 4-bromobenzyl bromide (2.65 g, 10.6 mmol) were combined with anhyd THF (50 mL) and the reaction mixture was stirred at 60° C. After 3 h the reaction mixture was concentrated in vacuo and the residue was washed into a separatory funnel with EtOAc and water. The organic layer was separated, dried (anhyd MgSO$_4$), and concentrated in vacuo to yield 1-bromo-4-methylthiomethyl-benzene. To a solution of this crude thioether in DCM (100 mL) was added 3-chloroperoxybenzoic acid (77%, 4.0 g) portionwise. After stirring overnight the reaction mixture was poured into a separatory funnel, washed with 1N NaOH, dried (Na$_2$SO$_4$), and concentrated in vacuo. The residue was crystallized from EtOAc-Hex to afford 1-bromo-4-methanesulfonylmethyl-benzene (2.02 g, 76%) as light tan needles:

$^1$H-NMR (CDCl$_3$) δ 7.56 (2H, d, J=8 Hz), 7.29 (2H, d, J=8 Hz), 4.20 (2H, s), 2.78 (3H, s); MS (ESI) m/z 249 and 251, both [M+H]$^+$.

The title compound was prepared from 1-bromo-4-methanesulfonylmethyl-benzene in a manner similar to that described for Example 12C: (DMSO-d$_6$) δ 9.52 (1H, s), 8.01 (1H, d, J=8.1), 7.91 (1H, app t, J=8.1), 7.81 (1H, app t, J=8.1), 7.77 (2H, d, J=8.6), 7.49 (1H, d, J=8.1), 7.33 (2H, d, J=8.6), 6.63 (1H, s), 4.41 (2H, s), 2.88 (3H, s), 2.13 (3H, s), 1.88 (3H, s); MS (ESI) m/z 451 [M+H]$^+$.

Example 13

PREPARATION OF 1-(3'-CHLORO-BIPHENYL-2-YL)-2,5-DIMETHYL-1H-PYRROLE-3-CARBOXYLIC ACID (4-METHANESULFONYL-PHENYL)-AMIDE

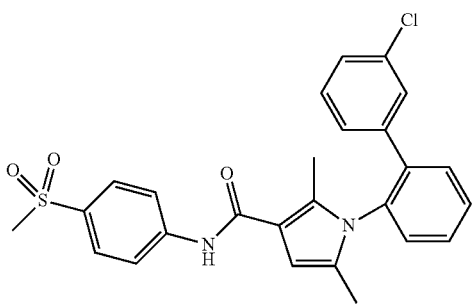 [SMILES: Cc1cc(C(=O)Nc2ccc(S(C)(=O)=O)cc2)c(C)n1-c1ccccc1-c1cccc(Cl)c1]

A. To a stirring solution of 1-(2-bromophenyl)-2,5-dimethyl-1H-pyrrole-3-carboxylic acid (4-methanesulfonyl-phenyl)-amide (100 mg, 0.23 mmol) and 3-chlorophenylboronic acid (0.95 g, 0.57 mmol) in DME/EtOH (2:1, 5 mL), 1M Na$_2$CO$_3$ (0.80 mL) and Pd(dppf)$_2$Cl$_2$ (38 mg, 0.046 mmol) were added. The reaction mixture was degassed and heated at 80° C. under Argon for 1 h and monitored by LC-MS. The mixture was diluted with DCM (20 mL) and washed with 15 mL of brine. The aqueous phase was extracted with DCM (20 mL) twice. The combined extracts were dried over anhyd Na$_2$SO$_4$ and concentrated under reduced pressure. The crude residue was purified by flash chromatography on silica gel, eluting with EtOAc-Hex (0-50%) to yield the title compound (53 mg, 48%) as a pale yellow solid. $^1$H-NMR (CDCl$_3$): δ 7.89 (2H, d), 7.80 (2H, d), 7.65 (1H, s), 7.57 (3H, m), 7.26 (3H, m), 7.04 (1H, t), 6.87 (1H, m), 6.13 (1H, s), 3.03 (3H, s), 2.23 (3H, s), 1.89 (3H, s). MS (ESI): 479 (MH$^+$).

B. In a manner similar to that described for Example 13A, the following compounds were prepared from the appropriate boronic acids:

1-(2'-Chloro-biphenyl-2-yl)-2,5-dimethyl-1H-pyrrole-3-carboxylic acid (4-methanesulfonyl-phenyl)-amide; MS (ESI): 479 (MH$^+$);

1-(4'-Chloro-biphenyl-2-yl)-2,5-dimethyl-1H-pyrrole-3-carboxylic acid (4-methanesulfonyl-phenyl)-amide; MS (ESI): 479 (MH$^+$);

1-(2',3'-Dichloro-biphenyl-2-yl)-2,5-dimethyl-1H-pyrrole-3-carboxylic acid (4-methanesulfonyl-phenyl)-amide; MS (ESI): 513 (MH$^+$);

1-(2',5'-Dichloro-biphenyl-2-yl)-2,5-dimethyl-1H-pyrrole-3-carboxylic acid (4-methanesulfonyl-phenyl)-amide; MS (ESI): 513 (MH$^+$);

1-(3'-Hydroxymethyl-biphenyl-2-yl)-2,5-dimethyl-1H-pyrrole-3-carboxylic acid (4-methanesulfonyl-phenyl)-amide; MS (ES): 475 (MH$^+$);

1-[2-(3,4-Dihydro-2H-benzo[b][1,4]dioxepin-7-yl)-phenyl]-2,5-dimethyl-1H-pyrrole-3-carboxylic acid (4-methanesulfonyl-phenyl)-amide; MS (ES): 517 (MH$^+$);

1-[2-((E)-3,3-Dimethyl-but-1-enyl)-phenyl]-2,5-dimethyl-1H-pyrrole-3-carboxylic acid (4-methanesulfonyl-phenyl)-amide; MS (ES): 451 (MH$^+$);

1-(3'-Diethylcarbamoyl-biphenyl-2-yl)-2,5-dimethyl-1H-pyrrole-3-carboxylic acid (4-methanesulfonyl-phenyl)-amide; MS (ES): 544 (MH$^+$);

1-[2-(5-Formyl-thiophen-2-yl)-phenyl]-2,5-dimethyl-1H-pyrrole-3-carboxylic acid (4-methanesulfonyl-phenyl)-amide; MS (ES): 479 (MH$^+$);

1-(4'-Methoxy-biphenyl-2-yl)-2,5-dimethyl-1H-pyrrole-3-carboxylic acid (4-methanesulfonyl-phenyl)-amide; MS (ES): 475 (MH$^+$);

1-(4'-Ethanesulfonyl-biphenyl-2-yl)-2,5-dimethyl-1H-pyrrole-3-carboxylic acid (4-methanesulfonyl-phenyl)-amide; MS (ES): 537 (MH$^+$);

1-(3'-Acetylamino-biphenyl-2-yl)-2,5-dimethyl-1H-pyrrole-3-carboxylic acid (4-methanesulfonyl-phenyl)-amide; MS (ES): 502 (MH$^+$);

1-(3'-tert-Butyl-5'-methylsulfanyl-biphenyl-2-yl)-2,5-dimethyl-1H-pyrrole-3-carboxylic acid (4-methanesulfonyl-phenyl)-amide; MS (ES): 547 (MH$^+$);

1-(4'-Methanesulfonyl-biphenyl-2-yl)-2,5-dimethyl-1H-pyrrole-3-carboxylic acid (4-methanesulfonyl-phenyl)-amide; MS (ES): 523 (MH$^+$);

1-(4'-Acetylamino-biphenyl-2-yl)-2,5-dimethyl-1H-pyrrole-3-carboxylic acid (4-methanesulfonyl-phenyl)-amide; MS (ES): 502 (MH$^+$);

1-(4'-Cyano-biphenyl-2-yl)-2,5-dimethyl-1H-pyrrole-3-carboxylic acid (4-methanesulfonyl-phenyl)-amide; MS (ES): 470 (MH+);

2'-[3-(4-Methanesulfonyl-phenylcarbamoyl)-2,5-dimethyl-pyrrol-1-yl]-biphenyl-4-carboxylic acid methyl ester; MS (ES): 503 (MH+);

1-(3'-Ethanesulfonyl-biphenyl-2-0)-2,5-dimethyl-1H-pyrrole-3-carboxylic acid (4-methanesulfonyl-phenyl)-amide; MS (ES): 537 (MH+);

2,5-Dimethyl-1-[3'-(pyrrolidine-1-carbonyl)-biphenyl-2-yl]-1H-pyrrole-3-carboxylic acid (4-methanesulfonyl-phenyl)-amide; MS (ES): 542 (MH+);

1-(5'-Ethyl-3'-methylsulfanyl-biphenyl-2-yl)-2,5-dimethyl-1H-pyrrole-3-carboxylic acid (4-methanesulfonyl-phenyl)-amide; MS (ES): 519 (MH+);

1-(4'-Ethoxy-3'-trifluoromethyl-biphenyl-2-yl)-2,5-dimethyl-1H-pyrrole-3-carboxylic acid (4-methanesulfonyl-phenyl)-amide; MS (ES): 557 (MH+);

1-(3'-Methoxy-biphenyl-2-yl)-2,5-dimethyl-1H-pyrrole-3-carboxylic acid (4-methanesulfonyl-phenyl)-amide; MS (ES): 475 (MH+);

2,5-Dimethyl-1-(2-thiophen-3-yl-phenyl)-1H-pyrrole-3-carboxylic acid (4-methanesulfonyl-phenyl)-amide; MS (ES): 451 (MH+);

1-(4'-Fluoro-2'-hydroxy-biphenyl-2-yl)-2,5-dimethyl-1H-pyrrole-3-carboxylic acid (4-methanesulfonyl-phenyl)-amide; MS (ES): 479 (MH+);

2,5-Dimethyl-1-(5'-propylsulfanyl-3'-trifluoromethyl-biphenyl-2-yl)-1H-pyrrole-3-carboxylic acid (4-methanesulfonyl-phenyl)-amide; MS (ES): 587 (MH+);

2,5-Dimethyl-1-[3'-trifluoromethyl-5'-(2-trimethylsilanyl-ethylsulfanyl)-biphenyl-2-yl]-1H-pyrrole-3-carboxylic acid (4-methanesulfonyl-phenyl)-amide; MS (ES): 645 (MH+);

1-(3'-Chloro-4'-methyl-biphenyl-2-yl)-2,5-dimethyl-1H-pyrrole-3-carboxylic acid (4-methanesulfonyl-phenyl)-amide; MS (ES): 493 (MH+);

1-(5'-Isopropylsulfanyl-3'-trifluoromethyl-biphenyl-2-yl)-2,5-dimethyl-1H-pyrrole-3-carboxylic acid (4-methanesulfonyl-phenyl)-amide; MS (ES): 587 (MH+);

1-(3'-Ethylcarbamoyl-biphenyl-2-yl)-2,5-dimethyl-1H-pyrrole-3-carboxylic acid (4-methanesulfonyl-phenyl)-amide; MS (ES): 516 (WO;

1-(3'-Carbamoyl-biphenyl-2-yl)-2,5-dimethyl-1H-pyrrole-3-carboxylic acid (4-methanesulfonyl-phenyl)-amide; MS (ES): 488 (MH+);

1-[2-(5-Cyano-6-ethoxy-pyridin-3-yl)-phenyl]-2,5-dimethyl-1H-pyrrole-3-carboxylic acid (4-methanesulfonyl-phenyl)-amide; MS (ES): 515 (MH+);

1-(4'-Hydroxymethyl-biphenyl-2-yl)-2,5-dimethyl-1H-pyrrole-3-carboxylic acid (4-methanesulfonyl-phenyl)-amide; MS (ES): 475 (MH+);

1-(4'-Ethoxy-3'-methanesulfonyl-biphenyl-2-yl)-2,5-dimethyl-1H-pyrrole-3-carboxylic acid (4-methanesulfonyl-phenyl)-amide; MS (ES): 567 (MH+);

2,5-Dimethyl-1-(2-pyrimidin-5-yl-phenyl)-1H-pyrrole-3-carboxylic acid (4-methanesulfonyl-phenyl)-amide; MS (ES): 447 (MH+);

2'-[3-(4-Methanesulfonyl-phenylcarbamoyl)-2,5-dimethyl-pyrrol-1-yl]-biphenyl-3-carboxylic acid methyl ester; MS (ES): 503 (MH+);

1-(3'-Hydroxy-biphenyl-2-yl)-2,5-dimethyl-1H-pyrrole-3-carboxylic acid (4-methanesulfonyl-phenyl)-amide; MS (ES): 461 (MH+);

1-(5'-Fluoro-2'-methoxy-biphenyl-2-yl)-2,5-dimethyl-1H-pyrrole-3-carboxylic acid (4-methanesulfonyl-phenyl)-amide; MS (ES): 493 (MH+);

1-(3'-Ethoxy-biphenyl-2-yl)-2,5-dimethyl-1H-pyrrole-3-carboxylic acid (4-methanesulfonyl-phenyl)-amide; MS (ES): 489 (MH+);

1-(2'-Fluoro-5'-methoxy-biphenyl-2-yl)-2,5-dimethyl-1H-pyrrole-3-carboxylic acid (4-methanesulfonyl-phenyl)-amide; MS (ES): 493 (MH+);

2,5-Dimethyl-1-[4'-(morpholine-4-carbonyl)-biphenyl-2-yl]-1H-pyrrole-3-carboxylic acid (4-methanesulfonyl-phenyl)-amide; MS (ES): 558 (MH+);

1-(4'-Ethylcarbamoyl-biphenyl-2-yl)-2,5-dimethyl-1H-pyrrole-3-carboxylic acid (4-methanesulfonyl-phenyl)-amide; MS (ES): 516 (MH+);

1-(2'-Acetyl-biphenyl-2-yl)-2,5-dimethyl-1H-pyrrole-3-carboxylic acid (4-methanesulfonyl-phenyl)-amide; MS (ES): 487 (MH+);

1-(4'-Methanesulfonylamino-biphenyl-2-yl)-2,5-dimethyl-1H-pyrrole-3-carboxylic acid (4-methanesulfonyl-phenyl)-amide; MS (ES): 538 (MH+);

2,5-Dimethyl-1-[4'-(piperidine-1-carbonyl)-biphenyl-2-yl]-1H-pyrrole-3-carboxylic acid (4-methanesulfonyl-phenyl)-amide; MS (ES): 556 (MH+);

1-(4'-Dimethylcarbamoyl-biphenyl-2-yl)-2,5-dimethyl-1H-pyrrole-3-carboxylic acid (4-methanesulfonyl-phenyl)-amide; MS (ES): 516 (MH+);

1-(3'-Acetyl-biphenyl-2-yl)-2,5-dimethyl-1H-pyrrole-3-carboxylic acid (4-methanesulfonyl-phenyl)-amide; MS (ES): 487 (MH+);

2,5-Dimethyl-1-[2-(5-methyl-furan-2-yl)-phenyl]-1H-pyrrole-3-carboxylic acid (4-methanesulfonyl-phenyl)-amide; MS (ES): 449 (MH+);

2'-[3-(4-Methanesulfonyl-phenylcarbamoyl)-2,5-dimethyl-pyrrol-1-yl]-biphenyl-4-carboxylic acid ethyl ester; MS (ES): 517 (MH+);

1-(3',4'-Dimethoxy-biphenyl-2-yl)-2,5-dimethyl-1H-pyrrole-3-carboxylic acid (4-methanesulfonyl-phenyl)-amide; MS (ES): 505 (MH+);

1-[2-(2,3-Dihydro-benzofuran-5-yl)-phenyl]-2,5-dimethyl-1H-pyrrole-3-carboxylic acid (4-methanesulfonyl-phenyl)-amide; MS (ES): 487 (MH+);

1-(2'-Acetylamino-biphenyl-2-yl)-2,5-dimethyl-1H-pyrrole-3-carboxylic acid (4-methanesulfonyl-phenyl)-amide; MS (ES): 502 (MH+);

2,5-Dimethyl-1-(3'-methylsulfanyl-biphenyl-2-yl)-1H-pyrrole-3-carboxylic acid (4-methanesulfonyl-phenyl)-amide; MS (ES): 491 (MH+).

Example 14

PREPARATION OF 2,5-DIMETHYL-1-[2-(TRIFLUOROMETHYL)PHENYL]-1H-PYRROLE-3-CARBOXYLIC ACID [4-(METHANESULFONYL)PHENYL]-METHYL-AMIDE

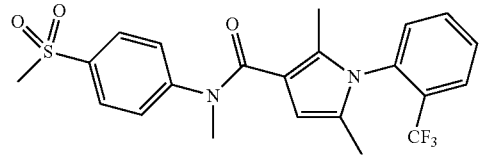 [SMILES: Cc1cc(C(=O)N(C)c2ccc(S(C)(=O)=O)cc2)c(C)n1-c1ccccc1C(F)(F)F]

To a solution of 4-methylsulfonyl-aniline (0.20 g, 1.2 mmol) in anhyd THF (2.0 mL) was added 1.43 M butyllithium in hexanes (0.82 mL, 1.2 mmol). The resulting suspension was sonicated to create a fine suspension and then iodomethane (80 µL, 1.29 mmol, 1.1 eq) was added. The suspension was sonicated for 0.5 h and then was washed into a separatory funnel with EtOAc and water. The organic layer was separated, dried (anhyd MgSO₄), and concentrated in vacuo to afford a 4:1 mixture of (4-methylsulfonyl-phenyl)-methyl-amine and (4-methylsulfonyl-phenyl)-dimethyl-amine as a tan solid (180 mg). The crude mixture was used directly in the next step without purification. The title compound was prepared from the crude sample of (4-methylsulfonyl-phenyl)-methyl-amine in a manner similar to that described in Example 1D; $^1$H NMR (CDCl$_3$): δ 7.77 (d, J=9 Hz, 2H), 7.72 (d, J=8 Hz, 1H), 7.61 (t, J=8 Hz, 1H), 7.52 (t, J=8 Hz, 1H), 7.24 (d, J=9 Hz, 2H), 7.12 (d, J=8 Hz, 1H), 5.49 (s, 1H), 3.44 (s, 3H), 2.97 (s, 3H), 1.82 (s, 3H), 1.66 (s, 3H); MS (ESI) m/z 451 [M+H]$^+$.

Example 15

PREPARATION OF 2,5-DIMETHYL-1-[2-(TRIFLUOROMETHYL)PHENYL]-1H-PYRROLE-3-CARBOXYLIC ACID (5-SULFAMOYL-[1,3,4]THIADIAZOL-2-YL)-AMIDE

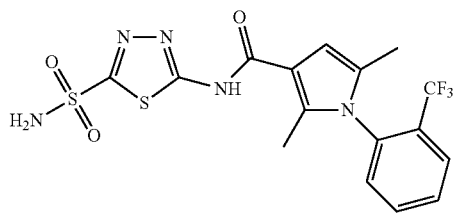 [SMILES: Cc1cc(C(=O)Nc2nnc(S(N)(=O)=O)s2)c(C)n1-c1ccccc1C(F)(F)F]

A. Acetazolamide (2.03 g, 9.13 mmol) was combined with 1N HCl (20 mL) and then heated at 100° C. The initial suspension became a clear solution within 3 h. After cooling to 0° C. the reaction mixture was carefully neutralized by the addition of solid KOH. Upon standing precipitates had formed and were collected by filtration. The solids were dried under high vacuum to afford 5-amino-[1,3,4]thiadiazole-2-sulfonic acid amide (1.2 g, 70%) as a colorless solid; $^1$H NMR (DMSO-d$_6$): δ 8.06 (s, 2H), 7.82 (s, 2H). Acetazolamide (2.03 g, 9.13 mmol) was combined with 1N HCl (20 mL) and then heated at 100° C. The initial suspension became a clear solution within 3 h. After cooling to 0° C. A.
The title compound was prepared from 5-amino-[1,3,4]thiadiazole-2-sulfonic acid amide in a manner similar to that described in Example 1D; $^1$H NMR (DMSO-d$_6$): δ 8.09 (s, 2H), 7.82 (d, J=8 Hz, 1H), 7.73 (t, J=8 Hz, 1H), 7.63 (t, J=8 Hz, 1H), 7.32 (d, J=8 Hz, 1H), 6.74 (s, 1H), 1.98 (s, 3H), 1.67 (s, 3H); MS (ESI) m/z 446 [M+H]$^+$.

PREPARATION OF 2,5-DIMETHYL-1-[2-(TRIFLUOROMETHYL)PHENYL]-1H-PYRROLE-3-CARBOXYLIC ACID (5-DIMETHYLSULFAMOYL-4-METHYL-THIAZOL-2-YL)-AMIDE

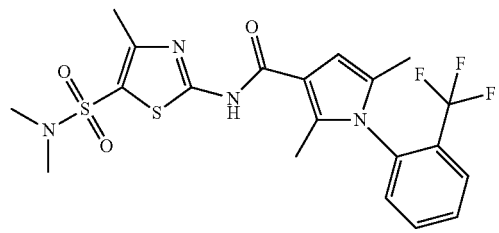 [SMILES: Cc1nc(NC(=O)c2cc(C)n(-c3ccccc3C(F)(F)F)c2C)sc1S(=O)(=O)N(C)C]

B. A 2.0 M solution (10 mL) of dimethylamine in THF, diisopropylethylamine (1.0 mL) and 2-acetamido-4-methyl-5-thiazolesulfonyl chloride (0.97 g, 3.8 mmol) were combined. After stirring 3 h the reaction mixture was concentrated in vacuo. The residue was partitioned between EtOAc and water. The organic layer was separated, dried (anhyd MgSO$_4$), and concentrated in vacuo to afford intermediate N-(5-dimethyl-sulfamoyl-4-methyl-thiazol-2-yl)-acetamide as a tan semi-solid. The intermediate was treated with 1N HCl (10 mL) and then heated at 95-100° C. After 2 h additional 1N HCl was added and heating was continued for another 2 h. The aqueous solution was cooled and was transferred to a separatory funnel, in which it was washed with DCM. The aqueous phase was made basic by the addition of 1N NaOH (30 mL) and then extracted with DCM. The combined extracts were dried (anhyd Na$_2$SO$_4$) and concentrated in vacuo to afford 2-amino-4-methyl-thiazole-5-sulfonic acid dimethylamide (0.48 g, 57%) as a light tan semi-crystalline solid; $^1$H-NMR (DMSO-d$_6$): δ 7.85 (s, 2H), 2.77 (s, 6H), 2.42 (s, 3H); MS (ESI) m/z 222 [M+H]$^+$.

The title compound was prepared from 2-amino-4-methyl-thiazole-5-sulfonic acid dimethylamide in a manner similar to that described in Example 1D; $^1$H NMR (CDCl$_3$): δ 9.36 (s, 1H), The title compound was prepared from 2-amino-4-methyl-thiazole-5-sulfonic acid dimethylamide in a manner similar to that described in Example 1D; $^1$H NMR (CDCl$_3$): δ 9.36 (s, 1H), 7.81 (d, J=8 Hz, 1H), 7.70 (t, J=8 Hz, 1H), 7.60 (t, J=8 Hz, 1H), 7.20 (d, J=8 Hz, 1H), 6.12 (s, 1H), 2.76 (s, 6H), 2.51 (s, 3H), 2.22 (s, 3H), 1.85 (s, 3H); MS (ESI) m/z 487 [M+H]$^+$.

Example 16

PREPARATION OF 2-CYANO-3-METHYL-4-OXO-4-(2-TRIFLUOROMETHYL-PHENYL)-BUTYRIC ACID METHYL ESTER

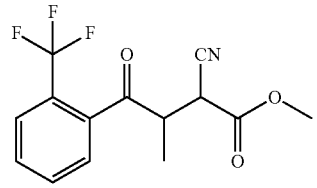 [SMILES: COC(=O)C(C#N)C(C)C(=O)c1ccccc1C(F)(F)F]

A. To a solution of 2'-trifluoromethyl-propiophenone (10 g, 48 mmol) in carbon tetrachloride (50 ml) was added a solution of bromine (2.72 mL, 52.8 mmol) in carbon tetrachloride (20 mL) dropwise. After the addition was complete, stirring was continued for another 2 h. The solution was washed with satd NaHCO$_3$ and water, dried (anhyd Na$_2$SO$_4$) and concentrated under reduced pressure to give 2-bromo-1-(2-trifluoromethyl-phenyl)-propan-1-one as an oil (12.8 g, 95%), which was used in the next step without purification. $^1$H-NMR (CDCl$_3$): δ 7.73 (m, 2H), 7.58-7.67 (m, 2H), 4.96 (q, 1H), 1.90 (d, 3H). To a solution of 2'-trifluoromethyl-propiophenone (10 g, 48 mmol) in carbon tetrachloride (50 ml) was added a solution of bromine (2.72 mL, 52.8 mmol) in carbon tetrachloride (20 m
To a suspension of NaH (60%, 2.88 g, 72 mmol) in anhyd THF (200 mL) was added methyl cyanoacetate (4.5 mL, 50 mmol). After this mixture was stirred for 3 h at 20° C., a solution of 2-bromo-1-(2-trifluoromethyl-phenyl)-propan-1-one (13.5 g, 48 mmol) was added and the mixture was stirred overnight at 20° C. The mixture was quenched with water and the organic layer was separated. The aqueous layer was extracted with EtOAc. The combined extracts were washed with brine, dried (anhyd $Na_2SO_4$) and concentrated under reduced pressure to afford the title compound as an oil (13.3 g, 93%), which was used in the next step without purification. MS (ES): 300 (MH$^+$).

PREPARATION OF 4-METHYL-5-(2-TRIFLUOROMETHYL-PHENYL)-1H-PYRROLE-3-CARBOXYLIC ACID METHYL ESTER

B. To a solution of 2-cyano-3-methyl-4-oxo-4-(2-trifluoromethyl-phenyl)-butyric acid methyl ester (13.27 g, 44.4 mmol) in formic acid (100 mL) was added freshly prepared Raney nickel [Al—Ni (1:1), 117 g] and the mixture was heated to reflux with stirring for 2 h. After cooling, the catalyst was removed by filtration and washed with ethanol. The combined filtrates were concentrated to give an oil, which was re-dissolved in DCM and filtered to remove residual solids. Evaporation of solvent gave 4-methyl-5-(2-trifluoromethyl-phenyl)-2,3-dihydro-1H-pyrrole-3-carboxylic acid methyl ester as an oil (10 g, 79%), which was used in the next step without purification. MS (ES): 286 (MH$^+$).

To a solution of 4-methyl-5-(2-trifluoromethyl-phenyl)-2,3-dihydro-1H-pyrrole-3-carboxylic acid methyl ester (10 g, 35 mmol) in toluene was added 10% Pd/C (3.3 g). The resulting suspension was heated to reflux for 3 days. After cooling, the solids were removed by filtration. The filtrate was washed with toluene and concentrated under reduced pressure to yield an oil, which was purified by column chromatography (silica), eluting with EtOAc-hexane (1:1) to give the title compound (2.9 g, 29%). MS (ES): 284 (MH$^+$).

PREPARATION OF 1,4-DIMETHYL-5-(2-TRIFLUOROMETHYL-PHENYL)-1H-PYRROLE-3-CARBOXYLIC ACID

C. To a solution of 4-methyl-5-(2-trifluoromethyl-phenyl)-1H-pyrrole-3-carboxylic acid methyl ester (2.9 g, 10.2 mmol) in anhyd THF (40 mL) was added lithium bis(trimethylsilyl)amide (1.0 M solution in THF, 12.3 mL, 12.3 mmol) slowly at 20° C. After stirring 0.5 h, iodomethane (0.96 mL, 15.4 mmol) was added and the mixture was stirred for 3 h at 20° C. After quenching with water, the organic layer was separated and the aqueous layer was extracted with EtOAc. The combined extracts were washed with water, dried (anhyd $Na_2SO_4$) and concentrated under reduced pressure to yield 1,4-dimethyl-5-(2-trifluoromethyl-phenyl)-1H-pyrrole-3-carboxylic acid methyl ester as an oil (2.8 g, 92%), which was used in the next step without purification. MS (ES): 298 (MH$^+$). To a solution of 4-methyl-5-(2-trifluoromethyl-phenyl)-1H-pyrrole-3-carboxylic acid methyl ester (2.9 g, 10.2 mmol) in anhyd THF (40 mL) was added lithium bis(trimethylsilyl)amide C.

To a solution of 1,4-dimethyl-5-(2-trifluoromethyl-phenyl)-1H-pyrrole-3-carboxylic acid methyl ester (2.5 g, 8.4 mmol) in MeOH (20 mL) was added 4N NaOH (10 mL) and the mixture was heated to reflux overnight. Evaporation of solvent gave a solid, which was re-dissolved in water. The solution was acidified with formic acid. The resulting solids were collected by filtration, washed with water and then dried under high vacuum to afford the title compound as an off-white solid (2.15 g, 90%). MS (ES): 284 (MH$^+$).

PREPARATION OF 1,4-DIMETHYL-5-(2-TRIFLUOROMETHYL-PHENYL)-1H-PYRROLE-3-CARBOXYLIC ACID (4-METHANESULFONYL-PHENYL)-AMIDE

D. To a solution of 1,4-dimethyl-5-(2-trifluoromethyl-phenyl)-1H-pyrrole-3-carboxylic acid (56 mg, 0.20 mmol) in DCM (4 mL) was added oxalyl chloride (22 pt, 0.25 mmol). After stirring 30 min, solvent was removed in vacuo to give an oil, which was re-dissolved in anhyd THF (4 mL). To this solution were added 4-methanesulfonyl-aniline (68 mg, 0.40 mmol) and DIEA (140 µL, 0.8 mmol) and the mixture was stirred at 60° C. overnight. After cooling, solvent was removed in vacuo to give a crude residue, which was purified by column chromatography on silica gel, eluted with EtOAc-hexane (0:100 to 25:75) to give the title compound (24 mg, 28%). $^1$H-NMR (CDCl$_3$): δ 7.89-7.91 (m, 2H), 7.80 (m, 3H), 7.57-7.66 (m, 3H), 7.33 (d, 1H), 7.30 (s, 1H), 3.32 (s, 3H), 3.05 (s, 3H), 2.12 (s, 3H). MS (ES): 437 (MH$^+$).

E. In a manner similar to that described for Example 16D, the following compounds were prepared from the appropriate anilines:

1,4-dimethyl-5-(2-trifluoromethyl-phenyl)-1H-pyrrole-3-carboxylic acid (4-methanesulfonyl-3-trifluoromethyl-phenyl)-amide; $^1$H-NMR (CDCl$_3$): δ 8.25 (1H, d), 8.08 (2H, m), 7.83 (1H, d), 7.77 (1H, s), 7.63 (2H, m), 7.33 (2H, m), 3.33 (3H, s), 3.18 (3H, m), 2.10 (3H, s); MS (ES): 505 (MH$^+$);

1,4-dimethyl-5-(2-trifluoromethyl-phenyl)-1H-pyrrole-3-carboxylic acid [4-(2-fluorobenzoyl)-phenyl]-amide; $^1$H-NMR (CDCl$_3$): δ 7.81-7.86 (3H, m), 7.72 (2H, m), 7.63 (3H, m), 7.52 (2H, m), 7.33 (1H, d), 7.29 (1H, s), 7.26 (1H, m), 7.16 (1H, m), 3.30 (3H, s), 2.08 (3H, s); MS (ES): 481 (MH$^+$);

1,4-dimethyl-5-(2-trifluoromethyl-phenyl)-1H-pyrrole-3-carboxylic acid (4-sulfamoyl-phenyl)-amide; $^1$H-NMR (DMSO-d$_6$): δ 9.84 (1H, s), 7.88 (3H, m), 7.79 (1H, m), 7.72 (3H, m), 7.67 (1H, s), 7.43 (1H, d), 7.21 (2H, s), 3.32 (3H, s), 1.92 (3H, s). MS (ES): 438 (MH$^+$);

1,4-dimethyl-5-(2-trifluoromethyl-phenyl)-1H-pyrrole-3-carboxylic acid (3-chloro-4-sulfoamoyl-phenyl)-amide; $^1$HNMR (CDCl$_3$): δ 8.04 (1H, d), 7.95 (1H, d), 7.83-7.79 (2H, m), 7.67-7.58 (2H, m), 7.45-7.43 (1H, dd), 7.33 (2H, m), 5.19 (2H, s), 3.33 (3H, s), 2.08 (3H, s). MS (ESI): 472 (MH$^+$).

F. In a manner similar to that described for Examples 16A-D, but replacing 2'-(trifluoromethyl)propiophenone with 4'-fluoro-2'-(trifluoromethyl)propiophenone, the following compound was prepared:

5-(4-fluoro-2-trifluoromethyl-phenyl)-1,4-dimethyl-1H-pyrrole-3-carboxylic acid (4-methanesulfonyl-phenyl)-amide; $^1$HNMR (CDCl$_3$): δ 7.90 (2H, m), 7.80 (2H, m), 7.68 (1H, s), 7.53 (1H, dd), 7.7.29-7.39 (3H, m), 3.32 (3H, s), 3.05 (3H, s), 2.08 (3H, s); MS (ES): 455 (MH$^+$).

G. In a manner similar to that described for Example 16F, the following compounds were prepared from the appropriate anilines:

5-(4-fluoro-2-trifluoromethyl-phenyl)-1,4-dimethyl-1H-pyrrole-3-carboxylic acid (3-chloro-4-sulfamoyl-phenyl)-amide; $^1$H-NMR (CDCl$_3$): δ 8.06 (1H, d), 7.98 (1H, d), 7.70 (1H, s), 7.54 (1H, dd), 7.44 (1H, dd), 7.35 (2H, m), 7.32 (1H, s), 5.14 (2H, s), 3.32 (3H, s), 2.08 (3H, s). MS (ES): 490 (MH$^+$);

5-(4-fluoro-2-trifluoromethyl-phenyl)-1,4-dimethyl-1H-pyrrole-3-carboxylic acid (3-trifluoromethyl-4-sulfamoyl-phenyl)-amide; $^1$H-NMR (CDCl$_3$): δ 8.22 (1H, d), 8.09 (1H, d), 7.98 (1H, dd), 7.73 (1H, s), 7.54 (1H, dd), 7.36 (2H, m), 7.31 (1H, s), 4.98 (2H, s), 3.33 (3H, s), 2.09 (3H, s). MS (ES): 524 (MH+).

Example 17

Preparation of ETHYL 5-BROMO-1,4-DIMETHYL-1H-PYRROLE-3-CARBOXYLATE

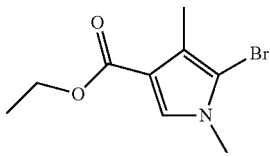

A. To a solution of ethyl 4-methyl-3-pyrrolecarboxylate (1.57 g, 10 mmol) in anhyd THF (30 mL) cooled to −78° C. was added NBS (1.9 g, 10 mmol). After stirring 1 h at −30° C., the reaction mixture was concentrated under reduced pressure. The residue was purified by column chromatography, eluting with EtOAc-Hex (0:100 to 30:70), to yield ethyl 5-bromo-4-methyl-1H-pyrrole-3-carboxylate (2.0, 86%) as a white solid. $^1$H-NMR (CDCl$_3$): δ 8.54 (1H, brs), 7.38 (1H, d), 4.27 (2H, q), 2.24 (3H, s), 1.33 (3H, t).

To a solution of ethyl 5-bromo-4-methyl-1H-pyrrole-3-carboxylate (2.0 g, 8.6 mmol) in anhyd DMF (30 mL) at 0° C. was added portionwise NaH (60% in mineral oil, 705 mg, 17.6 mmol) under nitrogen. After 1 h at ambient temperature, the reaction mixture was charged with iodomethane (1.5 mL, 24 mmol) and then stirred at ambient temperature overnight. The reaction mixture was quenched by cautious addition of water and then extracted with DCM. The combined extracts were washed with water, dried over Na$_2$SO$_4$, concentrated under reduced pressure, and purified by column chromatography, eluting with EtOAc-Hex (0:100 to 20:80), to provide the title compound (1.64 g, 78%) as a white solid. $^1$H-NMR (CDCl$_3$): δ 7.33 (1H, s), 4.25 (2H, q), 3.58 (3H, s), 2.24 (3H, s), 1.33 (3H, t).

PREPARATION OF 1,4-DIMETHYL-5-(4-FLUOROPHENYL)-1H-PYRROLE-3-CARBOXYLIC ACID (4-METHANESULFONYL-PHENYL) AMIDE

B. A mixture of ethyl 5-bromo-1,4-dimethyl-1H-pyrrole-3-carboxylate (246 mg, 1.0 mmol), 4-fluorophenyl-boronic acid (210 mg, 1.5 mmol), Na$_2$CO$_3$ (320 mg, 3.0 mmol) and Pd(PPh$_3$)$_4$ (116 mg, 0.10 mmol) in DMF/H$_2$O (10:1, 10 mL) was sparged with nitrogen for 10 min. The reaction vial was sealed and heated at 110° C. with stirring. After 18 h, the reaction mixture was diluted with DCM and then filtered. The filtrate was concentrated under reduced pressure and then purified by column chromatography, eluting with EtOAc-Hex (0:100 to 50:50), to give 1,4-dimethyl-5-(4-fluorophenyl)-1H-pyrrole-3-carboxylic acid ethyl ester (252 mg, 96%) as a pale yellow solid. $^1$H-NMR (CDCl$_3$): δ 7.30 (1H, s), 7.26-7.20 (2H, m), 7.15-7.10 (2H, m), 4.28 (2H, q), 3.48 (3H, s), 2.20 (3H, s), 1.36 (3H, t). MS (ESI): 262 (MH+).

The title compound was prepared from 1,4-dimethyl-5-(4-fluorophenyl)-1H-pyrrole-3-carboxylic acid ethyl ester in a manner similar to that described for Examples 16C-D.

$^1$H-NMR (DMSO-d$_6$): δ 9.94 (1H, s), 8.00-7.95 (2H, m), 7.87-7.84 (2H, d), 7.69 (1H, s), 7.43-7.39 (2H, m), 7.35-7.30 (2H, m), 3.52 (3H, s), 3.18 (3H, s), 2.15 (3H, s); MS (ESI): 387 (MH+).

C. In a manner similar to that described for Example 17B, but replacing 4-fluorophenylboronic acid with 1-naphthaleneboronic acid, the following compound was prepared:

1,4-dimethyl-5-(naphthalene-1-yl)-1H-pyrrole-3-carboxylic acid (4-methanesulfonyl-phenyl)amide; $^1$H-NMR (CDCl$_3$): δ 7.97-7.80 (7H, m), 7.59-7.41 (6H, m), 3.35 (3H, s), 3.06 (3H, s), 2.16 (3H, s); MS (ESI): 419 (MH+).

Example 18

A. Preparation of 2-BROMO-1,3-DI METHYL-1H-PYRROLE-4-CARBOXYLIC ACID [4-(SULFAMOYL)PHENYL]-AMIDE

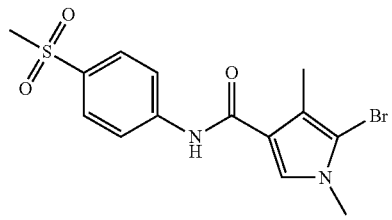 [SMILES: Cc1c(C(=O)Nc2ccc(S(C)(=O)=O)cc2)cn(C)c1Br]

Into a 250 mL round-bottom flask was weighed 2.06 g of 2-Bromo-1,3-dimethyl-1H-pyrrole-4-carboxylic acid methyl ester (8.88 mmol), 1.61 g (9.40 mmol) of 4-Aminophenyl methyl sulfone, and 20 mL of Toluene. To the resulting suspension was added 4.5 mL of 2.0 M trimethylaluminum in toluene. The resulting solution was heated to 100-105° C. for 1.5 h then the reaction was cooled and washed into a separatory funnel with ethyl acetate and saturated sodium-potassium tartrate. The ethyl acetate was separated, washed with saturated sodium-potassium tartrate and brine, then was dried (MgSO$_4$), and concentrated in vacuo. The residue was crystallized from ethanol to afford the 2-Bromo-1,3-dimethyl-1H-pyrrole-4-carboxylic acid [4-(sulfamoyl)phenyl]-amide as a faintly yellow semi-crystalline solid, yield: 2.81 g (85%). $^1$H NMR (DMSO-d$_6$): δ 10.06 (s, 1H), 8.04 (d, J=9 Hz, 2H), 7.94 (d, J=9 Hz, 2H), 7.88 (s, 1H), 3.72 (s, 3H), 3.26 (s, 3H), 2.28 (s, 3H); MS (ESI) m/z 371 and 373, each [M+H]+.

B. Preparation of 1,4-DIMETHYL-5-(2-PHENOXY-PHENYL)-1H-PYRROLE-3-CARBOXYLIC ACID (4-METHANESULFONYL-PHENYL)-AMIDE

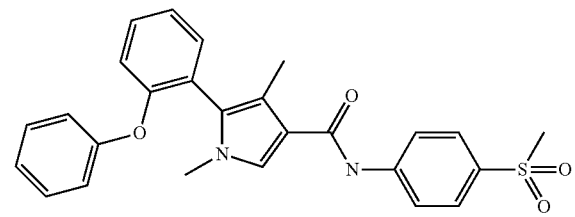 [SMILES: Cc1c(C(=O)Nc2ccc(S(C)(=O)=O)cc2)cn(C)c1-c1ccccc1Oc1ccccc1]

Into a 50 mL round bottom flask was weighed 100 mg of 2-Bromo-1,3-dimethyl-1H-pyrrole-4-carboxylic acid [4-(sulfamoyl)phenyl]-amide (0.27 mmol), 230 mg of (2-phenoxy)phenylboronic acid, potassium hydroxide (30.2 mg, 0.54 mmol), and DAPCy (J. Org Chem (2004), 69: 4330-4335) (6.2 mg, 4 Mol %) and Ethanol/DMF (3 ml, 50:50) was added. The solution was heated at 100° C. overnight. The reaction was cooled and washed into a separatory funnel with ethyl acetate and water. The ethyl acetate washed with water and brine, then was dried (MgSO$_4$), and concentrated in vacuo. The resulting residue was purified by flash chromatography (SiO$_2$), eluting with EtOAc/Hex 0-80% to afford the title compounds as a white solid (10 mg, 8%); $^1$H NMR (DMSO-d$_6$): δ 7.88 (d, J=9 Hz, 2H), 7.77 (d, J=9 Hz, 2H), 7.60 (s, 1H), 7.43-7.37 (m, 1H), 7.32-7.20 (m, 4H), 7.04 (d, J=9 Hz, 2H), 6.85 (d, J=8 Hz, 2H), 3.52 (s, 3H), 3.04 (s, 3H), 2.20 (s, 3H); MS (ESI) m/z 461 [M+H]$^+$ C. In a similar manner to that described in Example 18B, but replacing (2-phenoxy)phenylboronic acid with the appropriate boronic acid the following compounds were prepared:

1,4-Dimethyl-5-(4-trifluoromethyl-phenyl)-1H-pyrrole-3-carboxylic acid (4-methanesulfonyl-phenyl)-amide; MS (ES): 437 (MH+);
5-(2-Isopropoxy-phenyl)-1,4-dimethyl-1H-pyrrole-3-carboxylic acid (4-methanesulfonyl-phenyl)-amide; MS (ES): 427 (MH+);
5-(2-Benzyloxy-5-fluoro-phenyl)-1,4-dimethyl-1H-pyrrole-3-carboxylic acid (4-methanesulfonyl-phenyl)-amide; MS (ES): 493 (MH+);
5-(2-Butoxy-5-methyl-phenyl)-1,4-dimethyl-1H-pyrrole-3-carboxylic acid (4-methanesulfonyl-phenyl)-amide; MS (ES): 455 (MH+);
5-(3-Benzyloxy-phenyl)-1,4-dimethyl-1H-pyrrole-3-carboxylic acid (4-methanesulfonyl-phenyl)-amide; MS (ES): 475 (MH+);
5-(3-Bromo-2-methoxy-5-methyl-phenyl)-1,4-dimethyl-1H-pyrrole-3-carboxylic acid (4-methanesulfonyl-phenyl)-amide; MS (ES): 491 (MH+);
5-Benzo[b]thiophen-2-yl-1,4-dimethyl-1H-pyrrole-3-carboxylic acid (4-methanesulfonyl-phenyl)-amide; MS (ES): 425 (MH+);
5-(3-Bromo-2-butoxy-5-methyl-phenyl)-1,4-dimethyl-1H-pyrrole-3-carboxylic acid (4-methanesulfonyl-phenyl)-amide; MS (ES): 533 (MH+);
5-(5-Acetyl-thiophen-2-yl)-1,4-dimethyl-1H-pyrrole-3-carboxylic acid (4-methanesulfonyl-phenyl)-amide; MS (ES): 417 (MH+);
5-(3-Cyano-phenyl)-1,4-dimethyl-1H-pyrrole-3-carboxylic acid (4-methanesulfonyl-phenyl)-amide; MS (ES): 394 (MH+);
3-[4-(4-Methanesulfonyl-phenylcarbamoyl)-1,3-dimethyl-1H-pyrrol-2-yl]-benzoic acid methyl ester; MS (ES): 427 (MH+);
1,4-Dimethyl-5-(2-methylsulfanyl-phenyl)-1H-pyrrole-3-carboxylic acid (4-methanesulfonyl-phenyl)-amide; MS (ES): 415 (MH+);
5-(3,5-Bis-trifluoromethyl-phenyl)-1,4-dimethyl-1H-pyrrole-3-carboxylic acid (4-methanesulfonyl-phenyl)-amide; MS (ES): 505 (MH+);
5-((E)-3,3-Dimethyl-but-1-enyl)-1,4-dimethyl-1H-pyrrole-3-carboxylic acid (4-methanesulfonyl-phenyl)-amide; MS (ES): 375 (MH+);
5-(2-Amino-phenyl)-1,4-dimethyl-1H-pyrrole-3-carboxylic acid (4-methanesulfonyl-phenyl)-amide; MS (ES): 384 (MH+);
5-(2-Isopropoxy-5-methyl-phenyl)-1,4-dimethyl-1H-pyrrole-3-carboxylic acid (4-methanesulfonyl-phenyl)-amide; MS (ES): 441 (MH+);
5-Benzo[1,3]dioxol-5-yl-1,4-dimethyl-1H-pyrrole-3-carboxylic acid (4-methanesulfonyl-phenyl)-amide; MS (ES): 413 (MH+);
5-(1H-Indol-5-yl)-1,4-dimethyl-1H-pyrrole-3-carboxylic acid (4-methanesulfonyl-phenyl)-amide; MS (ES): 408 (MH+);
1,4-Dimethyl-5-naphthalen-1-yl-1H-pyrrole-3-carboxylic acid (4-methanesulfonyl-phenyl)-amide; MS (ES): 419 (MH+);
(E)-3-{3-[4-(4-Methanesulfonyl-phenylcarbamoyl)-1,3-dimethyl-1H-pyrrol-2-yl]-phenyl}-acrylic acid methyl ester; MS (ES): 453 (MH+);
5-(2-Butoxy-phenyl)-1,4-dimethyl-1H-pyrrole-3-carboxylic acid (4-methanesulfonyl-phenyl)-amide; MS (ES): 441 (MH+);
5-(3-Acetyl-phenyl)-1,4-dimethyl-1H-pyrrole-3-carboxylic acid (4-methanesulfonyl-phenyl)-amide; MS (ES): 411 (MH+);
5-Dibenzofuran-4-yl-1,4-dimethyl-1H-pyrrole-3-carboxylic acid (4-methanesulfonyl-phenyl)-amide; MS (ES): 459 (MH+);
5-(3-Benzylcarbamoyl-phenyl)-1,4-dimethyl-1H-pyrrole-3-carboxylic acid (4-methanesulfonyl-phenyl)-amide; MS (ES): 502 (MH+);
1,4-Dimethyl-5-(4-methyl-naphthalen-1-yl)-1H-pyrrole-3-carboxylic acid (4-methanesulfonyl-phenyl)-amide; MS (ES): 433 (MH+);
5-(2-Benzyloxy-phenyl)-1,4-dimethyl-1H-pyrrole-3-carboxylic acid (4-methanesulfonyl-phenyl)-amide; MS (ES): 475 (MH+);
5-(1-Benzenesulfonyl-1H-indol-3-yl)-1,4-dimethyl-1H-pyrrole-3-carboxylic acid (4-methanesulfonyl-phenyl)-amide; MS (ES): 548 (MH+);
5-(3-Carbamoyl-phenyl)-1,4-dimethyl-1H-pyrrole-3-carboxylic acid (4-methanesulfonyl-phenyl)-amide; MS (ES): 412 (MH+);
Carbonic acid tert-butyl ester 3-[4-(4-methanesulfonyl-phenylcarbamoyl)-1,3-dimethyl-1H-pyrrol-2-yl]-phenyl ester; MS (ES): 485 (MH+);
1,4-Dimethyl-5-pyrimidin-5-yl-1H-pyrrole-3-carboxylic acid (4-methanesulfonyl-phenyl)-amide; MS (ES): 371 (MH+);
5-Acenaphthen-5-yl-1,4-dimethyl-1H-pyrrole-3-carboxylic acid (4-methanesulfonyl-phenyl)-amide; MS (ES): 445 (MH+);
1,4-Dimethyl-5-(2,4,5-trimethyl-phenyl)-1H-pyrrole-3-carboxylic acid (4-methanesulfonyl-phenyl)-amide; MS (ES): 411 (MH+);
1,4-Dimethyl-5-(1-methyl-1H-indol-5-yl)-1H-pyrrole-3-carboxylic acid (4-methanesulfonyl-phenyl)-amide; MS (ES): 422 (MH+); and
5-(1-Benzyl-1H-pyrazol-4-yl)-1,4-dimethyl-1H-pyrrole-3-carboxylic acid (4-methanesulfonyl-phenyl)-amide; MS (ES): 449 (MH+).

Example 19

PREPARATION OF 3,5-DIMETHYL-4-(2-TRIFLUOROMETHYL-PHENYL)-1H-PYRROLE-2-CARBOXYLIC ACID ETHYL ESTER

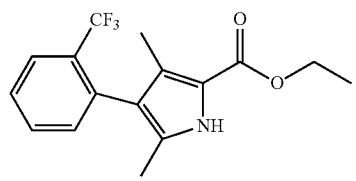 [SMILES: CCOC(=O)c1[nH]c(C)c(-c2ccccc2C(F)(F)F)c1C]

To a solution of ethyl 3,5-dimethyl-1H-pyrrole-2-carboxylate (3.42 g, 20 mmol) in carbon tetrachloride (40 mL) was added a solution of bromine in carbon tetrachloride (10 mL) dropwise at 20° C. After the addition was complete, stirring was continued for 2 h. The reaction mixture was diluted with DCM, washed with aqueous NaHCO$_3$ and water, and then dried over Na$_2$SO$_4$. Evaporation of solvent gave ethyl 4-bromo-3,5-dimethyl-1H-pyrrole-2-carboxylate as a solid (4.8 g), which was used in the next step without purification. $^1$H-NMR (CDCl$_3$): δ 9.36 (1H, s), 4.30 (2H, q), 228 (3H, s), 2.26 (3H, s), 1.36 (3H, t).

To a solution of ethyl 4-bromo-3,5-dimethyl-1H-pyrrole-2-carboxylate (2.4 g, 10 mmol) in DMF (25 mL) was added tetrakis(triphenylphosphine)palladium (2.3 g, 1 mmol). After stirring 15 min, the reaction mixture was charged with 2-(trifluoromethyl)-benzeneboronic acid (2.4 g, 12.5 mmol) and sodium carbonate (in 5 mL of water). The reaction mixture was heated to reflux overnight with stirring. After cooling, the reaction mixture was then diluted with water and extracted with DCM. The combined extracts were washed with water and dried over Na$_2$SO$_4$. Evaporation of solvent gave a crude material, which was purified by chromatography on silica gel column eluting with EtOAc-hexane (1:1) to give the title compound (1.5 g). MS (ES): 312 (MH$^+$);

PREPARATION OF 3,5-DIMETHYL-4-(2-TRIFLUOROMETHYL-PHENYL)-1H-PYRROLE-2-CARBOXYLIC ACID (4-METHANESULFONYL-PHENYL)-AMIDE

To a solution of 3,5-dimethyl-4-(2-trifluoromethyl-phenyl)-1H-pyrrole-2-carboxylic acid ethyl ester (0.96 g) in methanol was added 4 N NaOH (6 mL). The reaction mixture was then heated to reflux with stirring overnight. After cooling, solvent was removed and the crude material was diluted with water. Solids were removed by filtration and washed with water. The aqueous filtrate was acidified with formic acid to precipitate the product. The precipitates were collected by filtration and washed with water, and then dried under high vacuum to afford 3,5-dimethyl-4-(2-trifluoromethyl-phenyl)-1H-pyrrole-2-carboxylic acid (0.30 g). MS (ES): 284 (MH$^+$).

In a manner similar to that described in Example 16D, the title compound was prepared from 3,5-dimethyl-4-(2-trifluoromethyl-phenyl)-1H-pyrrole-2-carboxylic acid. $^1$H-NMR (CDCl$_3$): δ 9.68 (1H, s), 7.89 (2H, m), 7.79 (3H, m), 7.73 (1H, s), 7.59 (1H, m), 7.50 (1H, M), 7.24 (1H, d), 3.05 (3H, s), 3.05 (3H, s), 2.19 (3H, s), 2.06 (3H, s); MS (ES): 437 (MH$^+$).

Example 20

PREPARATION OF 5-(4-FLUOROPHENYL)-2-METHYL-1-(2-TRIFLUOROMETHYLPHENYL)-1H-PYRROLE-3-CARBOXYLIC ACID (4-METHANESULFONYL-PHENYL) AMIDE

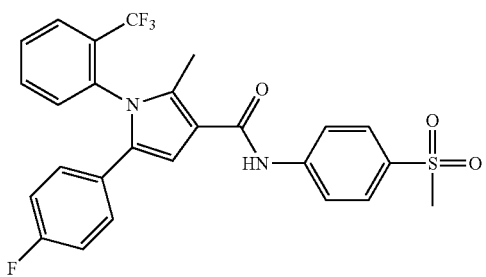 [SMILES: Cc1c(C(=O)Nc2ccc(S(C)(=O)=O)cc2)cc(-c2ccc(F)cc2)n1-c1ccccc1C(F)(F)F]

A. In a manner similar to that described for Examples 16C-D, the title compound was prepared from 5-(4-fluorophenyl)-2-methyl-1-(2-trifluoromethylphenyl)-1H-pyrrole-3-carboxylic acid ethyl ester, which was synthesized from 2-trifluoromethyl-aniline and 2-acetyl-4-(4-fluorophenyl)-4-oxobutyric acid ethyl ester using the procedures described in WO 03/027069. $^1$H-NMR (CDCl$_3$): δ 7.92-7.84 (5H, m), 7.77-7.69 (2H, m), 7.63-7.60 (1H, m), 7.42 (1H, d), 7.07-7.03 (2H, m), 6.88-6.84 (2H, m), 6.60 (1H, s), 3.05 (3H, s), 2.33 (3H, s). MS (ESI): 517 (MH$^+$).

B. In a manner similar to that described for Example 20A, but replacing 2-trifluoromethyl-aniline with 4-fluoroaniline, the following compound was prepared: 1,5-bis-(4-fluorophenyl)-2-methyl-1H-pyrrole-3-carboxylic acid (4-methanesulfonyl-phenyl) amide; $^1$HNMR (CDCl$_3$): δ 7.93-7.80 (5H, m), 7.25-7.11 (4H, m), 7.09-7.01 (2H, m), 6.93-6.87 (2H, m), 6.56 (1H, s), 3.04 (3H, s), 2.45 (3H, s). MS (ESI): 467 (MH$^+$).

C. In a manner similar to that described for Example 20A, but replacing 4-methanesulfonyl-aniline with the appropriate amines in the last step, the following compounds were prepared:

5-(4-fluoro-phenyl)-2-methyl-1-(2-trifluoromethyl-phenyl)-1H-pyrrole-3-carboxylic acid (3-methoxy-4-sulfamoyl-phenyl)-amide; MS (ES): 548 (MH+);

5-(4-fluoro-phenyl)-2-methyl-1-(2-trifluoromethyl-phenyl)-1H-pyrrole-3-carboxylic acid dimethylamide; MS (ES): 391 (MH+).

Example 21

PREPARATION OF 2-[3-(4-METHANESULFONYL-PHENYLCARBAMOYL)-2,5-DIMETHYL-PYRROL-1-YL]-BENZOIC ACID

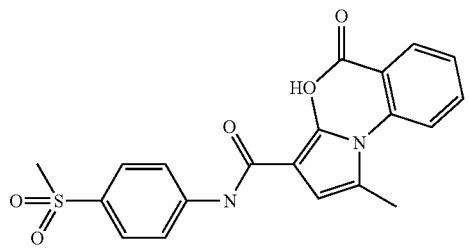 [SMILES: Cc1cc(C(=O)Nc2ccc(S(C)(=O)=O)cc2)c2oc(=O)c3ccccc3n12]

A. 2-[3-(4-Methanesulfonyl-phenylcarbamoyl)-2,5-dimethyl-pyrrol-1-yl]-benzoic acid methyl ester was prepared from methyl anthranilate in a manner similar to that described for Examples 1G. $^1$H-NMR (DMSO-d$_6$): δ 9.58 (1H, s), 7.83 (2H, d, J=8.8), 7.79 (1H, dd J=7.8, 1.5), 7.63 (2H, d, J=7.8), 7.58 (1H, dd, J=7.8, 1.5). 7.48 (1H, td, J=7.6, 1.3), 7.21 (1H, dd, J=7.8, 1.0), 7.15 (1H, s), 6.42 (1H, d, J=1.0), 3.43 (3H, s), 2.96 (3H, s), 1.94 (3H, s), 1.66 (3H, s); MS (ESI): 427 (MH$^4$).

To a solution of 2-[3-(4-methanesulfonyl-phenylcarbamoyl)-2,5-dimethyl-pyrrol-1-yl]-benzoic acid methyl ester (0.7 g, 1.6 mmol) in MeOH/THF (8 mL: 16 mL) was added LiOH (0.275 g, 6.4 mmol). After stirring 14 h at room temperature, the reaction mixture was concentrated in vacuo. The crude reaction mixture was re-dissolved in water and washed with EtOAc. The water layer was separated and then acidified with 1N HCl. The resulting suspension was extracted twice with EtOac. The combined extracts were dried (Na$_2$SO$_4$) and concentrated in vacuo to provide the title compound (0.67 g, 99%) as a white solid. $^1$H-NMR (DMSO-d$_6$): δ 13.03 (1H, s), 9.81 (1H, s), 8.06 (2H, d, J=9.1), 8.02 (1H, d J=7.8), 7.87 (2H, d, J=8.6), 7.78 (1H, t, J=7.3). 7.68 (1H, t, J=7.8), 7.39 (1H, d, J=7.6), 6.65 (1H, s), 3.20 (3H, s), 2.23 (3H, s), 1.92 (3H, s); MS (ESI): 413 (MH$^+$).

1-(2-CARBAMOYL-PHENYL)-2,5-DIMETHYL-1H-PYRROLE-3-CARBOXYLIC ACID (4-METHANESULFONYL-PHENYL)-AMIDE

B. In a manner similar to that described for Examples 1B-C, the title compound was prepared from 2-[3-(4-methanesulfonyl-phenylcarbamoyl)-2,5-dimethyl-pyrrol-1-yl]-benzoic acid and ammonia. $^1$H-NMR (DMSO-d$_6$): δ 9.82 (1H, s), 8.08 (2H, d, J=9.1), 7.90 (2H, d, J=9.1), 7.67 (4H, m), 7.39 (1H, s). 7.34 (1H, m), 6.63 (1H, s), 3.23 (3H, s), 2.27 (3H, s), 2.00 (3H, s); MS (ESI): 412 (MH$^+$).

C. In a manner similar to that described for Example 21B, the following compounds were prepared from the appropriate amines:

1-[2-((R)-2-Hydroxy-1-methyl-ethylcarbamoyl)-phenyl]-2,5-dimethyl-1H-pyrrole-3-carboxylic acid (4-methanesulfonyl-phenyl)-amide; MS (ES): 470 (MH$^4$);

1-[2-(3-Hydroxymethyl-piperidine-1-carbonyl)-phenyl]-2,5-dimethyl-1H-pyrrole-3-carboxylic acid (4-methanesulfonyl-phenyl)-amide; MS (ES): 510 (MH$^4$);

1-[2-(4-Acetyl-piperazine-1-carbonyl)-phenyl]-2,5-dimethyl-1H-pyrrole-3-carboxylic acid (4-methanesulfonyl-phenyl)-amide; MS (ES): 523 (MH$^+$);

1-{2-[(2-Cyano-ethyl)-cyclopropyl-carbamoyl]-phenyl}-2,5-dimethyl-1H-pyrrole-3-carboxylic acid (4-methanesulfonyl-phenyl)-amide; MS (ES): 505 (MH$^+$);

1-[2-(3-Ethoxy-phenylcarbamoyl)-phenyl]-2,5-dimethyl-1H-pyrrole-3-carboxylic acid (4-methanesulfonyl-phenyl)-amide; MS (ES): 532 (MH$^+$);

2,5-Dimethyl-1-[2-(3-nitro-phenylcarbamoyl)-phenyl]-1H-pyrrole-3-carboxylic acid (4-methanesulfonyl-phenyl)-amide; MS (ES): 533 (MH$^+$);

1-[2-(1H-Indazol-5-ylcarbamoyl)-phenyl]-2,5-dimethyl-1H-pyrrole-3-carboxylic acid (4-methanesulfonyl-phenyl)-amide; MS (ES): 528 (MH$^+$);

2,5-Dimethyl-1-[2-(2-methyl-1H-indol-5-ylcarbamoyl)-phenyl]-1H-pyrrole-3-carboxylic acid (4-methanesulfonyl-phenyl)-amide; MS (ES) 541 (MH$^+$)

1-[2-(2-Dimethylamino-1-methyl-ethylcarbamoyl)-phenyl]-2,5-dimethyl-1H-pyrrole-3-carboxylic acid (4-methanesulfonyl-phenyl)-amide; MS (ES): 497 (MH$^+$);

1-{2-[4-(2-Hydroxy-ethyl)-piperazine-1-carbonyl]-phenyl}-2,5-dimethyl-1H-pyrrole-3-carboxylic acid (4-methanesulfonyl-phenyl)-amide; MS (ES): 525 (MH$^+$);

1-[2-(3-Imidazol-1-yl-propylcarbamoyl)-phenyl]-2,5-dimethyl-1H-pyrrole-3-carboxylic acid (4-methanesulfonyl-phenyl)-amide; MS (ES): 520 (MH$^+$);

1-[2-((S)-1-Hydroxymethyl-3-methylsulfanyl-propylcarbamoyl)-phenyl]-2,5-dimethyl-1H-pyrrole-3-carboxylic acid (4-methanesulfonyl-phenyl)-amide; MS (ES): 530 (MH$^+$);

1-[2-(1,3-Dihydro-isobenzofuran-5-ylcarbamoyl)-phenyl]-2,5-dimethyl-1H-pyrrole-3-carboxylic acid (4-methanesulfonyl-phenyl)-amide; MS (ES): 530 (MH$^+$);

2,5-Dimethyl-1-[2-(2-methyl-aziridine-1-carbonyl)-phenyl]-1H-pyrrole-3-carboxylic acid (4-methanesulfonyl-phenyl)-amide; MS (ES): 452 (MH$^+$);

2,5-Dimethyl-1-{2-[1-(1-methyl-1H-pyrazol-4-yl)-ethylcarbamoyl]-phenyl}-1H-pyrrole-3-carboxylic acid (4-methanesulfonyl-phenyl)-amide; MS (ES): 520 (MH$^+$);

1-[2-((1R,2S)-2-Hydroxy-indan-1-ylcarbamoyl)-phenyl]-2,5-dimethyl-1H-pyrrole-3-carboxylic acid (4-methanesulfonyl-phenyl)-amide; MS (ES): 544 (MH$^+$);

1-[2-(1,1-Dioxo-tetrahydro-1-thiophen-3-ylcarbamoyl)-phenyl]-2,5-dimethyl-1H-pyrrole-3-carboxylic acid (4-methanesulfonyl-phenyl)-amide; MS (ES): 530 (MH$^+$);

1-[2-(3-Methanesulfonyl-pyrrolidine-1-carbonyl)-phenyl]-2,5-dimethyl-1H-pyrrole-3-carboxylic acid (4-methanesulfonyl-phenyl)-amide; MS (ES): 544 (MH$^+$);

1-[2-(3-Hydroxy-4-methyl-phenylcarbamoyl)-phenyl]-2,5-dimethyl-1H-pyrrole-3-carboxylic acid (4-methanesulfonyl-phenyl)-amide; MS (ES): 518 (MH$^+$);

2,5-Dimethyl-1-[2-([1,3,4]thiadiazol-2-ylcarbamoyl)-phenyl]-1H-pyrrole-3-carboxylic acid (4-methanesulfonyl-phenyl)-amide; MS (ES): 496 (MH$^+$);

1-[2-(4,5-Dimethyl-thiazol-2-ylcarbamoyl)-phenyl]-2,5-dimethyl-1H-pyrrole-3-carboxylic acid (4-methanesulfonyl-phenyl)-amide; MS (ES): 523 (MH$^+$);

(R)-3-Hydroxy-2-{2-[3-(4-methanesulfonyl-phenylcarbamoyl)-2,5-dimethyl-pyrrol-1-yl]-benzoylamino}-propionic acid methyl ester; MS (ES): 514 (MH$^+$);

2,5-Dimethyl-1-{2-[methyl-(4-methyl-thiazol-2-ylmethyl)-carbamoyl]-phenyl}-1H-pyrrole-3-carboxylic acid (4-methanesulfonyl-phenyl)-amide; MS (ES): 537 (MH$^+$);

3-{2-[3-(4-Methanesulfonyl-phenylcarbamoyl)-2,5-dimethyl-pyrrol-1-yl]-benzoylamino}-propionic acid ethyl ester; MS (ES): 512 (MH$^+$);

1-[2-(2-Ethylsulfanyl-ethylcarbamoyl)-phenyl]-2,5-dimethyl-1H-pyrrole-3-carboxylic acid (4-methanesulfonyl-phenyl)-amide; MS (ES): 500 (MH$^+$);

1-[2-((S)-1-Carbamoyl-3-methyl-butylcarbamoyl)-phenyl]-2,5-dimethyl-1H-pyrrole-3-carboxylic acid (4-methanesulfonyl-phenyl)-amide; MS (ES): 525 (MH$^+$);

1-[2-(4-Carbamoyl-phenylcarbamoyl)-phenyl]-2,5-dimethyl-1H-pyrrole-3-carboxylic acid (4-methanesulfonyl-phenyl)-amide; MS (ES): 531 (MH$^+$);

4-{2-[3-(4-Methanesulfonyl-phenylcarbamoyl)-2,5-dimethyl-pyrrol-1-yl]-benzoylamino}-cyclohexanecarboxylic acid; MS (ES): 538 (MH$^+$);

2,5-Dimethyl-1-{2-[(5-methyl-4H-[1,2,4]triazol-3-ylmethyl)-carbamoyl]-phenyl}-1H-pyrrole-3-carboxylic acid (4-methanesulfonyl-phenyl)-amide; MS (ES): 507 (MH$^+$);

1-{2-[3-(4-Methanesulfonyl-phenylcarbamoyl)-2,5-dimethyl-pyrrol-1-yl]-benzoyl}-piperidine-2-carboxylic acid methyl ester; MS (ES): 538 (MH$^+$);

1-{2-[2-(1H-Imidazol-4-yl)-ethylcarbamoyl]-phenyl}-2,5-dimethyl-1H-pyrrole-3-carboxylic acid (4-methanesulfonyl-phenyl)-amide; MS (ES): 506 (MH$^+$);

{2-[3-(4-Methanesulfonyl-phenylcarbamoyl)-2,5-dimethyl-pyrrol-1-yl]-benzoylamino}-acetic acid; MS (ES): 470 (MH$^+$);

2,5-Dimethyl-1-(2-methylcarbamoyl-phenyl)-1H-pyrrole-3-carboxylic acid (4-methanesulfonyl-phenyl)-amide; MS (ES): 426 (MH$^+$);

1-(2-Isopropylcarbamoyl-phenyl)-2,5-dimethyl-1H-pyrrole-3-carboxylic acid (4-methanesulfonyl-phenyl)-amide; MS (ES): 454 (MH$^+$); and 1-(2-Dimethylcarbamoyl-phenyl)-2,5-dimethyl-1H-pyrrole-3-carboxylic acid (4-methanesulfonyl-phenyl)-amide; MS (ES): 440 (MH$^+$).

Example 22

PREPARATION OF 4-METHYL-N-[4-(METHYLSULFONYL)PHENYL]-1-PHENYL-5-[2-(TRIFLUOROMETHYL)PHENYL]-1H-PYRROLE-3-CARBOXAMIDE

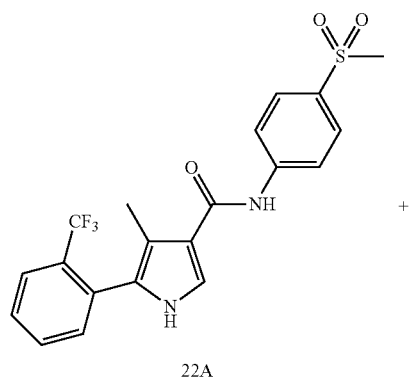

22A

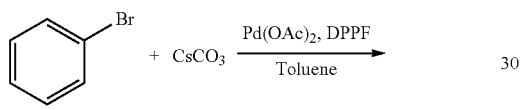

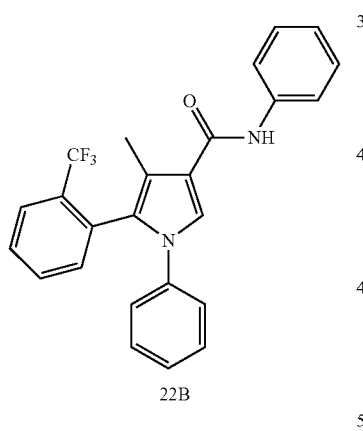

22B

A screw-capped vial was charged with 22A (4-methyl-N-[4-(methylsulfonyl)phenyl]-5-[2-(trifluoromethyl)phenyl]-1H-pyrrole-3-carboxamide) (175 mg, 0.41 mmol), bromobenzene (52 µL, 0.48 mmol), palladium acetate (31 mg, 0.046 mmol, 11 mol %), 1,1'-diphenylphosphino)ferrocene (DPPF) (32 mg, 0.058 mmol, 14 mol %), and cesium carbonate (200 mg, 0.61 mmol). Anhydrous toluene (20 mL) was added to the vial and the mixture was purged with $N_2$ for 5 minutes, after which time, the vial was capped. The reaction mixture was stirred at 105° C. for 12 hours. The product, 22B, was purified by silica column chromatography (1:1 EtOAc:Hex) in 8% yield.

$^1$H NMR (CDCl$_3$) δ 8.31 (s, 1H), 7.81 (d, 9.0 Hz, 3H), 7.65 (t, 7.8 Hz, 1H), 7.56-7.45 (m, 9H), 7.36 (s, 1H), 3.03 (m, 3H), 2.28 (s, 3H). LCMS: m/z 499 (M+H)$^+$.

Example 23

PREPARATION OF 1-(3-HYDROXYPROPYL)-4-METHYL-N-[4-(METHYL SULFONYL)PHENYL]-5-[2-(TRIFLUOROMETHYL)PHENYL]-1H-PYRROLE-3-CARBOXAMIDE

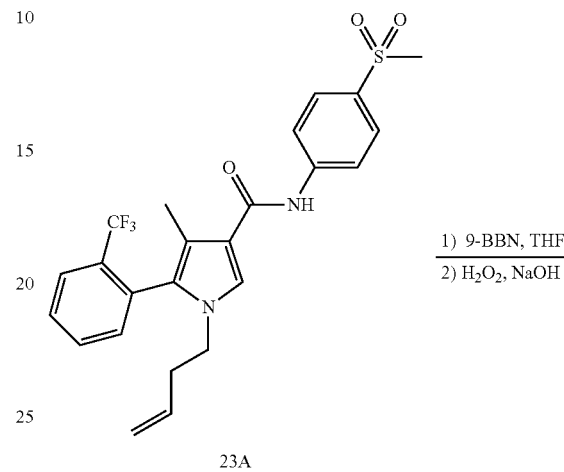

23A

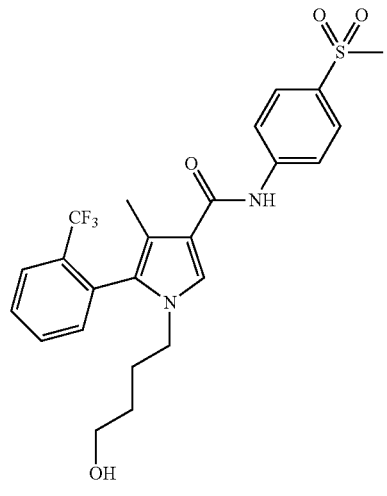

23B

A solution of 23A (4-methyl-N-[4-(methylsulfonyl)phenyl]-1-prop-2-en-1-yl-5-[2-trifluoromethyl)phenyl]-1H-pyrrole-3-carboxamide) (156 mg, 0.34 mmol) in THF (20 mL) was cooled to 0° C. 9-BBN (0.73 mL, 0.5 M solution in THF, 0.36 mmol) was added at 0° C. and the reaction mixture was warmed to RT. After 12 hours, NaOH (0.4 mL, 1 N solution, 0.4 mmol) and hydrogen peroxide (0.3 mL, 50% wt solution) were added to the reaction mixture and the mixture was stirred at RT for 3 hours, after which time, the mixture was diluted with EtOAc and extracted with water. The product, 23B, was purified by HPLC with NH$_4$Oac as eluent in 35% yield.

$^1$H NMR (DMSO-d$_6$) δ 9.92 (s, 1H), 7.96 (d, 9.0 Hz, 2H), 7.90-7.82 (m, 3H), 7.79-7.76 (m, 2H), 7.72-7.68 (m, 1H), 7.44 (d, 7.6 Hz, 1H), 4.51 (m, 1H), 3.72-3.65 (m, 1H), 3.63-

3.46 (m, 1H), 3.28 (s, 1H), 3.15 (s, 3H), 1.91 (s, 3H), 1.73-1.65 (m, 3H). LCMS: m/z 481 (M+H)+.

Example 24

Following the procedures set forth above in the foregoing preparations and examples, the following compounds of the invention were or may be prepared:

5-(2-Fluoro-phenyl)-4-methyl-1-pyridin-2-ylmethyl-1H-pyrrole-3-carboxylic acid (4-methanesulfonyl-phenyl)-amide.

1H NMR (400 MHz, CDCl$_3$) δ 8.50 (d, 1H), 7.91 (d, 2H), 7.80 (d, 2H), 7.23 (s, 1H), 7.58 (m, 1H), 7.45 (s, 1H), 7.39 (m, 1H), 7.17 (m, 4H), 6.71 (d, 1H), 5.08 (m, 2H), 3.06 (s, 3H), 2.25 (s, 3H); MS (EI) for $C_{25}H_{22}FN_3O_3S$: 464.3 (MH+).

5-(2-Fluoro-phenyl)-1-(2-hydroxy-ethyl)-4-methyl-1H-pyrrole-3-carboxylic acid (4-methanesulfonyl-phenyl)-amide.

1H NMR (400 MHz, CDCl$_3$) δ 7.91 (d, 2H), 7.81 (d, 2H), 7.74 (s, 1H), 7.49 (s, 1H), 7.44 (m, 1H), 7.28 (m, 2H), 7.20 (m, 1H), 3.93 (t, 2H), 3.72 (m, 2H) 3.06 (s, 3H), 2.22 (s, 3H), 1.62 (t, 1H); MS (EI) for $C_{21}H_{21}FN_2O_4S$: 417.2 (MH+).

1,4-Dimethyl-5-(2-trifluoromethyl-phenyl)-1H-pyrrole-3-carboxylic acid (1,1-dioxo-hexahydro-1l6-thiopyran-4-yl)-amide.

1H NMR (400 MHz, CDCl$_3$) δ 7.80 (d, 1H), 7.61 (m, 2H), 7.30 (d, 1H), 7.18 (s, 1H), 5.67 (d, 1H), 4.28 (m, 1H), 3.28 (s, 3H), 3.13 (m, 4H), 2.42 (m, 2H), 2.20 (m, 2H), 2.00 (s, 3H); MS (EI) for $C_{19}H_{21}F_3N_2O_3S$: 415.2 (MH+).

5-(2,6-Dimethyl-phenyl)-4-methyl-1H-pyrrole-3-carboxylic acid (4-methanesulfonyl-phenyl)-amide.

1H NMR (400 MHz, CDCl3) δ 8.12 (1H, s), 7.93-7.91 (2H, d), 7.84-7.82 (2H, d), 7.75 (1H, s), 7.46-7.45 (1H, d), 7.26-7.22 (1H, t), 7.14-7.15 (1H, d), 3.06 (3H, s), 2.14 (3H, s), 2.09 (6H, s); MS (EI) for $C_{21}H_{22}N_2O_3S$: 383 (MH+).

5-(2,6-Dimethyl-phenyl)-4-methyl-1-(2-morpholin-4-yl-ethyl)-1H-pyrrole-3-carboxylic acid (4-methanesulfonyl-phenyl)-amide.

1H NMR (400 MHz, CDCl$_3$) δ 7.92-7.89 (2H, d), 7.83-7.81 (2H, d), 7.76 (1H, s), 7.48 (1H, s), 7.25-7.23 (1H, d), 7.15-7.13 (2H, m), 3.64-3.61 (6H, m), 3.06 (3H, s), 2.47-2.44 (2H, t), 2.29-2.27 (4H, m), 2.09 (3H, s), 2.05 (6H, s); MS (EI) for $C_{27}H_{33}N_3O_4S$: 496 (MH+).

4-Methyl-1-(2-morpholin-4-yl-ethyl)-5-(2-phenoxy-phenyl)-1H-pyrrole-3-carboxylic acid (4-methanesulfonyl-phenyl)-amide.

1H NMR (400 MHz, CDCl$_3$) δ 7.90-7.88 (2H, d), 7.79-7.77 (2H, d), 7.63 (1H, s), 7.52-7.40 (1H, m), 7.38 (1H, s), 7.32-7.22 (4H, m), 7.06-7.02 (2H, t), 6.86-6.84 (2H, d), 4.00-3.85 (2H, m), 3.64-3.62 (4H, m), 3.04 (3H, s), 2.55-2.52 (2H, t), 2.33-2.29 (4H, m), 2.17 (3H, s); MS (EI) for $C_{31}H_{33}N_3O_5S$: 560 (MH+).

1-(2-Diethylamino-ethyl)-4-methyl-5-(2-phenoxy-phenyl)-1H-pyrrole-3-carboxylic acid (4-methanesulfonyl-phenyl)-amide.

1H NMR (400 MHz, CDCl$_3$) δ 7.87-7.84 (2H, d), 7.80-7.77 (3H, m), 7.40-7.38 (2H, m), 7.32-7.19 (4H, m), 7.05-7.01 (2H, m), 6.86-6.84 (2H, d), 3.91-3.82 (2H, m), 3.02 (3H, s), 2.60-2.54 (2H, m), 2.44-2.40 (4H, m), 2.17 (3H, s), 0.90-0.86 (6H, t); MS (EI) for $C_{31}H_{35}N_3O_4S$: 546 (MH+).

4-Methyl-5-(2-phenoxy-phenyl)-1-(2-piperidin-1-yl-ethyl)-1H-pyrrole-3-carboxylic acid (4-methanesulfonyl-phenyl)-amide.

1H NMR (400 MHz, CDCl3) δ7.88-7.86 (2H, d), 7.79-7.77 (2H, d), 7.71 (1H, s), 7.42-7.36 (2H, m), 7.31-7.19 (4H, m), 7.05-7.01 (2H, m), 6.86-6.84 (2H, d), 3.93-3.86 (2H, m), 3.03 (3H, s), 2.53-2.47 (2H, m), 2.27-2.22 (4H, m), 2.17 (3H, s), 1.54-1.49 (4H, m), 1.40-1.39 (2H, m); MS (EI) for $C_{32}H_{35}N_3O_4S$: 558 (MH+).

4-Methyl-5-(2-phenoxy-phenyl)-1-pyridin-3-ylmethyl-1H-pyrrole-3-carboxylic acid (4-methanesulfonyl-phenyl)-amide.

1H NMR (400 MHz, CDCl3) δ 8.45-844 (1H, m), 8.22 (1H, s), 7.91 (1H, s), 7.83-7.81 (2H, d), 7.75-7.73 (2H, d), 7.38-7.34 (1H, m), 7.30 (1H, s), 7.27-7.23 (3H, m), 7.19-7.12 (3H, m), 7.07-7.03 (1H, t), 6.98-6.96 (1H, d), 6.81-6.79 (2H, m), 4.99 (2H, s), 3.00 (3H, s), 2.20 (3H, s); MS (EI) for $C_{31}H_{27}N_3O_4S$: 538 (MH+).

4-Methyl-5-(2-phenoxy-phenyl)-1-(2-pyrrolidin-1-yl-ethyl)-1H-pyrrole-3-carboxylic acid (4-methanesulfonyl-phenyl)-amide.

1H NMR (400 MHz, CDCl3) δ 7.88-7.86 (2H, d), 7.79-7.77 (2H, d), 7.70 (1H, s), 7.41-7.38 (1H, m), 7.37 (1H, s), 7.31-7.19 (4H, m), 7.06-7.00 (2H, m), 6.86-6.84 (2H, d), 3.97-3.90 (2H, m), 3.03 (3H, s), 2.68-2.62 (2H, m), 2.42-2.36 (4H, m), 2.17 (3H, s), 1.74-1.72 (4H, m); MS (EI) for $C_{31}H_{33}N_3O_4S$: 544 (MH+).

1-(3-Dimethylamino-propyl)-4-methyl-5-(2-phenoxy-phenyl)-1H-pyrrole-3-carboxylic acid (4-methanesulfonyl-phenyl)-amide.

1H NMR (400 MHz, CDCl3) δ7.89-7.87 (2H, d), 7.81-7.78 (2H, d), 7.77 (1H, s), 7.41-7.36 (1H, m), 7.34 (1H, s), 7.30-7.19 (4H, m), 7.06-7.01 (2H, m), 6.87-6.85 (2H, d), 3.96-3.80 (2H, m), 3.03 (3H, s), 2.18-2.13 (11H, m), 1.77-1.73 (2H, t); MS (EI) for $C_{30}H_{33}N_3O_4S$: 532 (MH+).

1-(2-Hydroxy-ethyl)-4-methyl-5-(2-phenoxy-phenyl)-1H-pyrrole-3-carboxylic acid (4-methanesulfonyl-phenyl)-amide.

1H NMR (400 MHz, CDCl3) δ 9.00 (1H, s), 7.92-7.90 (2H, d), 7.85-7.83 (2H, d), 7.56 (1H, s), 7.39-7.18 (5H, m), 7.06-7.04 (1H, t), 6.99-6.96 (1H, d), 6.87-6.85 (2H, d), 4.01-3.88 (2H, m), 3.86-3.83 (1H, t), 3.78-3.64 (2H, m), 3.04 (3H, s), 2.19 (3H, s); MS (EI) for $C_{27}H_{26}N_2O_5S$: 491 (MH+).

5-(2,6-Dimethyl-phenyl)-1-(2-hydroxy-ethyl)-4-methyl-1H-pyrrole-3-carboxylic acid (4-methanesulfonyl-phenyl)-amide.

1H NMR (400 MHz, CDCl3) δ 791-7.89 (2H, d), 7.83-7.81 (2H, d), 7.77 (1H, s), 7.51 (1H, s), 7.25-7.23 (1H, m), 7.15-7.13 (2H, m) 3.69-3.66 (4H, m), 3.06 (3H, s), 2.09 (3H, s), 2.04 (6H, s); MS (EI) for $C_{23}H_{26}N_2O_4S$: 425 (MH−).

5-(2,6-Dimethyl-phenyl)-4-methyl-1-pyridin-3-ylmethyl-1H-pyrrole-3-carboxylic acid (4-methanesulfonyl-phenyl)-amide.

1H NMR (400 MHz, CDCl3) δ 8.48 (1H, m), 8.10-8.07 (2H, d), 7.87-7.85 (2H, d), 7.83-7.81 (2H, d), 7.52 (1H, s), 7.25-721 (2H, m), 7.18-7.10 (1H, m), 7.10-7.08 (2H, d), 4.68 (2H, s), 3.05 (3H, s), 2.08 (3H, s), 1.84 (6H, s); MS (EI) for $C_{27}H_{27}N_3O_3S$: 474 (MH+).

5-(2,6-Dimethyl-phenyl)-4-methyl-1-(2-pyrrolidin-1-yl-ethyl)-1H-pyrrole-3-carboxylic acid (4-methanesulfonyl-phenyl)-amide.

1H NMR (400 MHz, CDCl3) δ 7.91-7.88 (2H, d), 7.87 (1H, s), 7.85-7.82 (2H, d), 7.48 (1H, s), 7.26-7.22 (1H, m), 7.14-7.12 (2H, d), 3.67-3.64 (2H, t), 3.05 (3H, s), 2.62-2.58 (2H, t), 2.40-2.37 (4H, m), 2.08 (3H, s), 2.04 (6H, s), 1.74-1.71 (4H, m); MS (EI) for $C_{27}H_{33}N_3O_3S$: 480 (MH+).

5-(2,6-Dimethyl-phenyl)-4-methyl-1-(2-piperidin-1-yl-ethyl)-1H-pyrrole-3-carboxylic acid (4-methanesulfonyl-phenyl)-amide.

1H NMR (400 MHz, CDCl3) δ 7.90-7.88 (2H, d), 7.87 (1H, s), 7.85-7.82 (2H, d), 7.50 (1H, s), 7.26-7.22 (1H, m), 7.14-7.12 (2H, d), 3.65-3.61 (2H, t), 3.05 (3H, s), 2.45-2.41

5-(2,6-Dimethyl-phenyl)-1,4-dimethyl-1H-pyrrole-3-carboxylic acid (4-methanesulfonyl-phenyl)-amide.

1H NMR (400 MHz, CDCl3) δ 7.92-7.90 (2H, d), 7.83-7.81 (2H, d), 7.69 (1H, s), 7.36 (1H, s), 7.27-7.23 (1H, m), 7.15-7.13 (2H, d), 3.29 (3H, s), 3.06 (3H, s), 2.10 (3H, s), 2.02 (6H, s); MS (EI) for $C_{22}H_{24}N_2O_3S$: 397 (MH+).

5-(2,6-Dimethyl-phenyl)-4-methyl-1-pyridin-2-ylmethyl-1H-pyrrole-3-carboxylic acid (4-methanesulfonyl-phenyl)-amide.

1H NMR (400 MHz, CDCl3) δ 8.52-8.50 (1H, d), 7.92 (1H, s), 7.90-7.7.8 (2H, d), 7.84-7.81 (2H, d), 7.56-7.52 (2H, m), 7.25-7.21 (1H, t), 7.19-7.16 (1H, m), 7.09-7.07 (2H, m), 6.66-6.64 (1H, d), 4.79 (2H, s), 3.05 (3H, s), 2.09 (3H, s), 1.87 (6H, s); MS (EI) for $C_{27}H_{27}N_3O_3S$: 474 (MH+).

5-(4-Benzyloxy-2-methyl-phenyl)-1,4-dimethyl-1H-pyrrole-3-carboxylic acid (4-methanesulfonyl-phenyl)-amide.

1H NMR (400 MHz, CDCl3) δ 7.92-7.89 (2H, d), 7.83-7.80 (2H, d), 7.69 (1H, s), 7.48-7.36 (5H, m), 7.31 (1H, s), 7.10-7.07 (1H, d), 6.96 (1H, s), 6.90-6.87 (1H, m), 5.10 (2H, s), 3.35 (3H, s), 3.06 (3H, s), 2.15 (3H, s), 2.07 (3H, s); MS (EI) for $C_{28}H_{28}N_2O_4S$: 489 (MH+).

5-(4-Hydroxy-2-methyl-phenyl)-1,4-dimethyl-1H-pyrrole-3-carboxylic acid (4-methanesulfonyl-phenyl)-amide.

1H NMR (400 MHz, CDCl3) δ 7.91-7.89 (2H, d), 7.82-7.80 (2H, d), 7.68 (1H, s), 7.30 (1H, s), 7.04-7.02 (1H, d), 6.80 (1H, s), 6.75-6.72 (1H, m), 3.64 (3H, s), 3.05 (3H, s), 2.14 (3H, s), 2.04 (3H, s); MS (EI) for $C_{21}H_{22}N_2O_4S$: 399 (MH+).

1-[3-(4-Fluoro-phenoxy)-2-(R)-hydroxy-propyl]-4-methyl-5-(2-trifluoromethyl-phenyl)-1H-pyrrole-3-carboxylic acid (4-methanesulfonyl-phenyl)-amide. 1H NMR (400 MHz, CDCl3) δ 7.91-7.88 (2H, d), 7.83-7.82 (1H, d), 7.80-7.77 (2H, d), 7.71 (1H, s), 7.62-7.57 (2H, m), 7.51-7.48 (1H, d), 7.31-7.29 (1H, m), 6.98-6.94 (2H, t), 6.75-6.68 (2H, m), 4.13-4.01 (1H, m), 3.93-3.67 (4H, m), 3.05 (3H, s), 2.08 (3H, s); MS (EI) for $C_{29}H_{26}F_4N_2O_5S$: 591 (MH+).

1,4-Dimethyl-5-[2-methyl-4-(3-morpholin-4-yl-propoxy)-phenyl]-1H-pyrrole-3-carboxylic acid (4-methanesulfonyl-phenyl)-amide.

1H NMR (400 MHz, CDCl3) δ 7.90-7.88 (2H, d), 7.83-7.80 (2H, d), 7.74 (1H, s), 7.31 (1H, s), 7.26 (1H, s), 7.07-7.05 (1H, d), 6.86 (1H, s), 6.81-6.78 (1H, m), 4.08-4.05 (2H, t), 3.76-3.73 (4H, m), 3.34 (3H, s), 3.05 (3H, s), 2.59-2.55 (2H, t), 2.51 (4H, m), 2.13 (3H, s), 2.06 (3H, s), 2.03-2.00 (2H, t); MS (EI) for $C_{28}H_{35}N_3O_5S$: 526 (MH+).

1-Cyclopropylmethyl-4-methyl-5-(2-trifluoromethyl-phenyl)-1H-pyrrole-3-carboxylic acid (4-methanesulfonyl-phenyl)-amide.

1H NMR (400 MHz, CDCl3) δ 7.92-7.90 (2H, d), 7.83-7.81 (3H, m), 7.73 (1H, s), 7.67-7.58 (2H, m), 7.54 (1H, s), 7.37-7.35 (1H, d), 3.37-3.35 (2H, d), 3.05 (3H, s), 2.09 (3H, s), 1.04 (1H, m), 0.61-0.59 (2H, m), 0.25-0.14 (2H, m); MS (EI) for $C_{24}H_{23}F_3N_2O_3S$: 477 (MH+).

4-Methyl-1-prop-2-ynyl-5-(2-trifluoromethyl-phenyl)-1H-pyrrole-3-carboxylic acid (4-methanesulfonyl-phenyl)-amide.

1H NMR (400 MHz, CDCl3) δ 9.11 (1H, s), 7.97-7.94 (2H, d), 7.88-7.86 (2H, d), 7.82-7.80 (1H, d), 7.65-7.61 (2H, m), 7.60 (1H, s), 7.39-7.37 (1H, d), 6.39-6.36 (1H, t), 5.41-5.39 (2H, d), 3.05 (3H, s), 2.09 (3H, s), MS (EI) for $C_{23}H_{19}F_3N_2O_3S$: 461 (MH+).

5-(2-Chloro-phenyl)-1-[3-(4-fluoro-phenoxy)-2-(S)-hydroxy-propyl]-4-methyl-1H-pyrrole-3-carboxylic acid (4-methanesulfonyl-phenyl)-amide.

1H NMR (400 MHz, CDCl3) δ 8.02-7.99 (1H, d), 7.84-7.81 (2H, d), 7.78-7.75 (2H, m), 7.58-7.52 (1H, d), 7.51-7.47 (1H, m), 7.40-7.24 (3H, m), 6.94-6.90 (2H, m), 6.68-6.65 (2H, m), 4.07-3.78 (3H, m), 3.74-3.64 (2H, m), 3.03 (3H, s), 2.14 (3H, s); MS (EI) for $C_{26}H_{26}ClFN_2O_5S$: 557 (MH+).

5-(2-Chloro-phenyl)-1-[3-(4-fluoro-phenoxy)-2-(R)-hydroxy-propyl]-4-methyl-1H-pyrrole-3-carboxylic acid (4-methanesulfonyl-phenyl)-amide.

1H NMR (400 MHz, CDCl3) δ7.90-7.86 (2H, d), 7.79-7.71 (3H, m), 7.53-7.46 (2H, m), 7.41-7.27 (3H, m), 6.97-6.93 (2H, t), 6.72-6.68 (2H, m), 4.08-3.82 (3H, m), 3.78-3.73 (1H, m), 3.69-3.64 (1H, m), 3.05 (3H, s), 2.16 (3H, s); MS (EI) for $C_{26}H_{26}ClFN_2O_5S$: 557 (MH+).

5-(2-Chloro-phenyl)-1-cyclopropylmethyl-4-methyl-1H-pyrrole-3-carboxylic acid (4-methanesulfonyl-phenyl)-amide.

1H NMR (400 MHz, CDCl3) δ 7.90-7.81 (2H, d), 7.85-7.81 (3H, m), 7.53-7.51 (2H, m), 7.42-7.34 (2H, m), 7.32-7.28 (1H, m), 3.57-3.43 (2H, m), 3.05 (3H, s), 2.17 (3H, s), 1.02-0.98 (1H, m), 0.58-0.52 (2H, m), 0.18-0.09 (2H, m); MS (EI) for $C_{23}H_{23}ClN_2O_3S$: 443 (MH+).

5-(2-Methoxy-phenyl)-4-methyl-1-(2-piperidin-1-yl-ethyl)-1H-pyrrole-3-carboxylic acid (4-methanesulfonyl-phenyl)-amide.

1H NMR (400 MHz, d6-DMSO) δ 9.91 (s, 1H), 7.97 (d, 2H), 7.84 (d, 2H), 7.70 (s, 1H), 7.45 (t, 1H), 7.19 (m, 2H), 7.06 (t, 1H), 3.75 (s, 3H), 3.73 (m, 2H), 3.17 (s, 3H), 2.38 (t, 2H), 2.16 (m, 4H), 2.01 (s, 3H), 1.37 (m, 6H); MS (EI) for $C_{27}H_{33}N_3O_4S$: 496 (MH+).

5-(2-Methoxy-phenyl)-1,4-dimethyl-1H-pyrrole-3-carboxylic acid (4-methanesulfonyl-phenyl)-methyl-amide.

1H NMR (400 MHz, CDCl3) δ 7.86 (d, 2H), 7.39 (d, 2H), 7.37 (m, 1H), 7.06 (m, 1H), 6.96 (m, 2H), 6.39 (s, 1H), 3.74 (s, 3H), 3.51 (s, 3H), 3.23 (s, 3H), 3.06 (s, 3H), 1.89 (s, 3H); MS (EI) for $C_{22}H_{24}N_2O_4S$: 413 (MH+).

5-(2-Methoxy-phenyl)-4-methyl-1-(2-pyrrolidin-1-yl-ethyl)-1H-pyrrole-3-carboxylic acid (4-methanesulfonyl-phenyl)-amide.

1H NMR (400 MHz, d6-DMSO) δ 9.91 (s, 1H), 7.97 (d, 2H), 7.85 (d, 2H), 7.71 (s, 1H), 7.44 (m, 1H), 7.16 (m, 2H), 7.06 (m, 1H), 3.75 (s, 3H), 3.77 (m, 2H), 3.17 (s, 3H), 2.51 (m, 2H), 2.24 (m, 4H), 2.01 (s, 3H), 1.57 (m, 4H); MS (EI) for $C_{26}H_{31}N_3O_4S$: 482 (MH+).

1,4-Dimethyl-5-o-tolyl-1H-pyrrole-3-carboxylic acid (4-methanesulfonyl-phenyl)amide.

1H NMR (400 MHz, d6-DMSO) δ 9.94 (s, 1H), 7.98 (d, 2H), 7.85 (d, 2H), 7.69 (s, 1H), 7.37 (m, 2H), 7.29 (m, 1H), 7.18 (d, 1H), 3.17 (s, 3H), 2.07 (s, 3H), 1.99 (s, 3H); MS (EI) for $C_{21}H_{22}N_2O_3S$; 383 (MH+).

1-(2-Diethylamino-ethyl)-4-methyl-5-o-tolyl-1H-pyrrole-3-carboxylic acid (4-methane sulfonyl-phenyl)-amide.

1H NMR (400 MHz, d6-DMSO) δ 9.92 (s, 1H), 7.99 (d, 2H), 7.85 (d, 2H), 7.77 (s, 1H), 7.36 (m, 2H), 7.30 (m, 1H), 7.20 (m, 1H), 3.75 (m, 2H), 3.58 (m, 2H), 2.43 (m, 2H), 2.28 (q, 4H), 2.09 (s, 3H), 1.98 (s, 3H), 0.75 (t, 6H); MS (EI) for $C_{26}H_{33}N_3O_3S$; 468 (MH+).

4-Methyl-1-(2-pyrrolidin-1-yl-ethyl)-5-o-tolyl-1H-pyrrole-3-carboxylic acid (4-methane sulfonyl-phenyl)-amide.

1H NMR (400 MHz, d6-DMSO) δ 9.92 (s, 1H), 7.99 (d, 2H), 7.86 (d, 2H), 7.76 (s, 1H), 7.37 (m, 2H), 7.30 (m, 1H), 7.18 (m, 1H), 3.80 (m, 1H), 3.65 (m, 1H), 3.18 (s, 3H), 2.48 (m, 2H), 2.21 (m, 4H), 2.07 (s, 3H), 1.97 (s, 3H), 1.58 (m, 4H); MS (EI) for $C_{26}H_{31}N_3O_3S$: 466 (MH+).

4-Methyl-1-pyridin-2-yl-methyl-5-o-tolyl-1H-pyrrole-3-carboxylic acid (4-methane sulfonyl-phenyl)-amide.

1H NMR (400 MHz, d6-DMSO) δ 9.99 (s, 1H), 8.44 (m, 1H), 7.99 (d, 2H), 7.85 (m, 3H), 7.68 (m, 1H), 7.27 (m, 4H), 7.06 (m, 1H), 6.71 (m, 1H), 3.17 (s, 3H), 1.99 (s, 3H), 1.92 (s, 3H); MS (EI) for $C_{26}H_{25}N_3O_3S$: 460 (MH+).

1-(3-Dimethylamino-propyl)-4-methyl-5-o-tolyl-1H-pyrrole-3-carboxylic acid (4-methane sulfonyl-phenyl)-amide.

1H NMR (400 MHz, d6-DMSO) δ 9.91 (s, 1H), 7.99 (d, 2H), 7.85 (d, 2H), 7.75 (s, 1H), 7.36 (m, 2H), 7.29 (m, 1H), 7.20 (m, 1H), 3.73 (m, 1H), 3.60 (m, 1H), 3.17 (s, 3H), 2.06 (s, 3H), 2.04 (m, 2H), 1.97 (s, 3H), 1.95 (s, 3H), 1.57 (m, 2H); MS (EI) for $C_{26}H_{31}N_3O_3S$: 454 (MH+).

4-Methyl-1-(2-piperidin-1-yl-ethyl)-5-o-tolyl-1H-pyrrole-3-carboxylic acid (4-methane sulfonyl-phenyl)-amide.

1H NMR (400 MHz, d6-DMSO) 89.91 (s, 1H), 7.99 (d, 2H), 7.85 (d, 2H), 7.75 (s, 1H), 7.36 (m, 2H), 7.27 (m, 1H), 7.20 (m, 1H), 3.80 (m, 1H), 3.62 (m, 1H), 3.17 (s, 3H), 2.35 (m, 2H), 2.12 (m, 4H), 2.07 (s, 3H), 1.97 (s, 3H), 1.35 (m, 6H); MS (EI) for $C_{27}H_{33}N_3O_3S$; 480 (MH+).

4-Methyl-1-(2-morpholin-4-yl-ethyl)-5-o-tolyl-1H-pyrrole-3-carboxylic acid (4-methane sulfonyl-phenyl)-amide.

1H NMR (400 MHz, d6-DMSO) δ 9.92 (s, 1H), 7.99 (d, 2H), 7.86 (d, 2H), 7.77 (s, 1H), 7.36 (m, 2H), 7.32 (d, 1H), 7.20 (m, 1H), 3.82 (m, 1H), 3.65 (m, 1H), 3.46 (m, 4H), 3.17 (s, 3H), 2.40 (m, 2H), 2.16 (m, 4H), 2.08 (s, 3H), 1.98 (s, 3H); MS (EI) for $C_{26}H_{31}N_3O_4S$: 482 (MH+).

1-(2-Hydroxy-3-phenoxy-propyl)-4-methyl-5-o-tolyl-1H-pyrrole-3-carboxylic acid (4-methane sulfonyl-phenyl)-amide.

1H NMR (400 MHz, d6-DMSO) δ 9.95 (s, 1H), 8.00 (d, 2H), 7.85 (m, 3H), 7.24 (m, 6H), 6.91 (m, 1H), 6.73 (m, 2H), 5.45 (m, 1H), 3.70 (m, 5H), 3.17 (s, 3H), 2.03 (s, 3H), 1.98 (s, 3H); MS (EI) for $C_{29}H_{30}N_2O_5S$: 519 (MH+).

1-(2-Diethylamino-ethyl)-5-(2,6-difluoro-phenyl)-4-methyl-1H-pyrrole-3-carboxylic acid (4-methanesulfonyl-phenyl)-amide.

1H NMR (400 MHz, d6-DMSO) δ 9.98 (s, 1H), 7.99 (d, 2H), 7.86 (m, 3H), 7.61 (m, 1 H), 7.29 (m, 2H), 3.76 (m, 2H), 3.17 (s, 3H), 2.46 (m, 2H), 2.29 (q, 4H), 2.04 (s, 3H), 0.76 (t, 6H); MS (EI) for $C_{25}H_{29}F_2N_3O_3S$: 490 (MH+).

1-(2-Hydroxy-ethyl)-4-methyl-5-o-tolyl-1H-pyrrole-3-carboxylic acid (4-methanesulfonyl-phenyl)-amide.

1H NMR (400 MHz, d6-DMSO) δ 9.94 (s, 1H), 7.99 (d, 2H), 7.85 (d, 2H), 7.79 (s, 1H), 7.36 (m, 2H), 7.29 (m, 1H), 7.18 (m, 1H), 3.74 (m, 1H), 3.58 (m, 1H), 3.42 (m, 2H), 3.17 (s, 3H), 2.06 (s, 3H), 1.97 (s, 3H); MS (EI) for $C_{22}H_{24}F_2N_2O_4S$: 413 (MH+).

5-(2,6-Difluoro-phenyl)-4-methyl-1-(2-pyrrolidin-1-yl-ethyl)-1H-pyrrole-3-carboxylic acid (4-methanesulfonyl-phenyl)-amide.

1H NMR (400 MHz, d6-DMSO) δ 10.06 (s, 1H), 7.99 (d, 2H), 7.87 (m, 3H), 7.62 (m, 1 H), 7.30 (m, 2H), 3.88 (m, 2H), 3.17 (s, 3H), 2.64 (m, 2H), 2.33 (m, 2H), 2.04 (s, 3H), 1.62 (m, 4H); MS (EI) for $C_{25}H_{27}F_2N_3O_3S$: 488 (MH+).

5-(2,6-Difluoro-phenyl)-4-methyl-1-(2-piperidin-1-yl-ethyl)-1H-pyrrole-3-carboxylic acid (4-methanesulfonyl-phenyl)-amide.

1H NMR (400 MHz, d6-DMSO) δ 10.00 (s, 1H), 7.97 (d, 2H), 7.87 (m, 3H), 7.63 (m, 1H), 7.29 (m, 2H), 3.81 (m, 2H), 3.17 (s, 3H), 2.39 (m, 2H), 2.14 (m, 4H), 2.04 (s, 3H), 1.30 (m, 6H); MS (EI) for $C_{26}H_{29}F_2N_3O_3S$: 502 (MH+).

5-(2,6-Difluoro-phenyl)-4-methyl-1-pyridin-2-ylmethyl-1H-pyrrole-3-carboxylic acid (4-methanesulfonyl-phenyl)-amide.

1H NMR (400 MHz, d6-DMSO) δ 10.09 (s, 1H), 8.39 (m, 1H), 7.99 (m, 3H), 7.86 (d, 2 H), 7.67 (m, 1H), 7.51 (m, 1H), 7.17 (m, 3H), 6.75 (m, 1H), 5.09 (s, 2H), 3.17 (s, 3H), 2.05 (s, 3H); MS (EI) for $C_{25}H_{21}F_2N_3O_3S$: 482 (MH+).

5-(2,6-Dimethoxy-phenyl)-1,4-dimethyl-1H-pyrrole-3-carboxylic acid (4-methane sulfonyl-phenyl)-amide.

1H NMR (400 MHz, d6-DMSO) δ 9.89 (s, 1H), 7.97 (m, 2H), 7.84 (m, 2H), 7.62 (m, 1 H), 7.40 (m, 1H), 6.76 (m, 2H), 3.71 (s, 6H), 3.30 (s, 3H), 3.17 (s, 3H), 1.92 (s, 3H); MS (EI) for $C_{22}H_{24}F_2N_2O_5S$: 429 (MH+).

1,4-Dimethyl-5-(2-trifluoromethoxy-phenyl)-1H-pyrrole-3-carboxylic acid (4-methane sulfonyl-phenyl)-amide.

1H NMR (400 MHz, d6-DMSO) δ 10.00 (s, 1H), 7.98 (d, 2H), 7.85 (d, 2H), 7.74 (s, 1H), 7.62 (m, 1 H), 7.50 (m, 3H), 3.42 (s, 3H), 3.17 (s, 3H), 2.04 (s, 3H); MS (EI) for $C_{21}H_{19}F_3N_2O_4S$: 453 (MH+).

1-(2-Hydroxy-3-phenyl-propyl)-4-methyl-5-(2-trifluoromethyl-phenyl)-1H-pyrrole-3-carboxylic acid (4-methanesulfonyl-phenyl)-amide.

1H NMR (400 MHz, d6-DMSO) δ 10.00 (s, 1H), 8.00 (m, 2H), 7.80 (m, 6H), 7.40 (m, 1H), 7.15 (m, 4H), 6.90 (m, 1H), 3.72 (m, 1H), 3.62 (m, 1H), 3.54 (m, 1H), 3.38 (m, 1H), 3.17 (s, 3H), 2.55 (m, 2H), 1.191 (, 3H); MS (EI) for $C_{29}H_{27}F_3N_2O_4S$: 557 (MH+).

5-(2-Chloro-phenyl)-1-(2-hydroxy-2-phenyl-ethyl)-4-methyl-1H-pyrrole-3-carboxylic acid (4-methanesulfonyl-phenyl)-amide.

1H NMR (400 MHz, d6-DMSO) δ 10.00 (s, 1H), 8.01 (d, 2H), 7.85 (m, 3H), 7.64 (m, 1 H), 7.52 (m, 2H), 7.24 (m, 4H), 6.96 (m, 2H), 5.75 (m, 1H), 4.50 (m, 1H), 3.90 (m, 1 H), 3.66 (m, 1H), 3.17 (s, 3H), 2.02 (s, 3H); MS (EI) for $C_{27}H_{25}ClN_2O_4S$: 509 (MH+).

5-(2-Chloro-phenyl)-1-(2-hydroxy-3-methoxy-propyl)-4-methyl-1H-pyrrole-3-carboxylic acid (4-methanesulfonyl-phenyl)amide.

1H NMR (400 MHz, d6-DMSO) δ 9.99 (s, 1H), 7.99 (d, 2H), 7.84 (m, 3H), 7.62 (m, 1 H), 7.45 (m, 3H), 5.17 (br s, 1H), 3.75 (m, 2H), 3.54 (m, 1H), 3.17 (s, 3H), 2.01 (s, 3H); MS (EI) for $C_{23}H_{25}ClN_2O_5S$: 477 (MH+).

5-(2-Chloro-phenyl)-4-methyl-1-(3,3,3-trifluoro-2-hydroxy-propyl)-1H-pyrrole-3-carboxylic acid (4-methanesulfonyl-phenyl)-amide.

1H NMR (400 MHz, d6-DMSO) δ 10.02 (s, 1H), 8.01 (d, 2H), 7.88 (m, 3H), 7.65 (m, 1 H), 7.50 (m, 3H), 6.81 (m, 1H), 3.90 (m, 3H), 3.18 (s, 3H), 2.03 (s, 3H); MS (EI) for $C_{22}H_{20}ClF_3N_2O_4S$: 501 (MH+).

1-(3-tert-Butoxy-2-hydroxy-propyl)-5-(2-chloro-Phenyl)-4-methyl-1H-pyrrole-3-carboxylic acid (4-methanesulfonyl-phenyl)-amide.

1H NMR (400 MHz, CDCl₃) δ 7.84 (m, 5H), 7.51 (m, 2H), 7.39 (m, 2H), 7.30 (m, 1 H), 3.78 (m, 3H), 3.18 (m, 1H), 3.07 (m, 1H), 3.05 (s, 3H), 2.58 (m, 1H), 2.16 (s, 3H), 1.11 (s, 9H); MS (EI) for $C_{26}H_{31}ClN_2O_5S$: 519 (MH+).

5-(2-Chloro-phenyl)-1-(2-hydroxy-3-isopropoxy-propyl)-4-methyl-1H-pyrrole-3-carboxylic acid (4-methanesulfonyl-phenyl)-amide.

1H NMR (400 MHz, CDCl₃) δ 7.84 (m, 5H), 7.51 (m, 2H), 7.38 (m, 2H), 7.29 (m, 1 H), 3.79 (m, 3H), 3.50 (m, 1H), 3.26 (m, 1H), 3.10 (m, 1H), 3.05 (s, 3H), 2.16 (s, 3H), 1.09 (d, 6H); MS (EI) for $C_{25}H_{29}ClN_2O_5S$: 505 (MH+).

1-(2-Hydroxy-ethyl)-5-(4-methoxy-2-trifluoromethyl-phenyl)-4-methyl-1H-pyrrole-3-carboxylic acid (4-methanesulfonyl-phenyl)-amide.

1H NMR (400 MHz, CDCl₃) δ 8.02 (br s, 1H), 7.84 (m, 4H), 7.50 (m, 2H), 7.27 (m, 2H), 7.11 (m, 1H), 3.91 (s, 3H), 3.67 (m, 4H), 3.04 (s, 3H), 2.06 (s, 3H); MS (EI) for $C_{23}H_{23}F_3N_2O_5S$: 497 (MH+).

1,4-Dimethyl-5-[4-(3-morpholin-4-yl-propoxy)-2-trifluoromethyl-Phenyl]-1H-pyrrole-3-carboxylic acid (4-methanesulfonyl-phenyl)-amide.

¹H NMR (400 MHz, CDCl₃) δ 7.90 (d, 2H), 7.80 (d, 2H), 7.68 (m, 1H), 7.25 (m, 3H), 7.14 (m, 1H), 4.13 (m, 2H), 3.76

(m, 5H), 3.31 (s, 3H), 3.05 (s, 3H), 2.55 (m, 6H), 2.09 (s, 3H), 2.05 (m, 2H); MS (EI) for $C_{28}H_{32}F_3N_3O_5S$: 580 (MH+).

5-(2-Benzyloxy-4-fluoro-phenyl)-1-(2-dimethylamino-ethyl)-4-methyl-1H-pyrrole-3-carboxylic acid (4-methanesulfonyl-phenyl)-amide.

$^1$H NMR (400 MHz, CDCl$_3$): δ 9.07 (s, 1H), 8.11 (d, 2H), 7.88 (d, 2H) 7.68 (m, 1H), 7.35 (m, 2H), 7.18 (m, 1H), 6.93 (m, 1H), 6.84 (m, 1H), 5.04 (s, 2H), 4.35 (m, 1H), 4.21 (m, 2H), 3.46 (m, 2H), 3.33 (m, 2H), 3.05 (s, 3H), 2.96 (m, 2H), 2.35 (m, 1H), 2.22 (s, 2H) 1.64 (s, 6H); MS (EI) for $C_{31}H_{34}FN_3O_4S$: 564 (MH$^+$).

5-(2-Benzyloxy-4-fluoro-phenyl)-4-methyl-1-(2-pyrrolidin-1-yl-ethyl)-1H-pyrrole-3-carboxylic acid (4-methanesulfonyl-phenyl)-amide.

$^1$H NMR (400 MHz, CDCl$_3$): δ 8.78 (s, 1H), 8.00 (m, 2H), 7.89 (m, 2H) 7.60 (s, 1H), 7.33 (m, 2H), 7.22 (m, 2H), 7.16 (m, 1H), 6.84 (m, 1H), 5.02 (s, 2H), 3.80 (m, 2H), 3.05 (s, 3H), 2.59 (s, 2H), 2.42 (s, 2H), 2.20 (s, 2H), 2.96 (m, 2H), 2.35 (m, 1H), 2.22 (s, 2H) 1.64 (s, 6H); MS (EI) for $C_{32}H_{34}FN_3O_4S$: 576 (MH$^+$).

5-(2-Benzyloxy-4-fluoro-phenyl)-4-methyl-1-(2-piperidin-1-yl-ethyl)-1H-pyrrole-3-carboxylic acid (4-methanesulfonyl-phenyl)-amide.

$^1$H NMR (400 MHz, CDCl$_3$): δ7.91 (m, 2H), 7.84 (m, 2H), 7.46 (m, 1H) 7.60 (s, 1H), 7.31 (m, 2H), 7.23 (m, 2H), 7.16 (m, 2H), 6.78 (m, 2H), 5.05 (s, 2H), 3.83 (m, 2H), 3.45 (m, 1H), 3.05 (s, 3H), 2.24 (m, 2H), 2.18 (s, 3H), 2.07 (s, 1H), 1.80 (m, 5H), 1.50 (m, 2H) 1.37 (m, 2H); MS (EI) for $C_{33}H_{36}FN_3O_4S$: 590 (MH$^+$).

5-(2-chloro-phenyl)-1-(2-Methoxy-ethyl)-4-methyl-1H-pyrrole-3-carboxylic acid (4-methanesulfonyl-phenyl)-amide.

$^1$H NMR (400 MHz, CDCl$_3$): δ7.91 (m, 2H), 7.82 (m, 2H), 7.70 (s, 1H) 7.52 (m, 1H), 7.44 (m, 1H), 7.39 (m, 2H), 7.29 (m, 1H), 3.85 (m, 2H), 3.45 (m, 2H), 3.28 (s, 3H) 3.06 (s, 3H), 2.16 (s, 3H); MS (EI) for $C_{22}H_{23}ClN_2O_4S$: 447 (MH$^+$).

1-Allyl-5-(2-chloro-phenyl)-4-methyl-1H-pyrrole-3-carboxylic acid (4-methanesulfonyl-phenyl)-amide.

$^1$H NMR (400 MHz, CDCl$_3$): δ7.92 (m, 2H), 7.82 (m, 2H), 7.70 (s, 1H) 7.52 (m, 1H), 7.40 (m, 1H), 7.35 (m, 1H), 7.29 (m, 1H), 5.81 (m, 1H), 5.17 (m, 1H), 5.00 (m, 1H), 4.33 (m, 1H), 4.23 (m, 1H) 3.05 (s, 3H), 2.18 (s, 3H); MS (EI) for $C_{22}H_{21}ClN_2O_3S$: 429 (MH$^+$).

5-Biphenyl-2-yl-1-(2-diethylamino-ethyl)-4-methyl-1H-pyrrole-3-carboxylic acid (4-methanesulfonyl-phenyl)-amide.

$^1$H NMR (400 MHz, CDCl$_3$): δ7.92-7.04 (m, 14H), 3.42 (m, 2H), 3.26 (m, 2H), 3.05 (s, 3H), 2.29 (m, 4H), 2.21 (m, 3H), 0.82 (m, 6H); MS (EI) for $C_{31}H_{35}N_3O_3S$: 530 (MH$^+$).

5-Biphenyl-2-yl-4-methyl-1-(2-morpholin-4-yl-ethyl)-1H-pyrrole-3-carboxylic acid (4-methanesulfonyl-phenyl)-amide.

$^1$H NMR (400 MHz, CDCl$_3$): δ7.94-7.08 (m, 14H), 3.79 (m, 4H), 3.39 (m, 2H), 3.26 (m, 2H), 3.03 (s, 3H), 2.29 (m, 4H), 2.19 (m, 3H); MS (EI) for $C_{31}H_{33}N_3O_4S$: 544 (MH$^+$).

5-Biphenyl-2-yl-4-methyl-1-(2-pyrrolidin-1-yl-ethyl)-1H-pyrrole-3-carboxylic acid (4-methanesulfonyl-phenyl)-amide.

$^1$H NMR (400 MHz, CDCl$_3$): δ7.94-7.08 (m, 14H), 3.48 (m, 2H), 3.02 (s, 3H), 2.78-2.30 (m, 4H), 2.24 (m, 3H) 1.87 (m, 4H); MS (EI) for $C_{31}H_{33}N_3O_4S$: 528 (MH$^+$).

5-(2-Chloro-phenyl)-4-methyl-1-pyrazin-2-ylmethyl-1H-pyrrole-3-carboxylic acid (4-methanesulfonyl-phenyl)-amide.

$^1$H NMR (400 MHz, CDCl$_3$): δ8.62 (m, 2H), 7.99 (m, 2H), 7.91-7.79 (m, 4H) 7.52 (m, 2H), 7.43 (m, 1H), 7.39 (m, 1H), 7.27 (m, 2H), 7.18 (m, 1H), 5.05 (m, 2H), 3.06 (s, 3H), 2.16 (s, 3H); MS (EI) for $C_{24}H_{21}ClN_4O_3S$: 481 (MH$^+$).

5-(2-Chloro-phenyl)-4-methyl-1-pyrimidin-4-ylmethyl-1H-pyrrole-3-carboxylic acid (4-methanesulfonyl-phenyl)-amide.

$^1$H NMR (400 MHz, CDCl$_3$): δ9.07 (s, 1H), 8.61 (m, 1H), 8.02 (s, 1H), 7.87-7.79 (m, 4H) 7.52 (m, 2H), 7.43 (m, 1H), 7.39 (m, 1H), 7.27 (m, 1H), 7.18 (m, 2H), 6.69 (m, 1H), 5.07 (m, 2H), 3.07 (s, 3H), 2.16 (s, 3H); MS (EI) for $C_{24}H_{21}ClN_4O_3S$: 481 (MH$^+$).

1-(1-Hydroxy-2-methoxy-ethyl)-4-methyl-5-(2-trifluoromethyl-phenyl)-1H-pyrrole-3-carboxylic acid (4-methanesulfonyl-phenyl)-amide.

$^1$H NMR (400 MHz, CDCl$_3$): δ7.82-7.68 (m, 5H), 7.76-7.63 (m, 2H) 7.52 (m, 1H), 7.38 (m, 1H), 3.92 (m, 1H), 3.87-3.63 (m, 2H), 3.59-3.51 (m, 1H), 3.37-3.13 (m, 5H), 3.06 (s, 3H), 2.16 (s, 3H); MS (EI) for $C_{24}H_{25}F_3N_2O_5S$: 511 (MH$^+$).

4-Methyl-1-(tetrahydro-furan-2-ylmethyl)-5-(2-trifluoromethyl-phenyl)-1H-pyrrole-3-carboxylic acid (4-methanesulfonyl-phenyl)-amide.

$^1$H NMR (400 MHz, CDCl$_3$): δ7.94-7.29 (m, 9H), 4.07-3.43 (m, 5H), 3.06 (s, 3H), 2.16 (s, 3H), 1.78 (m, 4H); MS (EI) for $C_{25}H_{25}F_3N_2O_4S$: 507 (MH$^+$).

1-(3,3-Dimethyl-2-oxo-butyl)-4-methyl-5-(2-trifluoromethyl-phenyl)-1H-pyrrole-3-carboxylic acid (4-methanesulfonyl-phenyl)-amide.

$^1$H NMR (400 MHz, CDCl$_3$): δ7.91 (m, 2H), 7.82 (m, 3H), 7.59 (m, 2H), 7.22 (m, 3H), 4.59 (m, 2H), 3.03 (s, 3H), 2.09 (s, 3H), (0.97 (s, 9H); MS (EI) for $C_{26}H_{27}F_3N_2O_4S$: 521 (MH$^+$).

1-Furan-2-ylmethyl-4-methyl-5-(2-trifluoromethyl-phenyl)-1H-pyrrole-3-carboxylic acid (4-methanesulfonyl-phenyl)-amide.

$^1$H NMR (400 MHz, CDCl$_3$): δ7.95-7.62 (m, 6H), 7.29 (m, 2H), 7.59 (m, 2H), 7.22 (m, 2H), 6.30 (m, 1H), 6.05 (m, 1H), 4.65 (m, 2H), 3.05 (s, 3H), 2.09 (s, 3H); MS (EI) for $C_{26}H_{21}F_3N_2O_4S$: 503 (MH$^+$).

1-(3-Fluoro-pyridin-2-ylmethyl)-4-methyl-5-(2-trifluoromethyl-phenyl)-1H-pyrrole-3-carboxylic acid (4-methanesulfonyl-phenyl)-amide.

$^1$H NMR (400 MHz, CDCl$_3$): δ7.95-7.43 (m, 8H), 7.29 (m, 2H), 7.18 (m, 1H), 6.82 (m, 1H), 6.65 (m, 1H), 4.82 (m, 2H), 3.05 (s, 3H), 2.09 (s, 3H); MS (EI) for $C_{26}H_{21}F_4N_3O_3S$: 532 (MH$^+$).

5-(2-Chloro-phenyl)-1-(2-hydroxy-ethyl)-4-methyl-1H-pyrrole-3-carboxylic acid (3-chloro-4-sulfamoyl-phenyl)-amide.

$^1$H NMR (400 MHz, DMSO-d$_6$): δ10.01 (s, 1H), 8.17 (s, 1H), 7.95-7.39 (m, 8H), 3.81-3.39 (m, 6H), 2.05 (s, 3H); MS (EI) for $C_{20}H_{19}Cl_2N_3O_4S$: 468 (MH$^+$).

5-[4-fluoro-2-(trifluoromethyl)phenyl]-4-methyl-N-[4-(methylsulfonyl)phenyl]-1-(pyridin-2-ylmethyl)-1H-pyrrole-3-carboxamide.

$^1$H NMR (400 MHz, d$_6$-DMSO): 10.6 (s, 1H), 8.48 (dd, 1H), 8.02 (d, 2H), 7.88 (m, 3H), 7.82-7.72 (m, 2H), 7.5 (t, 1H), 7.3 (m, 1H), 7.2 (m, 1H), 6.94 (d, 1H), 5.15 (d, 1H), 4.75 (d, 1H), 3.2 (s, 3H), 1.95 (s, 3H); MS (EI) for $C_{26}H_{21}F_4N_3O_3S$: 532 (MH$^+$).

N-[4-(aminosulfonyl)-3-chlorophenyl]-5-[4-fluoro-2-(trifluoromethyl)phenyl]-4-methyl-1-(pyridin-3-ylmethyl)-1H-pyrrole-3-carboxamide.

$^1$H NMR (400 MHz, d$_6$-DMSO): 10.3 (s, 1H), 8.48 (dd, 1H), 8.2 (s, 1H), 8.08 (s, 1H), 7.91 (d, 1H), 7.83-7.76 (m, 3H), 7.56 (t, 1H), 7.5 (s, 2H), 7.42-7.32 (m, 2H), 7.28 (m, 1H), 5.05 (d, 1H), 4.75 (d, 1H), 1.94 (s, 3H); MS (EI) for $C_{26}H_{19}ClF_4N_4O_3S$: 567 (MH$^+$).

5-[4-fluoro-2-(trifluoromethyl)phenyl]-4-methyl-N-[4-(methylsulfonyl)phenyl]-1-(2-pyrrolidin-1-ylethyl)-1H pyrrole-3-carboxamide.

$^1$H NMR (400 MHz, d$_6$-DMSO): 9.98 (s, 1H), 8.0 (d, 2H), 7.86 (d, 2H), 7.83 (dd, 1H), 7.8 (s, 1H), 7.7 (t, 1H), 7.55 (m, 1H), 3.76 (m, 1H), 3.52 (m, 1H), 3.18 (s, 3H), 2.62 (m, 2H), 2.3 (m, 4H), 1.94 (s, 3H), 1.62 (t, 4H); MS (EI) for C$_{26}$H$_{27}$F$_4$N$_3$O$_3$S: 538 (MH$^+$).

1-[3-(dimethylamino)propyl]-5-[4-fluoro-2-(trifluoromethyl)phenyl]-4-methyl-N-[4-(methylsulfonyl)phenyl]-1H-pyrrole-3-carboxamide.

$^1$H NMR (400 MHz, d$_6$-DMSO): 9.96 (s, 1H), 8.0 (d, 2H), 7.86 (d, 2H), 7.83 (dd, 1H), 7.8 (s, 1H), 7.7 (dt, 1H), 7.57 (m, 1H), 3.66 (m, 1H), 3.48 (m, 1H), 3.18 (s, 3H), 2.1 (m, 2H), 2.05 (s, 6H), 1.94 (s, 3H); MS (EI) for C$_{26}$H$_{27}$F$_4$N$_3$O$_3$S: 526 (MH$^+$).

5-[4-fluoro-2-(trifluoromethyl)phenyl]-4-methyl-N-[4-(methylsulfonyl)phenyl]-1-(2-piperidin-1-ylethyl)-1H-pyrrole-3-carboxamide $^1$H NMR (400 MHz, d$_6$-DMSO): 9.97 (s, 1H), 7.98 (d, 2H), 7.8 (d, 2H), 7.84 (dd, 1H), 7.78 (s, 1H), 7.7 (dt, 1H), 7.56 (m, 1H), 3.75 (m, 1H), 3.5 (m, 1H), 3.18 (s, 3H), 2.46 (m, 2H), 2.2 (b, 4H), 1.93 (s, 3H), 1.45-1.3 (m, 6H); MS (EI) for C$_{27}$H$_{29}$F$_4$N$_3$O$_3$S: 552 (MH$^+$).

5-[4-fluoro-2-(trifluoromethyl)phenyl]-4-methyl-N-[4-(methylsulfonyl)phenyl]-1-(2-morpholin-4-ylethyl)-1H-pyrrole-3-carboxamide $^1$H NMR (400 MHz, d$_6$-DMSO): 9.97 (s, 1H), 7.98 (d, 2H), 7.86 (d, 2H), 7.83 (dd, 1H), 7.6 (dt, 1H), 7.56 (m, 1H), 3.78 (m, 1H), 3.56-3.48 (m, 5H), 3.18 (s, 3H), 2.5 (m, 2H), 2.24 (b, 4H), 1.92 (s, 3H); MS (EI) for C$_{26}$H$_{27}$F$_4$N$_3$O$_4$S: 554 (MH$^+$).

4-methyl-5-[2-(methyloxy)phenyl]-N-[4-(methylsulfonyl)phenyl]-1-(pyridin-3-ylmethyl)-1H-pyrrole-3-carboxamide $^1$H NMR (400 MHz, d$_6$-DMSO): 9.98 (s, 1H), 8.4 (t, 1H), 8.12 (s, 1H), 7.97 (d, 2H), 7.84 (d, 2H), 7.77 (s, 1H), 7.4 (dt, 1H), 7.27 (m, 2H), 7.12-6.96 (m, 3H), 5.03 (d, 1H), 4.9 (d, 1H), 3.68 (s, 3H), 3.18 (s, 3H), 2.03 (s, 3H); MS (EI) for C$_{26}$H$_{26}$N$_3$O$_4$S: 476 (MH$^+$).

4-methyl-5-[2-(methyloxy)phenyl]-N-[4-(methylsulfonyl)phenyl]-1-(2-morpholin-4-ylethyl)-1H-pyrrole-3-carboxamide $^1$H NMR (400 MHz, d$_6$-DMSO): 9.91 (s, 1H), 7.98 (d, 2H), 7.84 (d, 2H), 7.72 (s, 1H), 7.44 (dt, 1H), 7.2-7.04 (m, 3H), 3.86-3.66 (m, 2H), 3.76 (s, 3H), 3.46 (t, 4H), 3.16 (s, 3H), 2.42 (t, 2H), 2.18 (b, 4H), 2.0 (s, 3H); MS (EI) for C$_{26}$H$_{31}$N$_3$O$_5$S: 498 (MH$^+$).

1-[2-(diethylamino)ethyl]-4-methyl-5-[2-(methyloxy)phenyl]-N-[4-(methylsulfonyl)phenyl]-1H-pyrrole-3-carboxamide $^1$H NMR (400 MHz d$_6$-DMSO): 9.91 (s, 1H), 7.98 (d, 2H), 7.84 (d, 2H), 7.71 (s, 1H), 7.44 (dt, 1H), 7.2-7.03 (m, 3H), 3.8-3.6 (m, 2H), 3.75 (s, 3H), 3.17 (s, 1H), 2.42 (t, 2H), 2.3 (q, 4H), 2.02 (s, 3H), 0.75 (t, 4H); MS (EI) for C$_{26}$H$_{33}$N$_3$O$_4$S: 484 (MH$^+$).

4-methyl-5-[2-(methyloxy)phenyl]-N-[4-(methylsulfonyl)phenyl]-1-(pyridin-2-ylmethyl)-1H-pyrrole-3-carboxamide $^1$H NMR (400 MHz, d$_6$-DMSO): 9.98 (s, 1H), 8.42 (d, 1H), 8.0 (d, 2H), 7.84 (d, 2H), 7.82 (s, 1H), 7.68 (t, 1H), 7.37 (t, 1H), 7.22 (m, 1H), 7.04 (m, 1H), 6.92 (t, 1H), 6.7 (d, 1H), 5.08 (d, 1H), 4.92 (d, 1H), 3.66 (s, 3H), 3.17 (s, 3H), 2.05 (s, 3H); MS (EI) for C$_{26}$H$_{25}$N$_3$O$_4$S: 476 (MH$^+$).

5-(2,4-difluorophenyl)-4-methyl-N-[4-(methylsulfonyl)phenyl]-1H-pyrrole-3-carboxamide $^1$H NMR (400 MHz, d$_6$-DMSO): 11.6 (s, 1H), 10.0 (s, 1H), 8.1 (d, 2H), 7.84 (d, 2H), 7.8 (s, 1H), 7.47 (m, 1H), 7.4 (t, 1H), 7.2 (t, 1H), 3.18 (s, 3H), 2.2 (s, 3H); MS (EI) for C$_{19}$H$_{16}$F$_2$N$_2$O$_3$S: 391 (MH$^+$).

5-(2,4-difluorophenyl)-1,4-dimethyl-N-[4-(methylsulfonyl)phenyl]-1H-pyrrole-3-carboxamide $^1$H NMR (400 MHz, d$_6$-DMSO): 10.1 (s, 1H), 8.05 (d, 2H), 7.88 (s, 1H), 7.8 (d, 2H), 7.48 (m, 2H), 7.2 (t, 1H), 3.48 (s, 3H), 3.18 (s, 3H), 2.05 (s, 3H); MS (EI) for C$_{20}$H$_{18}$F$_2$N$_2$O$_3$S: 405 (MH$^+$).

1-[(6-chloropyridin-2-yl)methyl]-5-(2,4-difluorophenyl)-4-methyl-N-[4-(methylsulfonyl)phenyl]-1H-pyrrole-3-carboxamide $^1$H NMR (400 MHz, d6-DMSO): 10.2 (s, 1H), 8.0 (d, 2H), 7.9 (s, 1H), 7.86 (d, 2H), 7.77 (t, 1H), 7.4-7.28 (m, 3H), 7.12 (t, 1H), 6.7 (d, 1H), 5.2 (d, 1H), 5.05 (d, 1H), 3.18 (s, 3H), 2.05 (s, 3H); MS (EI) for C$_{25}$H$_{20}$ClF$_2$N$_3$O$_3$S: 516 (MH$^+$).

1-[2-(diethylamino)ethyl]-5-(2,4-difluorophenyl)-4-methyl-N-[4-(methylsulfonyl)phenyl]-1H-pyrrole-3-carboxamide $^1$H NMR (400 MHz, d$_6$-DMSO): 9.98 (s, 1H), 8.0 (d, 2H), 7.9-7.8 (m, 3H), 7.45 (m, 2H), 7.23 (t, 1H), 3.85 (d, 1H), 3.75 (d, 1H), 3.18 (s, 3H), 2.45 (s, 2H), 2.3 (m, 4H), 2.05 (s, 3H), 0.8 (t, 6H); MS (EI) for C$_{26}$H$_{29}$F$_2$N$_3$O$_3$S: 490 (MH$^+$).

5-(2,4-difluorophenyl)-4-methyl-N-[4-(methylsulfonyl)phenyl]-1-(2-pyrrolidin-1-ylethyl)-1H-pyrrole-3-carboxamide $^1$H NMR (400 MHz, d6-DMSO): 9.98 (s, 1H), 8.0 (d, 2H), 7.85 (d, 2H), 7.82 (s, 1H), 7.45 (m, 2H), 7.23 (t, 1H), 3.9 (m, 1H), 3.78 (m, 1H), 3.18 (s, 3H), 2.54 (m, 2H), 2.25 (t, 4H), 2.05 (s, 3H), 1.58 (t, 4H); MS (EI) for C$_{26}$H$_{27}$F$_2$N$_3$O$_3$S: 488 (MH$^+$).

1-[(6-aminopyridin-2-yl)methyl]-5-(2,4-difluorophenyl)-4-methyl-N-[4-(methylsulfonyl)phenyl]-1H-pyrrole-3-carboxamide $^1$H NMR (400 MHz, d$_6$-DMSO): 10.2 (s, 1H), 8.0 (d, 2H), 7.84 (m, 3H), 7.4 (m, 2H), 7.25 (t, 1H), 7.15 (t, 1H), 6.28 (d, 1H), 6.0 (s, 2H), 5.84 (d, 1H), 4.9 (d, 1H), 4.72 (d, 1H), 3.18 (s, 3H), 2.05 (s, 3H); MS (EI) for C$_{26}$H$_{22}$F$_2$N$_4$O$_3$S: 497 (MH$^+$).

1-[(6-aminopyridin-2-yl)methyl]-4-methyl-N-[4-(methylsulfonyl)phenyl]-5-[2-(trifluoromethyl)phenyl]-1H-pyrrole-3-carboxamide $^1$H NMR (400 MHz, d$_6$-DMSO): 10.2 (s, 1H), 8.05 (d, 2H), 7.97 (s, 1H), 7.9-7.8 (m, 3H), 7.77-7.65 (m, 3H), 7.27 (d, 2H), 6.84 (d, 1H), 6.12 (d, 1H), 5.2 (d, 1H), 4.78 (d, 1H), 3.18 (s, 3H), 1.98 (s, 3H); MS (EI) for C$_{26}$H$_{23}$F$_3$N$_4$O$_3$S: 529 (MH$^+$).

5-(2,4-difluorophenyl)-4-methyl-N-[4-(methylsulfonyl)phenyl]-1-[(6-pyrrolidin-1-ylpyridin-2-yl)methyl]-1H-pyrrole-3-carboxamide $^1$H NMR (400 MHz, d$_6$-DMSO): 10.0 (s, 1H), 8.0 (d, 2H), 7.85 (m, 3H), 7.5-7.35 (m, 3H), 7.2 (t, 1H), 6.25 (d, 1H), 6.0 (d, 1H), 4.95 (d, 1H), 4.78 (d, 1H), 3.3 (t, 4H), 3.18 (s, 3H), 2.08 (s, 3H), 1.9 (t, 4H); MS (EI) for C$_{29}$H$_{28}$F$_2$N$_4$O$_3$S: 551 (MH$^+$).

5-(2,4-difluorophenyl)-4-methyl-1-[(6-methylpyridin-2-yl)methyl]-N-[4-(methylsulfonyl)phenyl]-1H-pyrrole-3-carboxamide $^1$H NMR (400 MHz, d$_6$-DMSO): 10.1 (s, 1H), 8.0 (d, 2H), 7.93 (s, 1H), 7.84 (d, 2H), 7.6 (t, 1H), 7.4-7.3 (m, 2H), 7.1 (m, 2H), 6.6 (d, 1H), 5.15 (d, 1H), 4.95 (d, 1H), 3.18 (s, 3H), 2.38 (s, 3H), 2.05 (s, 31-1); MS (EI) for C$_{26}$H$_{23}$F$_2$N$_3$O$_3$S: 496 (MH$^+$).

methyl (6-{[2-(2,4-difluorophenyl)-3-methyl-4-({[4-(methylsulfonyl)phenyl]amino}carbonyl)-1H-pyrrol-1-yl]methyl}pyridin-2-yl)carbamate $^1$HNMR (400 MHz, d$_6$-DMSO): 10.12 (s, 2H), 8.02 (d, 2H), 7.94 (s, 1H), 7.85 (d, 2H), 7.68 (d, 2H), 7.4 (q, 1H), 7.35 (t, 1H), 7.13 (t, 1H), 6.41 (t, 1H), 5.1 (d, 1H), 4.9 (d, 1H), 3.64 (s, 3H), 3.18 (s, 3H), 2.08 (s, 3H); MS (EI) for C$_{27}$H$_{24}$F$_2$N$_4$O$_5$S: 555 (MH$^+$).

1-{[6-(acetylamino)pyridin-2-yl]methyl}-5-(2,4-difluorophenyl)-4-methyl-N-[4-(methylsulfonyl)phenyl]-1H-pyrrole-3-carboxamide $^1$H NMR (400 MHz, d$_6$-DMSO): 10.38 (s, 1H), 10.08 (s, 1H), 8.0 (d, 2H), 7.95-7.83 (m, 4H), 7.68 (t, 1H), 7.4-7.3 (m, 2H), 7.12 (t, 1H), 6.44 (d, 1H), 5.12 (d, 1H), 4.95 (d, 1H), 3.18 (s, 3H), 2.04 (s, 3H), 2.03 (s, 3H); MS (EI) for C$_{27}$H$_{24}$F$_2$N$_4$O$_4$S: 539 (MH$^+$).

1-({6-[bis(methylsulfonyl)amino]pyridin-2-yl}methyl)-5-(2,4-difluorophenyl)-4-methyl-N-[4-(methylsulfonyl)phenyl]-1H-pyrrole-3-carboxamide $^1$H NMR (400 MHz, d$_6$-DMSO): 10.07 (s, 1H), 8.0 d, 2H), 7.95 (s, 1H), 7.92 (t, 1H), 7.84 (d, 2H), 7.58 (d, 1H), 7.3 (t, 1H), 7.2 (q, 1H), 7.06 (d, 1H), 7.0 (t, 1H), 5.33 (d, 1H), 5.08 (d, 1H), 3.55 (s, 6H), 3.18 (s, 3H), 2.05 (s, 3H); MS (EI) for C$_{27}$H$_{26}$F$_2$N$_4$O$_7$S$_3$: 653 (MH$^+$).

5-(2-chlorophenyl)-1-[2-hydroxy-3-(4-methylpiperazin-1-yl)propyl]-4-methyl-N-[4-(methylsulfonyl)phenyl]-1H-pyrrole-3-carboxamide $^1$H NMR (400 MHz, d$_6$-DMSO): 10.0 (d, 1H), 8.0 (d, 2H), 7.85 (d, 2H), 7.8 (s, 1H), 7.6 (m, 1H), 7.5-7.38 (m, 3H), 5.0 (s, 1H), 4.0 (m, 1H), 3.6-3.4 (m, 2H), 3.18 (s, 3H), 2.3-2.0 (m, 14H), 1.8-1.7 (m, 2H); MS (EI) for C$_{27}$H$_{33}$ClN$_4$O$_4$S: 545 (MH$^+$).

5-(2-chlorophenyl)-1-{2-hydroxy-3-[(2-methylpropyl)amino]propyl}-4-methyl-N-[4-(methylsulfonyl)phenyl]-1H-pyrrole-3-carboxamide $^1$HNMR (400 MHz, d$_6$-DMSO): 9.98 (s, 1H), 8.0 (d, 2H), 7.86 (d, 2H), 7.8 (d, 1H), 7.62 (d, 1H), 7.52-7.42 (m, 2H), 7.4 (m, 1H), 5.0 (s, 1H), 3.9-3.73 (m, 1H), 3.7-3.4 (m, 2H), 3.18 (s, 3H), 2.3 (t, 2H), 2.2-2.0 (m, 2H), 2.02 (s, 3H), 1.5 (m, 1H), 0.75 (t, 6H); MS (EI) for C$_{26}$H$_{32}$ClN$_3$O$_4$S: 518 (MH$^+$).

5-(2-chlorophenyl)-1-{2-hydroxy-3-[(phenylmethyl)amino]propyl}-4-methyl-N-[4-(methylsulfonyl)phenyl]-1H-pyrrole-3-carboxamide $^1$HNMR (400 MHz, d$_6$-DMSO): 10.0 (s, 1H), 8.0 (d, 2H), 7.86 (d, 2H), 7.82 (d, 1H), 7.6 (d, 1H), 7.5-7.37 (m, 3H), 7.3-7.15 (m, 5H), 3.92-3.74 (m, 1H), 3.7-3.5 (m, 2H), 3.56-3.48 (m, 2H), 3.18 (s, 3H), 2.32-2.26 (m, 2H), 2.02 (d, 3H); MS (EI) for C$_{26}$H$_{30}$ClN$_3$O$_4$S: 552 (MH$^+$).

6: 1-(3-amino-2-hydroxypropyl)-5-(2-chlorophenyl)-4-methyl-N-[4-(methylsulfonyl)phenyl]-1H-pyrrole-3-carboxamide $^1$H NMR (400 MHz, d$_6$-DMSO): 10.0 (s, 1H), 8.0 (d, 2H), 7.87 (d, 2H), 7.83 (d, 1H), 7.62 (d, 1H), 7.52-7.38 (m, 3H), 4.95 (s, 1H), 3.84-3.6 (m, 1H), 3.54-3.3 (m, 2H), 3.18 (s, 3H), 2.4-2.23 (m, 2H), 2.02 (s, 3H); MS (EI) for C$_{22}$H$_{24}$ClN$_3$O$_4$S: 462 (MH$^+$).

4-methyl-1-{2-[(2-methylpropyl)amino]-2-oxoethyl}-N-[4-(methylsulfonyl)phenyl]-5-[2-(trifluoromethyl)phenyl]-1H-pyrrole-3-carboxamide $^1$H NMR (400 MHz, CDCl$_3$): 7.92 (d, 2H), 7.87-7.8 (m, 4H), 7.63 (t, 2H), 7.38 (s, 1H), 7.3 (m, 1H), 5.42 (t, 1H), 4.35 (d, 1H), 4.16 (d, 1H), 3.12-2.98 (m, 2H), 3.07 (s, 3H), 2.1 (s, 3H), 1.7 (m, 1H), 0.86 (d, 6H); MS (EI) for C$_{26}$H$_{28}$F$_3$N$_3$O$_4$S: 536 (MH$^+$).

N-[4-(aminosulfonyl)-3-chlorophenyl]-1,4-dimethyl-5-[2-(trifluoromethyl)phenyl]-1H-pyrrole-3-carboxamide $^1$H NMR (CDCl$_3$) .δ 808 (d, 2.2 Hz, 1H), 7.99 (d, 8.6 Hz, 1H), 7.83 (d, 7.2 Hz, 1H), 7.71 (s, 1H), 7.68-7.61 (m, 2H), 7.45 (dd, 8.8 Hz, 2.1 Hz, 1H), 7.35-7.26 (m, 2H), 5.13 (s, 2H), 3.32 (s, 3H), 2.09 (s, 3H). LCMS: m/z 472 (M+H)$^+$.

N-{4-[(acetylamino)sulfonyl]-3-chlorophenyl}-1,4-dimethyl-5-[2-(trifluoromethyl)phenyl]-1H-pyrrole-3-carboxamide $^1$H NMR (DMSO-d$_6$) .δ 12.3 (s, 1H), 10.03 (s, 1H), 8.10 (s, 1H), 7.96 (m, 1H), 7.86 (m, 1H), 7.71 (m, 4H), 7.41 (m, 1H), 3.29 (s, 3H), 1.92 (s, 3H), 1.88 (s, 3H). LCMS: m/z 514 (M+H)$^+$.

(N-{4-[(acetylamino-kappaN)sulfonyl]-3-chlorophenyl}-1,4-dimethyl-5-[2-(trifluoromethyl)phenyl]-1H-pyrrole-3-carboxamidato)sodium $^1$H NMR (DMSO-d$_6$) .δ 9.71 (s, 1H), 7.87 (d, 1H), 7.82 (d, 2.0 Hz, 1H), 7.78-7.68 (m, 3H), 7.63 (s, 1H), 7.54 (dd, 8.9 Hz, 2.0 Hz, 1H), 7.42 (d, 7.0 Hz, 1H), 3.24 (s, 3H), 1.88 (s, 3H), 1.61 (s, 3H). LCMS: m/z 514 (M+H)$^+$.

1-(2-hydroxyethyl)-4-methyl-N-[4-(methylsulfonyl)phenyl]-5-[2-(trifluoromethyl)phenyl]-1H-pyrrole-3-carboxamide $^1$H NMR (DMSO-d$_6$) .δ 9.97 (s, 1H), 7.97 (d, 9.0 Hz, 2H), 7.95-7.89 (m, 1H), 7.87-7.84 (m, 2H), 7.82-7.76 (m, 2H), 7.72-7.68 (m, 1H), 7.49-7.45 (m, 1H), 4.93 (t, 4.9 Hz, 1H), 3.69-3.65 (m, 1H), 3.55-3.44 (m, 3H), 3.16 (s, 3H), 1.91 (s, 3H). LCMS: m/z 467 (M+H)$^+$.

4-methyl-N-[4-(methylsulfonyl)phenyl]-1-(2-pyrrolidin-1-ylethyl)-5-[2-(trifluoromethyl)phenyl]-1H-pyrrole-3-carboxamide $^1$H NMR (DMSO-d$_6$) .δ 9.96 (s, 1H), 7.98 (d, 8.8 Hz, 2H), 7.92 (d, 7.6 Hz, 1H), 7.87-7.85 (m, 2H), 7.83-7.78 (m, 2H), 7.75-7.72 (m, 1H), 7.49-7.47 (m, 1H), 3.75 (m, 1H), 3.52 (m, 1H), 3.18 (s, 3H), 2.27 (m, 4H), 1.93 (s, 3H), 1.61 (br s, 4H), 1.23 (br s, 2H). LCMS: m/z 520 (M+H)$^+$.

4-methyl-N-[4-(methylsulfonyl)phenyl]-1-(2-morpholin-4-ylethyl)-5-[2-(trifluoromethyl)phenyl]-1H-pyrrole-3-carboxamide $^1$H NMR (DMSO-d$_6$) .δ 10.09 (s, 1H), 7.97-7.92 (m, 3H), 7.86-7.81 (m, 3H), 7.80-7.32 (m, 2H), 7.53 (d, 7.0 Hz, 1H), 4.05-3.21 (m, 12H), 3.16 (s, 3H), 1.90 (s, 3H). LCMS: m/z 536 (M+H)$^+$.

4-methyl-N-[4-(methylsulfonyl)phenyl]-1-(pyridin-2-ylmethyl)-5-[2-(trifluoromethyl)phenyl]-1H-pyrrole-3-carboxamide $^1$H NMR (DMSO-d$_6$) .δ 10.04 (s, 1H), 8.46 (d, 6.6 Hz, 1H), 7.99 (d, 7.0 Hz, 2H), 7.88-7.84 (m, 4H), 7.73 (td, 7.4 Hz, 1.6 Hz, 1H), 7.66 (t, 1H), 7.60 (t, 7.4 Hz, 1H), 7.28 (dd, 7.0 Hz, 4.3 Hz, 1H), 7.14 (d, 7.2 Hz, 1H), 6.87 (d, 8.0 Hz, 1H), 5.12 (d, 16 Hz, 1H), 4.70 (d, 16 Hz, 1H), 3.18 (s, 3H), 1.95 (s, 3H). LCMS: m/z 514 (M+H)$^+$.

1-[2-(diethylamino)ethyl]-4-methyl-N-[4-(methylsulfonyl)phenyl]-5-[2-(trifluoromethyl)phenyl]-1H-pyrrole-3-carboxamide $^1$H NMR (DMSO-d$_6$) .δ 9.95 (s, 1H), 7.99 (d, 8.8 Hz, 2H), 7.92 (d, 7.4 Hz, 1H), 7.87-7.78 (m, 4H), 7.74 (t, 7.8 Hz, 1H), 7.50 (d, 7.4 Hz, 1H), 3.74-3.67 (m, 1H), 3.47-3.40 (m, 1H), 3.18 (s, 3H), 2.53 (t, 7.8 Hz, 2H), 2.32 (q, 7.2 Hz, 4H), 1.94 (s, 3H), 0.78 (t, 7.0 Hz, 6H). LCMS: m/z 522 (M+H)$^+$.

ethyl-1,1-dimethyl-4-(phenylmethyl)-1,2,3,6-tetrahydroazepino[4,5-b]indole-5-carboxylate $^1$H NMR (DMSO-d$_6$) .δ 10.00 (s, 1H), 8.45 (dd, 4.7 Hz, 2.9 Hz, 1H), 8.13 (d, 1.6 Hz, 1H), 7.95 (d, 9.0 Hz, 2H), 7.88-7.80 (m, 4H), 7.68-7.63 (m, 2H), 7.37-7.30 (m, 2H), 7.18 (d, 6.8 Hz, 1H), 5.03 (d, 16 Hz, 1H) 4.69 (d, 16 Hz, 1H), 3.16 (s, 3H), 1.92 (s, 3H). LCMS: m/z 514 (M+H)$^+$.

4-methyl-N-[4-(methylsulfonyl)phenyl]-1-(2-piperidin-1-ylethyl)-5-[2-(trifluoromethyl)phenyl]-1H-pyrrole-3-carboxamide $^1$H NMR (DMSO-d$_6$) .δ 9.94 (s, 1H), 7.96 (d, 8.8 Hz, 2H), 7.89 (d, 7.2 Hz, 1H), 7.83 (d, 9.0 Hz, 1H), 7.81-7.69 (m, 4H), 7.46 (d, 7.2 Hz, 1H), 3.74-3.69 (m, 1H), 3.50-3.44 (m, 1H), 3.16 (s, 3H), 2.45-2.40 (m, 2H), 2.16 (br s, 4H), 1.91 (s, 3H), 1.37 (m, 4H), 1.29 (m, 2H). LCMS: m/z 534 (M+H)$^+$.

5-(2-chlorophenyl)-1-[2-hydroxy-3-(phenyloxy)propyl]-4-methyl-N4-[4-(methylsulfonyl)phenyl]-1H-pyrrole-3-carboxamide ¹H NMR (DMSO-d₆).89.90 (s, 1H), 7.99 (d, 8.6 Hz, 2H), 7.88-7.84 (m, 3H), 7.61-7.58 (m, 1H), 7.51-7.38 (m, 3H), 7.26-7.22 (m, 2H), 6.91 (t, 7.4 Hz, 1H), 6.73 (dd, 12 Hz, 7.8 Hz, 2H), 5.46 (d, 5.3 Hz, 1H), 4.01-3.82 (m, 2H), 3.78-3.65 (m, 3H), 3.18 (s, 3H), 2.02 (s, 3H) LCMS: m/z 539 (M+H)⁺.

5-(2-chlorophenyl)-1-(2,3-dihydroxypropyl)-4-methyl-N-[4-(methylsulfonyl)phenyl]-1H-pyrrole-3-carboxamide ¹H NMR (DMSO-d₆) δ 9.90 (s, 1H), 8.00 (d, 9.0 Hz, 2H), 7.86-7.80 (m, 3H), 7.61 (d, 7.4 Hz, 1H), 7.51-7.38 (m, 3H), 4.98 (m, 1H), 4.63 (m, 1H), 3.89-3.73 (m, 1H), 3.64-3.44 (m, 2H), 3.17 (s, 3H), 3.11 (m, 2H), 2.01 (s, 3H). LCMS: m/z 463 (M+H)⁺.

4-methyl-N-[4-(methylsulfonyl)phenyl]-5-[2-(trifluoromethyl)phenyl]-1H-pyrrole-3-carboxamide ¹H NMR (DMSO-d₆) δ 11.40 (s, 1H), 9.94 (s, 1H), 7.99 (d, 9.0 Hz, 2H), 7.88-7.84 (m, 3H), 7.76 (t, 7.2 Hz, 1H), 7.69-7.65 (m, 2H), 7.46 (d, 7.4 Hz, 1H), 3.18 (m, 3H), 2.03 (s, 3H). LCMS: m/z 423 (M+H)⁺.

4-methyl-N-[4-(methylsulfonyl)phenyl]-1-prop-2-en-1-yl-5-[2-(trifluoromethyl)phenyl]-1H-pyrrole-3-carboxamide ¹H NMR (DMSO-d₆) δ 10.00 (s, 1H), 7.99 (d, 9.0 Hz, 2H), 7.91-7.84 (m, 3H), 7.80-7.70 (m, 3H), 7.42 (d, 7.4 Hz, 1H), 5.87-5.79 (m, 1H), 5.15 (dd, 10 Hz, 1.4 Hz, 1H), 4.97 (dd, 17 Hz, 1.4 Hz, 1H), 4.31 (dd, 16 Hz, 5.7 Hz, 1H), 4.07 (dd, 16 Hz, 5.5 Hz, 1H), 3.18 (m, 3H), 1.95 (s, 3H). LCMS: m/z 463 (M+H)⁺.

1-{(2S)-3-[(4-fluorophenyl)oxy]-2-hydroxypropyl}-4-methyl-N-[4-(methylsulfonyl)phenyl]-5-[2-(trifluoromethyl)phenyl]-1H-pyrrole-3-carboxamide ¹H NMR (CDCl₃) .87.90 (d, 8.8 Hz, 2H), 7.84-7.77 (m, 3H), 7.67-7.57 (m, 3H), 7.49 (d, 12 Hz, 1H), 7.36-7.27 (m, 1H), 6.97 (t, 8.2 Hz, 2H), 6.76-6.69 (m, 2H), 4.12-3.92 (m, 1H), 3.90-3.67 (m, 4H), 3.05 (s, 3H), 2.38 (dd, 12 Hz, 5.5 Hz, 1H), 2.09 (s, 3H). LCMS: m/z 591 (M+H)⁺.

1-(4-hydroxybutyl)-4-methyl-N-[4-(methylsulfonyl)phenyl]-5-[2-(trifluoromethyl)phenyl]-1H-pyrrole-3-carboxamide ¹H NMR (DMSO-d₆) δ 7.96 (d, 9.0 Hz, 2H), 7.89 (d, 8.2 Hz, 1H), 7.85-7.77 (m, 5H), 7.71 (t, 7.6 Hz, 1H), 7.43 (d, 7.2 Hz, 1H), 4.39 (m, 1H), 3.62 (p, 7.4 Hz, 1H), 3.41 (p, 7.2 Hz, 1H), 3.32-3.25 (m, 2H), 3.16 (s, 3H), 1.91 (s, 3H), 1.58 (p, 7.0 Hz, 2H), 1.27 (p, 6.4 Hz, 2H). LCMS: m/z 495 (W+H)⁺.

4-methyl-N-[4-(methylsulfonyl)phenyl]-1-[2-(tetrahydro-2H-pyran-2-yloxy)ethyl]-5-[2-(trifluoromethyl)phenyl]-1H-pyrrole-3-carboxamide ¹H NMR (DMSO-d₆) δ 9.97 (d, 3.1 Hz, 1H), 7.96 (d, 8.8 z, 2H), 7.90-7.76 (m, 5H), 7.71 (t, 8.0 Hz, 1H), 7.44 (dd, 11 Hz, 7.6 Hz, 1H), 4.45 (d, 29 Hz, 1H), 3.88-3.43 (m, 6H), 3.15 (s, 3H), 1.91 (s, 3H), 1.64 (m, 1H), 1.55 (m, 1H), 1.41 (m, 4H). LCMS: m/z 551 (M+H)⁺.

1,4-dimethyl-N-[4-(methylsulfonyl)phenyl]-5-[2-(trifluoromethyl)phenyl]-1H-pyrrole-3-carboxamide ¹H NMR (CDCl₃) δ 7.91 (d, 8.8 Hz, 2H), 7.84-7.80 (m, 3H), 7.66-7.61 (m, 3H), 7.35 (d, 6.6 Hz, 1H), 7.27 (s, 1H), 3.32 (s, 3H), 3.06 (s, 3H), 2.10 (s, 3H). LCMS: m/z 435 (M+H)⁺.

N-[4-(aminosulfonyl)-3-chlorophenyl]-1-(2-hydroxyethyl)-4-methyl-5-[2-(trifluoromethyl)phenyl]-1H-pyrrole-3-carboxamide ¹H NMR (DMSO-d₆) δ 9.99 (s, 1H), 8.10 (d, 2.0 Hz, 1H), 7.92-7.90 (m, 2H), 7.82-7.78 (m, 3H), 7.72 (t, 7.6 Hz, 1H), 7.48-7.47 (m, 1H), 4.96 (t, 5.1 Hz, 1H), 3.70-3.67 (m, 1H), 3.54 (m, 3H), 1.92 (s, 3H). LCMS: m/z 502 (M+H)⁺.

4-methyl-1-[2-(4-methylpiperazin-1-yl)-2-oxoethyl]-N-[4-(methylsulfonyl)phenyl]-5-[2-(trifluoromethyl)phenyl]-1H-pyrrole-3-carboxamide ¹HNMR (400 MHz, d₆-DMSO): 10.6 (s, 1H), 8.0 (d, 2H), 7.88 (t, 1H), 7.85 (d, 2H), 7.8-7.68 (m, 2H), 7.63 (s, 1H), 7.32 (d, 1H), 4.9 (d, 1H), 4.3 (d, 1H), 3.18 (s, 3H), 1.92 (s, 3H); MS (EI) for C₂₇H₂₉F₃N₄O₄S: 563 (MH⁺).

1-(2-amino-2-oxoethyl)-4-methyl-N-[4-(methylsulfonyl)phenyl]-5-[2-(trifluoromethyl)phenyl]-1H-pyrrole-3-carboxamide ¹H NMR (400 MHz, d₆-DMSO): 10.3 (s, 1H), 8.01 (d, 2H), 7.9 (t, 1H), 7.85 (d, 2H), 7.8-7.69 (m, 3H), 7.36 (d, 2H), 7.27 (s, 1H), 7.1 (s, 1H), 4.5 (d, 1H), 3.98 (d, 1H), 3.18 (s, 3H), 1.93 (s, 3H); MS (EI) for C₂₂H₂₀F₃N₃O₄S: 480 (MH⁺).

1-[2-(butylamino)-2-oxoethyl]-4-methyl-N-[4-(methylsulfonyl)phenyl]-5-[2-(trifluoromethyl)phenyl]-1H-pyrrole-3-carboxamide ¹H NMR (400 MHz, d6-DMSO): 10.5 (s, 1H), 8.01 (d, 2H), 7.9-7.83 (m, 3H), 7.78 (t, 1H), 7.74-7.7 (M, 3H), 7.32 (m, 1H), 4.5 (d, 1H), 4.02 (d, 1H), 3.18 (s, 3H), 3.0 (m, 2H), 1.93 (s, 3H), 1.26 (t, 2H), 1.2 (t, 2H), 0.84 (t, 3H); MS (EI) for C₂₆H₂₈F₃N₃O₄S: 536 (MH⁺).

5-(2-chlorophenyl)-1,4-dimethyl-N-[4-(methylsulfonyl)phenyl]-1H-pyrrole-3-carboxamide ¹H NMR (400 MHz, d-CDCl₃) 7.94-7.88 (m, 2H), 7.84-7.78 (m, 2H), 7.68 (bs, 1H), 7.56-7.51 (m, 1H), 7.44-7.34 (m, 2H), 7.33-7.28 (m, 2H), 3.42 (s, 3H), 3.03 (s, 3H), 2.18 (s, 3H)

5-(2-fluorophenyl)-1,4-dimethyl-N-[4-(methylsulfonyl)phenyl]-1H-pyrrole-3-carboxamide ¹H NMR (400 MHz, d-CDCl₃) 7.94-7.88 (m, 2H), 7.84-7.78 (m, 2H), 7.68 (bs, 1H), 7.41-7.48 (m, 1H), 7.33 (s, 1H), 7.29-7.17 (m, 3H), 3.46 (s, 3H), 3.07 (s, 1H), 2.23 (s, 3H)

5-(2-chlorophenyl)-4-methyl-N-[4-(methylsulfonyl)phenyl]-1-(2-piperidin-1-ylethyl)-1H-pyrrole-3-carboxamide ¹H NMR (400 MHz, d-CDCl₃) 7.94-7.88 (m, 2H), 7.84-7.79 (m, 2H), 7.72 (bs, 1H), 7.51-7.54 (m, 1H), 7.46-7.28 (m, 4H), 3.03 (s, 3H), 2.46 (t, 2H), 2.23-2.20 (m, 4H), 2.16 (s, 3H), 2.1 (s, 2H), 1.61-1.35 (m, 6H)

5-(2-chlorophenyl)-4-methyl-N-[4-(methylsulfonyl)phenyl]-1-(2-morpholin-4-ylethyl)-1H-pyrrole-3-carboxamide ¹H NMR (400 MHz, d-CDCl₃) 7.95-7.99 (m, 2H), 7.84-7.79 (m, 2H), 7.68 (bs, 1H), 7.55-7.52 (m, 2H), 7.45-7.34 (m, 3H), 7.29-7.33 (m, 1H), 3.90-3.71 (m, 2H), 3.59-3.62 (t, 4H), 3.06 (s, 3H), 2.55-2.46 (t, 2H), 2.32-2.23 (m, 4H), 2.08 (s, 3H)

5-(2-chlorophenyl)-4-methyl-N-[4-(methylsulfonyl)phenyl]-1-(pyridin-2-ylmethyl)-1H-pyrrole-3-carboxamide ¹H NMR (400 MHz, d-CDCl₃) 8.51-8.44 (m, 1H), 7.94-7.88 (m, 2H), 7.83-7.78 (m, 2H), 7.72 (bs, 1H), 7.59-7.53 (m, 1H), 7.49-7.44 (m, 2H), 7.38-7.32 (m, 1H), 7.19-7.13 (m, 2H), 6.73-6.68 (m, 1H), 5.12-4.95 (m, 2H), 3.05 (s, 3H), 2.22 (s, 3H)

5-(2-chlorophenyl)-1-(2-hydroxyethyl)-4-methyl-N-[4-(methylsulfonyl)phenyl]-1H-pyrrole-3-carboxamide ¹H NMR (400 MHz, d-CDCl₃) 7.92-7.88 (m, 2H), 7.84-7.78 (m, 2H), 7.71 (bs, 1H), 7.52-7.55 (m, 1H), 7.46 (s, 1H), 7.44-7.35 (m, 2H), 7.33-7.30 (m, 1H), 3.95-3.81 (m, 2H), 3.78-3.61 (m, 2H), 3.21 (s, 3H), 2.16 (s, 3H)

N-[4-(aminosulfonyl)-3-chlorophenyl]-1,4-dimethyl-5-[2-(trifluoromethyl)phenyl]-1H-pyrrole-3-carboxamide ¹H NMR (400 MHz, d-CDCl₃) 8.10-8.07 (m, 1H), 8.02-7.98 (m, 1H), 7.85-7.81 (m, 1H), 7.70-7.58 (m, 3H), 7.47-7.42 (m, 1H), 7.36-7.31 (m, 2H), 5.13 (s, 2H), 3.33 (s, 3H), 2.08 (2, 3H).

5-(2-chlorophenyl)-4-methyl-N-[4-(methylsulfonyl)phenyl]-1-(2-pyrrolidin-1-ylethyl)-1H-pyrrole-3-carboxamide ¹H NMR (400 MHz, d-CDCl₃) 7.94-7.89 (m, 2H), 7.86-7.82 (m, 2H), 7.53-7.51 (m, 1H), 7.43 (bs, 1H), 7.42-7.32 (m, 2H), 7.31-7.26 (m, 2H), 3.95-3.82 (m, 2H), 3.05 (s, 3H), 2.65 (t, 2H), 2.49-2.38 (m, 2H), 2.18 (s, 3H), 1.82-1.52 (m, 6H)

5-(2-chlorophenyl)-1-[3-(dimethylamino)propyl]-4-methyl-N-[4-(methylsulfonyl)phenyl]-1H-pyrrole-3-carboxamide $^1$H NMR (400 MHz, d-CDCl$_3$) 7.94-7.88 (m, 2H), 7.84-7.78 (m, 2H), 7.69 (bs, 1H), 7.55-7.51 (m, 1H), 7.43-7.33 (m, 3H), 7.33-7.26 (m, 1H), 3.86-3.68 (m, 2H), 3.06 (s, 3H), 2.18 (s, 3H), 2.14-2.06 (m, 8H), 1.76 (t, 2H)

5-(2-chlorophenyl)-1-[2-(diethylamino)ethyl]-4-methyl-N-[4-(methylsulfonyl)phenyl]-1H-pyrrole-3-carboxamide $^1$H NMR (400 MHz, d-CDCl$_3$) 7.94-7.89 (m, 2H), 7.84-7.80 (m, 2H), 7.67 (bs, 1H), 7.54-7.52 (m, 1H), 7.44-7.34 (m, 3H), 7.34-7.30 (m, 1H), 3.82-3.64 (m, 2H), 3.07 (s, 3H), 2.53 (t, 2H), 2.42-2.34 (m, 4H), 2.18 (s, 3H), 0.88 (t, 6H)

1,4-dimethyl-N-[4-(methylsulfonyl)phenyl]-5-[2-(trifluoromethyl)phenyl]-1H-pyrrole-3-carboxamide $^1$H NMR (400 MHz, d-CDCl$_3$) 7.93-7.89 (m, 2H), 7.86-7.78 (m, 3H), 7.69-7.58 (m, 3H), 7.37-7.33 (m, 1H), 7.30 (s, 1H), 3.33 (s, 3H), 3.06 (s, 3H), 2.10 (s, 3H)

1-[(6-chloropyridin-2-yl)methyl]-4-methyl-N-[4-(methylsulfonyl)phenyl]-5-phenyl-1H-pyrrole-3-carboxamide $^1$H NMR (400 MHz, DMSO) 10.05 (s, 1H), 8.05-7.98 (m, 2H), 7.88-7.74 (m, 4H), 7.45-7.41 (m, 4H), 7.32-7.23 (m, 2H), 6.76-6.71 (m, 1H), 5.18 (s, 2H), 3.19 (s, 3H), 2.16 (s, 3H)

5-(2-chlorophenyl)-4-ethyl-1-methyl-N-[4-(methylsulfonyl)phenyl]-1H-pyrrole-3-carboxamide $^1$H NMR (400 MHz, d-CDCl$_3$) 7.92-7.89 (m, 2H), 7.82-7.78 (m, 2H), 7.68 (s, 1H), 7.55-7.53 (m, 1H), 7.45-7.30 (m, 3H), 7.27 (s, 1H), 3.41 (s, 3H), 3.03 (s, 3H), 2.61-2.52 (m, 2H), 1.12 (t, 3H)

Example 25

2,5-DIMETHYL-1-(2-TRIFLUOROMETHYL-PHENYL)-1H-PYRROLE-3-CARBOXYLIC ACID [3-(4-FLUORO-BENZYLOXY)-PHENYL]-AMIDE

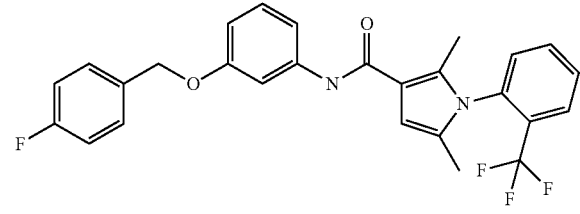 [SMILES: Cc1cc(C(=O)Nc2cccc(OCc3ccc(F)cc3)c2)c(C)n1-c1ccccc1C(F)(F)F]

A. 2,5-Dimethyl-1-(2-trifluoromethyl-phenyl)-1H-pyrrole-3-carboxylic acid (3-hydroxy-phenyl)-amide, previously described in Example 2C, was prepared as a white solid (0.92 g, 80%). $^1$H-NMR (DMSO-d$_6$): δ 9.15 (1H, s), 9.13 (1H, s), 7.86 (1H, d, J=7.8), 7.77 (1H, t, J=7.3), 7.66 (1H, t, J=7.8), 7.35 (1H, d, J=7.8), 7.20 (1H, t, J=2.0), 6.98 (1H, d, J=8.3), 6.91 (1H, t, J=7.8), 6.47 (1H, s), 6.29 (1H, d, J=7.8), 1.98 (3H, s), 1.73 (3H, s); MS (ESI): 375 (MH$^+$).

Into an oven-dried 1 dram vial was added 2,5-dimethyl-1-(2-trifluoromethyl-phenyl)-1H-pyrrole-3-carboxylic acid (3-hydroxy-phenyl)-amide (50 mg, 133 μmol), K$_2$CO$_3$ (22 mg, 160 μmol), 1-bromomethyl-4-fluoro-benzene (28 mg, 146 μmol) and 0.5 mL DMF. The vial was sealed and stirred 1 h at room temperature. The crude material was purified by reverse-phase chromatography (C18 column), eluting with 0.05% TFA in MeCN/H$_2$O (30:70 to 90:10) to yield the title compound (19 mg, 30%) as an off-white solid. $^1$H-NMR (DMSO-d$_6$): δ 9.43 (1H, s), 8.00 (1H, d, J=7.8), 7.90 (1H, t, J=7.8), 7.80 (1H, t, J=7.3), 7.58 (1H, m), 7.50 (3H, m), 7.35 (1H, d, J=8.6), 7.22 (3H, m), 6.69 (1H, d, J=8.3), 6.63 (1H, s), 5.07 (2H, s), 2.14 (3H, s), 1.88 (3H, s); MS (ESI): 483 (MH$^+$).

B. The following compounds were prepared in a similar manner described in 25A using the appropriate alkyl bromides:

2,5-Dimethyl-1-(2-trifluoromethyl-phenyl)-1H-pyrrole-3-carboxylic acid [3-(4-acetylamino-benzyloxy)-phenyl]-amide; MS (ES): 522 (MH$^+$);

2,5-Dimethyl-1-(2-trifluoromethyl-phenyl)-1H-pyrrole-3-carboxylic acid [3-(4-bromo-benzyloxy)-phenyl]-amide; MS (ES): 543 (MH$^+$);

2,5-Dimethyl-1-(2-trifluoromethyl-phenyl)-1H-pyrrole-3-carboxylic acid [3-(naphthalen-2-ylmethoxy)-phenyl]-amide; MS (ES): 515 (MH$^+$);

2,5-Dimethyl-1-(2-trifluoromethyl-phenyl)-1H-pyrrole-3-carboxylic acid [3-(benzo[1,2,5]oxadiazol-5-ylmethoxy)-phenyl]-amide; MS (ES): 507 (MH$^+$);

2,5-Dimethyl-1-(2-trifluoromethyl-phenyl)-1H-pyrrole-3-carboxylic acid [3-(2-methoxy-5-nitro-benzyloxy)-phenyl]-amide; MS (ES): 540 (MH$^+$);

2,5-Dimethyl-1-(2-trifluoromethyl-phenyl)-1H-pyrrole-3-carboxylic acid [3-(4-fluoro-2-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(4,5-dimethoxy-2-nitro-benzyloxy)-phenyl]-amide; MS (ES): 570 (MH$^+$);

2,5-Dimethyl-1-(2-trifluoromethyl-phenyl)-1H-pyrrole-3-carboxylic acid [3-(4-bromo-2-fluoro-benzyloxy)-phenyl]-amide; MS (ES): 561 (MH$^+$);

2,5-Dimethyl-1-(2-trifluoromethyl-phenyl)-1H-pyrrole-3-carboxylic acid [3-(2,6-dichloro-benzyloxy)-phenyl]-amide; MS (ES): 533 (MH$^+$);

2,5-Dimethyl-1-(2-trifluoromethyl-phenyl)-1H-pyrrole-3-carboxylic acid [3-(4-methanesulfonyl-benzyloxy)-phenyl]-amide; MS (ES): 543 (MH$^+$);

2,5-Dimethyl-1-(2-trifluoromethyl-phenyl)-1H-pyrrole-3-carboxylic acid [3-(6-chloro-benzo[1,2,5]thiadiazol-5-ylmethoxy)-phenyl]-amide; MS (ES): 557 (MH$^+$);

2,5-Dimethyl-1-(2-trifluoromethyl-phenyl)-1H-pyrrole-3-carboxylic acid [3-(3-nitro-benzyloxy)-phenyl]-amide; MS (ES): 510 (MH$^+$);

2,5-Dimethyl-1-(2-trifluoromethyl-phenyl)-1H-pyrrole-3-carboxylic acid [3-(benzo[1,2,5]thiadiazol-4-ylmethoxy)-phenyl]-amide; MS (ES): 523 (MH$^+$);

2,5-Dimethyl-1-(2-trifluoromethyl-phenyl)-1H-pyrrole-3-carboxylic acid [3-(3-methyl-5-phenyl-isoxazol-4-ylmethoxy)-phenyl]-amide; MS (ES): 546 (MH$^+$);

3-(3-{[2,5-Dimethyl-1-(2-trifluromethyl-phenyl)-1H-pyrrole-3-carbonyl]-amino}-phenoxymethyl)-benzoic acid methyl ester; MS (ES): 523 (MH$^+$);

2,5-Dimethyl-1-(2-trifluoromethyl-phenyl)-1H-pyrrole-3-carboxylic acid [3-(4-methyl-benzyloxy)-phenyl]-amide; MS (ES): 479 (MH$^+$);

2,5-Dimethyl-1-(2-trifluoromethyl-phenyl)-1H-pyrrole-3-carboxylic acid [3-(3-bromo-benzyloxy)-phenyl]-amide; MS (ES): 543 (MH$^+$);

2,5-Dimethyl-1-(2-trifluoromethyl-phenyl)-1H-pyrrole-3-carboxylic acid [3-(3,5-dimethyl-benzyloxy)-phenyl]-amide; MS (ES): 493 (MH$^+$);

2,5-Dimethyl-1-(2-trifluoromethyl-phenyl)-1H-pyrrole-3-carboxylic acid [3-(2,6-difluoro-benzyloxy)-phenyl]-amide; MS (ES): 501 (MH$^+$);

2,5-Dimethyl-1-(2-trifluoromethyl-phenyl)-1H-pyrrole-3-carboxylic acid [3-(4-chloro-benzyloxy)-phenyl]-amide; MS (ES): 499 (MH$^+$);

2,5-Dimethyl-1-(2-trifluoromethyl-phenyl)-1H-pyrrole-3-carboxylic acid [3-(2-chloro-4-fluoro-benzyloxy)-phenyl]-amide; MS (ES): 517 (MH$^+$);

2,5-Dimethyl-1-(2-trifluoromethyl-phenyl)-1H-pyrrole-3-carboxylic acid [3-(3,5-dimethoxy-benzyloxy)-phenyl]-amide; MS (ES): 525 (MH$^+$);

2,5-Dimethyl-1-(2-trifluoromethyl-phenyl)-1H-pyrrole-3-carboxylic acid [3-(3-chloro-2-fluoro-benzyloxy)-phenyl]-amide; MS (ES): 517 (MH$^+$);

2,5-Dimethyl-1-(2-trifluoromethyl-phenyl)-1H-pyrrole-3-carboxylic acid [3-(2-fluoro-6-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(2-bromo-benzyloxy)-phenyl]-amide; MS (ES): 543 (MH$^+$);

2,5-Dimethyl-1-(2-trifluoromethyl-phenyl)-1H-pyrrole-3-carboxylic acid [3-(2,3,5,6-tetrafluoro-4-methyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(2-bromo-5-methoxy-benzyloxy)-phenyl]-amide; MS (ES): 573 (MH$^+$);

2,5-Dimethyl-1-(2-trifluoromethyl-phenyl)-1H-pyrrole-3-carboxylic acid [3-(3,5-di-tert-butyl-benzyloxy)-phenyl]-amide; MS (ES): 577 (MH$^+$);

2,5-Dimethyl-1-(2-trifluoromethyl-phenyl)-1H-pyrrole-3-carboxylic acid [3-(benzothiazol-2-ylmethoxy)-phenyl]-amide; MS (ES): 522 (MH$^+$);

2,5-Dimethyl-1-(2-trifluoromethyl-phenyl)-1H-pyrrole-3-carboxylic acid [3-(5-methyl-2-phenyl-2H-[1,2,3]triazol-4-ylmethoxy)-phenyl]-amide; MS (ES): 546 (MH$^+$);

2,5-Dimethyl-1-(2-trifluoromethyl-phenyl)-1H-pyrrole-3-carboxylic acid [3-(5-trifluoromethyl-furan-2-ylmethoxy)-phenyl]-amide; MS (ES): 523 (MH$^+$);

2,5-Dimethyl-1-(2-trifluoromethyl-phenyl)-1H-pyrrole-3-carboxylic acid [3-(3-fluoro-5-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(2-chloro-3,6-difluoro-benzyloxy)-phenyl]-amide; MS (ES): 535 (MH$^+$);

2,5-Dimethyl-1-(2-trifluoromethyl-phenyl)-1H-pyrrole-3-carboxylic acid [3-(2,3,4-trifluoro-benzyloxy)-phenyl]-amide; MS (ES): 519 (MH$^+$);

2,5-Dimethyl-1-(2-trifluoromethyl-phenyl)-1H-pyrrole-3-carboxylic acid [3-(4-fluoro-3-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(2,4,5-trifluoro-benzyloxy)-phenyl]-amide; MS (ES): 519 (MH$^+$);

2,5-Dimethyl-1-(2-trifluoromethyl-phenyl)-1H-pyrrole-3-carboxylic acid [3-(2-chloro-6-fluoro-benzyloxy)-phenyl]-amide; MS (ES): 517 (MH$^+$);

2,5-Dimethyl-1-(2-trifluoromethyl-phenyl)-1H-pyrrole-3-carboxylic acid [3-(3-fluoro-2-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(4-tert-butyl-benzyloxy)-phenyl]-amide; MS (ES): 521 (MH$^+$);

2,5-Dimethyl-1-(2-trifluoromethyl-phenyl)-1H-pyrrole-3-carboxylic acid [3-(4-isopropyl-benzyloxy)-phenyl]-amide; MS (ES): 507 (MH$^+$);

2,5-Dimethyl-1-(2-trifluoromethyl-phenyl)-1H-pyrrole-3-carboxylic acid [3-(4-difluoromethoxy-benzyloxy)-phenyl]-amide; MS (ES): 531 (MH$^+$);

2,5-Dimethyl-1-(2-trifluoromethyl-phenyl)-1H-pyrrole-3-carboxylic acid [3-(3-methyl-benzyloxy)-phenyl]-amide; MS (ES): 479 (MH$^+$);

2,5-Dimethyl-1-(2-trifluoromethyl-phenyl)-1H-pyrrole-3-carboxylic acid [3-(3,5-difluoro-benzyloxy)-phenyl]-amide; MS (ES): 501 (MH$^+$);

2,5-Dimethyl-1-(2-trifluoromethyl-phenyl)-1H-pyrrole-3-carboxylic acid [3-(2-methyl-benzyloxy)-phenyl]-amide; MS (ES): 479 (MH$^+$);

2,5-Dimethyl-1-(2-trifluoromethyl-phenyl)-1H-pyrrole-3-carboxylic acid [3-(2-fluoro-benzyloxy)-phenyl]-amide; MS (ES): 483 (MH$^+$);

2,5-Dimethyl-1-(2-trifluoromethyl-phenyl)-1H-pyrrole-3-carboxylic acid [3-(2,3-difluoro-benzyloxy)-phenyl]-amide; MS (ES): 501 (MH$^+$);

2,5-Dimethyl-1-(2-trifluoromethyl-phenyl)-1H-pyrrole-3-carboxylic acid [3-(2,4-difluoro-benzyloxy)-phenyl]-amide; MS (ES): 501 (MH$^+$);

2,5-Dimethyl-1-(2-trifluoromethyl-phenyl)-1H-pyrrole-3-carboxylic acid [3-(3-trifluoromethyl-benzyloxy)-phenyl]-amide; MS (ES): 533 (MH$^+$);

2,5-Dimethyl-1-(2-trifluoromethyl-phenyl)-1H-pyrrole-3-carboxylic acid [3-(2-difluoromethoxy-benzyloxy)-phenyl]-amide; MS (ES): 531 (MH$^+$);

2,5-Dimethyl-1-(2-trifluoromethyl-phenyl)-1H-pyrrole-3-carboxylic acid [3-(2-fluoro-4-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(2-fluoro-3-methyl-benzyloxy)-phenyl]-amide; MS (ES): 497 (MH$^+$);

2,5-Dimethyl-1-(2-trifluoromethyl-phenyl)-1H-pyrrole-3-carboxylic acid [3-(3-chloro-2,6-difluoro-benzyloxy)-phenyl]-amide; MS (ES): 535 (MH$^+$);

2,5-Dimethyl-1-(2-trifluoromethyl-phenyl)-1H-pyrrole-3-carboxylic acid [3-(2,5-difluoro-benzyloxy)-phenyl]-amide; MS (ES): 501 (MH$^+$);

2,5-Dimethyl-1-(2-trifluoromethyl-phenyl)-1H-pyrrole-3-carboxylic acid [3-(2-trifluoromethoxy-benzyloxy)-phenyl]-amide; MS (ES): 549 (MH$^+$);

2,5-Dimethyl-1-(2-trifluoromethyl-phenyl)-1H-pyrrole-3-carboxylic acid [3-(biphenyl-2-ylmethoxy)-phenyl]-amide; MS (ES): 541 (MH$^+$);

2,5-Dimethyl-1-(2-trifluoromethyl-phenyl)-1H-pyrrole-3-carboxylic acid [3-(5-chloro-benzo[b]thiophen-3-ylmethoxy)-phenyl]-amide; MS (ES): 555 (MH$^+$);

2,5-Dimethyl-1-(2-trifluoromethyl-phenyl)-1H-pyrrole-3-carboxylic acid [3-(2,3,6-trifluoro-benzyloxy)-phenyl]-amide; MS (ES): 519 (MH$^+$);

2,5-Dimethyl-1-(2-trifluoromethyl-phenyl)-1H-pyrrole-3-carboxylic acid [3-(2-trifluoromethyl-benzyloxy)-phenyl]-amide; MS (ES): 533 (MH$^+$);

4-(3-{[2,5-Dimethyl-1-(2-trifluoromethyl-phenyl)-1H-pyrrole-3-carbonyl]-amino}-phenoxymethyl)-benzoic acid methyl ester; MS (ES): 523 (MH$^+$);

2,5-Dimethyl-1-(2-trifluoromethyl-phenyl)-1H-pyrrole-3-carboxylic acid [3-(3-fluoro-4-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(3-trifluoromethoxy-benzyloxy)-phenyl]-amide; MS (ES): 549 (MH$^+$);

2,5-Dimethyl-1-(2-trifluoromethyl-phenyl)-1H-pyrrole-3-carboxylic acid [3-(2-chloro-5-fluoro-benzyloxy)-phenyl]-amide; MS (ES): 517 (MH$^4$);

2,5-Dimethyl-1-(2-trifluoromethyl-phenyl)-1H-pyrrole-3-carboxylic acid [3-(2-fluoro-5-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(2-fluoro-3-trifluoromethyl-benzyloxy)-phenyl]-amide; MS (ES): 551 (MH$^+$);

2,5-Dimethyl-1-(2-trifluoromethyl-phenyl)-1H-pyrrole-3-carboxylic acid [3-(2-chloro-5-trifluoromethyl-benzyloxy)-phenyl]-amide; MS (ES): 567 (MH⁺);

2,5-Dimethyl-1-(2-trifluoromethyl-phenyl)-1H-pyrrole-3-carboxylic acid [3-(2-chloro-benzyloxy)-phenyl]-amide; MS (ES): 499 (MH⁺);

2,5-Dimethyl-1-(2-trifluoromethyl-phenyl)-1H-pyrrole-3-carboxylic acid [3-(2,5-dichloro-benzyloxy)-phenyl]-amide; MS (ES): 533 (MH⁺);

4-(3-{[2,5-Dimethyl-1-(2-trifluoromethyl-phenyl)-1H-pyrrole-3-carbonyl]-amino}-phenoxymethyl)-benzoic acid ethyl ester; MS (ES): 537 (MH⁺);

2,5-Dimethyl-1-(2-trifluoromethyl-phenyl)-1H-pyrrole-3-carboxylic acid [3-(4-[1,2,4]triazol-1-yl-benzyloxy)-phenyl]-amide; MS (ES): 532 (MH⁺);

2,5-Dimethyl-1-(2-trifluoromethyl-phenyl)-1H-pyrrole-3-carboxylic acid [3-(3-pyrrol-1-yl-benzyloxy)-phenyl]-amide; MS (ES): 530 (MH⁺).

Example 26

1-[4-(2,4-BIS-TRIFLUOROMETHYL-BENZOYLAMINO)-2-TRIFLUOROMETHYL-PHENYL]-2,5-DIMETHYL-1H-PYRROLE-3-CARBOXYLIC ACID (4-METHANESULFONYL-PHENYL)-AMIDE

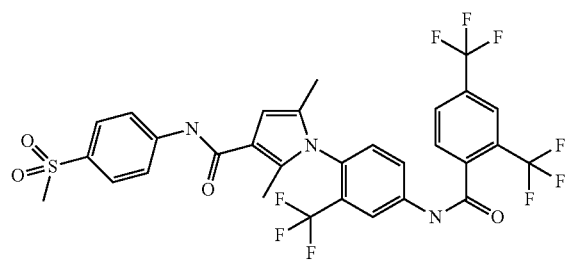 [SMILES: Cc1cc(C(=O)Nc2ccc(S(C)(=O)=O)cc2)c(C)n1-c1ccc(NC(=O)c2ccc(C(F)(F)F)cc2C(F)(F)F)cc1C(F)(F)F]

A.  1-[4-Bromo-2-(trifluoromethyl)phenyl]-2,5-dimethyl-1H-pyrrole-3-carboxylic acid [4-(methanesulfonyl)phenyl]-amide was prepared as described in Example 1G.

Into an oven-dried 1 dram vial was added 1-[4-Bromo-2-(trifluoromethyl)phenyl]-2,5-dimethyl-1H-pyrrole-3-carboxylic acid [4-(methanesulfonyl)phenyl]-amide (26 mg, 50 µmol), 2,4-Bis(Trifluoromethyl)benzamide (13 mg, µmol) Copper (1) Iodide (50 mg, 260 µmol), K₂CO₃ (50 mg, 360 µmol), N,N'-Dimethylenediamine (9 mg, 100 µmol), and 0.4 mL of Toluene. The vial was sealed and stirred for 18 h at 110° C. The reaction was worked up by addition of a 1:1 solution of 2.0 M NaOH: 0.5M EDTA (1 ml) and Ethyl Acetate (1 ml). The vial was vortexed and the Ethyl Acetate was removed and dried in Vacuo. The crude material was purified by reverse-phase chromatography (C18 column), eluting with 0.05% TFA in MeCN/H₂O (30:70 to 90:10) to yield the title compound (6.9 mg, 10%) as a white solid. ¹H-NMR (DMSO-d₆): δ 11.24 (1H, s), 9.78 (1H, s), 8.28 (1H, d, J=2 Hz), 8.22 (1H, d, J=8 Hz), 8.19 (1H, s), 8.02 (4H, m), 7.76 (2H, d, J=9 Hz), 7.44 (2H, d, J=9 Hz), 6.59 (1H, s), 3.09 (3H, s), 2.10 (3H, s), 1.84 (3H, s); MS (ESI): 692 (MH⁺).

Example 27

GAL4-MR Cell Based Assay

Compound activity was determined in a cell-based assay using a GAL4-MR chimera to identify compounds with the ability to modulate MR activity.

The pCMX-GAL4-MR expression plasmid was constructed by cloning nucleotides encoding amino acids 671 to 984 of human MR (see GenBank sequence AAA59571) into the vector pCMX-GAL4 (Perlmann et al., 1993, Genes & Development 7:1411-1422) comprising nucleotides encoding for amino acids 1-147 of the GAL4 DNA binding domain.

The TK-MH100x4-Luc (GAL4$_{UAS}$-TK-Luciferase) reporter construct was constructed by insertion of four copies of the Gal4 UAS (Kang et al. 1993, J. Biol. Chem. 268:9629-9635) into the Hind III site of TK-Luc. The parental plasmid, TK-Luc, was prepared by insertion of the Herpes simplex virus thymidine kinase gene promoter (−105 to +51) obtained from the plasmid pBLCAT2 by digestion with HindIII and XhoI (described in Luckow et al., 1987, Nuc. Acid. Res. 15:5490) into the plasmid MMTV-LUC described by Hollenberg and Evans, 1988, Cell 55:899-906) after removal of MMTV-LTR promoter sequence from MMTV-LUC via digestion with HindIII and XhoI. Correct cloning was confirmed by restriction digestion and/or sequencing.

Assays were performed using CV-1 (African Green Monkey Kidney Cells) (ATCC) cells grown in T175 flasks at a density of 3×10⁶ cells/flask in DMEM with 5% FBS. Cells were transfected one day after plating at 70-80 percent confluency with a DNA mixture containing (per T175 flask) 9 µg pCMX-GAL4-MR, 9 µg TK-MH100x4-Luc, and 2 µg pCMX β-Gal using the transfection reagent FuGENE6 (Roche Molecular Biochemicals, Indianapolis, Ind.) following recommended protocols and instructions provided by the manufacturer, and incubated with transfection reagents for 5 hours at 37° C.

For the antagonist format, compounds were diluted in media containing aldosterone (30 nM) and dispensed into the assay plates using a Multimek (Beckman, Fullerton, Calif.). Approximately 5 µl of media containing compound and aldosterone was dispensed into each well of the 384-well plate to achieve a final concentration of approximately 10 µM for compounds and 3 nM for aldosterone. Transfected cells were trypsinized, resuspended in media, and 45 µL was added to assay plates at a density of approximately 5,000 cells/well using a Multiprop dispenser (MTX Lab Systems, Inc., VA). The assay plates containing both compounds and screening cells were incubated for approximately 20 hours at 37° C. and 5% CO₂ in a tissue culture incubator.

After incubation of the transfected cells with compounds, Lysis buffer (1%/o Triton X-100, 10% Glycerol, 5 mM DTT, 1 mM EGTA, 25 mM Tricine, pH 7.8) and Luciferin assay buffer (0.73 mM ATP, 22.3 mM Tricine, 0.11 mM EDTA, 33.3 mM DTT, 0.2M MgSO₄, 11 mM Luciferin, 6.1 mM Coenzyme A, 0.01 mM HEPES, pH 7.8) were prepared. Media was removed from the plates and lysis buffer and luciferin assay buffer mixed in a 1:1 ratio and then 30 µl of the mixture was added to each well using a Multidrop dispenser. Plates were read on the Northstar (Applied Biosystems, Foster City, Calif.) and data was analyzed using ActivityBase (ID Business Solutions, Ltd., Guildford, Surrey, UK). If required, luciferase values may be normalized for transfection efficiency by measuring (β-galactosidase activity based on expression from the pCMX-pGal expression plasmid as described previously (Willy et al., 1995, Gene & Development, 9:1033-1045).

In certain cases, compounds were also evaluated for activity in selectivity assays with other steroid hormone receptor members, including AR, ER, GR and PR, as well as GAL4 alone. Steroid receptors used for selectivity assays were essentially generated as described above for pCMX-GAL4-MR, and comprised the LBD and a portion of the hinge region of the nuclear receptor of interest cloned in frame into the vector pCMX-GAL4 (Perlmann et al., 1993, Genes & Development 7:1411-1422) as described above.

Assays run in antagonist mode included agonists as follows: AR; 25 nM dihydrotestosterone (DHT), ER; 4.5 nM estradiol, GR; 20 nM dexamethasone, and PR; 2 nM medroxyprogesterone (MPA), respectively. Assays run in agonist mode contained no supplemental compounds.

Example 28

Scintillation Proximity Assay

Compound activity was also characterized via the use of a scintillation proximity assay (SPA assay). The assay measures the ability of the compound to displace $^3$H-aldosterone binding to the human MR-ligand binding domain (MR-LBD).

Required Materials:
[$^3$H]-Aldosterone (Perkin-Elmer, Cat # NET419, 1 mCi/ml, 2.56TBq/mmol, 70.0Ci/mmol) MR-LBD lysate
SPA beads: Ysi copper His-tag (2 □M) SPA beads (Amersham, Cat # RPNQ0096)
Plates: Non-binding surface 96-well plate (Corning, Cat#3604)
MR lysate buffer: (20 mM Tris-HCl pH 7.3, 1 mM EDTA, 10% Glycerol, 20 mM Sodium Tungstate).
SPA Buffer with EDTA: (10 mM $k_2HPO_4/KH_2PO_4$, pH7.3, 50 mM NaCl, 0.025% Tween 20, 10% Glycerol, 2 mM EDTA)
SPA Buffer w/o EDTA: (10 mM $K_2HPO_4/KH_2PO_4$, pH7.3, 50 mM NaCl, 0.025% Tween 20, 10% Glycerol)
Stock Solutions:
0.5 M $K_2HPO_4/KH_2PO_4$ pH 7.3
0.5 M EDTA pH 8.0
5 M NaCl
10% Tween-20
Glycerol
2×SPA Buffer (with EDTA)
2×SPA Buffer (without EDTA)
Preparation of Protein Lysates:
A baculovirus expression plasmid for human MR LBD was made by cloning a DNA fragment encoding amino acids 671-984 of human MR into the pBlueBacHis2, baculovirus transfer vector (Invitrogen, CA) following standard procedures. Insertion of the cDNAs into the pBlueBacHis2 vector polylinker created an in frame fusion to the cDNA to an N-terminal poly-His tag present in pBlueBacHis2 to yield vector pBlueBacHis2-MR-LBD. Viral plaques were formed by co-transformation of pBlueBacHis2-MR-LBD with linearized Bac-N-Blue (Invitrogen, CA) into sf9 insect cells following the instructions provided with the reagents. Recombination between the two vectors resulted in the creation of MR-LBD baculovirus plaque. The virus stock was prepared following the manufacturers recommended protocols and used at a titer of $10^9$ pfu/ml. Expression was confirmed by SDS-PAGE analysis after purification using Ni-NTA Resin (Qiagen) and western blotting using an anti-his antibody (Invitrogen, CA) using standard procedures. Correct cloning was confirmed by PCR and sequencing using specific primers.

Cell lysates were prepared by infecting healthy, Sf9 insect cells at a density of approximately $1.8\times10^6$/ml at 27° C., in a total volume of 500 mL per spinner flask. Sf9 cells were infected use virus at an M.O.I of approximately 5 and incubated for 48 hours at 27° C. with constant stirring prior to harvesting.

After incubation, cells were harvested by centrifugation and pelleted. Cell pellets were resuspended in ice-cold freshly prepared extraction buffer at 1/50 volumes of original culture (20 mM Tris-HCl pH 7.3, 1 mM EDTA, 10% Glycerol, 20 mM Sodium Tungstate, containing one EDTA free protease inhibitor tablet (Roche Catalog No: 1836170) per 10 ml of MR lysate buffer).

Cells were lysed on ice using a Branson Sonifier 450 set at an output of 1.5, 80% constant, for five sets of 15 beats to achieve 80-90% cell lysis. The homogenate was centrifuged in a pre-chilled rotor (SW55 or SW28, or equivalent) at 40,000 rpm for 20 minutes at 4° C. Aliquots of the supernatant were frozen on dry ice and stored frozen at −80° C. until quantification and quality control. Aliquots of the lysates were tested in the SPA assay to ensure lot to lot consistency, and adjusted for protein concentration and expression level prior to use in screening assays.

Preparation of Screening Reagents:

[$^3$H]-aldosterone ([$^3$H]-Aldo) solution: For each 96-well plate (or 100 wells), 4.5 μL of [$^3$H]-Aldo (70 Ci/mmol, 1 mCi/mL) was added to 3.6 mL of SPA Buffer with EDTA to provide for a final concentration of 14.7 nM. The ([$^3$H]-Aldo solution for each additional 96-well plate is prepared identically immediately prior to use. The final concentration of [$^3$H]-Aldo in the well was 4.4 nM.

MR-LBD lysate (prepared as above) was diluted with MR lysate buffer. 1.5 mL of diluted MR-LBD lysate was prepared per 96-well plate, (or 100 wells). The MR lysate solution for each additional 96-well plate is prepared identically immediately prior to use. SPA bead solution: For a 96-well plate (or 100 wells), 600 μL of Ysi His-tag SPA beads (vortex well before taking) and 5.6 mL SPA buffer w/o EDTA were mixed together. The SPA bead solution for each additional 96-well plate is prepared identically immediately prior to use.

Procedure:

Appropriate dilutions of each compound were prepared and 10 μL was pipetted into the appropriate well(s) of a non-binding surface multiwell plate.

30 μL of [$^3$H]-Aldo was added to each well of the multiwell plate.

10 μl of diluted MR-LBD lysate was added to each well of the multiwell plate.

50 μL of SPA bead solution was added to each well of the multiwell plate.

The plates were covered with clear sealer and placed in the Wallac Microbeta at ambient temperature for 30 minutes to one hour. After incubation plates were analyzed using a scintillation plate reader (Wallac Microbeta) using the program Robin96well3H. The settings for Robin96well3H were: Counting Mode: DPM/Sample Type: SPA/ParaLux Mode: low background/Count time: 2 minutes.

The determined Ki represents the average of at least two independent dose response experiments. The binding affinity for each compound may be determined by non-linear regression analysis using the one site competition formula to determine the $IC_{50}$ where:

$$Y = \text{Bottom} + \frac{(\text{Top} - \text{Bottom})}{(1 + 10^{X - \log IC_{50}})}$$

The Ki is then calculated using the Cheng and Prusoff equation where:

$$Ki = IC_{50}/(1+[\text{concentration of ligand}]/Kd \text{ of Ligand})$$

For this assay, typically the concentration of ligand=4.4 nM and the Kd of Aldo for the receptor is 5 nM as determined by saturation binding. The compounds of the invention demonstrated the ability to bind to hMR-LBD when tested in this assay.

Example 29

AR-Receptor Hydroxylapatite Binding Assay

Compound binding to AR was assessed by measuring the displacement of tritiated R1881 (an AR selective ligand) using a hydroxylapatite (HAP) binding assay to separate bound and free ligand using partially purified AR obtained from a cell lysate. Partially purified AR was obtained from the MDA-kb2 cell line (ATCC) that endogenously expresses the full length AR. MDA-kb2 cells were grown in DMEM with 5% FBS in T175 flasks. When the cells reached about 80% confluency they were harvested and centrifuged at 1000 rpm for 5 min. The cell pellet was resuspended in AR buffer (10 mM TRIS, 10% glycerol, 1.5 mM EDTA, 1.0 mM sodium molybdate, 1 mM PMSF, 1.0 mM dithiothreotol, pH 7.4 at 4° C.) and sonicated using a sonic probe (Sonifier 450, Branson) at a setting of 1.5, (80% constant) for five sets of 15 beats to achieve 80-90% cell lysis. After sonication, cells were incubated on ice for 10 minutes and then centrifuged in a pre-chilled rotor (SW55 or SW28, or equivalent) at 40,000 rpm for 20 minutes at 4° C. The supernatant was collected and placed on ice.

For the binding assay, MDA cell lysate (prepared as above) was diluted 1:2 in AR buffer and 300 µl pipetted into a 1.2 ml microcentrifuge tube. 50 µl of triamcinolone (a selective GR antagonist) (Sigma, St. Louis, Mo.) was included in all assay tubes at a final concentration of 60 µM. Compounds to be tested were prepared in DMSO at a starting concentration of 945 µM and 10 µM were added to the lysate preparation. [$^3$H]R1881 (NEN, Boston, Mass.) and was first diluted in AR buffer to create a stock concentration of 94.5 nM. 5 µl of the stock [$^3$H]R1881 was then added to the lysate mixture to initiate binding. Non-specific binding was determined using cold R1881 at a 100-fold molar excess over the concentration of labeled [$^3$H]R1881. The tubes were gently vortexed and incubated overnight at 4° C.

Following overnight incubation (18 hrs), the lysates were washed to remove unbound ligand. This was achieved by adding 100 µl of the lysate prep to 500 µl of a 50% hydroxylapatite slurry contained in a 12×75 mm polypropylene tube. The tubes were then vortex mixed three times for 20 sec, allowing the tubes to incubate for five minutes between vortex mixings. After the final mixing, the tubes were centrifuged at 1780 rpm at 4° C. for 5 minutes. The supernatant was decanted and the slurry was resuspended in AR buffer. This wash step was repeated four times. Following the final wash with AR buffer, the pellet was resuspended in 1.5 ml ethanol. The tubes were then vortex mixed for 20 sec every 5 minutes at room temperature. This was repeated four times.

After the final mix the tubes were centrifuged at 1780 rpm at 4° C. for 20 minutes. The supernatant was decanted into a 20 ml glass scintillation vial and 15 ml of Ecolume scintillation fluid was added. Samples were counted on a Beckman LS3801 scintillation counter (Fullerton, Calif.).

Example 30

Formulation and Experimental Design

A. Solution Formulation

Test article was administered intravenously at 3 mg/kg formulated in carrier dosage vehicle suitable for IV administration of the test article. Oral solution (or suspension) doses of 3, 10, 30, 100, 300 and 1000 mg/kg were administered using a suitable carrier dosage vehicle. The compound was also administered at 10 mg/kg as a solid in gelatin capsules. Experimental groups were comprised of five animals for each dose group. Blood was collected (100 µL) in heparinized tubes via a jugular catheter at 0.02, 0.08, 0.25, 0.5, 1, 2, 4, 6, 8, 10, 12, 24, 32, 48 and 72 hours post-dosing for the IV groups. Samples were similarly collected at 0.08, 0.25, 0.5, 1, 2, 4, 6, 8, 10, 12, 24, 32, 48 and 72 hours post-dosing for the PO groups. The plasma obtained was stored at −80° C. and a volume of 50 µL was used for analysis.

B. Solid Dosage

Torpac size 9 porcine gelatin mini capsules were used to orally dose test article in solid form at 3 or 10 mg/kg. Capsules were filled with powdered compound based on body weight. Capsules were administered directly into the rat's stomach with the use of a stainless steel dosing device similar to an oral gavage needle. Pilot studies with empty capsules revealed that capsules dissolve in less than 7 minutes in the stomach.

Bioanalytical Analysis

The concentration of test article in plasma and tissue samples was determined by HPLC/MS/MS analysis using sample preparation and analytical conditions appropriate for the test article quantification by this method. A non-compartmental model was applied to calculate pharmacokinetic (PK) parameters for all routes of administration using WinNonlin 3.1 software (Pharsight Co., Mountain View, Calif.).

The compounds of the present invention exhibited greatly enhanced and improved pharmacokinetic properties.

Example 31

Kinetic Solubility Assay

The kinetic solubility of test compounds in buffer was evaluated using a 96 well filtration plate format. A 500 µM assay solution in PBS, pH7.4 (or other assay buffer, as needed) was generated form a DMSO stock solution (up to 10 mM). Samples were transferred to a 96 Millipore Multi-Screen HTS 96-well Filter plate (Cat# MSSLBPCIO) mixed by shaking for 1.5 hours and processed by filtration prior to quantitation by HPLC-UV. Amiodarone and testosterone were used as reference controls. In-house historical data shows that the solubility of amiodarone is between 3-5 µM and testosterone is approximately 330 µM. An Agilent Chemstation using a Waters 4×23 mm threaded cartridge YMC/AQ S-5 120A C18 column was used for separation of analytes at a mobile phase flow rate of 2.2 mL/min. The mobile phase was 0.1% TFA in water (solvent A) and 0.1% TFA in acetonitrile (solvent B). The column was maintained at 37° C. and detection of analytes was achieved by UV signal quantification at 220 nm and 254 nm following a 10 µL injection volume.

The compounds demonstrated kinetic solubility in the range of for example, about 500 µM or less, 400 µM or less, 300 µM or less, 200 µM or less, 100 µM or less. In an advantageous embodiment, the kinetic solubility is about 50 µM or less, 20 or less, 10 µM or less, 5 µM or less, 2.5 µM or less, or 1 µM or less.

Example 32

The following table provides in vitro MR activity data of representative compounds described in the Examples. Average IC$_{50}$ values for antagonist activity in the GAL4-MR assay are provided as follows: V: less than 0.5 µM; W: 0.5 µM-1 µM; X: 1 µM to 5 µM. Average percent inhibition with respect to MR activity relative to a maximally effective concentration of Spironolactone (as determined in a dose response curve in the presence of 3 nM aldosterone), are provided as follows; A: 100-120% of control and B: 80-100% of control.

TABLE II

| Example | MR IC50 | % control |
|---|---|---|
| 2,5-dimethyl-1-(2-trifluoromethyl-phenyl)-1H-pyrrole-3-carboxylic acid [2-(3-chloro-phenyl)-ethyl]-amide | X | B |
| 2,5-dimethyl-1-(2-trifluoromethyl-phenyl)-1H-pyrrole-3-carboxylic acid 4-phenoxy-benzylamide | X | B |
| 2,5-dimethyl-1-(2-trifluoromethyl-phenyl)-1H-pyrrole-3-carboxylic acid (2-fluoro-5-trifluoromethyl-phenyl)-amide | X | B |
| 1-[4-(2,4-bis-trifluoromethyl-benzoylamino)-2-trifluoromethyl-phenyl]-2,5-dimethyl-1H-pyrrole-3-carboxylic acid (4-methanesulfonyl-phenyl)-amide | X | B |
| 2,5-dimethyl-1-[2-(trifluoromethyl)phenyl]-1H-pyrrole-3-carboxylic acid (4-ethylsulfamoyl-phenyl)-amide | X | B |
| 2,5-dimethyl-1-[2-(trifluoromethy)phenyl]-1H-pyrrole-3-carboxylic acid (4-guanidinosulfonyl-phenyl)-amide | X | B |
| 2,5-dimethyl-1-(2-trifluoromethyl-phenyl)-1H-pyrrole-3-carboxylic acid (2-thiophen-2-yl-ethyl)-amide | W | B |
| 2,5-dimethy1-1-(2-trifluoromethyl-phenyl)-1H-pyrrole-3-carboxylic acid [2-(2-chloro-phenyl)-ethyl]-amide | W | B |
| 2,5-dimethyl-1-(2-trifluoromethyl-phenyl)-1H-pyrrole-3-carboxylic acid (3-fluoro-4-methyl-phenyl)-amide | W | B |
| 2,5-dimethyl-1-[2-(3-nitro-phenylcarbamoyl)-phenyl]-1H-pyrrole-3-carboxylic acid (4-methanesulfonyl-phenyl)-amide | W | B |
| 2,5-dimethyl-1-(2-trifluoromethyl-phenyl)-1H-pyrrole-3-carboxylic acid [4-(propane-2-sulfonyl)-phenyl]-amide | W | B |
| 2,5-dimethy]-1-(2-trifluoromethyl-phenyl)-1H-pyrrole-3-carboxylic acid (4-methanesulfonylamino-phenyl)-amide | W | B |
| 2,5-dimethyl-1-(2-trifluoromethyl-phenyl)-1H-pyrrole-3-carboxylic acid phenethyl-amide | V | A |
| 2,5-dimethyl-1-(2-trifluoromethyl-phenyl)-1H-pyrrole-3-carboxylic acid (3-chloro-4-methyl-phenyl)-amide | V | A |
| 2,5-dimethyl-1-(2-trifluoromethyl-phenyl)-1H-pyrrole-3-carboxylic acid (5-methyl-thiazol-2-yl)-amide | V | B |
| 2,5-dimethyl-1-(2-trifluoromethyl-phenyl)-1H-pyrrole-3-carboxylic acid naphthalen-2-ylamide | V | A |
| 2,5-dimethyl-1-(2-trifluoromethyl-phenyl)-1H-pyrrole-3-carboxylic acid (4-sulfamoyl-phenyl)-amide | V | B |
| 2,5-dimethyl-1-(2-trifluoromethyl-phenyl)-1H-pyrrole-3-carboxylic acid (3-methoxy-4-sulfamoyl-phenyl)-amide | V | A |
| 5-(4-fluorophenyl)-2-methyl-1-(2-trifluoromethylphenyl)-1H-pyrrole-3-carboxylic acid (4-methanesulfonyl-phenyl) amide | V | A |
| 2,5-dimethyl-1-naphthalen-1-yl-1H-pyrrole-3-carboxylic acid (4-methanesulfonyl-phenyl)-amide | V | A |
| 1,4-dimethyl-5-(2-trifluoromethyl-phenyl)-1H-pyrrole-3-carboxylic acid (4-sulfamoyl-phenyl)-amide | V | A |
| 3,5-dimethyl-4-(2-trifluoromethyl-phenyl)-1H-pyrrole-2-carboxylic acid (4-methanesulfonyl-phenyl)-amide | V | A |
| 1-[2-((E)-3,3-dimethyl-but-1-enyl)-phenyl]-2,5-dimethyl-1H-pyrrole-3-carboxylic acid 4-methanesulfonyl-phenyl)-amide | V | A |

We claim:

1. A method for the treatment of a disease, or disorder mediated by, or otherwise affected by one or more steroid nuclear receptors, or in which steroid nuclear receptor activity is implicated, wherein said steroid nuclear receptor is the mineralocorticoid receptor, the method comprising:
   administering to a patient in need thereof a pharmacologically active composition comprising a compound of formula (III);

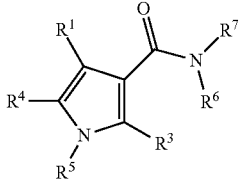

(III)

or a pharmaceutically acceptable salt thereof, wherein:
$R^1$ is optionally substituted alkyl;
$R^3$ is independently hydrogen or optionally substituted alkyl;
$R^4$ is aryl, optionally substituted by one or more substituents selected from the group consisting of optionally substituted alkyl, optionally substituted alkenyl, optionally substituted alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, $-R^8-OR^9$, $-R^8-SR^9$, $-R^8-S(O)_tR^{10}$ (where t is 1 or 2), $-R^8-N(R^9)_2$, $-R^8-CN$, $-R^8-C(O)R^9$, $-R^8-C(S)R^9$, $-R^8-C(NR^9)R^9$, $-R^8-C(O)OR^9$, $-R^8-C(S)OR^9$, $-R^8-C(NR^9)OR^9$, $-R^8-C(O)N(R^9)_2$, $-R^8-C(S)N(R^9)_2$, $-R^8-C(NR^9)N(R^9)_2$, $-R^8-C(O)SR^9$, $-R^8-C(S)SR^9$, $-R^8-C(NR^9)SR^9$, $-R^8-S(O)_tOR^9$ (where t is 1 or 2), $-R^8-S(O)_tN(R^9)_2$ (where t is 1 or 2), $-R^8-S(O)_tN(R^9)N(R^9)_2$ (where t is 1 or 2), $-R^8-S(O)_tN(R^9)N=C(R^9)_2$, $-R^8-S(O)_tN(R^9)C(O)R^{10}$ (where t is 1 or 2), $-R^8-S(O)_tN(R^9)C(O)N(R^9)_2$ (where t is 1 or 2), $-R^8-S(O)_tN(R^9)C(NR^9)N(R^9)_2$ (where t is 1 or 2), $-R^8-N(R^9)C(O)R^{10}$, $-R^8-N(R^9)C(O)OR^{10}$, $-R^8-N(R^9)C(O)SR^{10}$, $-R^8-N(R^9)C(NR^9)SR^{10}$, $-R^8-N(R^9)C(S)SR^{10}$, $-R^8-N(R^9)C(O)N(R^9)_2$, $-R^8-N(R^9)C(NR^9)N(R^9)_2$, $-R^8-N(R^9)C(S)N(R^9)_2$, $-R^8-N(R^9)S(O)_tR^{10}$ (where t is 1 or 2), $-R^8-OC(O)R^{10}$, $-R^8-OC(NR^9)R^{10}$, $-R^8-OC(S)R^{10}$, $-R^8-OC(O)OR^{10}$, $-R^8-OC(NR^9)OR^{10}$, $-R^8-OC(S)OR^{10}$, $-R^8-OC(O)SR^9$, $-R^8-OC(O)N(R^9)_2$, $-R^8-OC(NR^9)N(R^9)_2$, $-R^8-OC(S)N(R^9)_2$, $-R^8-C(O)-R^{11}-C(O)R^9$, $-R^8-C(O)-R^{11}-C(S)R^9$, $-R^8-C(O)-R^{11}-C(NR^9)R^9$, $-R^8-C(O)-R^{11}-C(O)OR^9$, $-R^8-C(O)-R^{11}-C(S)OR^9$, $-R^8-C(O)-R^{11}-C(NR^9)OR^9$, $-R^{11}-C(O)-R^{11}-C(O)N(R^9)_2$, $-R^{11}-C(O)-R^{11}-C(S)N(R^9)_2$, $-R^8-C(O)-R^{11}-C(NR^9)N(R^9)_2$, $-R^8-C(O)-R^{11}-C(O)SR^9$, $-R^8-C(O)-R^{11}-C(S)SR^9$ and $-R^8-C(O)-R^{11}-C(NR^9)SR^9$;

$R^5$ is alkyl optionally substituted by one or more substituents selected from the group consisting of halo, haloalkyl, haloalkoxy, nitro, $-OR^9$, $-SR^9$, $-S(O)_tR^{10}$ (where t is 1 or 2), $-N(R^9)_2$, $-CN$, $-C(O)R^9$, $-C(S)R^9$, $-C(NR^9)R^9$, $-C(O)OR^9$, $-C(S)OR^9$, $-C(NR^9)OR^9$, $-C(O)N(R^9)_2$, $-C(S)N(R^9)_2$, $-C(NR^9)N(R^9)_2$, $-C(O)SR^9$, $-C(S)SR^9$, $-C(NR^9)SR^9$, $-S(O)_tOR^9$ (where t is 1 or 2), $-S(O)_tN(R^9)_2$ (where t is 1 or 2), $-S(O)_tN(R^9)N(R^9)_2$ (where t is 1 or 2), $-S(O)_tN(R^9)N=C(R^9)_2$, $-S(O)_tN(R^9)C(O)R^{10}$ (where t is 1 or 2), $-S(O)_tN(R^9)C(O)N(R^9)_2$ (where t is 1 or 2), $-R^8-S(O)_tN(R^9)C(NR^9)N(R^9)_2$ (where t is 1 or 2), $-N(R^9)C(O)R^{10}$, $-N(R^9)C(O)OR^{10}$, $-N(R^9)C(O)SR^{10}$, $-N(R^9)C(NR^9)SR^{10}$, $-N(R^9)C(S)SR^{10}$, $-N(R^9)C(O)N(R^9)_2$, $-N(R^9)C(NR^9)N(R^9)_2$, $-N(R^9)C(S)N(R^9)_2$, $-N(R^9)S(O)_tR^{10}$ (where t is 1 or 2), $-OC(O)R^{10}$, $-OC(NR^9)R^{10}$, $-OC(S)R^{10}$, $-OC(O)OR^{10}$, $-OC(NR^9)OR^{11}$, $-OC(S)OR^{10}$, $-OC(O)SR^9$, $-OC(O)N(R^9)_2$, $-OC(NR^9)N(R^9)_2$, $-OC(S)N(R^9)_2$, $-C(O)-R^{11}-C(O)R^9$, $-C(O)-R^{11}-C(S)R^9$, $-C(O)-R^{11}-C(NR^9)R^9$, $-C(O)-R^{11}-C(O)OR^9$, $-C(O)-R^{11}-C(S)OR^9$, $-C(O)-R^{11}-C(NR^9)OR^9$, $-C(O)-R^{11}-C(O)N(R^9)_2$, $-C(O)-R^{11}-C(S)N(R^9)_2$, $-C(O)-R^{11}-C(NR^9)N(R^9)_2$, $-C(O)-R^{11}-C(O)SR^9$, $-C(O)-R^{11}-C(S)SR^9$ and $-C(O)-R^{11}-C(NR^9)SR^9$;

$R^6$ is hydrogen or optionally substituted alkyl;

$R^7$ is aryl, optionally substituted by one or more substituents selected from the group consisting of optionally substituted alkenyl, optionally substituted alkynyl, halo, haloalkyl, haloalkenyl, haloalkoxy, nitro, dioxo, optionally substituted cycloalkyl, optionally substituted cycloalkylalkyl, optionally substituted cycloalkenyl, optionally substituted cycloalkenylalkyl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, $-R^{13}-OR^{14}$, $-R^{13}-SR^{14}$, $-R^{13}-S(O)_tR^{15}$ (where t is 1 or 2), $-R^{13}-N(R^{14})_2$, $-R^{13}-CN$, $-R^{13}-C(O)R^{14}$, $-R^{13}-C(S)R^{14}$, $-R^{13}-C(NR^{14})R^{14}$, $-R^{13}-C(S)OR^{14}$, $-R^{13}-C(NR^{14})OR^{14}$, $-R^{13}-C(S)N(R^{14})_2$, $-R^{13}-C(NR^{14})N(R^{14})_2$, $-R^{13}-C(O)SR^{14}$, $-R^{13}-C(S)SR^{14}$, $-R^{13}-C(NR^{14})SR^{14}$, $-R^{13}-S(O)_tOR^{14}$ (where t is 1 or 2), $-R^{13}-S(O)_tN(R^{14})_2$ (where t is 1 or 2), $-R^{13}-S(O)_tN(R^{14})N(R^{14})_2$ (where t is 1 or 2), $-R^{13}-S(O)_tN(R^{14})N=C(R^{14})_2$, $-R^{13}-S(O)_tN(R^{14})C(O)R^{15}$, $-R^{13}-S(O)_tN(R^{14})C(O)N(R^{14})_2$ (where t is 1 or 2), $-R^{13}-S(O)_tN(R^{14})C(NR^{14})N(R^{14})_2$ (where t is 1 or 2), $-R^{13}-N(R^{14})C(O)R^{15}$, $-R^{13}-N(R^{14})C(O)OR^{15}$, $-R^{13}-N(R^{14})C(O)SR^{15}$, $-R^{13}-N(R^{14})C(NR^{14})SR^{15}$, $-R^{13}-N(R^{14})C(S)SR^{15}$, $-R^{13}-N(R^{14})C(O)N(R^{14})_2$, $-R^{13}-N(R^{14})C(NR^{14})N(R^{14})_2$, $-R^{13}-N(R^{14})C(S)N(R^{14})_2$, $-R^{13}-N(R^{14})S(O)_tR^{15}$ (where t is 1 or 2), $-R^{13}-OC(O)R^{15}$, $-R^{13}-OC(NR^{14})R^{15}$, $-R^{13}-OC(S)R^{15}$, $-R^{13}-OC(O)OR^{15}$, $-R^{13}-OC(NR_{14})OR^{15}$, $-R^{13}-OC(S)OR^{15}$, $-R^{13}-OC(O)SR^{14}$, $-R^{13}-OC(O)N(R^{14})_2$, $-R^{13}-OC(NR^{14})N(R^{14})_2$, $-R^{13}-OC(S)N(R^{14})_2$, $-R^{13}-C(O)-R^{16}-C(O)R^{14}$, $-R^{13}-C(O)-R^{16}-C(S)R^{14}$, $-R^{13}-C(O)-R^{16}-C(NR^{14})R^{14}$, $-R^{13}-C(O)-R^{16}-C(O)OR^{14}$, $-R^{13}-C(O)-R^{16}-C(S)OR^{14}$, $-R^{13}-C(O)-R^{16}-C(NR^{14})OR^{14}$, $-R^{13}-C(O)-R^{16}-C(O)N(R^{14})_2$, $-R^{13}-C(O)-R^{16}-C(S)N(R^{14})_2$, $-R^{13}-C(O)-R^{16}-C(NR^{14})N(R^{14})_2$, $-R^{13}-C(O)-R^{16}-C(O)SR^{14}$, $-R^{13}-C(O)-R^{16}-C(S)SR^{14}$ and $-R^{13}-C(O)-R^{16}-C(NR^{14})SR^{14}$;

where each $R^8$ and $R^{13}$ are independently a direct bond, an optionally substituted straight or branched alkylene chain, or an optionally substituted straight or branched alkenylene chain;

where each $R^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^9$s, together with the nitrogen atom to which they are attached, form an optionally substituted heterocyclyl;

where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^{14}$s, together with the nitrogen atom to which they are attached, form an optionally substituted heterocyclyl;

where each $R^{10}$ and $R^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each $R^{11}$ and $R^{16}$ are independently an optionally substituted straight or branched alkylene chain or an optionally substituted straight or branched alkenylene chain.

2. The method of claim 1, wherein the diseases or disorder is related to one or more metabolic syndromes.

3. The method of claim 1, wherein the disease or disorder is related to bone or cartilage dysfunction.

4. The method of claim 1, wherein the disease or disorder is related to cognitive dysfunction.

5. The method of claim 1, wherein the disease or disorder is related to high blood pressure.

6. The method of claim 1, wherein the diseases or disorder is related to renal disease.

7. The method of claim 1, wherein the diseases or disorder is related to fibrosis.

8. The method of claim 1, wherein the disease or disorder is related to epidermal dysfunction.

9. The method of claim 1, wherein the diseases or disorder is related to muscle wasting.

10. The method of claim 1
wherein:
$R^1$ is optionally substituted alkyl;
$R^3$ is hydrogen;
$R^4$ is aryl optionally substituted by one or more substituents selected from the group consisting of halo, nitro, optionally substituted alkyl, optionally substituted alkenyl, optionally substituted alkynyl, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^9)_2$, —$R^8$—CN, —$R^8$—$C(O)R^9$, —$R^8$—$C(S)R^9$, —$R^8$—$C(NR^9)R^9$, —$R^8$—$C(O)OR^9$, —$R^8$—$C(S)OR^9$, —$R^8$—$C(NR^9)OR^9$, —$R^8$—$C(O)N(R^9)_2$, —$R^8$—$C(S)N(R^9)_2$, —$R^8$—$C(NR^9)N(R^9)_2$, —$R^8$—$C(O)SR^9$, —$R^8$—$C(S)SR^9$, —$R^8$—$C(NR^9)SR^9$, —$R^8$—$S(O)_tOR^9$ (where t is 1 or 2), —$R^8$—$S(O)_tN(R^9)_2$ (where t is 1 or 2), —$R^8$—$S(O)_tN(R^9)N(R^9)_2$ (where t is 1 or 2), —$R^8$—$S(O)_tN(R^9)N=C(R^9)_2$, —$R^8$—$S(O)_tN(R^9)C(O)R^{10}$ (where t is 1 or 2), —$R^8$—$S(O)_tN(R^9)C(O)N(R^9)_2$ (where t is 1 or 2), —$R^8$—$S(O)_tN(R^9)C(NR^9)N(R^9)_2$ (where t is 1 or 2), —$R^8$—$N(R^9)C(O)R^{10}$, —$R^8$—$N(R^9)C(O)OR^{10}$, —$R^8$—$N(R^9)C(O)SR^{10}$, —$R^8$—$N(R^9)C(NR^9)SR^{10}$, —$R^8$—$N(R^9)C(S)SR^{10}$, —$R^8$—$N(R^9)C(O)N(R^9)_2$, —$R^8$—$N(R^9)C(NR^9)N(R^9)_2$, —$R^8$—$N(R^9)C(S)N(R^9)_2$, —$R^8$—$N(R^9)S(O)_tR^{10}$ (where t is 1 or 2), —$R^8$—$OC(O)R^{10}$, —$R^8$—$OC(NR^9)R^{10}$, —$R^8$—$OC(S)R^{10}$, —$R^8$—$OC(O)OR^{10}$, —$R^8$—$OC(NR^9)OR^{10}$, —$R^8$—$OC(S)OR^{10}$, —$R^8$—$OC(O)SR^9$, —$R^8$—$OC(O)N(R^9)_2$, —$R^8$—$OC(NR^9)N(R^9)_2$, —$R^8$—$OC(S)N(R^9)_2$; —$R^8$—$C(O)$—$R^{11}$—$C(O)R^{14}$, —$R^8$—$C(O)$—$R^{11}$—$C(S)R^{14}$, —$R^8$—$C(O)$—$R^{11}$—$C(NR^{14})R^{14}$, —$R^8$—$C(O)$—$R^{11}$—$C(O)OR^{14}$, —$R^8$—$C(O)$—$R^{11}$—$C(S)OR^{14}$, —$R^8$—$C(O)$—$R^{11}$—$C(NR^4)OR^4$, —$R^8$—$C(O)$—$R^{11}$—$C(O)N(R^{14})_2$, —$R^8$—$C(O)$—$R^{11}$—$C(S)N(R^{14})_2$, —$R^8$—$C(O)R^{11}$—$C(NR^{14})N(R^{14})_2$, —$R^8$—$C(O)$—$R^{11}$—$C(O)SR^{14}$, —$R^8$—$C(O)$—$R^{11}$—$C(S)SR^{14}$ and —$R^8$—$C(O)$—$R^{11}$—$C(NR^{14})SR^{14}$;

$R^5$ is alkyl, optionally substituted by one or more substituents selected from the group consisting of halo, nitro, —$OR^9$, —$SR^9$, —$S(O)_tR^{10}$ (where t is 1 or 2), —$N(R^9)_2$, —CN, —$C(O)R^9$, —$C(S)R^9$, —$C(NR^9)R^9$, —$C(O)OR^9$, —$C(S)OR^9$, —$C(NR^9)OR^9$, —$C(O)N(R^9)_2$, —$C(S)N(R^9)_2$, —$C(NR^9)N(R^9)_2$, —$C(O)SR^9$, —$C(S)SR^9$, —$C(NR^9)SR^9$, —$S(O)_tOR^9$ (where t is 1 or 2), —$S(O)_tN(R^9)_2$, (where t is 1 or 2), —$S(O)_tN(R^9)N(R^9)_2$ (where t is 1 or 2), —$S(O)_tN(R^9)N=C(R^9)_2$, —$S(O)_tN(R^9)C(O)R^{10}$ (where t is 1 or 2), —$S(O)_tN(R^9)C(O)N(R^9)_2$ (where t is 1 or 2), —$R^8$—$S(O)_tN(R^9)C(NR^9)N(R^9)_2$ (where t is 1 or 2), —$N(R^9)C(O)R^{10}$, —$N(R^9)C(O)OR^{10}$, —$N(R^9)C(O)SR^{10}$, —$N(R^9)C(NR^9)SR^{10}$, —$N(R^9)C(S)SR^{10}$, —$N(R^9)C(O)N(R^9)_2$, —$N(R^9)C(NR^9)N(R^9)_2$, —$N(R^9)C(S)N(R^9)_2$, —$N(R^9)S(O)_tR^{10}$ (where t is 1 or 2), —$OC(O)R^{10}$, —$OC(NR^9)R^{10}$, —$OC(S)R^{10}$, —$OC(O)OR^{10}$, —$OC(NR^9)OR^{10}$, —$OC(S)OR^{10}$, —$OC(O)SR^9$, —$OC(O)N(R^9)_2$, —$OC(NR^9)N(R^9)_2$, —$OC(S)N(R^9)_2$, —$C(O)$—$R^{11}$—$C(O)R^9$, —$C(O)$—$R^{11}$—$C(S)R^9$, —$C(O)$—$R^{11}$—$C(NR^9)R^9$, —$C(O)$—$R^{11}$—$C(O)OR^9$, —$C(O)$—$R^{11}$—$C(S)OR^9$, —$C(O)$—$R^{11}$—$C(NR^9)OR^9$, —$C(O)$—$R^{11}$—$C(O)N(R^9)_2$, —$C(O)$—$R^{11}$—$C(S)N(R^9)_2$, —$C(O)$—$R^{11}$—$C(NR^9)N(R^9)_2$, —$C(O)$—$R^{11}$—$C(O)SR^9$, —$C(O)$—$R^{11}$—$C(S)SR^9$ and —$C(O)$—$R^{11}$—$C(NR^9)SR^9$;

$R^6$ is hydrogen or optionally substituted alkyl;

$R^7$ is aryl optionally substituted by one or more substituents selected from the group consisting of halo, nitro, optionally substituted alkenyl, optionally substituted alkynyl, optionally substituted cycloalkyl, optionally substituted cycloalkylalkyl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^{13}$—$OR^{14}$, —$R^{13}$—$SR^{14}$, —$R^{13}$—$S(O)_tR^{15}$ (where t is 1 or 2), —$R^{13}$—$N(R^{14})_2$, —$R^{13}$—CN, —$R^{13}$—$C(O)R^{14}$, —$R^{13}$—$C(S)R^{14}$, —$R^{13}$—$C(NR^{14})R^{14}$, —$R^{13}$—$C(S)OR^{14}$, —$R^{13}$—$C(NR^{14})OR^{14}$, —$R^{13}$—$C(S)N(R^{14})_2$, —$R^{13}$—$C(NR^{14})N(R^{14})_2$, —$R^{13}$—$C(O)SR^{14}$, —$R^{13}$—$C(S)SR^{14}$, —$R^{13}$—$C(NR^{14})SR^{14}$, —$R^{13}$—$S(O)_tOR^{14}$ (where t is 1 or 2), —$R^{13}$—$S(O)_tN(R^{14})_2$ (where t is 1 or 2), —$R^{13}$—$S(O)_tN(R^{14})N(R^{14})_2$ (where t is 1 or 2), —$R^{13}$—$S(O)_tN(R^{14})N=C(R^{14})_2$, —$R^{13}$—$S(O)_tN(R^{14})C(O)R^{15}$ (where t is 1 or 2), —$R^{13}$—$S(O)_tN(R^{14})C(O)N(R^{14})_2$ (where t is 1 or 2), —$R^{13}$—$S(O)_tN(R^{14})C(NR^{14})N(R^{14})_2$ (where t is 1 or 2) and —$R^{13}$—$N(R^{14})S(O)_tR^{15}$ (where t is 1 or 2);

where each $R^8$ and $R^{13}$ are independently a direct bond, an optionally substituted straight or branched alkylene chain, or an optionally substituted straight or branched alkenylene chain;

where each $R^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^9$s, together with the nitrogen atom to which they are attached, form an optionally substituted heterocyclyl; and where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^{14}$s, together with the nitrogen atom to which they are attached, form an optionally substituted heterocyclyl;

where each $R^{10}$ and $R^{15}$ are independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each $R^{11}$ is independently an optionally substituted straight or branched alkylene chain or an optionally substituted straight or branched alkenylene chain;

or as a pharmaceutically acceptable salt thereof.

11. The method of claim 1 wherein $R^7$ is aryl, substituted by $R^{26}$ and optionally substituted by $R^{25}$;

wherein:

$R^{25}$ is selected from the group consisting of halo, nitro, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aralkyl, optionally substituted aralkenyl, optionally substituted heteroaralkenyl, —$R^{13}$—$OR^{14}$; —$R^{13}$—$SR^{14}$, —$R^{13}$—$S(O)_tR^{15}$ (where t is 1 or 2), —$R^{13}$—$N(R^{14})_2$, —$R^{13}$—$CN$, —$R^{13}$—$C(O)R^{14}$, —$R^{13}$—$S(O)_tN(R^{14})_2$ (where t is 1 or 2), —$R^{13}$—$S(O)_tN(R^{14})C(O)R^{15}$, (where t is 1 or 2), —$R^{13}$—$S(O)_tN(R^{14})C(O)N(R^{14})_2$ (where t is 1 or 2), —$R^{13}$—$S(O)_tN(R^{14})C(NR^{14})N(R^{14})_2$ (where t is 1 or 2), —$R^{13}$—$N(R^{14})C(O)R^5$, —$R^{13}$—$N(R^{14})S(O)_tR^{15}$ (where t is 1 or 2), —$R^{13}$—$C(O)$—$R^{16}$—$C(O)R^{14}$, —$R^{13}$—$C(O)$—$R^{16}$—$C(S)R^{14}$ and —$R^{13}$—$C(O)$—$R^{16}$—$C(O)N(R^{14})_2$;

$R^{26}$ is selected from the group consisting of —$R^{13}$—$C(O)R^{14}$, —$R^{13}$—$S(O)_tR^{15}$ (where t is 1 or 2), —$R^{13}$—$S(O)_tN(R^{14})_2$ (where t is 1 or 2) and —$R^{13}$—$S(O)_tN(R^{14})C(O)R^{15}$ (where t is 1 or 2);

where each $R^{13}$ is independently a direct bond, an optionally substituted straight or branched alkylene chain, or an optionally substituted straight or branched alkenylene chain;

where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or where two $R^{14}$s, together with the nitrogen atom to which they are attached, form an optionally substituted heterocyclyl;

where each $R^{15}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and where each $R^{16}$ is independently an optionally substituted straight or branched alkylene chain or an optionally substituted straight or branched alkenylene chain.

12. The method of claim 11 wherein $R^7$ is:

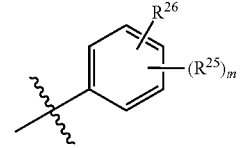

wherein:

m is 0 to 1;

$R^{25}$ is selected from the group consisting of halo, nitro, optionally substituted cycloalkyl, optionally substituted heteroaralkenyl, optionally substituted aralkyl, optionally substituted heterocyclyl, optionally substituted heteroaryl, —$R^{13}$—$OR^{14}$; —$R^{13}$—$SR^{14}$, —$R^{13}$—$S(O)_tR^{15}$ (where t is 1 or 2), —$R^{13}$—$N(R^{14})_2$, —$R^{13}$—$CN$, —$R^{13}$—$C(O)R^{14}$, —$R^{13}$—$S(O)_tN(R^{14})_2$ (where t is 1 or 2), —$R^{13}$—$S(O)_tN(R^{14})C(O)R^{15}$, (where t is 1 or 2), —$R^{13}$—$S(O)_tN(R^{14})C(O)N(R^{14})_2$ (where t is 1 or 2), —$R^{13}$—$S(O)_tN(R^{14})C(NR^{14})N(R^{14})_2$ (where t is 1 or 2), —$R^{13}$—$N(R^{14})C(O)R^{15}$, and —$R^{13}$—$N(R^{14})S(O)_tR^{15}$ (where t is 1 or 2); and $R^{26}$ is selected from the group consisting of —$R^{13}$—$S(O)_tR^{15}$ (where t is 1 or 2), —$R^8$—$C(O)R^{14}$ and —$R^{13}$—$S(O)_tN(R^{14})_2$ (where t is 1 or 2);

where each $R^{13}$ is independently a direct bond or an optionally substituted straight or branched alkylene chain;

where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; or where two $R^{14}$s, together with the nitrogen atom to which they are attached, form an optionally substituted heterocyclyl;

where each $R^{15}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; and where each $R^{16}$ is independently an optionally substituted straight or branched alkylene chain or an optionally substituted straight or branched alkenylene chain.

13. The method of claim 12 wherein $R^{26}$ is in the para position.

14. The method of Claim 1 wherein $R^7$ is aryl except phenyl, substituted by $R^{26}$ and optionally substituted by $R^{25}$ wherein:
  $R^{25}$ is selected from the group consisting of halo, nitro, optionally substituted cycloalkyl, optionally substituted heteroaralkenyl, optionally substituted aralkyl, optionally substituted heterocyclyl, optionally substituted heteroaryl, —$R^{13}$—$OR^{14}$; —$R^{13}$—$SR^{14}$, —$R^{13}$—$S(O)_tR^{15}$ (where t is 1 or 2), —$R^{13}$—$N(R^{14})_2$, —$R^{13}$—CN, —$R^{13}$—$C(O)R^{14}$, —$R^{13}$—$S(O)_tN(R^{14})_2$ (where t is 1 or 2), —$R^{13}$—$S(O)_tN(R^{14})C(O)R^{15}$, (where t is 1 or 2), —$R^{13}$—$S(O)_tN(R^{14})C(O)N(R^{14})_2$ (where t is 1 or 2), —$R^{13}$—$S(O)_tN(R^{14})C(NR^{14})N(R^{14})_2$ (where t is 1 or 2), —$R^{13}$—$N(R^{14})C(O)R^{15}$, and —$R^{13}$—$N(R^{14})S(O)_tR^{15}$ (where t is 1 or 2); and
  $R^{26}$ is selected from the group consisting of —$S(O)_tR^{15}$ (where t is 1 or 2), —$N(R^{14})_2$, —$C(O)R^{14}$ and —$S(O)_tN(R^{14})_2$ (where t is 1 or 2);
  where each $R^{13}$ is independently a direct bond, an optionally substituted straight or branched alkylene chain, or an optionally substituted straight or branched alkenylene chain;
  where each $R^{14}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; or
  where two $R^{14}$s, together with the nitrogen atom to which they are attached, form an optionally substituted heterocyclyl; and
  where each $R^{15}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl.

15. The method of claim 1 wherein $R^1$ and $R^5$ are each alkyl.

16. The method of claim 1 wherein $R^4$ is aryl optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^9)_2$, —$R^8$—CN, —$R^8$—$C(O)R^9$, —$R^8$—$C(S)R^9$, —$R^8$—$C(NR^9)R^9$, —$R^8$—$C(O)OR^9$, —$R^8$—$C(S)OR^9$, —$R^8$—$C(NR^9)OR^9$, —$R^8$—$C(O)N(R^9)_2$, —$R^8$—$C(S)N(R^9)_2$, —$R^8$—$C(NR^9)N(R^9)_2$, —$R^8$—$C(O)SR^9$, —$R^8$—$C(S)SR^9$, —$R^8$—$C(NR^9)SR^9$, —$R^8$—$S(O)_tOR^9$ (where t is 1 or 2), —$R^8$—$S(O)_tN(R^9)_2$ (where t is 1 or 2), —$R^8$—$S(O)_tN(R^9)N(R^9)_2$ (where t is 1 or 2), —$R^8$—$S(O)_tN(R^9)N=C(R^9)_2$, —$R^8$—$S(O)_tN(R^9)C(O)R^{10}$ (where t is 1 or 2), —$R^8$—$S(O)_tN(R^9)C(O)N(R^9)_2$ (where t is 1 or 2), —$R^8$—$S(O)_tN(R^9)C(NR^9)N(R^9)_2$ (where t is 1 or 2), —$R^8$—$N(R^9)C(O)R^{10}$, —$R^8$—$N(R^9)C(O)OR^{10}$, —$R^8$—$N(R^9)C(O)SR^{10}$, —$R^8$—$N(R^9)C(NR^9)SR^{10}$, —$R^8$—$N(R^9)C(S)SR^{10}$, —$R^8$—$N(R^9)C(O)N(R^9)_2$, —$R^8$—$N(R^9)C(NR^9)N(R^9)_2$, —$R^8$—$N(R^9)C(S)N(R^9)_2$, —$R^8$—$N(R^9)S(O)_tR^{10}$ (where t is 1 or 2), —$R^8$—$OC(O)R^{10}$, —$R^8$—$OC(NR^9)R^{10}$, —$R^8$—$OC(S)R^{10}$, —$R^8$—$OC(O)OR^{10}$, —$R^8$—$OC(NR^9)OR^{10}$, —$R^8$—$OC(S)OR^{10}$, —$R^8$—$OC(O)SR^9$, —$R^8$—$OC(O)N(R^9)_2$, —$R^8$—$OC(NR^9)N(R^9)_2$, —$R^8$—$OC(S)N(R^9)_2$, —$R^8$—$C(O)$—$R^{11}$—$C(O)R^9$, —$R^8$—$C(O)$—$R^{11}$—$C(S)R^9$, —$R^8$—$C(O)$—$R^{11}$—$C(NR^9)R^9$, —$R^8$—$C(O)$—$R^{11}$—$C(O)OR^9$, —$R^8$—$C(O)$—$R^{11}$—$C(S)OR^9$, —$R^8$—$C(O)$—$R^{11}$—$C(NR^9)OR^9$, —$R^8$—$C(O)$—$R^{11}$—$C(O)N(R^9)_2$, —$R^8$—$C(O)$—$R^{11}$—$C(S)N(R^9)_2$, —$R^8$—$C(O)$—$R^{11}$—$C(NR^9)N(R^9)_2$, —$R^8$—$C(O)$—$R^{11}$—$C(O)SR^9$, —$R^8$—$C(O)$—$R^{11}$—$C(S)SR^9$ and —$R^8$—$C(O)$—$R^{11}$—$C(NR^9)SR^9$;
  where each $R^8$ is independently a direct bond, an optionally substituted straight or branched alkylene chain, or an optionally substituted straight or branched alkenylene chain;
  where each $R^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; or
  where two $R^9$s, together with the nitrogen atom to which they are attached, form an optionally substituted heterocyclyl;
  where each $R^{10}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and
  where each $R^{11}$ is independently an optionally substituted straight or branched alkylene chain or an optionally substituted straight or branched alkenylene chain.

17. The method of Claim 16 wherein said compound is selected from the group consisting of:
  5-(1H-Indol-5-yl)-1,4-dimethyl-1H-pyrrole-3-carboxylic acid (4-methanesulfonyl-phenyl)-amide;
  5-Acenaphthen-5-yl-1,4-dimethyl-1H-pyrrole-3-carboxylic acid (4-methanesulfonyl-phenyl)-amide;
  5-Biphenyl-2-yl-1-(2-diethylamino-ethyl)-4-methyl-1H-pyrrole-3-carboxylic acid (4-methanesulfonyl-phenyl)-amide;
  5-Biphenyl-2-yl-4-methyl-1-(2-pyrrolidin-1-yl-ethyl)-1H-pyrrole-3-carboxylic acid (4-methanesulfonyl-phenyl)-amide;
  5-Biphenyl-2-yl-4-methyl-1-(2-morpholin-4-yl-ethyl)-1H-pyrrole-3-carboxylic acid (4-methanesulfonyl-phenyl)-amide;
  5-(2-Benzyloxy-4-fluoro-phenyl)-4-methyl-1-(2-pyrrolidin-yl-ethyl)-1H-pyrrole-3-carboxylic acid (4-methanesulfonyl-phenyl)-amide;

5-(2-Benzyloxy-4-fluoro-phenyl)-1-(2-dimethylamino-ethyl)-4-methyl-1H-pyrrole-3-carboxylic acid (4-methanesulfonyl-phenyl)-amide;
5-(2-Benzyloxy-4-fluoro-phenyl)-4-methyl-1-(2-piperidin-yl-ethyl)-1H-pyrrole-3-carboxylic acid (4-methanesulfonyl-phenyl)-amide;
4-Methyl-1-(2-morpholin-4-yl-ethyl)-5-(2-phenoxy-phenyl)-1H-pyrrole-3-carboxylic acid (4-methanesulfonyl-phenyl)-amide;
1-(2-Diethylamino-ethyl)-4-methyl-5-(2-phenoxy-phenyl)-1H-pyrrole-3-carboxylic acid (4-methanesulfonyl-phenyl)-amide;
4-Methyl-5-(2-phenoxy-phenyl)-1-(2-piperidin-1-yl-ethyl)-1H-pyrrole-3-carboxylic acid (4-methanesulfonyl-phenyl)-amide;
4-Methyl-5-(2-phenoxy-phenyl)-1-(2-pyrrolidin-1-yl-ethyl)-1H-pyrrole-3-carboxylic acid (4-methanesulfonyl-phenyl)-amide;
1-(3-Dimethylamino-propyl)-4-methyl-5-(2-phenoxy-phenyl)-1H-pyrrole-3-carboxylic acid (4-methanesulfonyl-phenyl)-amide;
1-(2-Hydroxy-ethyl)-4-methyl-5-(2-phenoxy-phenyl)-1H-pyrrole-3-carboxylic acid (4-methanesulfonyl-phenyl)-amide;
5-(4-Benzyloxy-2-methyl-phenyl)-1,4-dimethyl-1H-pyrrole-3-carboxylic acid (4-methanesulfonyl-phenyl)-amide;
5-(4-Hydroxy-2-methyl-phenyl)-1,4-dimethyl-1H-pyrrole-3-carboxylic acid (4-methanesulfonyl-phenyl)-amide;
1,4-Dimethyl-5-[2-methyl-4-(3-morpholin-4-yl-propoxy)-phenyl]-1H-pyrrole-3-carboxylic acid (4-methanesulfonyl-phenyl)-amide;
1,4-Dimethyl-5-[4-(3-morpholin-4-yl-propoxy)-2-trifluoromethyl-phenyl]-1H-pyrrole-3-carboxylic acid (4-methanesulfonyl-phenyl)-amide, or
a pharmaceutically acceptable salt of any of the foregoing.

18. The method of claim 16 wherein $R^4$ is:

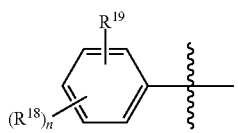

wherein:
n is 0 to 4;
$R^{18}$ is halo, optionally substituted heterocyclyl, optionally substituted aryl, optionally substituted heteroaryl or optionally substituted aralkenyl;
$R^{19}$ is selected from the group consisting of haloalkyl, optionally substituted heterocyclyl, optionally substituted aryl, optionally substituted heteroaryl, —$R^8$—$OR^9$ or —$R^8$—C(O)N($R^9$)$_2$;
where $R^8$ is a direct bond, an optionally substituted straight or branched alkylene chain, or an optionally substituted straight or branched alkenylene chain; and
where each $R^9$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroaralkyl; or where two $R^9$s, together with the nitrogen atom to which they are attached, form an optionally substituted heterocyclyl.

19. The method of Claim 1 wherein said compound is selected from the group consisting of:
1,4-dimethyl-5-(2-trifluoromethyl-phenyl)-1H-pyrrole-3-carboxylic acid (4-methanesulfonyl-phenyl)-amide;
1,4-dimethyl-5-(2-trifluoromethyl-phenyl)-1H-pyrrole-3-carboxylic acid [4-(2-fluoro-benzoyl)-phenyl]-amide;
1,4-dimethyl-5-(2-trifluoromethyl-phenyl)-1H-pyrrole-3-carboxylic acid (4-methanesulfonyl-3-trifluoromethyl-phenyl)-amide;
1,4-dimethyl-5-(2-trifluoromethyl-phenyl)-1H-pyrrole-3-carboxylic acid (4-sulfamoyl-phenyl)-amide;
5-(4-fluoro-2-trifluoromethyl-phenyl)-1,4-dimethyl-1H-pyrrole-3-carboxylic acid (4-methanesulfonyl-phenyl)-amide;
1,4-dimethyl-5-(2-trifluoromethyl-phenyl)-1H-pyrrole-3-carboxylic acid (3-chloro-4-sulfamoyl-phenyl)-amide;
5-(4-fluoro-phenyl)-1,4-dimethyl-1H-pyrrole-3-carboxylic acid (4-methanesulfonyl-phenyl)-amide;
5-(4-fluoro-2-trifluoromethyl-phenyl)-1,4-dimethyl-1H-pyrrole-3-carboxylic acid (3-chloro-4-sulfamoyl-phenyl)-amide;
5-(4-fluoro-2-trifluoromethyl-phenyl)-1,4-dimethyl-1H-pyrrole-3-carboxylic acid (4-sulfamoyl-3-trifluoromethyl-phenyl)-amide;
1,4-Dimethyl-5-(2-phenoxy-phenyl)-1H-pyrrole-3-carboxylic acid (4-methanesulfonyl-phenyl)-amide;
1,4-Dimethyl-5-(4-trifluoromethyl-phenyl)-1H-pyrrole-3-carboxylic acid (4-methanesulfonyl-phenyl)-amide;
5-(2-Isopropoxy-phenyl)-1,4-dimethyl-1H-pyrrole-3-carboxylic acid (4-methanesulfonyl-phenyl)-amide;
5-(2-Benzyloxy-5-fluoro-phenyl)-1,4-dimethyl-1H-pyrrole-3-carboxylic acid (4-methanesulfonyl-phenyl)-amide;
5-(2-Butoxy-5-methyl-phenyl)-1,4-dimethyl-1H-pyrrole-3-carboxylic acid (4-methanesulfonyl-phenyl)-amide;
5-(3-Benzyloxy-phenyl)-1,4-dimethyl-1H-pyrrole-3-carboxylic acid (4-methanesulfonyl-phenyl)-amide;
5-(3-Bromo-2-methoxy-5-methyl-phenyl)-1,4-dimethyl-1H-pyrrole-3-carboxylic acid (4-methanesulfonyl-phenyl)-amide;
5-(3-Bromo-2-butoxy-5-methyl-phenyl)-1,4-dimethyl-1H-pyrrole-3-carboxylic acid (4-methanesulfonyl-phenyl)-amide;
3-[4-(4-Methanesulfonyl-phenylcarbamoyl)-1,3-dimethyl-1H-pyrrol-2-yl]-benzoic acid methyl ester;
5-(3,5-Bis-trifluoromethyl-phenyl)-1,4-dimethyl-1H-pyrrole-3-carboxylic acid (4-methanesulfonyl-phenyl)-amide;
5-(2-Isopropoxy-5-methyl-phenyl)-1,4-dimethyl-1H-pyrrole-3-carboxylic acid (4-methanesulfonyl-phenyl)-amide;
5-(2-Butoxy-phenyl)-1,4-dimethyl-1H-pyrrole-3-carboxylic acid (4-methanesulfonyl-phenyl)-amide;
5-(3-Benzylcarbamoyl-phenyl)-1,4-dimethyl-1H-pyrrole-3-carboxylic acid (4-methanesulfonyl-phenyl)-amide;
5-(2-Benzyloxy-phenyl)-1,4-dimethyl-1H-pyrrole-3-carboxylic acid (4-methanesulfonyl-phenyl)-amide; and
5-(3-Carbamoyl-phenyl)-1,4-dimethyl-1H-pyrrole-3-carboxylic acid (4-methanesulfonyl-phenyl)-amide;
N-[4-(aminosulfonyl)-3-chlorophenyl]-5-[4-fluoro-2-(trifluoromethyl)phenyl]-4-methyl-1-(pyridin-3-ylmethyl)-1H-pyrrole-3-carboxamide;

5-[4-fluoro-2-(trifluoromethyl)phenyl]-4-methyl-N-[4-(methylsulfonyl)phenyl]-1-(2-pyrrolidin-1-ylethyl)-1H pyrrole-3-carboxamide;

1-[3-(dimethylamino)propyl]-5-[4-fluoro-2-(trifluoromethyl)phenyl]-4-methyl-N-[4-(methylsulfonyl)phenyl]-1H-pyrrole-3-carboxamide;

5-[4-fluoro-2-(trifluoromethyl)phenyl]-4-methyl-N-[4-(methylsulfonyl)phenyl]-1-(pyridin-2-ylmethyl)-1H-pyrrole-3-carboxamide;

1-[3-(dimethylamino)propyl]-5-[4-fluoro-2-(trifluoromethyl)phenyl]-4-methyl-N-[4-(methylsulfonyl)phenyl]-1H-pyrrole-3-carboxamide;

5-[4-fluoro-2-(trifluoromethyl)phenyl]-4-methyl-N-[4-(methylsulfonyl)phenyl]-1-(2-piperidin-1-ylethyl)-1H-pyrrole-3-carboxamide;

5-[4-fluoro-2-(trifluoromethyl)phenyl]-4-methyl-N-[4-(methylsulfonyl)phenyl]-1-(2-morpholin-4-ylethyl)-1H-pyrrole-3-carboxamide;

4-methyl-5-[2-(methyloxy)phenyl]-N-[4-(methylsulfonyl)phenyl]-1-(pyridin-3-ylmethyl)-1H-pyrrole-3-carboxamide;

4-methyl-5-[2-(methyloxy)phenyl]-N-[4-(methylsulfonyl)phenyl]-1-(2-morpholin-4-ylethyl)-1H-pyrrole-3-carboxamide;

1-[2-(diethylamino)ethyl]-4-methyl-5-[2-(methyloxy)phenyl]-N-[4-(methylsulfonyl)phenyl]-1H-pyrrole-3-carboxamide;

1-[(6-chloropyridin-2-yl)methyl]-5-(2,4-difluorophenyl)-4-methyl-N-[4-(methylsulfonyl)phenyl]-1H-pyrrole-3-carboxamide;

5-(2,4-difluorophenyl)-1,4-dimethyl-N-[4-(methylsulfonyl)phenyl]-1H-pyrrole-3-carboxamide;

1-[(6-aminopyridin-2-yl)methyl]-5-(2,4-difluorophenyl)-4-methyl-N-[4-(methylsulfonyl)phenyl]-1H-pyrrole-3-carboxamide;

1-[2-(diethylamino)ethyl]-5-(2,4-difluorophenyl)-4-methyl-N-[4-(methylsulfonyl)phenyl]-1H-pyrrole-3-carboxamide;

5-(2,4-difluorophenyl)-4-methyl-N-[4-(methylsulfonyl)phenyl]-1-(2-pyrrolidin-1-ylethyl)-1H-pyrrole-3-carboxamide;

1-[(6-aminopyridin-2-yl)methyl]-4-methyl-N-[4-(methylsulfonyl)phenyl]-5-[2-(trifluoromethyl)phenyl]-1H-pyrrole-3-carboxamide;

5-(2,4-difluorophenyl)-4-methyl-N-[4-(methylsulfonyl)phenyl]-1-[(6-pyrrolidin-1-ylpyridin-2-yl)methyl]-1H-pyrrole-3-carboxamide;

5-(2,4-difluorophenyl)-4-methyl-1-[(6-methylpyridin-2-yl)methyl]-N-[4-(methylsulfonyl)phenyl]-1H-pyrrole-3-carboxamide; methyl (6-{[2-(2,4-difluorophenyl)-3-methyl-4-({[4-(methylsulfonyl)phenyl]amino}carbonyl)-1H-pyrrol-1-yl]methyl}pyridin-2-yl)carbamate;

1-{[6-(acetylamino)pyridin-2-yl]methyl}-5-(2,4-difluorophenyl)-4-methyl-N-[4-(methylsulfonyl)phenyl]-1H-pyrrole-3-carboxamide;

5-(2-chlorophenyl)-1-[2-hydroxy-3-(4-methylpiperazin-1-yl)propyl]-4-methyl-N-[4-(methylsulfonyl)phenyl]-1H-pyrrole-3-carboxamide;

5-(2-chlorophenyl)-1-{2-hydroxy-3-[(2-methylpropyl)amino]propyl}-4-methyl-N-[4-(methylsulfonyl)phenyl]-1H-pyrrole-3-carboxamide;

5-(2-chlorophenyl)-1-{2-hydroxy-3-[(phenylmethyl)amino]propyl}-4-methyl-N-[4-(methylsulfonyl)phenyl]-1H-pyrrole-3-carboxamide;

1-(3-amino-2-hydroxypropyl)-5-(2-chlorophenyl)-4-methyl-N-[4-(methylsulfonyl)phenyl]-1H-pyrrole-3-carboxamide;

4-methyl-1-{2-[(2-methylpropyl)amino]-2-oxoethyl}-N-[4-(methylsulfonyl)phenyl]-5-[2-(trifluoromethyl)phenyl]-1H-pyrrole-3-carboxamide;

4-methyl-1-[2-(4-methylpiperazin-1-yl)-2-oxoethyl]-N-[4-(methylsulfonyl)phenyl]-5-[2-(trifluoromethyl)phenyl]-1H-pyrrole-3-carboxamide;

1-(2-amino-2-oxoethyl)-4-methyl-N-[4-(methylsulfonyl)phenyl]-5-[2-(trifluoromethyl)phenyl]-1H-pyrrole-3-carboxamide;

1-[2-(butylamino)-2-oxoethyl]-4-methyl-N-[4-(methylsulfonyl)phenyl]-5-[2-(trifluoromethyl)phenyl]-1H-pyrrole-3-carboxamide;

5-(2-chlorophenyl)-1,4-dimethyl-N-[4-(methylsulfonyl)phenyl]-1H-pyrrole-3-carboxamide;

5-(2-fluorophenyl)-1,4-dimethyl-N-[4-(methylsulfonyl)phenyl]-1H-pyrrole-3-carboxamide;

5-(2-chlorophenyl)-4-methyl-N-[4-(methylsulfonyl)phenyl]-1-(2-morpholin-4-ylethyl)-1H-pyrrole-3-carboxamide;

5-(2-chlorophenyl)-4-methyl-N-[4-(methylsulfonyl)phenyl]-1-(2-piperidin-1-ylethyl)-1H-pyrrole-3-carboxamide;

5-(2-chlorophenyl)-4-methyl-N-[4-(methylsulfonyl)phenyl]-1-(pyridin-2-ylmethyl)-1H-pyrrole-3-carboxamide;

5-(2-chlorophenyl)-1-(2-hydroxyethyl)-4-methyl-N-[4-(methylsulfonyl)phenyl]-1H-pyrrole-3-carboxamide;

5-(2-chlorophenyl)-4-methyl-N-[4-(methylsulfonyl)phenyl]-1-(2-piperidin-1-ylethyl)-1H-pyrrole-3-carboxamide;

5-(2-chlorophenyl)-4-methyl-N-[4-(methylsulfonyl)phenyl]-1-(2-pyrrolidin-1-ylethyl)-1H-pyrrole-3-carboxamide;

5-(2-chlorophenyl)-1-[3-(dimethylamino)propyl]-4-methyl-N-[4-(methylsulfonyl)phenyl]-1H-pyrrole-3-carboxamide;

5-(2-chlorophenyl)-1-[2-(diethylamino)ethyl]-4-methyl-N-[4-(methylsulfonyl)phenyl]-1H-pyrrole-3-carboxamide;

1-[(6-chloropyridin-2-yl)methyl]-4-methyl-N-[4-(methylsulfonyl)phenyl]-5-phenyl-1H-pyrrole-3-carboxamide;

5-(2-chlorophenyl)-4-ethyl-1-methyl-N-[4-(methylsulfonyl)phenyl]-1H-pyrrole-3-carboxamide;

5-(2-Fluoro-phenyl)-4-methyl-1-pyridin-2-ylmethyl-1H-pyrrole-3-carboxylic acid (4-methanesulfonyl-phenyl)-amide;

5-(2-Fluoro-phenyl)-1-(2-hydroxy-ethyl)-4-methyl-1H-pyrrole-3-carboxylic acid (4-methanesulfonyl-phenyl)-amide;

5-(2-Chloro-phenyl)-4-methyl-1-pyrazin-2-ylmethyl-1H-pyrrole-3-carboxylic acid (4-methanesulfonyl-phenyl)-amide;

1-(3-Fluoro-pyridin-2-ylmethyl)-4-methyl-5-(2-trifluoromethyl-phenyl)-1H-pyrrole-3-carboxylic acid (4-methanesulfonyl-phenyl)-amide;

4-Methyl-1-(tetrahydro-furan-2-ylmethyl)-5-(2-trifluoromethyl-phenyl)-1H-pyrrole-3-carboxylic acid (4-methanesulfonyl-phenyl)-amide;

1-(1-Hydroxy-2-methoxy-ethyl)-4-methyl-5-(2-trifluoromethyl-phenyl)-1H-pyrrole-3-carboxylic acid (4-methanesulfonyl-phenyl)-amide;

1-(3,3-Dimethyl-2-oxo-butyl)-4-methyl-5-(2-trifluoromethyl-phenyl)-1H-pyyrrole-3-carboxylic acid (4-methanesulfonyl-phenyl)-amide;

1-Furan-2-ylmethyl-4-methyl-5-(2-trifluoromethyl-phenyl)-1H-pyrrole-3-carboxylic acid (4-methanesulfonyl-phenyl)-amide;

5-(2-Chloro-phenyl)-1-(2-hydroxy-ethyl)-4-methyl-1H-pyrrole-3-carboxylic acid (3-chloro-4-sulfamoyl-phenyl)-amide;

1-(2-hydroxyethyl)-4-methyl-N-[4-(methylsulfonyl)phenyl]-5-[2-(trifluoromethyl)phenyl]-1H-pyrrole-3-carboxamide;

4-methyl-N-[4-(methylsulfonyl)phenyl]-1-(2-pyrrolidin-1-ylethyl)-5-[2-(trifluoromethyl)phenyl]-1H-pyrrole-3-carboxamide;

4-methyl-N-[4-(methylsulfonyl)phenyl]-1-(2-morpholin-4-ylethyl)-5-[2-(trifluoromethyl)phenyl]-1H-pyrrole-3-carboxamide;

4-methyl-N-[4-(methylsulfonyl)phenyl]-1-(pyridin-2-ylmethyl)-5-[2-(trifluoromethyl)phenyl]-1H-pyrrole-3-carboxamide;

1-[2-(diethylamino)ethyl]-4-methyl-N-[4-(methylsulfonyl)phenyl]-5-[2-(trifluoromethyl)phenyl]-1H-pyrrole-3-carboxamide;

4-methyl-N-[4-(methylsulfonyl)phenyl]-1-(2-piperidin-1-ylethyl)-5-[2-(trifluoromethyl)phenyl]-1H-pyrrole-3-carboxamide;

5-(2-chlorophenyl)-1-[2-hydroxy-3-(phenyloxy)propyl]-4-methyl-N-[4-(methylsulfonyl)phenyl]-1H-pyrrole-3-carboxamide;

5-(2-chlorophenyl)-1-(2,3-dihydroxypropyl)-4-methyl-N-[4-(methylsulfonyl)phenyl]-1H-pyrrole-3-carboxamide;

4-methyl-N-[4-(methylsulfonyl)phenyl]-1-prop-2-en-1-yl-5-[2-(trifluoromethyl)phenyl]-1H-pyrrole-3-carboxamide;

1-(3-hydroxypropyl)-4-methyl-N-[4-(methylsulfonyl)phenyl]-5-[2-(trifluoromethyl)phenyl]-1H-pyrrole-3-carboxamide;

1-{(2S)-3-[(4-fluorophenyl)oxy]-2-hydroxypropyl}-4-methyl-N-[4-(methylsulfonyl)phenyl]-5-[2-(trifluoromethyl)phenyl]-1H-pyrrole-3-carboxamide;

1-(4-hydroxybutyl)-4-methyl-N-[4-(methylsulfonyl)phenyl]-5-[2-(trifluoromethyl)phenyl]-1H-pyrrole-3-carboxamide;

4-methyl-N-[4-(methylsulfonyl)phenyl]-1-[2-(tetrahydro-2H-pyran-2-yloxy)ethyl]-5-[2-(trifluoromethyl)phenyl]-1H-pyrrole-3-carboxamide;

N-[4-(aminosulfonyl)-3-chlorophenyl]-1-(2-hydroxyethyl)-4-methyl-5-[2-(trifluoromethyl)phenyl]-1H-pyrrole-3-carboxamide;

5-(2-chloro-phenyl)-1-(2-Methoxy-ethyl)-4-methyl-1H-pyrrole-3-carboxylic acid (4-methanesulfonyl-phenyl)-amide;

(2-chlorophenyl)-4-methyl-N-[4-(methylsulfonyl)phenyl]-1-prop-2-en-1-yl-1H-pyrrole-3-carboxamide;

5-(2,6-Dimethyl-phenyl)-1-(2-hydroxy-ethyl)-4-methyl-1H-pyrrole-3-carboxylic acid (4-methanesulfonyl-phenyl)-amide;

5-(2,6-Dimethyl-phenyl)-4-methyl-1-pyridin-3-ylmethyl-1H-pyrrole-3-carboxylic acid (4-methanesulfonyl-phenyl)-amide;

5-(2,6-Dimethyl-phenyl)-4-methyl-1-(2-pyrrolidin-1-yl-ethyl)-1H-pyrrole-3-carboxylic acid (4-methanesulfonyl-phenyl)-amide;

5-(2,6-Dimethyl-phenyl)-4-methyl-1-(2-piperidin-1-yl-ethyl)-1H-pyrrole-3-carboxylic acid (4-methanesulfonyl-phenyl)-amide;

5-(2,6-Dimethyl-phenyl)-1,4-dimethyl-1H-pyrrole-3-carboxylic acid (4-methanesulfonyl-phenyl)-amide;

5-(2,6-Dimethyl-phenyl)-4-methyl-1-pyridin-2-ylmethyl-1H-pyrrole-3-carboxylic acid (4-methanesulfonyl-phenyl)-amide;

1-[3-(4-Fluoro-phenoxy)-2-(R)-hydroxy-propyl]-4-methyl-5-(2-trifluoromethyl-phenyl)-1H-pyrrole-3-carboxylic acid (4-methanesulfonyl-phenyl)-amide;

1-Cyclopropylmethyl-4-methyl-5-(2-trifluoromethyl-phenyl)-1H-pyrrole-3-carboxylic acid (4-methanesulfonyl-phenyl)-amide;

4-Methyl-1-prop-2-ynyl-5-(2-trifluoromethyl-phenyl)-1H-pyrrole-3-carboxylic acid (4-methanesulfonyl-phenyl)-amide;

(2-Chloro-phenyl)-1-[3-(4-fluoro-phenoxy)-2-(S)-hydroxy-propyl]-4-methyl-1H-pyrrole-3-carboxylic acid (4-methanesulfonyl-phenyl)-amide;

5-(2-Chloro-phenyl)-1-[3-(4-fluoro-phenoxy)-2-(R)-hydroxy-propyl]-4-methyl-1H-pyrrole-3-carboxylic acid (4-methanesulfonyl-phenyl)-amide;

5-(2-Chloro-phenyl)-1-cyclopropylmethyl-4-methyl-1H-pyrrole-3-carboxylic acid (4-methanesulfonyl-phenyl)-amide;

4-methyl-5-[2-(methyloxy)phenyl]-N-[4-(methylsulfonyl)phenyl-1(2-piperidin-1-ylethyl)-1H-pyrrole-3-carboxamide;

5-(2-Methoxy-phenyl)-1,4-dimethyl-1H-pyrrole-3-carboxylic acid (4-methanesulfonyl-phenyl)-methyl-amide;

5-(2-Methoxy-phenyl)-4-methyl-1-(2-pyrrolidin-1-yl-ethyl)-1H-pyrrole-3-carboxylic acid (4-methanesulfonyl-phenyl)-amide;

1,4-Dimethyl-5-o-tolyl-1H-pyrrole-3-carboxylic acid (4-methanesulfonyl-phenyl)-amide;

1-(2-Diethylamino-ethyl)-4-methyl-5-o-tolyl-1H-pyrrole-3-carboxylic acid (4-methanesulfonyl-phenyl)-amide;

4-Methyl-1-(2-pyrrolidin-1-yl-ethyl)-5-o-tolyl-1H-pyrrole-3-carboxylic acid (4-methanesulfonyl-phenyl)-amide;

4-Methyl-1-pyridin-2-yl-methyl-5-o-tolyl-1H-pyrrole-3-carboxylic acid (4-methanesulfonyl-phenyl)-amide;

1-(3-Dimethylamino-propyl)-4-methyl-5-o-tolyl-1H-pyrrole-3-carboxylic acid (4-methanesulfonyl-phenyl)-amide;

4-Methyl-1-(2-piperidin-1-yl-ethyl)-5-o-tolyl-1H-pyrrole-3-carboxylic acid (4-methanesulfonyl-phenyl)-amide;

4-Methyl-1-(2-morpholin-4-yl-ethyl)-5-o-tolyl-1H-pyrrole-3-carboxylic acid (4-methanesulfonyl-phenyl)-amide;

1-(2-Hydroxy-3-phenoxy-propyl)-4-methyl-5-o-tolyl-1H-pyrrole-3-carboxylic acid (4-methanesulfonyl-phenyl)-amide;

1-(2-Diethylamino-ethyl)-5-(2,6-difluoro-phenyl)-4-methyl-1H-pyrrole-3-carboxylic acid (4-methanesulfonyl-phenyl)-amide;

1-(2-Hydroxy-ethyl)-4-methyl-5-o-tolyl-1H-pyrrole-3-carboxylic acid (4-methanesulfonyl-phenyl)-amide;

5-(2,6-Difluoro-phenyl)-4-methyl-1-(2-pyrrolidin-1-yl-ethyl)-1H-pyrrole-3-carboxylic acid (4-methanesulfonyl-phenyl)-amide;

5-(2,6-Difluoro-phenyl)-4-methyl-1-(2-piperidin-1-yl-ethyl)-1H-pyrrole-3-carboxylic acid (4-methanesulfonyl-phenyl)-amide;

5-(2,6-Difluoro-phenyl)-4-methyl-1-pyridin-2-ylmethyl-1H-pyrrole-3-carboxylic acid (4-methanesulfonyl-phenyl)-amide;

5-(2,6-Dimethoxy-phenyl)-1,4-dimethyl-1H-pyrrole-3-carboxylic acid (4-methanesulfonyl-phenyl)-amide;

1,4-Dimethyl-5-(2-trifluoromethoxy-phenyl)-1H-pyrrole-3-carboxylic acid (4-methanesulfonyl-phenyl)-amide;

1-(2-Hydroxy-3-phenyl-propyl)-4-methyl-5-(2-trifluoromethyl-phenyl)-1H-pyrrole-3-carboxylic acid (4-methanesulfonyl-phenyl)-amide;

5-(2-Chloro-phenyl)-1-(2-hydroxy-2-phenyl-ethyl)-4-methyl-1H-pyrrole-3-carboxylic acid (4-methanesulfonyl-phenyl)-amide;

5-(2-Chloro-phenyl)-1-(2-hydroxy-3-methoxy-propyl)-4-methyl-1H-pyrrole-3-carboxylic acid (4-methanesulfonyl-phenyl)-amide;

5-(2-Chloro-phenyl)-4-methyl-1-(3,3,3-trifluoro-2-hydroxy-propyl)-1H-pyrrole-3-carboxylic acid (4-methanesulfonyl-phenyl)-amide;

1-(3-tert-Butoxy-2-hydroxy-propyl)-5-(2-chloro-phenyl)-4-methyl-1H-pyrrole-3-carboxylic acid (4-methanesulfonyl-phenyl)-amide;

5-(2-Chloro-phenyl)-1-(2-hydroxy-3-isopropoxy-propyl)-4-methyl-1H-pyrrole-3-carboxylic acid (4-methanesulfonyl-phenyl)-amide;

1-(2-Hydroxy-ethyl)-5-(4-methoxy-2-trifluoromethyl-phenyl)-4-methyl-1H-pyrrole-3-carboxylic acid (4-methanesulfonyl-phenyl)-amide, or a pharmaceutically acceptable salt of any of the foregoing.

20. The method of claim 16 wherein $R^4$ is naphthyl optionally substituted by one or more substituents selected from the group consisting of alkyl, alkenyl, alkynyl, halo, haloalkyl, haloalkenyl, haloalkoxy, nitro, optionally substituted cycloalkyl, optionally substituted cycloalkylalkyl, optionally substituted cycloalkenyl, optionally substituted cycloalkenylalkyl, optionally substituted aryl, optionally substituted aralkyl, optionally substituted aralkenyl, optionally substituted heterocyclyl, optionally substituted heterocyclylalkyl, optionally substituted heterocyclylalkenyl, optionally substituted heteroaryl, optionally substituted heteroaralkyl, optionally substituted heteroaralkenyl, —$R^8$—$OR^9$, —$R^8$—$SR^9$, —$R^8$—$S(O)_tR^{10}$ (where t is 1 or 2), —$R^8$—$N(R^9)_2$, —$R^8$—CN, —$R^8$—$C(O)R^9$, —$R^8$—$C(S)R^9$, —$R^8$—$C(NR^9)R^9$, —$R^8$—$C(O)OR^9$, —$R^8$—$C(S)OR^9$, —$R^8$—$C(NR^9)OR^9$, —$R^8$—$C(O)N(R^9)_2$, —$R^8$—$C(S)N(R^9)_2$, —$R^8$—$C(NR^9)N(R^9)_2$, —$R^8$—$C(O)SR^9$, —$R^8$—$C(S)SR^9$, —$R^8$—$C(NR^9)SR^9$, —$R^8$—$S(O)_tOR^9$ (where t is 1 or 2), —$R^8$—$S(O)_tN(R^9)_2$ (where t is 1 or 2), —$R^8$—$S(O)_tN(R^9)N(R^9)_2$ (where t is 1 or 2), —$R^8$—$S(O)_tN(R^9)N=C(R^9)_2$, —$R^8$—$S(O)_tN(R^9)C(O)R^{10}$ (where t is 1 or 2), —$R^8$—$S(O)_tN(R^9)C(O)N(R^9)_2$, (where t is 1 or 2), —$R^8$—$S(O)_tN(R^9)C(NR^9)N(R^9)_2$ (where t is 1 or 2), —$R^8$—$N(R^9)C(O)R^{10}$, —$R^8$—$N(R^9)C(O)OR^{10}$, —$R^8$—$N(R^9)C(O)SR^{10}$, —$R^8$—$N(R^9)C(NR^9)SR^{10}$, —$R^8$—$N(R^9)C(S)SR^{10}$, —$R^8$—$N(R^9)C(O)N(R^9)_2$, —$R^8$—$N(R^9)C(NR^9)N(R^9)_2$, —$R^8$—$N(R^9)C(S)N(R^9)_2$, —$R^8$—$N(R^9)S(O)_tR^{10}$ (where t is 1 or 2), —$R^8$—$OC(O)R^{10}$, —$R^8$—$OC(NR^9)R^{10}$, —$R^8$—$OC(S)R^{10}$, —$R^8$—$OC(O)OR^{10}$, —$R^8$—$OC(NR^9)OR^{10}$, —$R^8$—$OC(S)OR^{10}$, —$R^8$—$OC(O)SR^9$, —$R^8$—$OC(O)N(R^9)_2$, —$R^8$—$OC(NR^9)N(R^9)_2$, —$R^8$—$OC(S)N(R^9)_2$, —$R^8$—$C(O)$—$R^{11}$—$C(O)R^9$, —$R^8$—$C(O)$—$R^{11}$—$C(S)R^9$, —$R^8$—$C(O)$—$R^{11}$—$C(NR^9)R^9$, —$R^8$—$C(O)$—$R^{11}$—$C(O)OR^9$, —$R^8$—$C(O)$—$R^{11}$—$C(S)OR^9$, —$R^8$—$C(O)$—$R^{11}$—$C(NR^9)OR^9$, —$R^8$—$C(O)$—$R^{11}$—$C(O)N(R^9)_2$, —$R^{11}$—$C(O)$—$R^{11}$—$C(S)N(R^9)_2$, —$R^8$—$C(O)$—$R^{11}$—$C(NR^9)N(R^9)_2$, —$R^8$—$C(O)$—$R^{11}$—$C(O)SR^9$, —$R^8$—$C(O)$—$R^{11}$—$C(S)SR^9$ and —$R^8$—$C(O)$—$R^{11}$—$C(NR^9)SR^9$.

21. The method of claim 20 wherein said compound is selected from the group consisting of:
1,4-dimethyl-5-naphthalen-1-yl-1H-pyrrole-3-carboxylic acid (4-methane sulfonyl-phenyl)-amide; and
1,4-dimethyl-5-(4-methyl-naphthalen-1-yl)-1H-pyrrole-3-carboxylic acid (4-methanesulfonyl-phenyl)-amide, or
a pharmaceutically acceptable salt of any of the foregoing.

22. The method of claim 1 wherein the diseases or disorder is related to heart disease.

23. The method of claim 1 wherein the disease or disorder is related to hypertension.

24. The method of claim 1 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

25. The method of claim 2 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

26. The method of claim 3 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

27. The method of claim 4 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

28. The method of claim 5 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

29. The method of claim 7 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

30. The method of claim 8 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

31. The method of claim 9 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

32. The method of claim 22 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

33. The method of claim 23 wherein the compound is 1-(2-hydroxy-ethyl)-4-methyl-N-[4-(methylsulfonyl)phenyl]-5-[2-(trifluoromethyl)phenyl]-1H-pyrrole-3-carboxamide, or a pharmaceutically acceptable salt thereof.

* * * * *